United States Patent
Berdini et al.

(10) Patent No.: US 8,691,806 B2
(45) Date of Patent: *Apr. 8, 2014

(54) PYRAZOLE DERIVATIVES AS PROTEIN KINASE MODULATORS

(75) Inventors: Valerio Berdini, Cambridge (GB); Gordon Saxty, Cambridge (GB); Marinus Leendert Verdonk, Burwell (GB); Steven John Woodhead, Cambridge (GB); Paul Graham Wyatt, Perth (GB); Robert George Boyle, Cambridge (GB); Hannah Fiona Sore, Cambridge (GB); David Winter Walker, Linton (GB); Ian Collins, Redhill (GB); Robert Downham, Newmarket (GB); Robin Arthur Ellis Carr, Bassingbourn (GB)

(73) Assignees: Astex Therapeutics Limited, Cambridge (GB); The Institute of Cancer Research: Royal Cancer Hospital, London (GB); Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,174

(22) Filed: Jun. 28, 2012

(65) Prior Publication Data

US 2013/0005702 A1    Jan. 3, 2013

Related U.S. Application Data

(63) Continuation of application No. 10/596,788, filed as application No. PCT/GB2004/005464 on Dec. 23, 2004, now Pat. No. 8,247,576.

(60) Provisional application No. 60/532,199, filed on Dec. 23, 2003, provisional application No. 60/577,843, filed on Jun. 8, 2004.

(30) Foreign Application Priority Data

Dec. 23, 2003   (GB) .................................. 0329617.5

(51) Int. Cl.
  *A61K 31/397*  (2006.01)
  *C07D 231/12*  (2006.01)

(52) U.S. Cl.
  USPC ..... 514/210.2; 514/406; 514/326; 548/377.1; 548/373.1; 548/356.1; 548/100

(58) Field of Classification Search
  None
  See application file for complete search history.

(56) References Cited

U.S. PATENT DOCUMENTS

| | | | | |
|---|---|---|---|---|
| 2,438,106 | A * | 3/1948 | Alburn et al. | 514/192 |
| 2,596,069 | A * | 5/1952 | Fox | 514/354 |
| 2,645,594 | A * | 7/1953 | Tabern | 514/297 |
| 2,736,681 | A * | 2/1956 | Tishler | 514/180 |
| 5,532,356 | A | 7/1996 | Smyser et al. | |
| 5,922,744 | A | 7/1999 | Harrison et al. | |
| 6,010,837 | A | 1/2000 | Clark et al. | |
| 6,015,825 | A | 1/2000 | Bell et al. | |
| 6,020,357 | A | 2/2000 | Pinto et al. | |
| 6,200,978 | B1 | 3/2001 | Maw et al. | |
| 7,393,842 | B2 | 7/2008 | Makriyannis et al. | |
| 7,799,782 | B2 | 9/2010 | Munson et al. | |
| 8,247,576 | B2 | 8/2012 | Berdini et al. | |
| 8,343,953 | B2 * | 1/2013 | Davies et al. | 514/210.2 |
| 8,497,294 | B2 | 7/2013 | Woodhead et al. | |
| 2002/0091116 | A1 | 7/2002 | Zhu et al. | |
| 2004/0122230 | A1 | 6/2004 | Welsh et al. | |
| 2005/0261315 | A1 | 11/2005 | Mehta et al. | |
| 2010/0166699 | A1 | 7/2010 | Thompson et al. | |
| 2011/0144080 | A1 | 6/2011 | Berdini et al. | |
| 2011/0269808 | A1 | 11/2011 | Woodhead et al. | |
| 2013/0005702 | A1 | 1/2013 | Berdini et al. | |

FOREIGN PATENT DOCUMENTS

| | | |
|---|---|---|
| EP | 1024138 A1 | 8/2000 |
| GB | 2427406 A | 12/2006 |
| JP | 2000-016984 A | 1/2000 |
| WO | 90/09381 A1 | 8/1990 |
| WO | 91/11445 A1 | 8/1991 |

(Continued)

OTHER PUBLICATIONS

Taylor, S.S. et al., PKA: a portrait of protein kinase dynamics, Biochemica et Biophysica, 1697, 2004, pp. 259-269.

(Continued)

*Primary Examiner* — Brandon Fetterolf
*Assistant Examiner* — Theodore R West
(74) *Attorney, Agent, or Firm* — Heslin Rothenberg Farley & Mesiti P.C.

(57) ABSTRACT

The invention provides compounds of the formula (I) having protein kinase B inhibiting activity:

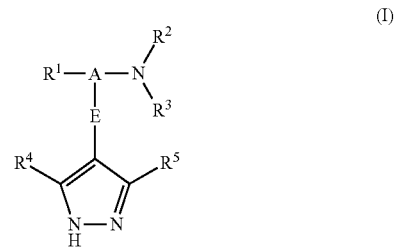

(I)

Also provided are pharmaceutical compositions containing the compounds, methods for preparing the compounds and their use as anticancer agents.

20 Claims, No Drawings

(56) References Cited

FOREIGN PATENT DOCUMENTS

| | | | |
|---|---|---|---|
| WO | 94/29300 | A1 | 12/1994 |
| WO | 95/10513 | A1 | 4/1995 |
| WO | 97/01552 | A1 | 1/1997 |
| WO | 97/36886 | A1 | 10/1997 |
| WO | 98/04528 | A2 | 2/1998 |
| WO | 98/25617 | A1 | 6/1998 |
| WO | 99/38508 | A1 | 8/1999 |
| WO | 00/07996 | A2 | 2/2000 |
| WO | 00/14066 | A1 | 3/2000 |
| WO | 00/31063 | A1 | 6/2000 |
| WO | 00/39091 | A1 | 7/2000 |
| WO | 00/66562 | A1 | 11/2000 |
| WO | 00/69859 | A1 | 11/2000 |
| WO | 01/19788 | A2 | 3/2001 |
| WO | 01/19798 | A2 | 3/2001 |
| WO | 01/32653 | A1 | 5/2001 |
| WO | 01/64642 | A2 | 9/2001 |
| WO | 01/91754 | A1 | 12/2001 |
| WO | 02/088090 | A2 | 11/2002 |
| WO | 03/011855 | A2 | 2/2003 |
| WO | 03/028686 | A1 | 4/2003 |
| WO | 03/030898 | A1 | 4/2003 |
| WO | 03/048081 | A2 | 6/2003 |
| WO | 03/048158 | A1 | 6/2003 |
| WO | 03/059884 | A1 | 7/2003 |
| WO | 03/068230 | A1 | 8/2003 |
| WO | 03/080545 | A2 | 10/2003 |
| WO | 03/086247 | A1 | 10/2003 |
| WO | 03/090680 | A2 | 11/2003 |
| WO | 2004/011460 | A2 | 2/2004 |
| WO | 2004/110350 | A2 | 12/2004 |
| WO | 2005/003101 | A2 | 1/2005 |
| WO | 2005/012256 | A1 | 2/2005 |
| WO | 2005/035506 | A1 | 4/2005 |
| WO | 2005/061460 | A1 | 7/2005 |
| WO | 2005/061463 | A1 | 7/2005 |
| WO | 2005/117909 | A2 | 12/2005 |
| WO | 2006/046023 | A1 | 5/2006 |
| WO | 2006/071819 | A1 | 7/2006 |
| WO | 2006/091450 | A1 | 8/2006 |
| WO | 2006/136821 | A1 | 12/2006 |
| WO | 2006/136823 | A1 | 12/2006 |
| WO | 2006/136829 | A2 | 12/2006 |
| WO | 2006/136830 | A1 | 12/2006 |
| WO | 2006/136837 | A2 | 12/2006 |
| WO | 2008/110846 | A2 | 9/2008 |

OTHER PUBLICATIONS

Hill, Michelle M. et al., Inhibition of protein kinase B/Akt: implications for cancer therapy, Pharmacology & Therapeutics, 93, 2002, pp. 243-251.

Barnett, Stanley F. et al., The Akt/PKB Family of Protein Kinases: A Review of Small Molecule Inhibitors and Progress Towards Target Validation, Current Topics in Medicinal Chemistry, 5, 2005, pp. 109-125.

Nagarajan, K. et al., Mechanism of Formation of p-Substituted Products in Displacement Reactions on α-Chlorodiphenylacetamides, Tetrahedron Letters, No. 22, 1968, pp. 2717-2720.

Simig, Gyula et al., Single Electron Transfer Inititated Thermal Reactions of Arylmethyl Halides, X, Acta Chimica Hungarica, 118(4), 1985, pp. 309-314.

Ajmani Subhash et al., A comprehensive structure-activity analysis of protein kinase B-alpha (Akt1) inhibitors, Journal of Molecular Graphics and Modelling, 28(7), 2010, pp. 683-694.

Murray Andrew J., Pharmacological PKA Inhibition: All May Not Be What It Seems, Science Signaling, Jun. 3, 2008, vol. 1, issue 22, pp. 1-6.

Dorwald, Florencio Zaragoza, Side Reactions in Organic Synthesis, Wiley-VCH, 2005, p. 1 and preface.

Drewry et al. CAS 143 229871 (2005).

Schrijvers et al., Docetaxel, cisplatin and 5-fluorouracil in patients with locally advanced unresectable head and neck cancer: a phase I-II feasibility study, Annals of Oncology, vol. 15, 638-645, 2004.

Yap et al.; AT13148 Is a Novel, Oral Multi-AGC Kinase Inhibitor with Potent Pharmacodynamic and Antitumor Activity; *Clin Cancer Re*; Jul. 15, 2012; 18(14).

Marshall, Chris; Effective inhibition of actomyosin contractility by a new series of Rho-kinase inhibitors blocks multiple modes of melanoma cell migration and metastasis; PowerPoint Presentation at Antitumoral Targets Upstream and Downstream of RAS GTPases Meeting; Santander, Spain; Oct. 8-9, 2012.

Lala & Orucevic, Role of nitric oxide in tumor progression: Lessons from experimental tumors, Cancer and Metastasis Reviews 1998 17(1) 91-106.

Golub et al., Molecular Classification of Cancer: Class Discovery and Class Prediction by Gene Expression Monitoring, Science (1999) vol. 286 531-537.

Cancer online retrieved Jul. 6, 2007 retrieved from the internet http://www.nlm.nih.gov/medlineplus/cancer.html.

Cancer online retrieved Jul. 6, 2007 retrieved from the internet http://en.wikipedia.org/wiki/Cancer.

\* cited by examiner

PYRAZOLE DERIVATIVES AS PROTEIN KINASE MODULATORS

CROSS REFERENCE TO RELATED APPLICATIONS

This application is continuation of U.S. application Ser. No. 10/596,788 (which published as U.S. 2011-0144080 on Jun. 16, 2011), which is a national phase filing under 35 U.S.C. §371 of PCT International Application PCT/GB2004/005464, filed Dec. 23, 2004, and published under PCT Article 21(2) in English as WO 2005/061463 on Jul. 7, 2005, which claimed benefit of priority under 35 U.S.C. §119(a) from British application 03 29617.5, filed Dec. 23, 2003, and under 35 U.S.C. §119(e) from U.S. Provisional Application Nos. 60/532,199, filed Dec. 23, 2003 and 60/577,843, filed Jun. 8, 2004. The entire contents of each of the prior applications are incorporated herein by reference.

This invention relates to pyrazole-containing aryl- and heteroaryl-alkylamine compounds that inhibit or modulate the activity of protein kinase B (PKB) and protein kinase A (PKA), to the use of the compounds in the treatment or prophylaxis of disease states or conditions mediated by PKB and PKA, and to novel compounds having PKB and PKA inhibitory or modulating activity. Also provided are pharmaceutical compositions containing the compounds and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Apoptosis or programmed cell death is an important physiological process which removes cells no longer required by an organism. The process is important in early embryonic growth and development allowing the non-necrotic controlled breakdown, removal and recovery of cellular components. The removal of cells by apoptosis is also important in the maintenance of chromosomal and genomic integrity of growing cell populations. There are several known checkpoints in the cell growth cycle at which DNA damage and genomic integrity are carefully monitored. The response to the detection of anomalies at such checkpoints is to arrest the growth of such cells and initiate repair processes. If the damage or anomalies cannot be repaired then apoptosis is initiated by the damaged cell in order to prevent the propagation of faults and errors. Cancerous cells consistently contain numerous mutations, errors or rearrangements in their chromosomal DNA. It is widely believed that this occurs in part because the majority of tumours have a defect in one or more of the processes responsible for initiation of the apoptotic process. Normal control mechanisms cannot kill the cancerous cells and the chromosomal or DNA coding errors continue to be propagated. As a consequence restoring these pro-apoptotic signals or suppressing unregulated survival signals is an attractive means of treating cancer.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzyme PI3K is activated by a range of growth and survival factors e.g. EGF, PDGF and through the generation of polyphosphatidylinositols, initiates the activation of the downstream signalling events including the activity of the kinases PDK1 and protein kinase B (PKB) also known as Akt. This is also true in host tissues, e.g. vascular endothelial cells as well as neoplasias. PKB is a protein ser/thr kinase consisting of a kinase domain together with an N-terminal PH domain and C-terminal regulatory domain. The enzyme PKB itself is phosphorylated on Thr 308 by PDK1 and on Ser 473 by an as yet unidentified kinase. Full activation requires phosphorylation at both sites whilst association between PIP3 and the PH domain is required for anchoring of the enzyme to the cytoplasmic face of the lipid membrane providing optimal access to substrates.

Activated PKB in turn phosphorylates a range of substrates contributing to the overall survival response. Whilst we cannot be certain that we understand all of the factors responsible for mediating the PKB dependent survival response, some important actions are believed to be phosphorylation and inactivation of the pro-apoptotic factor BAD and caspase 9, phosphorylation of Forkhead transcription factors e.g. FKHR leading to their exclusion from the nucleus, and activation of the NfkappaB pathway by phosphorylation of upstream kinases in the cascade.

In addition to the anti-apoptotic and pro-survival actions of the PKB pathway, the enzyme also plays an important role in promoting cell proliferation. This action is again likely to be mediated via several actions, some of which are thought to be phosphorylation and inactivation of the cyclin dependent kinase inhibitor of $p21^{Cip1/WAF1}$, and phosphorylation and activation of mTOR, a kinase controlling several aspects of cell growth.

The phosphatase PTEN which dephosphorylates and inactivates polyphosphatidyl-inositols is a key tumour suppressor protein which normally acts to regulate the PI3K/PKB survival pathway. The significance of the PI3K/PKB pathway in tumourigenesis can be judged from the observation that PTEN is one of the most common targets of mutation in human tumours, with mutations in this phosphatase having been found in ~50% or more of melanomas (Guldberg et al 1997, Cancer Research 57, 3660-3663) and advanced prostate cancers (Cairns et al 1997 Cancer Research 57, 4997). These observations and others suggest that a wide range of tumour types are dependent on the enhanced PKB activity for growth and survival and would respond therapeutically to appropriate inhibitors of PKB.

There are 3 closely related isoforms of PKB called alpha, beta and gamma, which genetic studies suggest have distinct but overlapping functions. Evidence suggests that they can all independently play a role in cancer. For example PKB beta has been found to be over-expressed or activated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330), PKB alpha is amplified in human gastric, prostate and breast cancer (Staal 1987, PNAS 84, 5034-5037; Sun et al 2001, Am. J. Pathol. 159, 431-437) and increased PKB gamma activity has been observed in steroid independent breast and prostate cell lines (Nakatani et al 1999, J. Biol. Chem. 274, 21528-21532).

The PKB pathway also functions in the growth and survival of normal tissues and may be regulated during normal physiology to control cell and tissue function. Thus disorders associated with undesirable proliferation and survival of normal cells and tissues may also benefit therapeutically from treatment with a PKB inhibitor. Examples of such disorders are disorders of immune cells associated with prolonged expansion and survival of cell population leading to a prolonged or up regulated immune response. For example, T and B lymphocyte response to cognate antigens or growth factors such as interleukin-2 activates the PI3K/PKB pathway and is responsible for maintaining the survival of the antigen specific lymphocyte clones during the immune response. Under conditions in which lymphocytes and other immune cells are responding to inappropriate self or foreign antigens, or in which other abnormalities lead to prolonged activation, the PKB pathway contributes an important survival signal preventing the normal mechanisms by which the immune response is terminated via apoptosis of the activated cell population. There is a considerable amount of evidence demonstrating the expansion of lymphocyte populations responding to self antigens in autoimmune conditions such as multiple sclerosis and arthritis. Expansion of lymphocyte populations responding inappropriately to foreign antigens is a feature of another set of conditions such as allergic responses and asthma. In summary inhibition of PKB could provide a beneficial treatment for immune disorders.

Other examples of inappropriate expansion, growth, proliferation, hyperplasia and survival of normal cells in which PKB may play a role include but are not limited to atherosclerosis, cardiac myopathy and glomerulonephritis.

In addition to the role in cell growth and survival, the PKB pathway functions in the control of glucose metabolism by insulin. Available evidence from mice deficient in the alpha and beta isoforms of PKB suggests that this action is mediated by the beta isoform. As a consequence, modulators of PKB activity may also find utility in diseases in which there is a dysfunction of glucose metabolism and energy storage such as diabetes, metabolic disease and obesity.

Cyclic AMP-dependent protein kinase (PKA) is a serine/threonine protein kinase that phosphorylates a wide range of substrates and is involved in the regulation of many cellular processes including cell growth, cell differentiation, ion-channel conductivity, gene transcription and synaptic release of neurotransmitters. In its inactive form, the PKA holoenzyme is a tetramer comprising two regulatory subunits and two catalytic subunits.

PKA acts as a link between G-protein mediated signal transduction events and the cellular processes that they regulate. Binding of a hormone ligand such as glucagon to a transmembrane receptor activates a receptor-coupled G-protein (GTP-binding and hydrolyzing protein). Upon activation, the alpha subunit of the G protein dissociates and binds to and activates adenylate cyclase, which in turn converts ATP to cyclic-AMP (cAMP). The cAMP thus produced then binds to the regulatory subunits of PKA leading to dissociation of the associated catalytic subunits. The catalytic subunits of PKA, which are inactive when associated with the regulatory sub-units, become active upon dissociation and take part in the phosphorylation of other regulatory proteins.

For example, the catalytic sub-unit of PKA phosphorylates the kinase Phosphorylase Kinase which is involved in the phosphorylation of Phosphorylase, the enzyme responsible for breaking down glycogen to release glucose. PKA is also involved in the regulation of glucose levels by phosphorylating and deactivating glycogen synthase. Thus, modulators of PKA activity (which modulators may increase or decrease PKA activity) may be useful in the treatment or management of diseases in which there is a dysfunction of glucose metabolism and energy storage such as diabetes, metabolic disease and obesity.

PKA has also been established as an acute inhibitor of T cell activation. Anndahl et al, have investigated the possible role of PKA type I in HIV-induced T cell dysfunction on the basis that T cells from HIV-infected patients have increased levels of cAMP and are more sensitive to inhibition by cAMP analogues than are normal T cells. From their studies, they concluded that increased activation of PKA type I may contribute to progressive T cell dysfunction in HIV infection and that PKA type I may therefore be a potential target for immunomodulating therapy. Aandahl, E. M., Aukrust, P., Skålhegg, B. S., Müller, F., Frøland, S. S., Hansson, V., Taskén, K. *Protein kinase A type I antagonist restores immune responses of T cells from HIV-infected patients.* FASEB J. 12, 855-862 (1998).

It has also been recognised that mutations in the regulatory sub-unit of PKA can lead to hyperactivation in endocrine tissue.

Because of the diversity and importance of PKA as a messenger in cell regulation, abnormal responses of cAMP can lead to a variety of human diseases such as irregular cell growth and proliferation (Stratakis, C. A., Cho-Chung, Y. S.; Protein Kinase A and human diseases. *Trends Endrocri. Metab.* 2002, 13, 50-52). Over-expression of PKA has been observed in a variety of human cancer cells including those from ovarian, breast and colon patients. Inhibition of PKA would therefore be an approach to treatment of cancer (Li, Q.; Zhu, G-D., *Current Topics in Medicinal Chemistry,* 2002, 2, 939-971).

For a review of the role of PKA in human disease, see for example, *Protein Kinase A and Human Disease,* Edited by Constantine A. Stratakis, Annals of the New York Academy of Sciences, Volume 968, 2002, ISBN 1-57331-412-9.

Several classes of compounds have been disclosed as having PKA and PKB inhibitory activity.

For example, a class of isoquinolinyl-sulphonamido-diamines having PKB inhibitory activity is disclosed in WO 01/91754 (Yissum).

WO0/07996 (Chiron) discloses substituted pyrazoles having estrogen receptor agonist activity. The compounds are described as being useful in treating or preventing inter alia estrogen-receptor mediated breast cancer. PKB inhibitory activity is not disclosed.

WO 00/31063 (Searle) discloses substituted pyrazole compounds as p38 kinase inhibitors.

WO 01/32653 (Cephalon) discloses a class of pyrazolone kinase inhibitors. WO 03/059884 (X-Ceptor Therapeutics) discloses N-substituted pyridine compounds as modulators of nuclear receptors.

WO 03/068230 (Pharmacia) discloses substituted pyridones as p38 MAP kinase modulators.

WO 00/66562 (Dr Reddy's Research Foundation) discloses a class of 1-phenyl-substituted pyrazoles for use as anti-inflammatory agents. The 1-phenyl group is substituted by a sulphur-containing substituent as a sulphonamide or sulphonyl group.

SUMMARY OF THE INVENTION

The invention provides compounds that have protein kinase B (PKB) and protein A (PKA) inhibiting or modulating activity, and which it is envisaged will be useful in preventing or treating disease states or conditions mediated by PKB or PKA.

In a first aspect, the invention provides a compound of the formula (I):

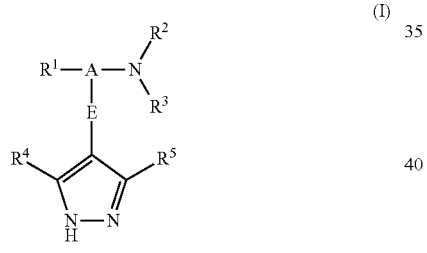

or a salt, solvate, tautomer or N-oxide thereof;
wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom α with respect to the $NR^2R^3$ group and provided that the oxo group when present is located at a carbon atom α with respect to the $NR^2R^3$ group;

E is a monocyclic or bicyclic carbocyclic or heterocyclic group;

$R^1$ is an aryl or heteroaryl group;

$R^2$ and $R^3$ are independently selected from hydrogen, $C_{1-4}$ hydrocarbyl and $C_{1-4}$ acyl wherein the hydrocarbyl and acyl moieties are optionally substituted by one or more substituents selected from fluorine, hydroxy, amino, methylamino, dimethylamino and methoxy;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N;

or $NR^2R^3$ and the carbon atom of linker group A to which it is attached together form a cyano group;

$R^4$ is selected from hydrogen, halogen, $C_{1-5}$ saturated hydrocarbyl, $C_{1-5}$ saturated hydrocarbyloxy, cyano, and $CF_3$; and $R^5$ is selected from selected from hydrogen, halogen, $C_{1-5}$ saturated hydrocarbyl, $C_{1-5}$ saturated hydrocarbyloxy, cyano, $CONH_2$, $CONHR^9$, $CF_3$, $NH_2$, $NHCOR^9$ or $NHCONHR^9$;

$R^9$ is a group $R^{9a}$ or $(CH_2)R^{9a}$, wherein $R^{9a}$ is a monocyclic or bicyclic group which may be carbocyclic or heterocyclic;

the carbocyclic group or heterocyclic group $R^{9a}$ being optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

The invention also provides a compound of the formula (Ia):

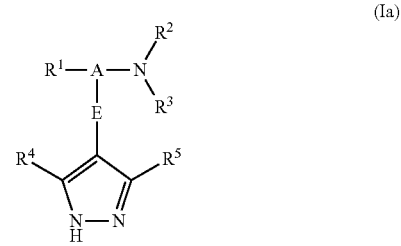

or a salt, solvate, tautomer or N-oxide thereof;
wherein A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from oxo, fluorine and hydroxy, provided that the hydroxy group when present is not located at a carbon atom α with respect to the NR²R³ group and provided that the oxo group when present is located at a carbon atom α with respect to the NR²R³ group;

E is a monocyclic or bicyclic carbocyclic or heterocyclic group;

R¹ is an aryl or heteroaryl group;

R² and R³ are independently selected from hydrogen, $C_{1-4}$ hydrocarbyl and $C_{1-4}$ acyl;

or R² and R³ together with the nitrogen atom to which they are attached form a saturated monocyclic heterocyclic group having 4-7 ring members and optionally containing a second heteroatom ring member selected from O and N;

or one of R² and R³ together with the nitrogen atom to which they are attached and one or more atoms from the linker group A form a saturated monocyclic heterocyclic group having 4-7 ring members and optionally containing a second heteroatom ring member selected from O and N;

or NR²R³ and the carbon atom of linker group A to which it is attached together form a cyano group;

R⁴ is selected from hydrogen, halogen, $C_{1-5}$ saturated hydrocarbyl, cyano and $CF_3$; and R⁵ is selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

R⁹ is phenyl or benzyl each optionally substituted by one or more substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$.

Also provided are compounds of the general formula (Ib):

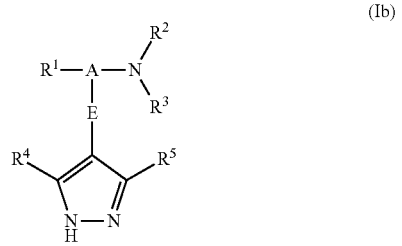

(Ib)

or salts, solvates, tautomers or N-oxides thereof;

wherein A is a saturated hydrocarbon linker group containing from 1 to 7 carbon atoms, the linker group having a maximum chain length of 5 atoms extending between R¹ and NR²R³ and a maximum chain length of 4 atoms extending between E and NR²R³, wherein one of the carbon atoms in the linker group may optionally be replaced by an oxygen or nitrogen atom, and wherein the carbon atoms of the linker group A may optionally bear one or more substituents selected from fluorine and hydroxy, provided that the hydroxy group is not located at a carbon atom α with respect to the NR²R³ group;

E is a monocyclic or bicyclic carbocyclic or heterocyclic group;

R¹ is an aryl or heteroaryl group;

R² and R³ are independently selected from hydrogen, $C_{1-4}$ hydrocarbyl and $C_{1-4}$ acyl;

or R² and R³ together with the nitrogen atom to which they are attached form a saturated monocyclic heterocyclic group having 4-7 ring members and optionally containing a second heteroatom ring member selected from O and N;

or one of R² and R³ together with the nitrogen atom to which they are attached and one or more atoms from the linker group A form a saturated monocyclic heterocyclic group having 4-7 ring members and optionally containing a second heteroatom ring member selected from O and N;

or NR²R³ and the carbon atom of linker group A to which it is attached together form a cyano group;

R⁴ is selected from hydrogen, halogen, $C_{1-5}$ saturated hydrocarbyl, cyano, and $CF_3$; and R⁵ is selected from selected from hydrogen, halogen, $C_{1-5}$ saturated hydrocarbyl, cyano, $CONH_2$, $CF_3$, $NH_2$, $NHCOR^9$ or $NHCONHR^9$;

R⁹ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$, $R^c$ is selected from hydrogen and $C_{1-4}$ hydrocarbyl; and $X^1$ is O, S or $NR^c$ and $X^2$ is =O, =S or =$NR^c$.

The invention further provides:

A compound per se of the formula (II), (III), (IV), (V) or any other sub-group or embodiment of the formula (I) as defined herein.

A compound of the formula (I), (Ia), (Ib), (II), (III), (IV), (V) or any sub-group thereof as defined herein for use in the prophylaxis or treatment of a disease state or condition mediated by protein kinase B.

The use of a compound of formula (I), (Ia), (Ib), (II), (III), (IV), (V) or any sub-group thereof as defined herein for the manufacture of a medicament for the prophylaxis or treatment of a disease state or condition mediated by protein kinase B.

A method for the prophylaxis or treatment of a disease state or condition mediated by protein kinase B, which method comprises administering to a subject in need thereof a compound of the formula (I), (Ia), (Ib), (II), (III), (IV), (V) or any sub-group thereof as defined herein.

A method for treating a disease or condition comprising or arising from abnormal cell growth or abnormally arrested cell death in a mammal, the method comprising administering to the mammal a compound of the formula (I), (Ia), (Ib), (II), (III), (IV), (V) or any sub-group thereof as defined herein in an amount effective to inhibit protein kinase B activity.

A method of inhibiting protein kinase B, which method comprises contacting the kinase with a kinase-inhibiting compound of the formula (I), (Ia), (Ib), (II), (III), (IV), (V) or any sub-group thereof as defined herein.

A method of modulating a cellular process (for example cell division) by inhibiting the activity of a protein kinase B using a compound of the formula (I), (Ia), (Ib), (II), (III), (IV), (V) or any sub-group thereof as defined herein.

A compound of the formula (I), (Ia), (Ib), (II), (III), (IV), (V) or any sub-group or embodiment thereof as defined herein for use in the prophylaxis or treatment of a disease state or condition mediated by protein kinase A.

The use of a compound of formula (I), (Ia), (Ib), (II), (III), (IV), (V) or any sub-group or embodiment thereof as defined herein for the manufacture of a medicament for the prophylaxis or treatment of a disease state or condition mediated by protein kinase A.

A method for the prophylaxis or treatment of a disease state or condition mediated by protein kinase A, which method comprises administering to a subject in need thereof a compound of the formula (I), (Ia), (Ib), (II), (III), (IV), (V) or any sub-group or embodiment thereof as defined herein.

A method for treating a disease or condition comprising or arising from abnormal cell growth or abnormally arrested cell death in a mammal, the method comprising administering to the mammal a compound of the formula (I), (Ia), (Ib), (II), (III), (IV), (V) or any sub-group or embodiment thereof as defined herein in an amount effective to inhibit protein kinase A activity.

A method of inhibiting protein kinase A, which method comprises contacting the kinase with a kinase-inhibiting compound of the formula (I), (Ia), (Ib), (II), (III), (IV), (V) or any sub-group or embodiment thereof as defined herein.

A method of modulating a cellular process (for example cell division) by inhibiting the activity of a protein kinase A using a compound of the formula (I), (Ia), (Ib), (II), (III), (IV), (V) or any sub-group or embodiment thereof as defined herein.

The use of a compound of the formula (I), (Ia), (Ib), (II), (III), (IV), (V) or any sub-group thereof as defined herein for the manufacture of a medicament for the prophylaxis or treatment of a disease state or condition arising from abnormal cell growth or abnormally arrested cell death.

A method for treating a disease or condition comprising or arising from abnormal cell growth in a mammal, which method comprises administering to the mammal a compound of the formula (I), (Ia), (Ib), (II), (III), (IV), (V) or any sub-group thereof as defined herein in an amount effective in inhibiting abnormal cell growth or abnormally arrested cell death.

A method for alleviating or reducing the incidence of a disease or condition comprising or arising from abnormal cell growth or abnormally arrested cell death in a mammal, which method comprises administering to the mammal a compound of the formula (I), (Ia), (Ib), (II), (III), (IV), (V) or any sub-group thereof as defined herein in an amount effective in inhibiting abnormal cell growth.

A pharmaceutical composition comprising a novel compound of the formula (I), (Ia), (Ib), (II), (III), (IV), (V) or any sub-group thereof as defined herein and a pharmaceutically acceptable carrier.

A compound of the formula (I), (Ia), (Ib), (II), (III), (IV), (V) or any sub-group thereof as defined herein for use in medicine.

The use of a compound of the formula (I), (Ia), (Ib), (II), (III), (IV), (V) or any sub-group thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a compound (e.g. a therapeutically effective amount) of the formula (I), (Ia), (Ib), (II), (III), (IV), (V) or any sub-group thereof as defined herein.

A method for alleviating or reducing the incidence of a disease state or condition disclosed herein, which method comprises administering to a patient (e.g. a patient in need thereof) a compound (e.g. a therapeutically effective amount) of the formula (I), (Ia), (Ib), (II), (III), (IV), (V) or any sub-group thereof as defined herein.

A method for the diagnosis and treatment of a disease state or condition mediated by protein kinase B, which method comprises (i) screening a patient to determine whether a disease or condition from which the patient is or may be suffering is one which would be susceptible to treatment with a compound having activity against protein kinase B; and (ii) where it is indicated that the disease or condition from which the patient is thus susceptible, thereafter administering to the patient a compound of the formula (I), (Ia), (Ib), (II), (III), (IV), (V) or any sub-group thereof as defined herein.

The use of a compound of the formula (I), (Ia), (Ib), (II), (III), (IV), (V) or any sub-group thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase B.

A method for the diagnosis and treatment of a disease state or condition mediated by protein kinase A, which method comprises (i) screening a patient to determine whether a disease or condition from which the patient is or may be suffering is one which would be susceptible to treatment with a compound having activity against protein kinase A; and (ii) where it is indicated that the disease or condition from which the patient is thus susceptible, thereafter administering to the patient a compound of the formula (I), (Ia), (Ib), (II), (III), (IV), (V) or any sub-group or embodiment thereof as defined herein.

The use of a compound of the formula (I), (Ia), (Ib), (II), (III), (IV), (V) or any sub-group or embodiment thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase A.

GENERAL PREFERENCES AND DEFINITIONS

The following general preferences and definitions shall apply to each of the moieties A, E and $R^1$ to $R^5$ and $R^9$ and any sub-definition, sub-group or embodiment thereof, unless the context indicates otherwise.

Any references to Formula (I) herein shall be taken also to refer to formulae (Ia), (Ib), (II), (III), (IV), (V) and any other sub-group of compounds within formula (I) unless the context requires otherwise.

References to "carbocyclic" and "heterocyclic" groups as used herein shall, unless the context indicates otherwise, include both aromatic and non-aromatic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term non-aromatic group embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C═C, C≡C or N═C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings. Each ring may contain up to about four heteroatoms typically selected from nitrogen, sulphur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Examples of bicyclic heteroaryl groups containing a six membered ring fused to a five membered ring include but are not limited to benzfuran, benzthiophene, benzimidazole, benzoxazole, benzisoxazole, benzthiazole, benzisothiazole, isobenzofuran, indole, isoindole, indolizine, indoline, isoindoline, purine (e.g., adenine, guanine), indazole, benzodioxole and pyrazolopyridine groups.

Examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur.

The heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulfolane and sulfolene), cyclic sulphoxides, cyclic sulphonamides and combinations thereof (e.g. thiomorpholine). Other examples of non-aromatic heterocyclic groups include cyclic amide moieties (e.g. as in pyrrolidone) and cyclic ester moieties (e.g. as in butyrolactone).

Examples of monocyclic non-aromatic heterocyclic groups include 5-, 6- and 7-membered monocyclic heterocyclic groups. Particular examples include morpholine, thiomorpholine and its S-oxide and S,S-dioxide (particularly thiomorpholine), piperidine (e.g. 1-piperidinyl, 2-piperidinyl 3-piperidinyl and 4-piperidinyl), N-alkyl piperidines such as N-methyl piperidine, piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine, N-ethyl piperazine and N-isopropylpiperazine.

One sub-group of monocyclic non-aromatic heterocyclic groups includes morpholine, piperidine (e.g. 1-piperidinyl, 2-piperidinyl 3-piperidinyl and 4-piperidinyl), piperidone, pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include piperidine, pyrrolidine, azetidine, morpholine, piperazine and N-alkyl piperazines. A further particular example of a non-aromatic heterocyclic group, which also forms part of the above group of preferred non-aromatic heterocyclic groups, is azetidine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Each of the definitions of carbocyclic and heterocyclic groups in this specification may optionally exclude any one or any combination of two or more of the following moieties:
 substituted or unsubstituted pyridone rings;
 substituted or unsubstituted pyrrolo[1,2-a]pyrimid-4-ones;
 substituted or unsubstituted pyrazolones.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$—$R^b$ wherein $R^a$ is a bond, O, CO, $X^1C(X^2)$, $C(X^2)$ $X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;
 $R^c$ is selected from hydrogen and $C_{1-4}$ hydrocarbyl; and
 $X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

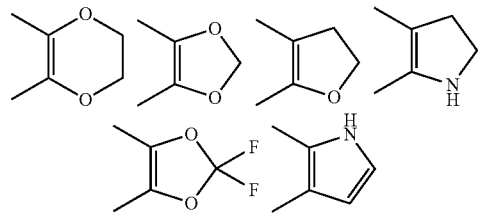

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone, except where otherwise stated. In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, can be substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl, naphthyl, indane and indene groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The definition "$R^a$—$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, $C(O)O$, $C(O)S$, $C(O)NR^c$, $C(S)O$, $C(S)S$, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^c(S)O$, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(NR^c)S$, $NR^cC(NR^c)S$, $OC(O)NR^c$, $SC(O)NR^c$, $NR^c(O)NR^c$, $OC(S)NR^c$, $SC(S)NR^c$, $NR^cC(S)NR^c$, $OC(NR^c)NR^c$, $SC(NR^c)NR^c$, $NR^cC(NR^cNR^c$, S, SO, $SO_2$ $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by, for example, a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$—$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl, difluoromethyl, 2,2,2-trifluoroethyl and perfluoroalkyl groups such as trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl, phenethyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$—$R^b$ where $R^a$ is $SO_2$ include alkylsulphonyl, heteroarylsulphonyl and arylsulphonyl groups, particularly monocyclic aryl and hetero aryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$—$R^b$ where $R^a$ is $NR^c$ include amino, $C_{1-4}$ alkylamino (e.g. methylamino, ethylamino, propylamino, isopropylamino, tert-butylamino), alkylamino (e.g. dimethylamino and diethylamino) and cycloalkylamino (e.g. cyclopropylamino, cyclopentylamino and cyclohexylamino).

Specific Embodiments of and Preferences for A, E, $R^1$ to $R^5$ and $R^9$

The Group "A"

In formula (I), A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$. Within these constraints, the moieties E and $R^1$ can each be attached at any location on the group A.

The term "maximum chain length" as used herein refers to the number of atoms lying directly between the two moieties in question, and does not take into account any branching in the chain or any hydrogen atoms that may be present. For example, in the structure A shown below:

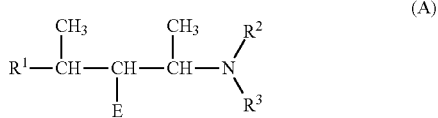

(A)

the chain length between $R^1$ and $NR^2R^3$ is 3 atoms whereas the chain length between E and $NR^2R^3$ is 2 atoms.

In general it is presently preferred that the linker group has a maximum chain length of 3 atoms (for example 1 or 2 atoms).

In one embodiment, the linker group has a chain length of 1 atom extending between $R^1$ and $NR^2R^3$.

In another embodiment, the linker group has a chain length of 2 atoms extending between $R^1$ and $NR^2R^3$.

In a further embodiment, the linker group has a chain length of 3 atoms extending between $R^1$ and $NR^2R^3$.

It is preferred that the linker group has a maximum chain length of 3 atoms extending between E and $NR^2R^3$.

In one particularly preferred group of compounds, the linker group has a chain length of 2 or 3 atoms extending between $R^1$ and $NR^2R^3$ and a chain length of 2 or 3 atoms extending between E and $NR^2R^3$.

One of the carbon atoms in the linker group may optionally be replaced by an oxygen or nitrogen atom.

When present, the nitrogen atom may be linked directly to the group E.

In one embodiment, the carbon atom to which the group $R^1$ is attached is replaced by an oxygen atom.

In another embodiment, $R^1$ and E are attached to the same carbon atom of the linker group, and a carbon atom in the chain extending between E and $NR^2R^3$ is replaced by an oxygen atom.

When a nitrogen atom or oxygen atom are present, it is preferred that the nitrogen or oxygen atom and the $NR^2R^3$ group are spaced apart by at least two intervening carbon atoms.

In one particular group of compounds within formula (I), the linker atom linked directly to the group E is a carbon atom and the linker group A has an all-carbon skeleton.

The carbon atoms of the linker group A may optionally bear one or more substituents selected from oxo, fluorine and hydroxy, provided that the hydroxy group is not located at a carbon atom α with respect to the $NR^2R^3$ group, and provided also that the oxo group is located at a carbon atom α with respect to the $NR^2R^3$ group. Typically, the hydroxy group, if present, is located at a position β with respect to the $NR^2R^3$ group. In general, no more than one hydroxy group will be present. Where fluorine is present, it may be present as a single fluorine substituent or may be present in a difluoromethylene or trifluoromethyl group, for example. In one embodiment, a fluorine atom is located at a position β with respect to the $NR^2R^3$ group.

It will be appreciated that that when an oxo group is present at the carbon atom adjacent the $NR^2R^3$ group, the compound of the formula (I) will be an amide.

In one embodiment of the invention, no fluorine atoms are present in the linker group A.

In another embodiment of the invention, no hydroxy groups are present in the linker group A.

In a further embodiment, no oxo group is present in the linker group A.

In one group of compounds of the formula (I) neither hydroxy groups nor fluorine atoms are present in the linker group A, e.g. the linker group A is unsubstituted.

Preferably, when a carbon atom in the linker group A is replaced by a nitrogen atom, the group A bears no more than one hydroxy substituent and more preferably bears no hydroxy substituents.

When there is a chain length of four atoms between E and $NR^2R^3$, it is preferred that the linker group A contains no nitrogen atoms and more preferably has an all carbon skeleton.

In order to modify the susceptibility of the compounds to metabolic degradation in vivo, the linker group A can have a branched configuration at the carbon atom attached to the $NR^2R^3$ group. For example, the carbon atom attached to the $NR^2R^3$ group can be attached to a pair of gem-dimethyl groups.

In one particular group of compounds of the formula (I), the portion $R^1$-A-$NR^2R^3$ of the compound is represented by the formula $R^1$-$(G)_k$-$(CH_2)_m$—W—$O_b$—$(CH_2)_n$—$(CR^6R^7)_p$—$NR^2R^3$ wherein G is NH, NMe or O; W is attached to the group E and is selected from $(CH_2)_j$—$CR^{20}$, $(CH_2)_j$—N and $(NH)_j$—CH; b is 0 or 1, j is 0 or 1, k is 0 or 1, m is 0 or 1, n is 0, 1, 2, or 3 and p is 0 or 1; the sum of b and k is 0 or 1; the sum of j, k, m, n and p does not exceed 4; $R^6$ and $R^7$ are the same or different and are selected from methyl and ethyl, or $CR^6R^7$ forms a cyclopropyl group; and $R^{20}$ is selected from hydrogen, methyl, hydroxy and fluorine;

In another sub-group of compounds of the formula (I), the portion $R^1$-A-$NR^2R^3$ of the compound is represented by the formula $R^1$-$(G)_k$-$(CH_2)_m$—X—$(CH_2)_n$—$(CR^6R^7)_p$—$NR^2R^3$ wherein G is NH, NMe or O; X is attached to the group E and is selected from $(CH_2)_j$—CH, $(CH_2)_j$—N and $(NH)_j$—CH; j is 0 or 1, k is 0 or 1, m is 0 or 1, n is 0, 1, 2, or 3 and p is 0 or 1, and the sum of j, k, m, n and p does not exceed 4; and $R^6$ and $R^7$ are the same or different and are selected from methyl and ethyl, or $CR^6R^7$ forms a cyclopropyl group.

A particular group $CR^6R^7$ is $C(CH_3)_2$.

Preferably X is $(CH_2)_j$—CH.

Particular configurations where the portion $R^1$-A-$NR^2R^3$ of the compound is represented by the formula $R^1$-$(G)_k$-$(CH_2)_m$—X—$(CH_2)_n$—$(CR^6R^7)_p$—$NR^2R^3$ are those wherein:

k is 0, m is 0 or 1, n is 0, 1, 2 or 3 and p is 0.
k is 0, m is 0 or 1, n is 0, 1 or 2 and p is 1.
X is $(CH_2)_j$—CH, k is 1, m is 0, n is 0, 1, 2 or 3 and p is 0.
X is $(CH_2)_j$—CH, k is 1, m is 0, n is 0, 1 or 2 and p is 1.
X is $(CH_2)_j$—CH, G is 0, k is 1, m is 0, n is 0, 1, 2 or 3 and p is 0.

Particular configurations wherein the portion $R^1$-A-$NR^2R^3$ of the compound is represented by the formula $R^1$-$(G)_k$-$(CH_2)_m$—W—$O_b$—$(CH_2)_n$—$(CR^6R^7)_p$—$NR^2R^3$ are those wherein:

k is 0, m is 0, W is $(CH_2)_j$—$CR^{20}$, j is 0, $R^{20}$ is hydrogen, b is 1, n is 2 and p is 0.
k is 0, m is 0, W is $(CH_2)_j$—$CR^{20}$, j is 0, $R^{20}$ is hydroxy, b is 0, n is 1 and p is 0.
k is 0, m is 0, W is $(CH_2)_j$—$CR^{20}$, j is 0, $R^{20}$ is methyl, b is 0, n is 1 and p is 0.
k is 0, m is 0, W is $(CH_2)_j$—$CR^{20}$, j is 0, $R^{20}$ is fluorine, b is 0, n is 1 and p is 0.

In one preferred configuration, the portion $R^1$-A-$NR^2R^3$ of the compound is represented by the formula $R^1$—X—$(CH_2)_n$—$NR^2R^3$ wherein X is attached to the group E and is a group CH, and n is 2.

Particular examples of the linker group A, together with their points of attachment to the groups $R^1$, E and $NR^2R^3$, are shown in Table 1 below.

TABLE 1

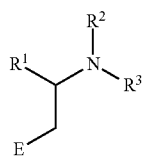    A1

TABLE 1-continued

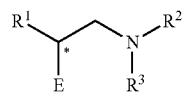    A2

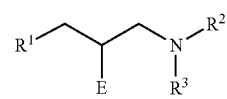    A3

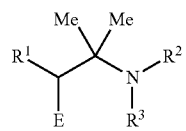    A4

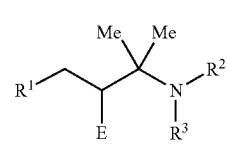    A5

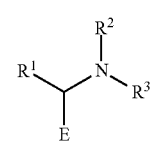    A6

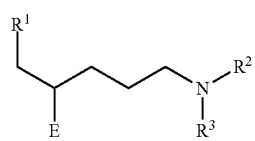    A7

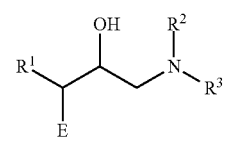    A8

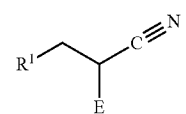    A9

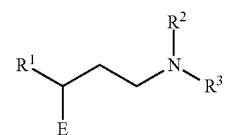    A10

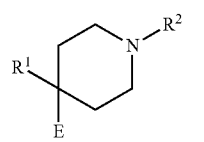    A11

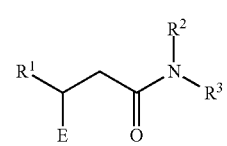    A12

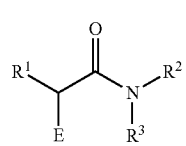    A13

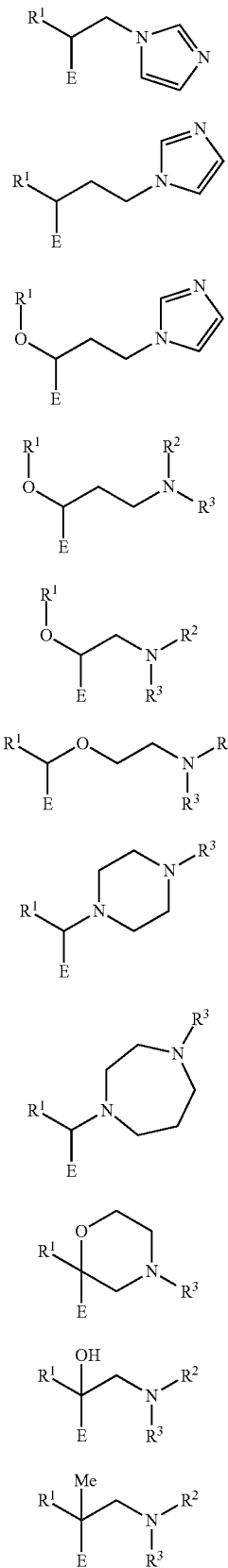
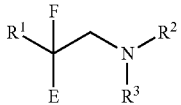

Currently preferred groups include A1, A2, A3, A6, A10, A11, A22 and A23.

One particular set of groups includes A1, A2, A3, A10 and A11.

A further particular set of groups includes A2 and A11.

Another particular set of groups includes A6, A22 and A23.

A further set of groups includes A1, A2 and A3.

In group A2, the asterisk designates a chiral centre. Compounds having the R configuration at this chiral centre represent one preferred sub-group of compounds of the invention.

$R^1$

The group $R^1$ is an aryl or heteroaryl group and may be selected from the list of such groups set out in the section headed General Preferences and Definitions.

$R^1$ can be monocyclic or bicyclic and, in one preferred embodiment, is monocyclic. Particular examples of monocyclic aryl and heteroaryl groups are six membered aryl and heteroaryl groups containing up to 2 nitrogen ring members, and five membered heteroaryl groups containing up to 3 heteroatom ring members selected from O, S and N.

Examples of such groups include phenyl, naphthyl, thienyl, furan, pyrimidine and pyridine, with phenyl being presently preferred.

The group $R^1$ can be unsubstituted or substituted by up to 5 substituents, and examples of substituents are those listed in group $R^{10}$ above.

Particular substituents include hydroxy; $C_{1-4}$ acyloxy; fluorine; chlorine; bromine; trifluoromethyl; cyano; $CONH_2$; nitro; $C_{1-4}$ hydrocarbyloxy and $C_{1-4}$ hydrocarbyl each optionally substituted by $C_{1-2}$ alkoxy, carboxy or hydroxy; $C_{1-4}$ acylamino; benzoylamino; pyrrolidinocarbonyl; piperidinocarbonyl; morpholinocarbonyl; piperazinocarbonyl; five and six membered heteroaryl and heteroaryloxy groups containing one or two heteroatoms selected from N, O and S; phenyl; phenyl-$C_{1-4}$ alkyl; phenyl-$C_{1-4}$ alkoxy; heteroaryl-$C_{1-4}$ alkyl; heteroaryl-$C_{1-4}$ alkoxy and phenoxy, wherein the heteroaryl, heteroaryloxy, phenyl, phenyl-$C_{1-4}$ alkyl, phenyl-$C_{1-4}$ alkoxy, heteroaryl-$C_{1-4}$ alkyl, heteroaryl-$C_{1-4}$ alkoxy and phenoxy groups are each optionally substituted with 1, 2 or 3 substituents selected from $C_{1-2}$ acyloxy, fluorine, chlorine, bromine, trifluoromethyl, cyano, $CONH_2$, $C_{1-2}$ hydrocarbyloxy and $C_{1-2}$ hydrocarbyl each optionally substituted by methoxy or hydroxy.

Preferred substituents include hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; phenyl; pyridyl; and phenoxy wherein the phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

In one sub-group of compounds, the substituents for $R^1$ are chosen from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

Although up to 5 substituents may be present, more typically there are 0, 1, 2, 3 or 4 substituents, preferably 0, 1, 2 or 3, and more preferably 0, 1 or 2.

In one embodiment, the group $R^1$ is unsubstituted or substituted by up to 5 substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

In a further embodiment, the group $R^1$ can have one or two substituents selected from hydroxy, fluorine, chlorine, cyano, phenyloxy, pyrazinyloxy, benzyloxy, methyl and methoxy.

In another embodiment, the group $R^1$ can have one or two substituents selected from fluorine, chlorine, trifluoromethyl, methyl and methoxy.

When $R^1$ is a phenyl group, particular examples of substituent combinations include mono-chlorophenyl and dichlorophenyl.

Further examples of substituent combinations include those wherein $R^1$ is hydroxyphenyl, fluorochlorophenyl, cyanophenyl, methoxyphenyl, methoxy-chlorophenyl, fluorophenyl, difluorophenyl, phenoxyphenyl, pyrazinyloxyphenyl or benzyloxyphenyl.

When $R^1$ is a six membered aryl or heteroaryl group, a substituent may advantageously be present at the para position on the six-membered ring. Where a substituent is present at the para position, it is preferably larger in size than a fluorine atom.

$R^2$ and $R^3$

In one group of compounds of the formula (I), $R^2$ and $R^3$ are independently selected from hydrogen, $C_{1-4}$ hydrocarbyl and $C_{1-4}$ acyl wherein the hydrocarbyl and acyl moieties are optionally substituted by one or more substituents selected from fluorine, hydroxy, amino, methylamino, dimethylamino and methoxy.

When the hydrocarbyl moiety is substituted by a hydroxy, amino, methylamino, dimethylamino or methoxy group, typically there are at least two carbon atoms between the substituent and the nitrogen atom of the group $NR^2R^3$. Particular examples of substituted hydrocarbyl groups are hydroxyethyl and hydroxypropyl.

In another group of compounds of the invention, $R^2$ and $R^3$ are independently selected from hydrogen, $C_{1-4}$ hydrocarbyl and $C_{1-4}$ acyl.

Typically the hydrocarbyl group, whether substituted or unsubstituted, is an alkyl group, more usually a $C_1$, $C_2$ or $C_3$ alkyl group, and preferably a methyl group. In one particular sub-group of compounds, $R^2$ and $R^3$ are independently selected from hydrogen and methyl and hence $NR^2R^3$ can be an amino, methylamino or dimethylamino group. In one particular embodiment, $NR^2R^3$ can be an amino group. In another particular embodiment, $NR^2R^3$ can be a methylamino group.

In an alternative embodiment, the $C_{1-4}$ hydrocarbyl group can be a cyclopropyl, cyclopropylmethyl or cyclobutyl group.

In another group of compounds, $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N.

In a further group of compounds, $R^2$ and $R^3$ together with the nitrogen atom to which they are attached form a saturated monocyclic heterocyclic group having 4-7 ring members and optionally containing a second heteroatom ring member selected from O and N.

The saturated monocyclic heterocyclic group can be unsubstituted or substituted by one or more substituents $R^{10}$ as defined above in the General Preferences and Definitions section of this application. Typically, however, any substituents on the heterocyclic group will be relatively small substituents such as $C_{1-4}$ hydrocarbyl (e.g. methyl, ethyl, n-propyl, i-propyl, cyclopropyl, n-butyl, sec-butyl and tert-butyl), fluorine, chlorine, hydroxy, amino, methylamino, ethylamino and dimethylamino. Particular substituents are methyl groups.

The saturated monocyclic ring can be an azacycloalkyl group such as an azetidine, pyrrolidine, piperidine or azepane ring, and such rings are typically unsubstituted. Alternatively, the saturated monocyclic ring can contain an additional heteroatom selected from O and N, and examples of such groups include morpholine and piperazine. Where an additional N atom is present in the ring, this can form part of an NH group or an N—$C_{1-4}$alkyl group such as an N-methyl, N-ethyl, N-propyl or N-isopropyl group.

Where $NR^2R^3$ forms an imidazole group, the imidazole group can be unsubstituted or substituted, for example by one or more relatively small substituents such as $C_{1-4}$ hydrocarbyl (e.g. methyl, ethyl, propyl, cyclopropyl and butyl), fluorine, chlorine, hydroxy, amino, methylamino, ethylamino and dimethylamino. Particular substituents are methyl groups.

In a further group of compounds, one of $R^2$ and $R^3$ together with the nitrogen atom to which they are attached and one or more atoms from the linker group A form a saturated monocyclic heterocyclic group having 4-7 ring members and optionally containing a second heteroatom ring member selected from O and N.

Examples of such compounds include compounds wherein $NR^2R^3$ and A form a unit of the formula:

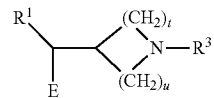

where t and u are each 0, 1, 2 or 3 provided that the sum of t and u falls within the range of 2 to 4.

Further examples of such compounds include compounds wherein $NR^2R^3$ and A form a cyclic group of the formula:

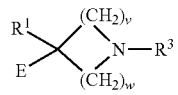

where v and w are each 0, 1, 2 or 3 provided that the sum of v and w falls within the range of 2 to 5. Particular examples of cyclic compounds are those in which v and w are both 2.

Further examples of such compounds include compounds wherein $NR^2R^3$ and A form a cyclic group of the formula:

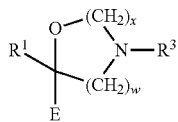

where x and w are each 0, 1, 2 or 3 provided that the sum of x and w falls within the range of 2 to 4. Particular examples of cyclic compounds are those in which x is 2 and w is 1.

$R^4$

In formula (I), $R^4$ is selected from hydrogen, halogen, $C_{1-5}$ saturated hydrocarbyl, $C_{1-5}$ saturated hydrocarbyloxy, cyano, and $CF_3$.

More typically, $R^4$ is selected from hydrogen, halogen, $C_{1-5}$ saturated hydrocarbyl, cyano and $CF_3$. Preferred values for $R^4$ include hydrogen and methyl. In a particular embodiment, $R^4$ is hydrogen.

$R^5$

In formula (I), $R^5$ is selected from hydrogen, halogen, $C_{1-5}$ saturated hydrocarbyl, $C_{1-5}$ saturated hydrocarbyloxy, cyano, $CONH_2$, $CONHR^9$, $CF_3$, $NH_2$, $NHCOR^9$ and $NHCONHR^9$; $NHCONHR^9$ where $R^9$ is a group $R^{9a}$ or $(CH_2)R^{9a}$, wherein $R^{9a}$ is an optionally substituted monocyclic or bicyclic group which may be carbocyclic or hetero cyclic.

Examples of carbocyclic and heterocyclic groups are set out above in the General Preferences and Definitions section.

Typically the carbocyclic and heterocyclic groups are monocyclic.

Preferably the carbocyclic and heterocyclic groups are aromatic.

Particular examples of the group $R^9$ are optionally substituted phenyl or benzyl.

Preferably, $R^5$ is selected from selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$ where $R^9$ is optionally substituted phenyl or benzyl.

More preferably, $R^5$ is selected from selected from hydrogen, halogen, $C_{1-5}$ saturated hydrocarbyl, cyano, $CF_3$, $NH_2$, $NHCOR^9$ and $NHCONHR^9$ where $R^9$ is optionally substituted phenyl or benzyl.

The group $R^9$ is typically unsubstituted phenyl or benzyl, or phenyl or benzyl substituted by 1, 2 or 3 substituents selected from halogen; hydroxy; trifluoromethyl; cyano; carboxy; $C_{1-4}$alkoxycarbonyl; $C_{1-4}$ acyloxy; amino; mono- or di-$C_{1-4}$ alkylamino; $C_{1-4}$ alkyl optionally substituted by halogen, hydroxy or $C_{1-2}$ alkoxy; $C_{1-4}$ alkoxy optionally substituted by halogen, hydroxy or $C_{1-2}$ alkoxy; phenyl, five and six membered heteroaryl groups containing up to 3 heteroatoms selected from O, N and S; and saturated carbocyclic and heterocyclic groups containing up to 2 heteroatoms selected from O, S and N.

Particular examples of the moiety $R^5$ include hydrogen, fluorine, chlorine, bromine, methyl, ethyl, hydroxyethyl, methoxymethyl, cyano, $CF_3$, $NH_2$, $NHCOR^{9b}$ and $NHCONHR^{9b}$ where $R^{9b}$ is phenyl or benzyl optionally substituted by hydroxy, $C_{1-4}$ acyloxy, fluorine, chlorine, bromine, trifluoromethyl, cyano, $C_{1-4}$ hydrocarbyloxy (e.g. alkoxy) and $C_{1-4}$ hydrocarbyl (e.g. alkyl) optionally substituted by $C_{1-2}$ alkoxy or hydroxy.

Preferred examples of $R^5$ include hydrogen, methyl and cyano. Preferably $R^5$ is hydrogen or methyl.

The Group "E"

In formula (I), E is a monocyclic or bicyclic carbocyclic or heterocyclic group and can be selected from the groups set out above in the section headed General Preferences and Definitions.

Preferred groups E are monocyclic and bicyclic aryl and heteroaryl groups and, in particular, groups containing a six membered aromatic or heteroaromatic ring such as a phenyl, pyridine, pyrazine, pyridazine or pyrimidine ring, more particularly a phenyl, pyridine, pyrazine or pyrimidine ring, and more preferably a pyridine or phenyl ring.

Examples of bicyclic groups include benzo-fused and pyrido-fused groups wherein the group A and the pyrazole ring are both attached to the benzo- or pyrido-moiety.

In one embodiment, E is a monocyclic group.

Particular examples of monocyclic groups include monocyclic aryl and heteroaryl groups such as phenyl, thiophene, furan, pyrimidine, pyrazine and pyridine, phenyl being presently preferred.

One subset of monocyclic aryl and heteroaryl groups comprises phenyl, thiophene, furan, pyrimidine and pyridine.

Examples of non-aromatic monocyclic groups include cycloalkanes such as cyclohexane and cyclopentane, and nitrogen-containing rings such as piperazine and piperazone.

It is preferred that the group A and the pyrazole group are not attached to adjacent ring members of the group E. For example, the pyrazole group can be attached to the group E in a meta or para relative orientation. Examples of such groups E include 1,4-phenylene, 1,3-phenylene, 2,5-pyridylene and 2,4-pyridylene, 1,4-piperazinyl, and 1,4-piperazonyl. Further examples include 1,3-disubstituted five membered rings.

The groups E can be unsubstituted or can have up to 4 substituents $R^8$ which may be selected from the group $R^{10}$ as hereinbefore defined. More typically however, the substituents $R^8$ are selected from hydroxy; oxo (when E is non-aromatic); halogen (e.g. chlorine and bromine); trifluoromethyl; cyano; $C_{1-4}$ hydrocarbyloxy optionally substituted by $C_{1-2}$ alkoxy or hydroxy; and $C_{1-4}$ hydrocarbyl optionally substituted by $C_{1-2}$ alkoxy or hydroxy.

Preferably there are 0-3 substituents, more preferably 0-2 substituents, for example 0 or 1 substituent. In one embodiment, the group E is unsubstituted.

E may be other than:
a substituted pyridone group;
a substituted thiazole group;
a substituted or unsubstituted pyrazole or pyrazolone group;
a substituted or unsubstituted bicyclic fused pyrazole group;
a phenyl ring fused to a thiophene ring or a six membered nitrogen-containing heteroaryl ring fused to a thiophene ring;
a substituted or unsubstituted piperazine group;

The group E can be an aryl or heteroaryl group having five or six members and containing up to three heteroatoms selected from O, N and S, the group E being represented by the formula:

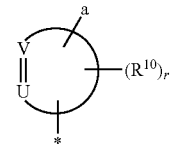

where * denotes the point of attachment to the pyrazole group, and "a" denotes the attachment of the group A, r is 0, 1 or 2;
U is selected from N and $CR^{12a}$; and
V is selected from N and $CR^{12b}$; where $R^{12a}$ and $R^{12b}$ are the same or different and each is hydrogen or a substituent containing up to ten atoms selected from C, N, O, F, Cl and S provided that the total number of non-hydrogen atoms present in $R^{12a}$ and $R^{12b}$ together does not exceed ten;
or $R^{12a}$ and $R^{12b}$ together with the carbon atoms to which they are attached form an unsubstituted five or six membered saturated or unsaturated ring containing up to two heteroatoms selected from O and N; and $R^{10}$ is as hereinbefore defined.

In one preferred group of compounds, E is a group:

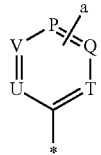

where * denotes the point of attachment to the pyrazole group, and "a" denotes the attachment of the group A;

P, Q and T are the same or different and are selected from N, CH and $NCR^{10}$, provided that the group A is attached to a carbon atom; and U, V and $R^{10}$ are as hereinbefore defined.

Examples of $R^{12a}$ and $R^{12b}$ include hydrogen and substituent groups $R^{10}$ as hereinbefore defined having no more than ten non-hydrogen atoms. Particular examples of $R^{12a}$ and $R^{12b}$ include methyl, ethyl, propyl, isopropyl, cyclopropyl, cyclobutyl, cyclopentyl, fluorine, chlorine, methoxy, trifluoromethyl, hydroxymethyl, hydroxyethyl, methoxymethyl, difluoromethoxy, trifluoromethoxy, 2,2,2-trifluoroethyl, cyano, amino, methylamino, dimethylamino, $CONH_2$, $CO_2Et$, $CO_2H$, acetamido, azetidinyl, pyrrolidino, piperidine, piperazino, morpholino, methylsulphonyl, aminosulphonyl, mesylamino and trifluoroacetamido.

Preferably, when U is $CR^{12a}$ and/or V is $CR^{12b}$ the atoms or groups in $R^{12a}$ and $R^{12b}$ that are directly attached to the carbon atom ring members C are selected from H, O (e.g. as in methoxy), NH (e.g. as in amino and methylamino) and $CH_2$ (e.g. as in methyl and ethyl).

Particular examples of the linker group E, together with their points of attachment to the group A ($^a$) and the pyrazole ring (*) are shown in Table 2 below.

TABLE 2

| | |
|---|---|
| 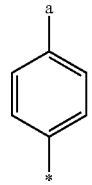 | B1 |
| 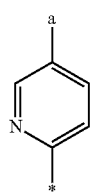 | B2 |
| 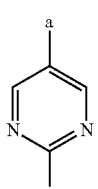 | B3 |

TABLE 2-continued

| | |
|---|---|
| 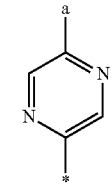 | B4 |
| 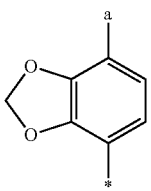 | B5 |
| 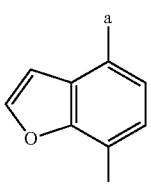 | B6 |
| 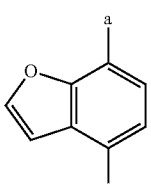 | B7 |
| 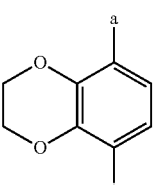 | B8 |
| 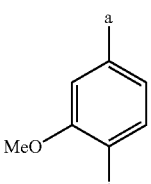 | B9 |
| 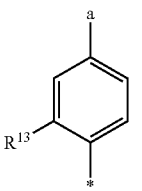 | B10 |

TABLE 2-continued

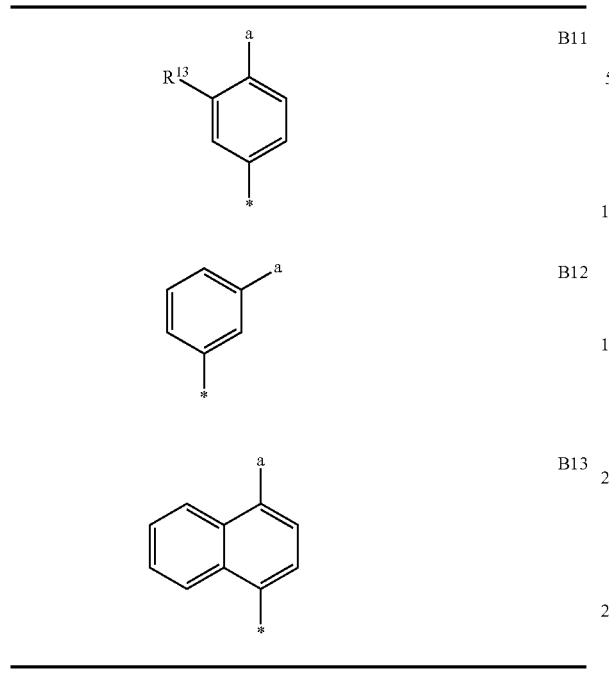

| | |
|---|---|
| B11 | (R13-substituted phenyl) |
| B12 | (meta-substituted phenyl) |
| B13 | (naphthyl) |

In the table, the substituent group $R^{13}$ is selected from methyl, chlorine, fluorine and trifluoromethyl.

The following optional exclusions may apply to the definition of E in any of formulae (I), (Ia), (Ib), (II), (III), (IV) and (V) and any sub-groups or sub-definitions thereof as defined herein:

E may be other than a phenyl group having a sulphur atom attached to the position para with respect to the pyrazole group.

E may be other than a substituted or unsubstituted benzimidazole, benzoxazole or benzthiazole group.

One sub-group of compounds of the formula (I) has the general formula (II):

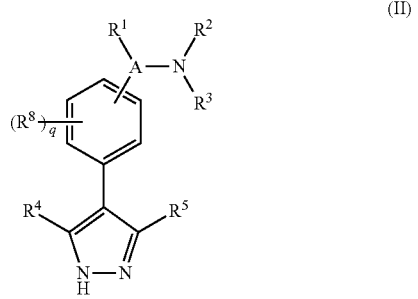

(II)

wherein the group A is attached to the meta or para position of the benzene ring, q is 0-4; $R^1$, $R^2$, $R^3$, $R^4$ and $R^5$ are as defined herein in respect of formula (I) and sub-groups, examples and preferences thereof; and $R^8$ is a substituent group as hereinbefore defined. In formula (II), q is preferably 0, 1 or 2, more preferably 0 or 1 and most preferably 0. Preferably the group A is attached to the para position of the benzene ring.

Within formula (II), one particular sub-group of compounds of the invention is represented by the formula (III):

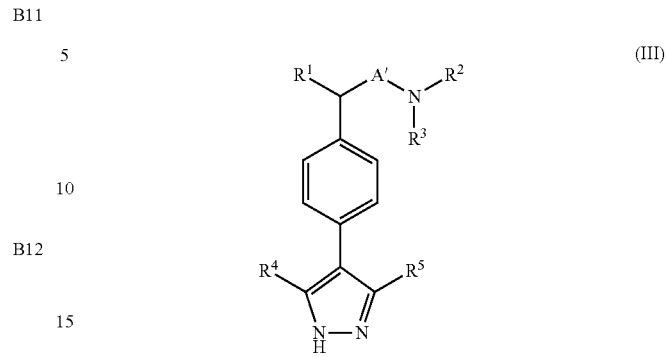

(III)

where A' is the residue of the group A and $R^1$ to $R^5$ are as defined herein.

Within formula (III), one preferred group of compounds is presented by the formula (IV):

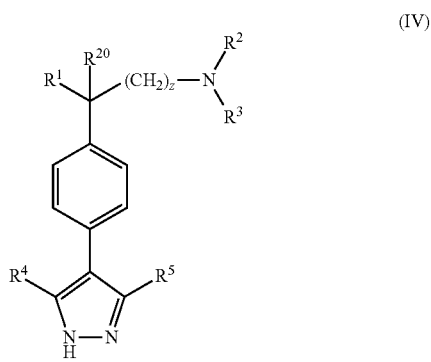

(IV)

wherein z is 0, 1 or 2, $R^{20}$ is selected from hydrogen, methyl, hydroxy and fluorine and $R^1$ to $R^5$ are as defined herein, provided that when z is 0, $R^{20}$ is other than hydroxy.

Another group of compounds within formula (III) is represented by formula (V):

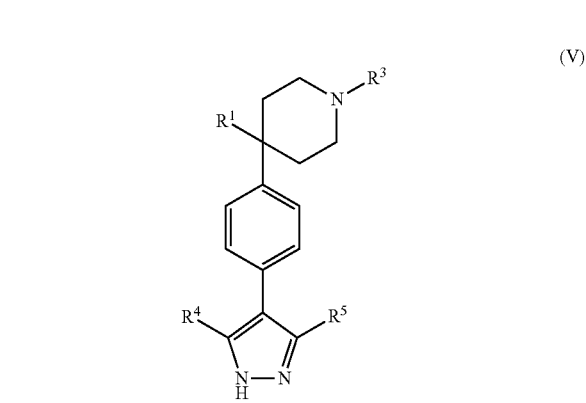

(V)

wherein and $R^1$ and $R^3$ to $R^5$ are as defined herein.

In formula (V), $R^3$ is preferably selected from hydrogen and $C_{1-4}$ hydrocarbyl, for example $C_{1-4}$ alkyl such as methyl, ethyl and isopropyl. More preferably $R^3$ is hydrogen.

In each of formulae (II) to (V), $R^1$ is preferably an optionally substituted phenyl group as defined herein.

In another sub-group of compounds of the invention, A is a saturated hydrocarbon linker group containing from 1 to 7 carbon atoms, the linker group having a maximum chain length of 5 atoms extending between $R^1$ and $NR^2R^3$ and a maximum chain length of 4 atoms extending between E and $NR^2R^3$, wherein one of the carbon atoms in the linker group may optionally be replaced by an oxygen or nitrogen atom; and wherein the carbon atoms of the linker group A may optionally bear one or more substituents selected from fluorine and hydroxy, provided that the hydroxy group when present is not located at a carbon atom α with respect to the $NR^2R^3$ group; and $R^5$ is selected from selected from hydrogen, $C_{1-5}$ saturated hydrocarbyl, cyano, $CONH_2$, $CF_3$, $NH_2$, $NHCOR^9$ and $NHCONHR^9$.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^9$ and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below and are selected from:

2-phenyl-2-[4-(1H-pyrazol-4-yl)-phenyl]-ethylamine;
3-phenyl-2-[3-(1H-pyrazol-4-yl)-phenyl]-propionitrile;
2-[4-(3,5-dimethyl-1H-pyrazol-4-yl)-phenyl]-2-phenyl-ethylamine;
2-(4-chloro-phenyl)-2-[4-(1H-pyrazol-4-yl)-phenyl]-ethylamine;
2-[3-(3,5-dimethyl-1H-pyrazol-4-yl)-phenyl]-1-phenyl-ethylamine;
3-phenyl-2-[3-(1H-pyrazol-4-yl)-phenyl]-propylamine;
3-phenyl-2-[4-(1H-pyrazol-4-yl)-phenyl]-propylamine;
{3-(4-chloro-phenyl)-3-[4-(1H-pyrazol-4-yl)-phenyl]-propyl}-methyl-amine;
{3-(3,4-difluoro-phenyl)-3-[4-(1H-pyrazol-4-yl)-phenyl]-propyl}-methyl-amine;
{3-(3-chloro-phenyl)-3-[4-(1H-pyrazol-4-yl)-phenyl]-propyl}-methyl-amine;
3-(4-chloro-phenyl)-3-[4-(1H-pyrazol-4-yl)-phenyl]-propionamide;
3-(4-chloro-phenyl)-3-[4-(1H-pyrazol-4-yl)-phenyl]-propylamine;
3-(3,4-dichloro-phenyl)-3-[4-(1H-pyrazol-4-yl)-phenyl]-propylamine;
4-(4-chloro-phenyl)-4-[4-(1H-pyrazol-4-yl)-phenyl]-piperidine;
4-(4-methoxy-phenyl)-4-[4-(1H-pyrazol-4-yl)-phenyl]-piperidine;
4-(4-chloro-phenyl)-1-methyl-4-[4-(1H-pyrazol-4-yl)-phenyl]-piperidine;
4-phenyl-4-[4-(1H-pyrazol-4-yl)-phenyl]-piperidine;
4-[4-(3,5-dimethyl-1H-pyrazol-4-yl)-phenyl]-4-phenyl-piperidine;
dimethyl-{3-[4-(1H-pyrazol-4-yl)-phenyl]-3-pyridin-2-yl-propyl}-amine;
{2-(4-chloro-phenyl)-2-[4-(1H-pyrazol-4-yl)-phenyl] ethyl}-dimethyl-amine;
{2-(4-chloro-phenyl)-2-[4-(1H-pyrazol-4-yl)-phenyl] ethyl}-methyl-amine;
{2-(4-chloro-phenyl)-2-[4-(1H-pyrazol-4-yl)-phenyl] ethyl}-methyl-amine (R);
{2-(4-chloro-phenyl)-2-[4-(1H-pyrazol-4-yl)-phenyl]-ethyl}-methyl-amine (S);
4-{2-(4-chloro-phenyl)-2-[4-(1H-pyrazol-4-yl)-phenyl]-ethyl}-morpholine;
4-{4-[1-(4-chloro-phenyl)-2-pyrrolidin-1-yl-ethyl]-phenyl}-1H-pyrazole;
{2-(4-chloro-phenyl)-2-[4-(1H-pyrazol-4-yl)-phenyl] ethyl}-isopropyl-amine;
dimethyl-{2-phenyl-2-[4-(1H-pyrazol-4-yl)-phenyl]-ethyl}-amine;
{2,2-bis-[4-(1H-pyrazol-4-yl)-phenyl]-ethyl}-dimethyl-amine;
{2,2-bis-[4-(1H-pyrazol-4-yl)-phenyl]-ethyl}-methyl-amine;
2-(4-chloro-phenyl)-2-[4-(1H-pyrazol-4-yl)-phenyl]-ethylamine (R);
2-(4-chloro-phenyl)-2-[4-(1H-pyrazol-4-yl)-phenyl]-ethylamine (S);
2-(4-chloro-phenyl)-2-[4-(1H-pyrazol-4-yl)-phenyl]-acetamide;
1-{2-(4-chloro-phenyl)-2-[4-(1H-pyrazol-4-yl)-phenyl] ethyl}-piperazine;
1-{2-(4-chloro-phenyl)-2-[4-(1H-pyrazol-4-yl)-phenyl] ethyl}-piperidine;
4-{4-[2-azetidin-1-yl-1-(4-chloro-phenyl)-ethyl]-phenyl}-1H-pyrazole;
1-phenyl-2-[4-(1H-pyrazol-4-yl)-phenyl]-ethylamine;
2-(4-chloro-phenyl)-N-methyl-2-[4-(1H-pyrazol-4-yl)-phenyl]-acetamide;
N-methyl-2,2-bis-[4-(1H-pyrazol-4-yl)-phenyl]acetamide;
{2-(4-chloro-phenyl)-2-[4-(1H-pyrazol-4-yl)-phenyl] ethyl}-methyl-amine;
{2-(4-chloro-phenyl)-2-[4-(1H-pyrazol-4-yl)-phenyl] ethyl}-ethyl-amine;
4-{4-[1-(4-chloro-phenyl)-2-imidazol-1-yl-ethyl]-phenyl}-1H-pyrazole;
methyl-{2-(4-phenoxy-phenyl)-2-[4-(1H-pyrazol-4-yl)-phenyl]-ethyl}-amine;
{2-(4-methoxy-phenyl)-2-[4-(1H-pyrazol-4-yl)-phenyl]-ethyl}-methyl-amine;
methyl-{2-[4-(pyrazin-2-yloxy)-phenyl]-2-[4-(1H-pyrazol-4-yl)-phenyl]ethyl}-amine;
methyl-{2-phenoxy-2-[4-(1H-pyrazol-4-yl)-phenyl]-ethyl}-amine;
2-{(4-chloro-phenyl)-[4-(1H-pyrazol-4-yl)-phenyl]-methoxy}-ethylamine;
4-{4-[1-(4-chloro-phenyl)-3-pyrrolidin-1-yl-propyl]-phenyl}-1H-pyrazole;
4-{4-[3-azetidin-1-yl-1-(4-chloro-phenyl)-propyl]-phenyl}-1H-pyrazole;
methyl-{3-naphthalen-2-yl-3-[4-(1H-pyrazol-4-yl)-phenyl]-propyl}-amine;
dimethyl-(4-{3-methylamino-1-[4-(1H-pyrazol-4-yl)-phenyl]-propyl}-phenyl)-amine;
{3-(4-fluoro-phenyl)-3-[4-(1H-pyrazol-4-yl)-phenyl]-propyl}-methyl-amine;
4-{4-[4-(4-chloro-phenyl)-piperidin-4-yl]-phenyl}-1H-pyrazole-3-carbonitrile;
3-(4-phenoxy-phenyl)-3-[4-(1H-pyrazol-4-yl)-phenyl]-propylamine;
1-{(4-chloro-phenyl)-[4-(1H-pyrazol-4-yl)-phenyl]-methyl}-piperazine;

1-methyl-4-{phenyl-[4-(1H-pyrazol-4-yl)-phenyl]methyl}-[1,4]diazepane;
{3-(3-chloro-phenoxy)-3-[4-(1H-pyrazol-4-yl)-phenyl]-propyl}-methyl-amine;
methyl-{2-phenyl-2-[6-(1H-pyrazol-4-yl)-pyridin-3-yl]-ethyl}-amine;
4-{4-[1-(4-chloro-phenyl)-3-imidazol-1-yl-propyl]-phenyl}-1H-pyrazole;
4-[4-(3-imidazol-1-yl-1-phenoxy-propyl)-phenyl]-1H-pyrazole;
4-{4-[4-(1H-pyrazol-4-yl)-phenyl]-piperidin-4-yl}-phenol;
1-{(4-chloro-phenyl)-[4-(1H-pyrazol-4-yl)-phenyl]-methyl}-piperazine;
{2-(4-fluoro-phenyl)-2-[4-(1H-pyrazol-4-yl)-phenyl]-ethyl}-methyl-amine;
{2-(3-chloro-phenyl)-2-[4-(1H-pyrazol-4-yl)-phenyl]ethyl}-methyl-amine;
4-[4-(2-methoxy-ethoxy)-phenyl]-4-[4-(1H-pyrazol-4-yl)-phenyl]-piperidine;
4-[4-(3-methoxy-propoxy)-phenyl]-4-[4-(1H-pyrazol-4-yl)-phenyl]-piperidine;
3-(3,4-dichloro-phenyl)-3-[4-(1H-pyrazol-4-yl)-phenyl]-propionamide;
2-(4-{2-methylamino-1-[4-(1H-pyrazol-4-yl)-phenyl]-ethyl}-phenoxy)-isonicotinamide;
{2-(3-chloro-phenoxy)-2-[4-(1H-pyrazol-4-yl)-phenyl]ethyl}-methyl-amine;
3-{2-(4-chloro-phenyl)-2-[4-(1H-pyrazol-4-yl)-phenyl]-ethylamino}-propan-1-ol;
2-{2-(4-chloro-phenyl)-2-[4-(1H-pyrazol-4-yl)-phenyl]ethylamino}-ethanol;
3-{2-(4-chloro-phenyl)-2-[4-(1H-pyrazol-4-yl)-phenyl]ethylamino}-propan-1-ol;
2-{2-(4-chloro-phenyl)-2-[4-(1H-pyrazol-4-yl)-phenyl]ethylamino}-ethanol;
{2-(4-Chloro-phenyl)-2-[4-(1H-pyrazol-4-yl)-phenyl]-ethyl}-cyclopropylmethyl-amine;
methyl-[2-[4-(1H-pyrazol-4-yl)-phenyl]-2-(4-pyridin-3-yl-phenyl)-ethyl]amine;
4-{3-methylamino-1-[4-(1H-pyrazol-4-yl)-phenyl]-propyl}-phenol;
3-(4-methoxy-phenyl)-3-[4-(1H-pyrazol-4-yl)-phenyl]-propylamine;
4-(4-chloro-phenyl)-4-[4-(3-methyl-1H-pyrazol-4-yl)-phenyl]-piperidine;
2-(4-chloro-phenyl)-2-[4-(1H-pyrazol-4-yl)-phenyl]-morpholine;
(4-{4-[4-(1H-pyrazol-4-yl)-phenyl]-piperidin-4-yl}-phenoxy)-acetic acid,
(4-{4-[4-(1H-pyrazol-4-yl)-phenyl]-piperidin-4-yl}-phenoxy)-acetic acid, methyl ester;
4-{4-[4-(1H-pyrazol-4-yl)-phenyl]-piperidin-4-yl}-benzonitrile;
{2-(4-chloro-phenyl)-2-[4-(1H-pyrazol-4-yl)-phenyl]-propyl}-methyl-amine;
1-(4-chloro-phenyl)-2-methylamino-1-[4-(1H-pyrazol-4-yl)-phenyl]-ethanol;
2-amino-1-(4-chloro-phenyl)-1-[4-(1H-pyrazol-4-yl)-phenyl]-ethanol;
4-(3,4-dichloro-phenyl)-4-[4-(1H-pyrazol-4-yl)-phenyl]-piperidine;
4-(3-chloro-4-methoxy-phenyl)-4-[4-(1H-pyrazol-4-yl)-phenyl]-piperidine;
4-(4-chloro-3-fluoro-phenyl)-4-[4-(1H-pyrazol-4-yl)-phenyl]-piperidine;
4-{4-[4-(1H-pyrazol-4-yl)-phenyl]-piperidin-4-yl}-benzoic acid;
4-[4-(1H-pyrazol-4-yl)-phenyl]-1,2,3,4,5,6-hexahydro-[4,4']bipyridinyl;
3-(3-chloro-phenyl)-3-[4-(1H-pyrazol-4-yl)-phenyl]-propylamine;
2-methylamino-1-(4-nitro-phenyl)-1-[4-(1H-pyrazol-4-yl)-phenyl]ethanol;
2-(3-chloro-4-methoxy-phenyl)-2-[4-(1H-pyrazol-4-yl)-phenyl]-ethylamine;
2-(4-chloro-phenyl)-2-fluoro-2-[4-(1H-pyrazol-4-yl)-phenyl]-ethylamine;
3-(3,4-dichloro-phenyl)-3-[6-(1H-pyrazol-4-yl)-pyridin-3-yl]-propylamine;
2-(4-chloro-3-fluoro-phenyl)-2-[4-(1H-pyrazol-4-yl)-phenyl]-ethylamine;
4-(2-chloro-3-fluoro-phenyl)-4-[4-(1H-pyrazol-4-yl)-phenyl]-piperidine;
1-{(3,4-dichloro-phenyl)-[4-(1H-pyrazol-4-yl)-phenyl]methyl}-piperazine;
2-(3,4-dichloro-phenyl)-2-[4-(1H-pyrazol-4-yl)-phenyl]-ethylamine;
{2-(3-chloro-4-methoxy-phenyl)-2-[4-(1H-pyrazol-4-yl)-phenyl]ethyl}-methyl-amine;
4-{4-[2-azetidin-1-yl-1-(4-chloro-phenoxy)-ethyl]-phenyl}-1H-pyrazole;
3-(3-chloro-4-methoxy-phenyl)-3-[4-(1H-pyrazol-4-yl)-phenyl]-propylamine;
{3-(3-chloro-4-methoxy-phenyl)-3-[4-(1H-pyrazol-4-yl)-phenyl]-propyl}-methyl-amine;
1-{(3,4-dichloro-phenyl)-[4-(1H-pyrazol-4-yl)-phenyl]-methyl}-piperazine; and
C-(4-chloro-phenyl)-C-[4-(1H-pyrazol-4-yl)-phenyl]methylamine;
and salts, solvates, tautomers and N-oxides thereof.

In one embodiment, the compound of the formula (I) is selected from the group consisting of:
{2-(4-chloro-phenyl)-2-[4-(1H-pyrazol-4-yl)-phenyl]ethyl}-methyl-amine (R);
4-(4-chloro-phenyl)-4-[4-(1H-pyrazol-4-yl)-phenyl]-piperidine;
3-(4-chloro-phenyl)-3-[4-(1H-pyrazol-4-yl)-phenyl]-propylamine;
3-(3,4-dichloro-phenyl)-3-[4-(1H-pyrazol-4-yl)-phenyl]-propylamine;
{3-(4-chloro-phenyl)-3-[4-(1H-pyrazol-4-yl)-phenyl]-propyl}-methyl-amine;
{2-(4-chloro-phenyl)-2-[4-(1H-pyrazol-4-yl)-phenyl]ethyl}-dimethyl-amine; and
2-(4-chloro-phenyl)-2-[4-(1H-pyrazol-4-yl)-phenyl]-ethylamine.

A further subset of compounds of the formula (I) consists of
4-(3-chloro-4-methoxy-phenyl)-4-[4-(1H-pyrazol-4-yl)-phenyl]-piperidine;
2-(4-chloro-phenyl)-2-[4-(1H-pyrazol-4-yl)-phenyl]-ethylamine (R isomer);
and salts, solvates, tautomers and N-oxides thereof.

Salts, Solvates, Tautomers, Isomers, N-Oxides, Esters, Prodrugs and Isotopes

In this section, as in all other sections of this application, unless the context indicates otherwise, references to formula (I) included references to formulae (Ia), (Ib), (II), (III), (IV) and (V) and all other sub-groups, preferences and examples thereof as defined herein.

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to formula (I) should be taken to refer also to formula (II) and sub-groups thereof unless the context indicates otherwise.

Salt forms may be selected and prepared according to methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. For example, acid addition salts may be prepared by dissolving the free base in an organic solvent in which a given salt form is insoluble or poorly soluble and then adding the required acid in an appropriate solvent so that the salt precipitates out of solution.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), D-oxoglutaric, glycolic, hippuric, hydrobromic, hydrochloric, hydriodic, isethionic, lactic (e.g. (+)-L-lactic and (±)-DL-lactic), lactobionic, maleic, malic, (−)-L-malic, malonic, (±)-DL-mandelic, methanesulphonic, naphthalene sulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated ammo acids and cation exchange resins.

One particular group of acid addition salts includes salts formed with hydrochloric, hydriodic, phosphoric, nitric, sulphuric, citric, lactic, succinic, maleic, malic, isethionic, fumaric, benzene sulphonic, toluenesulphonic, methanesulphonic, ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compounds of the invention may exist as mono- or di-salts depending upon the pKa of the acid from which the salt is formed. In stronger acids, the basic pyrazole nitrogen, as well as the nitrogen atom in the group NR²R³, may take part in salt formation. For example, where the acid has a pKa of less than about 3 (e.g. an acid such as hydrochloric acid, sulphuric acid or trifluoroacetic acid), the compounds of the invention will typically form salts with 2 molar equivalents of the acid.

If the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

Where the compounds of the formula (I) contain an amine function, these may form quaternary ammonium salts, for example by reaction with an alkylating agent according to methods well known to the skilled person. Such quaternary ammonium compounds are within the scope of formula (I).

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4ᵗʰ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) the pyrazole group may take either of the following two tautomeric forms A and B.

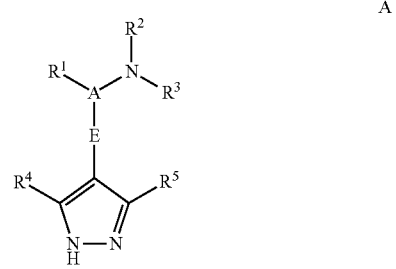

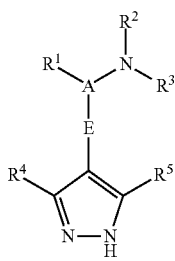

B

For simplicity, the general formula (I) illustrates form A but the formula is to be taken as embracing both form A and form B.

Where compounds of the formula (I) contain one or more chiral centres, and can exist in the form of two or more optical isomers, references to compounds of the formula (I) include all optical isomeric forms thereof (e.g. enantiomers and diastereoisomers), either as individual optical isomers, or mixtures or two or more optical isomers, unless the context requires otherwise.

For example, the group A can include one or more chiral centres. Thus, when E and $R^1$ are both attached to the same carbon atom on the linker group A, the said carbon atom is typically chiral and hence the compound of the formula (I) will exist as a pair of enantiomers (or more than one pair of enantiomers where more than one chiral centre is present in the compound).

The optical isomers may be characterised and identified by their optical activity (i.e. as + and − isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluloyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Esters such as carboxylic acid esters and acyloxy esters of the compounds of formula (I) bearing a carboxylic acid group or a hydroxyl group are also embraced by Formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu);
$C_{1-7}$ amino alkyl (e.g., amino ethyl; 2-(N,N-diethylamino) ethyl;
2-(4-morpholino)ethyl); and
acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl, (4-tetrahydropyranyloxy) carbonyloxymethyl; 1-(4-tetrahydropyranyloxy)-carbonyloxyethyl; (4-tetrahydropyranyl)carbonyloxymethyl, and 1-(4-tetrahydropyranyl)-carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT). For example, the prodrug may be a sugar derivative or other glycoside conjugate, or may be an amino acid ester derivative.

Methods for the Preparation of Compounds of the Formula (I)

In this section, as in all other sections of this application, unless the context indicates otherwise, references to formula (I) included references to formulae (Ia), (Ib), (II), (III), (IV) and (V) and all other sub-groups, preferences and examples thereof as defined herein.

Compounds of the formula (I) can be prepared by reaction of a compound of the formula (X) with a compound of the formula (XI) or an N-protected derivative thereof:

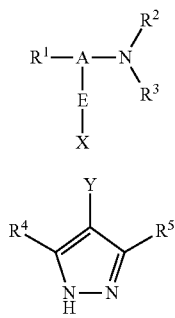

wherein A, E, and $R^1$ to $R^5$ are as hereinbefore defined, one of the groups X and Y is chlorine, bromine or iodine or a trifluoromethanesulphonate (triflate) group, and the other one of the groups X and Y is a boronate residue, for example a boronate ester or boronic acid residue.

The reaction can be carried out under typical Suzuki Coupling conditions in the presence of a palladium catalyst such as bis(tri-t-butylphosphine)palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C.

An illustrative synthetic route involving a Suzuki coupling step is shown in Scheme 1. The starting material for the synthetic route shown in scheme 1 is the halo-substituted aryl- or heteroarylmethyl nitrile (XII) m which X is a chlorine, bromine or iodine atom or a triflate group. The nitrile (XII) is condensed with the aldehyde $R^1$CHO in the presence of an alkali such as sodium or potassium hydroxide in an aqueous solvent system such as aqueous ethanol. The reaction can be carried out at room temperature.

The resulting substituted acrylonitrile derivative (XIII) is then treated with a reducing agent that will selectively reduce the alkene double bond without reducing the nitrile group. A borohydride such as sodium borohydride may be used for this purpose to give the substituted acetonitrile derivative (XIV). The reduction reaction is typically carried out in a solvent such as ethanol and usually with heating, for example to a temperature up to about 65° C.

The reduced nitrile (XIV) is then coupled with the pyrazole boronate ester (XV) under the Suzuki coupling conditions described above to give a compound of the formula (I) in which A-NR²R³ is a substituted acetonitrile group.

Scheme 1

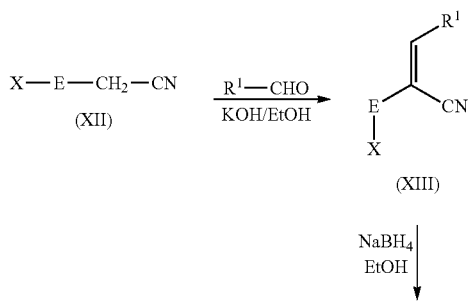

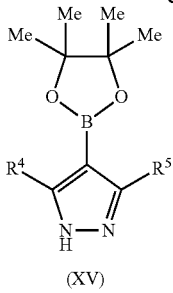

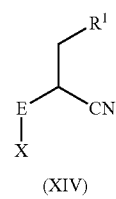

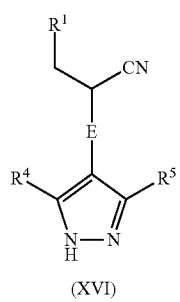

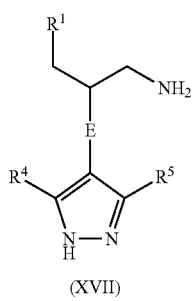

The substituted acetonitrile compound (XVI) may then be reduced to the corresponding amine (XVII) by treatment with a suitable reducing agent such as Raney nickel and ammonia in ethanol.

The synthetic route shown in Scheme 1 gives rise to amino compounds of the formula (I) in which the aryl or heteroaryl group E is attached to the β-position of the group A relative to the amino group. In order to give amino compounds of the formula (I) in which $R^1$ is attached to the β-position relative to the amino group, the functional groups on the two starting materials in the condensation step can be reversed so that a compound of the formula X-E-CHO wherein X is bromine, chlorine, iodine or a triflate group is condensed with a compound of the formula $R^1$—$CH_2$—CN to give a substituted acrylonitrile derivative which is then reduced to the corresponding acetonitrile derivative before coupling with the pyrazole boronate (XV) and reducing the cyano group to an amino group.

Compounds of the formula (I) in which $R^1$ is attached to the α-position relative to the amino group can be prepared by the sequence of reactions shown in Scheme 2.

In Scheme 2, the starting material is a halo-substituted aryl- or heteroarylmethyl Grignard reagent (XVIII, X=bromine or chlorine) which is reacted with the nitrile $R^1$—CN in a dry ether such as diethyl ether to give an intermediate imine (not shown) which is reduced to give the amine (XIX) using a reducing agent such as lithium aluminium hydride. The amine (XIX) can be reacted with the boronate ester (XV) under the Suzuki coupling conditions described above to yield the amine (XX).

Scheme 2

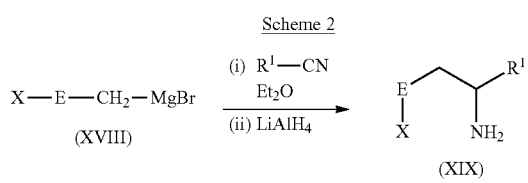

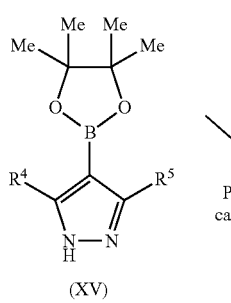

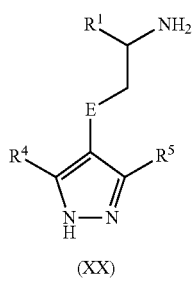

Compounds of the formula (I) can also be prepared from the substituted nitrile compound (XXI):

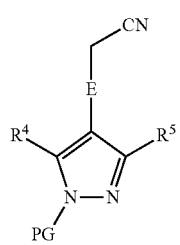

wherein PG is a protecting group such as a tetrahydropyranyl group. The nitrile (XXI) can be condensed with an aldehyde of the formula $R^1$—$(CH_2)_r$—CHO, wherein r is 0 or 1, and the resulting substituted acrylonitrile subsequently reduced to the corresponding substituted nitrile under conditions analogous to those set out in Scheme 1 above. The protecting group PG can then be removed by an appropriate method. The nitrile compound may subsequently be reduced to the corresponding amine by the use of a suitable reducing agent as described above.

The nitrile compound (XXI) may also be reacted with a Grignard reagent of the formula $R^1$—$(CH_2)_r$—MgBr under standard Grignard reaction conditions followed by deprotection to give an amino compound of the invention which has the structure shown in formula (XXII).

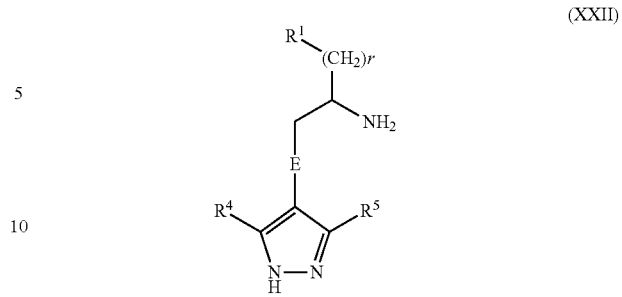

In the preparative procedures outlined above, the coupling of the aryl or heteroaryl group E to the pyrazole is accomplished by reacting a halo-pyrazole or halo-aryl or heteroaryl compound with a boronate ester or boronic acid in the presence of a palladium catalyst and base. Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Compounds of the formula (I) in which the group A contains a nitrogen atom attached to the group E can be prepared by well known synthetic procedures from compounds of the formula (XXIII) or a protected form thereof. Compounds of the formula (XXIII) can be obtained by a Suzuki coupling reaction of a compound of the formula (XV) (see Scheme 1) with a compound of the formula Br-E-$NH_2$ such as 4-bromoaniline.

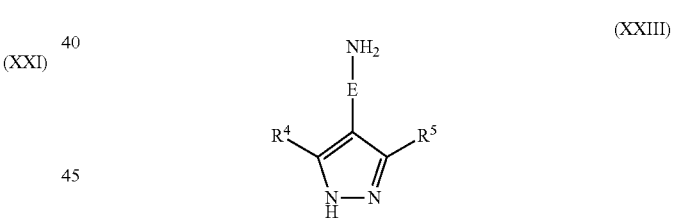

Compounds of the formula (I) in which $R^1$ and E are connected to the same carbon atom can be prepared as shown in Scheme 3.

Scheme 3

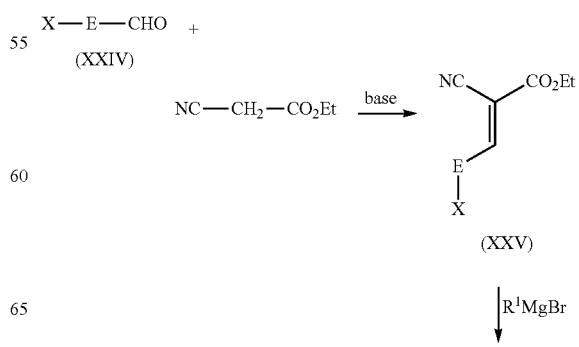

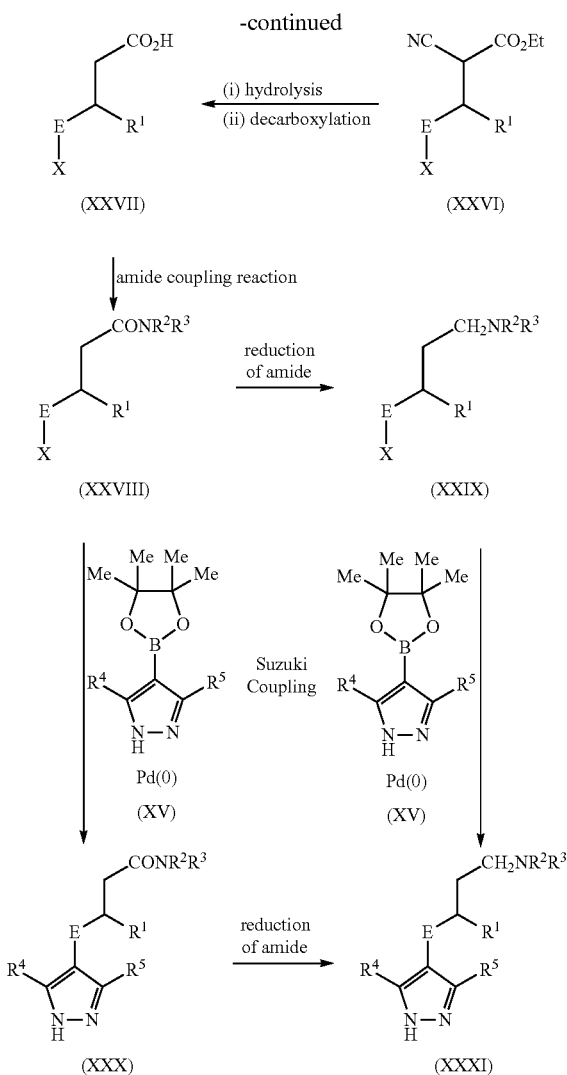

In Scheme 3, an aldehyde compound (XXIV) where X is bromine, chlorine, iodine or a triflate group is condensed with ethyl cyanoacetate in the presence of a base to give a cyanoacrylate ester intermediate (XXV). The condensation is typically carried out in the presence of a base, preferably a non-hydroxide such as piperidine, by heating under Dean Stark conditions.

The cyanoacrylate intermediate (XXV) is then reacted with a Grignard reagent $R^1MgBr$ suitable for introducing the group $R^1$ by Michael addition to the carbon-carbon double bond of the acrylate moiety. The Grignard reaction may be carried out in a polar non-protic solvent such as tetrahydrofuran at a low temperature, for example at around 0° C. The product of the Grignard reaction is the cyano propionic acid ester (XXVI) and this is subjected to hydrolysis and decarboxylation to give the propionic acid derivative (XXVII). The hydrolysis and decarboxylation steps can be effected by heating in an acidic medium, for example a mixture of sulphuric acid and acetic acid.

The propionic acid derivative (XXVII) is converted to the amide (XXVIII) by reaction with an amine $HNR^2R^3$ under conditions suitable for forming an amide bond. The coupling reaction between the propionic acid derivative (XXVII) and the amine $HNR^2R^3$ is preferably carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC m combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Where the amine $HNR^2R^3$ is ammonia, the amide coupling reaction can be carried out using 1,1'-carbonyldiimidazole (CDI) to activate the carboxylic acid before addition of the ammonia.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

The amide (XXVIII) can be converted to a compound of the formula (XXX) (which corresponds to a compound of the formula (I) wherein A has an oxo substituent next to the $NR^2R^3$ group) by reaction with a boronate (XV) under Suzuki coupling conditions as described above. The amide (XXX) can subsequently be reduced using a hydride reducing agent such as lithium aluminium hydride in the presence of aluminium chloride to give an amine of the formula (XXXI) (which corresponds to a compound of the formula (I) wherein A is CH—$CH_2$—$CH_2$—). The reduction reaction is typically carried out in an ether solvent, for example diethyl ether, with heating to the reflux temperature of the solvent.

Rather than reacting the amide (XXVIII) with the boronate (XV), the amide may instead be reduced with lithium aluminium hydride/aluminium chloride, for example in an ether solvent at ambient temperature, to give the amine (XXIX) which is then reacted with the boronate (XV) under the Suzuki coupling conditions described above to give the amine (XXX).

In order to obtain the homologue of the amine (XXIX) containing one fewer methylene group, the carboxylic acid (XXVII) can be converted to the azide by standard methods and subjected to a Curtius rearrangement in the presence of an alcohol such as benzyl alcohol to give a carbamate (see *Advanced Organic Chemistry*, 4$^{th}$ edition, by Jerry March, John Wiley & sons, 1992, pages 1091-1092). The benzylcarbamate can function as a protecting group for the amine during the subsequent Suzuki coupling step, and the benzyloxycarbonyl moiety in the carbamate group can then be removed by standard methods after the coupling step. Alternatively, the benzylcarbamate group can be treated with a hydride reducing agent such as lithium aluminium hydride to give a compound in which $NR^2R^3$ is a methylamino group instead of an ammo group.

Intermediate compounds of the formula (X) where the moiety X is a chlorine, bromine or iodine atom and A is a group $CH-CH_2-$ can be prepared by the reductive amination of an aldehyde compound of the formula (XXXII):

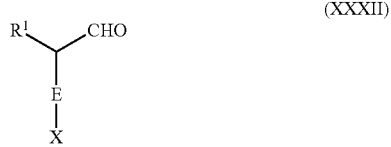
(XXXII)

with an amine of the formula $HNR^2R^3$ under standard reductive amination conditions, for example in the presence of sodium cyanoborohydride in an alcohol solvent such as methanol or ethanol.

The aldehyde compound (XXXII) can be obtained by oxidation of the corresponding alcohol (XXXIII) using, for example, the Dess-Martin periodinane (see Dess, D. B.; Martin, J. C. *J. Org. Soc.*, 1983, 48, 4155 and *Organic Syntheses*, Vol. 77, 141).

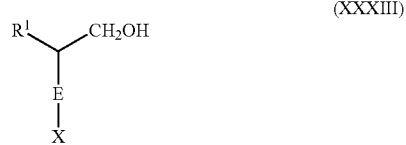
(XXXIII)

Compounds of the formula (I) where A, N and $R^2$ together form a cyclic group can be formed by the Suzuki coupling of a boronate compound of the formula (XV) with a cyclic intermediate of the formula (XXXIV) or an N-protected derivative thereof

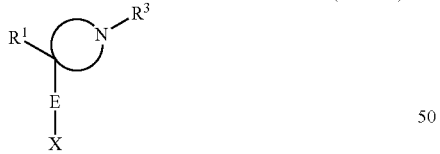
(XXXIV)

Cyclic intermediates of the formula (XXXIV), where $R^1$ is an aryl group such as an optionally substituted phenyl group, can be formed by Friedel Crafts alkylation of an aryl compound $R^1-H$ with a compound of the formula (XXXV):

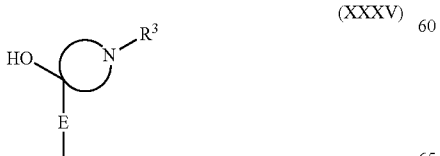
(XXXV)

The alkylation is typically carried out in the presence of a Lewis acid such as aluminium chloride at a reduced temperature, for example less than 5° C.

The Friedel Crafts reaction has been found to be of general applicability to the preparation of a range of intermediates of the formula (X). Accordingly, in a general method of making compounds of the formula (X), a compound of the formula (LXX):

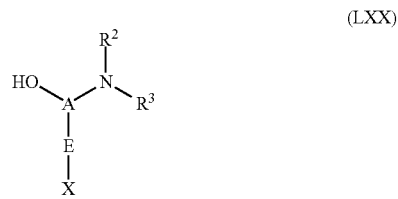
(LXX)

is reacted with a compound of the formula $R^1-H$ under Friedel Crafts alkylation conditions, for example in the presence of an aluminium, halide (e.g. $AlCl_3$).

In a further method for the preparation of a compound of the formula (I) wherein the moiety $NR^2R^3$ is attached to a $CH_2$ group of the moiety A, an aldehyde of the formula (XXXVI) can be coupled with an amine of the formula $HNR^2R^3$ under reductive amination conditions as described above. In the formulae (XXXVI) and (XXXVII), A' is the residue of the group A—i.e. the moieties A' and $CH_2$ together form the group A. The aldehyde (XXXVII) can be formed by oxidation of the corresponding alcohol using, for example, Dess-Martin periodinane.

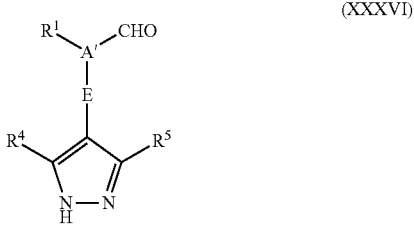
(XXXVI)

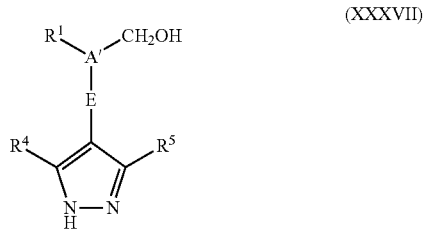
(XXXVII)

A Friedel Crafts alkylation procedure of the type described above for the synthesis of intermediates of the formula (XXXIV) can also be used to prepare intermediates of the formula (X) wherein X is bromine. An example of such a procedure is shown in Scheme 4.

Scheme 4

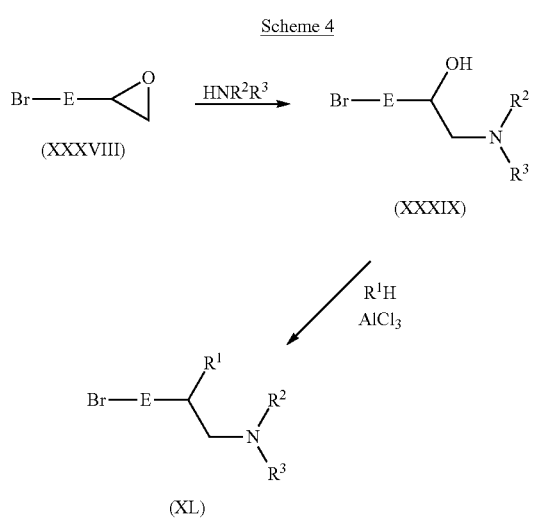

The starting material for the synthetic route shown in Scheme 4 is the epoxide (XXXVIII) which can either be obtained commercially or can be made by methods well known to the skilled person, for example by reaction of the aldehyde Br-E-CHO with trimethylsulphonium iodide. The epoxide (XXXVIII) is reacted with an amine $HNR^2R^3$ under conditions suitable for a ring-opening reaction with the epoxide to give a compound of the formula (XXXIX). The ring opening reaction can be carried out in a polar solvent such as ethanol at room temperature or optionally with mild heating, and typically with a large excess of the amine.

The amine (XXXIX) is then reacted with an aryl compound $R^1H$, typically a phenyl compound, capable of taking part in a Friedel Crafts alkylation (see for example *Advanced Organic Chemistry*, by Jerry March, pages 534-542). Thus, the amine of formula (XXXIX) is typically reacted with the aryl compound $R^1H$ in the presence of an aluminium chloride catalyst at or around room temperature. Where the aryl compound $R^1H$ is a liquid, e.g. as in the case of a methoxybenzene (e.g. anisole) or a halobenzene such as chlorobenzene, the aryl compound may serve as the solvent. Otherwise, a less reactive solvent such as nitrobenzene may be used. The Friedel Crafts alkylation of the compound $R^1H$ with the amine (XXXIX) gives a compound of the formula (XL) which corresponds to a compound of the formula (X) wherein X is bromine and A is $CHCH_2$.

The hydroxy intermediate (XXXIX) in Scheme 4 can also be used to prepare compounds of the formula (X) in which the carbon atom of the hydrocarbon linker group A adjacent the group $R^1$ is replaced by an oxygen atom. Thus the compound of formula (XXXIX), or an N-protected derivative thereof (where $R^2$ or $R^3$ are hydrogen) can be reacted with a phenolic compound of the formula $R^1$—OH under Mitsunobu alkylation conditions, e.g. in the presence of diethyl azodicarboxylate and triphenylphosphine. The reaction is typically carried out in a polar non-protic solvent such as tetrahydrofuran at a moderate temperature such as ambient temperature.

A further use of the hydroxy-intermediate (XXXIX) is for the preparation of the corresponding fluoro-compound. Thus, the hydroxy group can be replaced by fluorine by reaction with pyridine:hydrogen fluoride complex (Olah's reagent). The fluorinated intermediate can then be subjected to a Suzuki coupling reaction to give a compound of the formula (I) with a fluorinated hydrocarbon group A. A fluorinated compound of the formula (I) could alternatively be prepared by first coupling the hydroxy intermediate (XXXIX), or a protected form thereof, with a pyrazole boronic acid or boronate under Suzuki conditions and then replacing the hydroxy group in the resulting compound of formula (I) with fluorine using pyridine:hydrogen fluoride complex.

Compounds of the formula (I) in which the moiety:

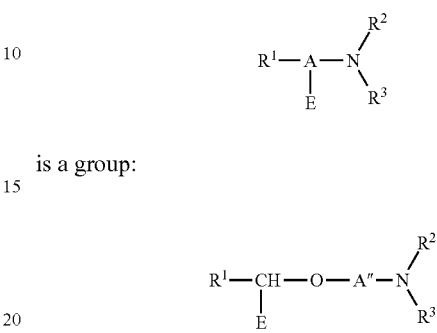

is a group:

$$R^1-CH-O-A''-N\begin{matrix}R^2\\ \\R^3\end{matrix}$$
$$\phantom{R^1-CH}|\phantom{-O-A''-N}$$
$$\phantom{R^1-CH}E$$

where A" is the hydrocarbon residue of the group A, can be prepared by the sequence of reactions shown in Scheme 5.

Scheme 5

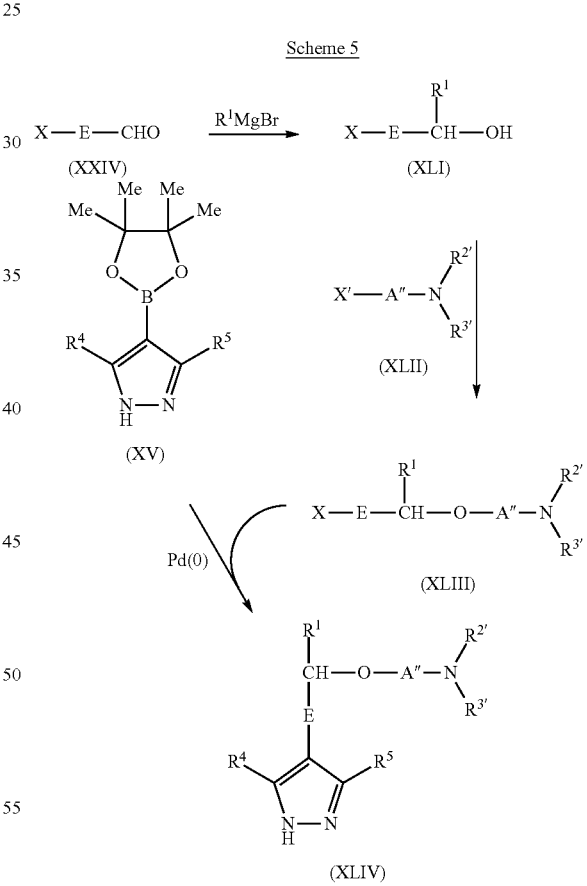

As shown in Scheme 5, the aldehyde (XXIV) is reacted with a Grignard reagent $R^1MgBr$ under standard Grignard conditions to give the secondary alcohol (XLI). The secondary alcohol can then be reacted with a compound of the formula (XLII) in which $R^{2'}$ and $R^{3'}$ represent the groups $R^2$ and $R^3$ or an amine-protecting group, A" is the residue of the group A, and X' represents a hydroxy group or a leaving group.

The amine protecting group can be, for example, a phthalolyl group in which case NR²'R³' is a phthalimido group.

When X' is a hydroxy group, the reaction between compound (XLI) and (XLII) can take the form of an toluene sulphonic acid catalysed condensation reaction. Alternatively, when X' is a leaving group such as halogen, the alcohol (XLI) can first be treated with a strong base such as sodium hydride to form the alcoholate which then reacts with the compound (XLII).

The resulting compound of the formula (XLIII) is then subjected to a Suzuki coupling reaction with the pyrazole boronate reagent (XV) under typical Suzuki coupling conditions of the type described above to give a compound of the formula (XLIV). The protecting group can then be removed from the protected amine group NR²'R³' to give a compound of the formula (I).

Compounds of the formula (I) in which the moiety:

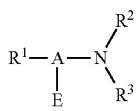

is a group:

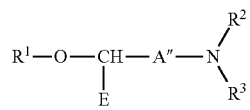

where A" is the hydrocarbon residue of the group A, can be prepared by the sequence of reactions shown in Scheme 6.

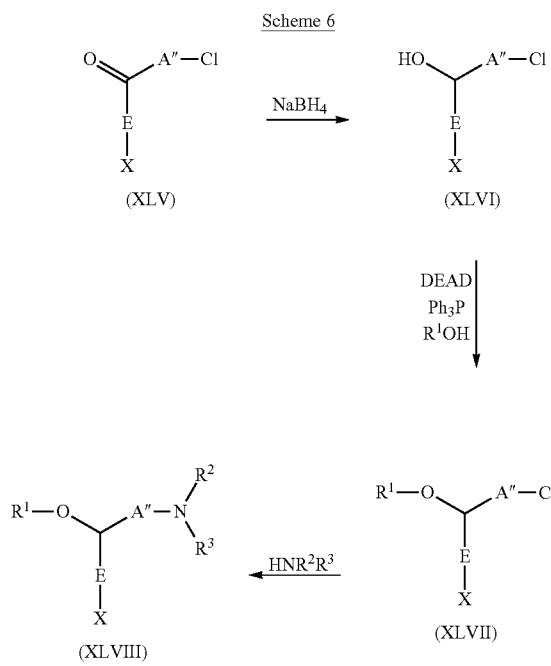

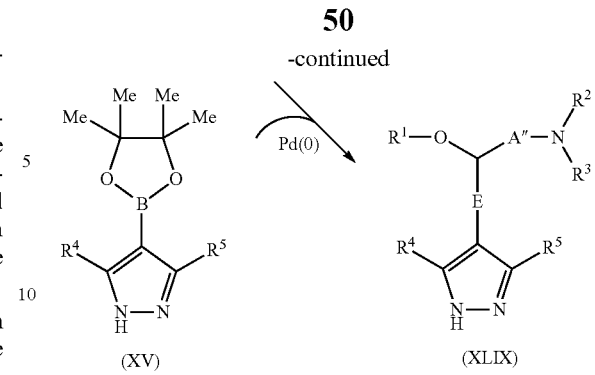

The starting material in Scheme 6 is the chloroacyl compound (XLV) which can be prepared by literature methods (e.g. the method described in *J. Med. Chem.*, 2004, 47, 3924-3926) or methods analogous thereto. Compound (XLV) is converted into the secondary alcohol (XLVI) by reduction with a hydride reducing agent such as sodium borohydride in a polar solvent such as water/tetrahydrofuran.

The secondary alcohol (XLVI) can then be reacted with a phenolic compound of the formula R¹—OH under Mitsunobu alkylation conditions, e.g. in the presence of diethyl azodicarboxylate and triphenylphosphine, as described above, to give the aryl ether compound (XLVII).

The chorine atom in the aryl ether compound (XLVII) is then displaced by reaction with an amine HNR²R³ to give a compound of the formula (XLVIII). The nucleophilic displacement reaction may be carried out by heating the amine with the aryl ether in a polar solvent such as an alcohol at an elevated temperature, for example approximately 100° C. The heating may advantageously be achieved using a microwave heater. The resulting amine (XLVIII) can then be subjected to a Suzuki coupling procedure with a boronate of the formula (XV) as described above to give the compound (XLIX).

In a variation on the reaction sequence shown in Scheme 6, the secondary alcohol (XLVI) can be subjected to a nucleophilic displacement reaction with an amine HNR²R³ before introducing the group R¹ by means of the Mitsunobu ether-forming reaction.

Another route to compounds of the formula (I) in which E and R¹ are attached to the same carbon atom in the group A is illustrated in Scheme 7.

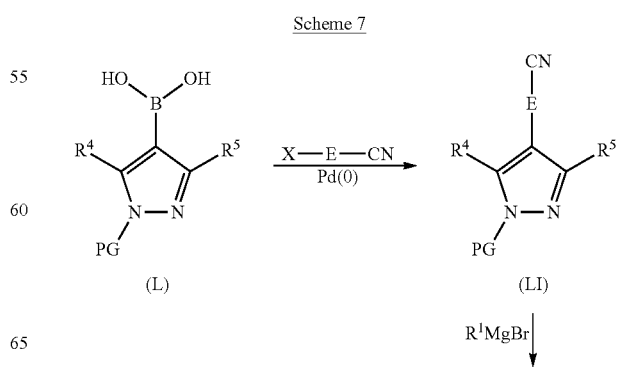

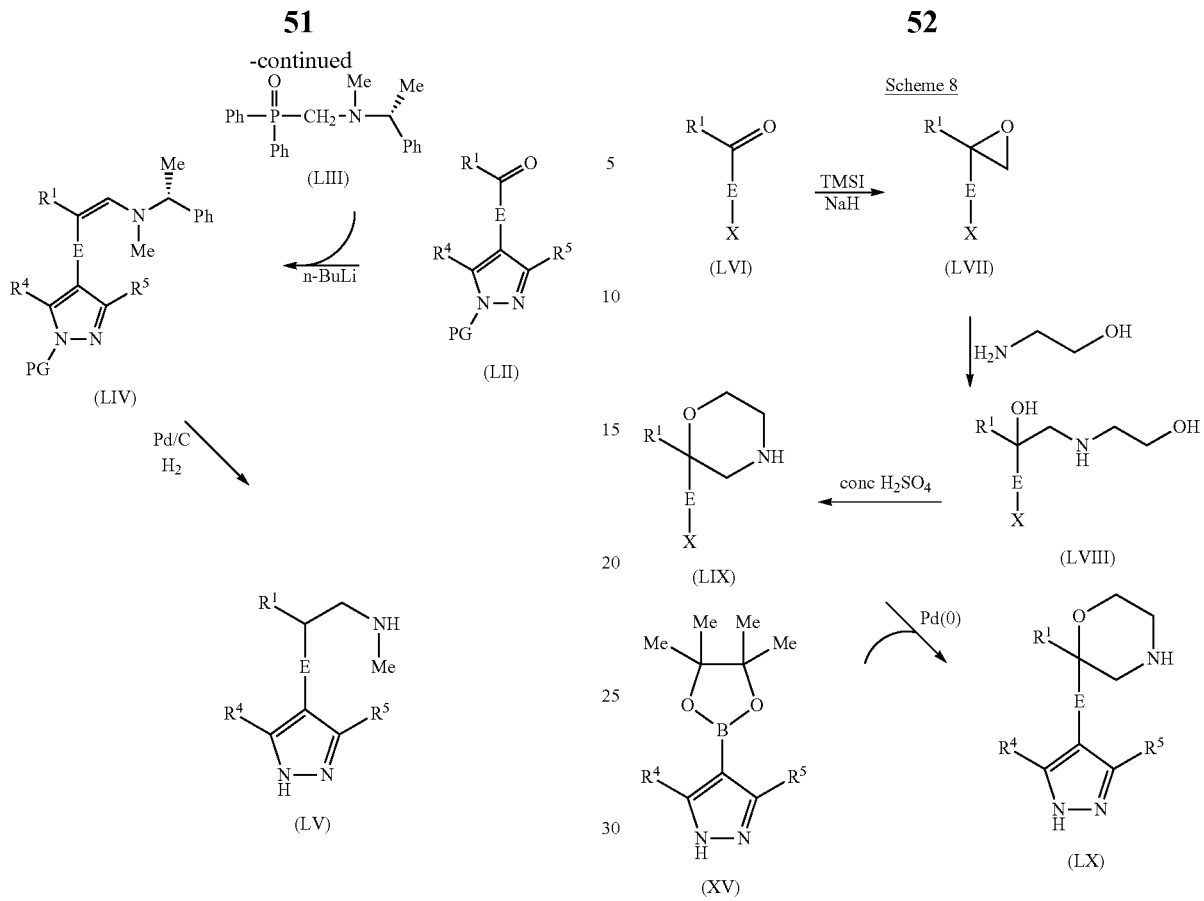

In Scheme 7, an N-protected pyrazolyl boronic acid (L) is reacted under Suzuki coupling conditions with the cyano compound X-E-CN in which X is typically a halogen such as bromine or chlorine. The protecting group PG at the 1-position of the pyrazole ring may be, for example, a triphenylmethyl (trityl) group. The boronic acid (L) can be prepared using the method described in EP 1382603 or methods analogous thereto.

The resulting nitrile (LI) may then be reacted with a Grignard reagent $R^1$—MgBr to introduce the group $R^1$ and form the ketone (LII). The ketone (LII) is converted to the enamine (LIV) by reaction with the diphenylphosphinoylmethylamine (LIII) in the presence of a strong base such as an alkyl lithium, particularly butyl lithium.

The enamine (LIV) is then subjected to hydrogenation over a palladium on charcoal catalyst to reduce the double bond of the enamine and remove the 1-phenethyl group. Where the protecting group PG is a trityl group, hydrogenation also removes the trityl group, thereby yielding a compound of the formula (LV).

Alternatively, the enamine (LIV) can be reduced with a hydride reducing agent under the conditions described in *Tetrahedron: Asymmetry* 14 (2003) 1309-1316 and subjected to a chiral separation. Removal of the protecting 2-phenethyl group and the protecting group PG then gives an optically active form of the compound of formula (LV).

Intermediates of the formula (X) wherein A and $R^2$ link to form a ring containing an oxygen atom can be prepared by the general method illustrated in Scheme 8.

In Scheme 8, a ketone (LVI) is reacted with trimethylsulphonium iodide to form the epoxide (LVII). The reaction is typically carried out in the presence of a hydride base such as sodium hydride in a polar solvent such as dimethylsulphoxide.

The epoxide (LVII) is subjected to a ring opening reaction with ethanolamine in the presence of a non-interfering base such as triethylamine in a polar solvent such as an alcohol (e.g. isopropanol), usually with mild heating (e.g. up to approximately 50° C. The resulting secondary alcohol is then cyclised to form the morpholine ring by treatment with concentrated sulphuric acid in a solvent such as ethanolic dichloromethane.

The morpholine intermediate (LIX) can then reacted with the boronate (XV) under Suzuki coupling conditions to give the compound of formula (LX), which corresponds to a compound of the formula (I) in which A-$NR^2R^3$ forms a morpholine group.

Instead of reacting the epoxide (LVII) with ethanolamine, it may instead be reacted with mono- or dialkylamines thereby providing a route to compounds containing the moiety:

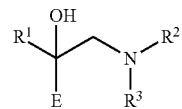

Compounds wherein $R^2$ and $R^3$ are both hydrogen can be prepared by reacting the epoxide (LVII) with potassium phthalimide in a polar solvent such as DMSO. During the Suzuki coupling step, the phthalimide group may undergo partial hydrolysis to give the corresponding phthalamic acid which can be cleaved using hydrazine to give the amino group $NH_2$. Alternatively, the phthalamic acid can be recyclised to the phthalimide using a standard amide-forming reagent and the phthaloyl group then removed using hydrazine to give the amine.

A further synthetic route to compounds of the formula (I) wherein A and $NR^2R^3$ combine to form a cyclic group is illustrated in Scheme 9.

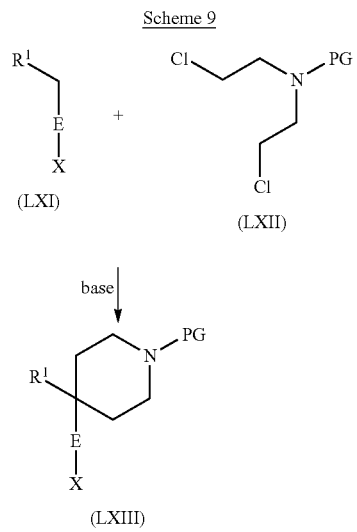

In Scheme 9, the starting material (LXI) is typically a di-aryl/heteroaryl methane in which one or both of the aryl/heteroaryl groups is capable of stabilising or facilitating formation of an anion formed on the methylene group between E and $R^1$. For example, $R^1$ may advantageously be a pyridine group. The starting material (LXI) is reacted with the N-protected bis-2-chloroethylamine (LXII) in the presence of a non-interfering strong base such as sodium hexamethyldisilazide in a polar solvent such as tetrahydrofuran at a reduced temperature (e.g. around 0° C.) to give the N-protected cyclic intermediate (LXIII). The protecting group can be any standard amine-protecting group such as a Boc group. Following cyclisation, the intermediate (LXIII) is coupled to a boronate of the formula (XV) under Suzuki coupling conditions and then deprotected to give the compound of the formula (I).

Compounds of the formula (I) in which the moiety:

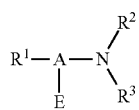

is a group:

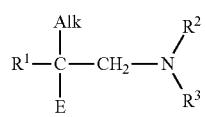

wherein "Alk" is a small alkyl group such as methyl or ethyl can be formed by the synthetic route illustrated in Scheme 10.

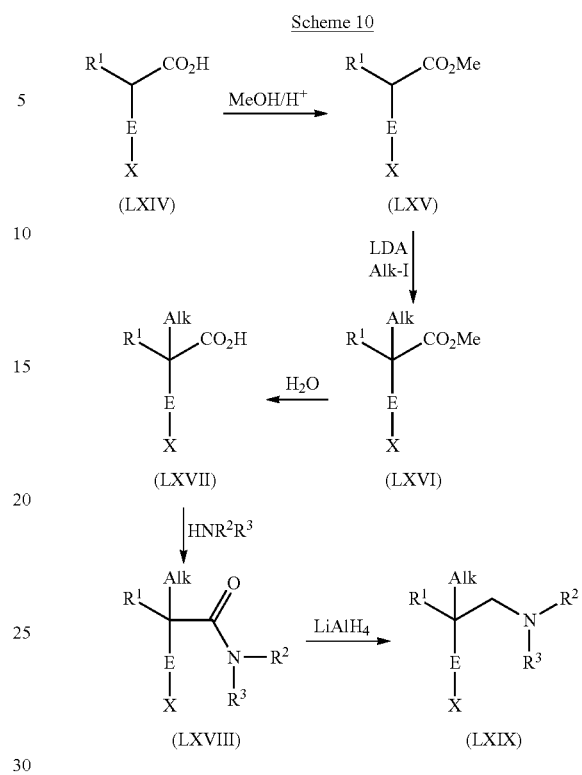

In Scheme 10, a carboxylic acid of the formula (LXIV) is esterified by treatment with methanol in the presence of an acid catalyst such as hydrochloric acid. The ester (LXV) is then reacted with a strong base such as lithium diisopropylamide (LDA) and an alkyl iodide such as methyl iodide at reduced temperature (e.g. between 0° C. and −78° C.). The branched ester (LXVI) is then hydrolysed to the acid (LXVII) and coupled with an amine $HNR^2R^3$ under standard amide forming conditions of the type described above. The amide (LXVIII) can then be reduced to the amine (LXIX) using lithium aluminium hydride, and the amine (LXIX) is then reacted with a pyrazole boronate or boronic acid under Suzuki coupling conditions to give a compound of the formula (I).

Once formed, many compounds of the formula (I) can be converted into other compounds of the formula (I) using standard functional group interconversions. For example, compounds of the formula (I) in which the $NR^2R^3$ forms part of a nitrile group can be reduced to the corresponding amine. Compounds in which $NR^2R^3$ is an $NH_2$ group can be converted to the corresponding alkylamine by reductive alkylation, or to a cyclic group. Compounds wherein $R^1$ contains a halogen atom such as chlorine or bromine can be used to introduce an aryl or heteroaryl group substituent into the $R^1$ group by means of a Suzuki coupling reaction. Further examples of interconversions of one compound of the formula (I) to another compound of the formula (I) can be found in the examples below. Additional examples of functional group interconversions and reagents and conditions for carrying out such conversions can be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN, 0-471-58283-2), and *Organic Syntheses*, Volumes 1-8, John Wiley, edited by Jeremiah P. Freeman (ISBN: 0-471-31192-8).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (diphenylmethyl)ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2-(phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

The 1(H) position of the pyrazole group in the compounds of the formula (I) or its precursors can be protected by a variety of groups, the protecting group being selected according to the nature of the reaction conditions to which the group is exposed. Examples of protecting groups for the pyrazole N—H include tetrahydropyranyl, benzyl and 4-methoxybenzyl groups.

Many of the chemical intermediates described above are novel and such novel intermediates form a further aspect of the invention.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g. lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 1 nanogram to 2 milligrams, for example 0.1 milligrams to 2 grams of active ingredient, more usually from 10 milligrams to 1 gram, e.g. 50 milligrams to 500 milligrams, or 0.1 milligrams to 2 milligrams.

The active compound will be administered to a patient in need thereof (for example a human or animal patient) in an amount sufficient to achieve the desired therapeutic effect.

Protein Kinase Inhibitory Activity

The activity of the compounds of the invention as inhibitors of protein kinase A and protein kinase B can be measured using the assays set forth in the examples below and the level of activity exhibited by a given compound can be defined in terms of the IC50 value. Preferred compounds of the present invention are compounds having an $IC_{50}$ value of less than 1 µM, more preferably less than 0.1 µM, against protein kinase B.

Therapeutic Uses

Prevention or Treatment of Proliferative Disorders

The compounds of the formula (I) are inhibitors of protein kinase A and protein kinase B. As such, they are expected to be useful in providing a means of preventing the growth of or inducing apoptosis of neoplasias. It is therefore anticipated that the compounds will prove useful in treating or preventing proliferative disorders such as cancers. In particular tumours with deletions or inactivating mutations in PTEN or loss of PTEN expression or rearrangements in the (T-cell lymphocyte) TCL-1 gene may be particularly sensitive to PKB inhibitors. Tumours which have other abnormalities leading to an upregulated PKB pathway signal may also be particularly sensitive to inhibitors of PKB. Examples of such abnormalities include but are not limited to overexpression of one or more PI3K subunits, over-expression of one or more PKB isoforms, or mutations in PI3K, PDK1, or PKB which lead to an increase in the basal activity of the enzyme in question, or upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families.

It is also envisaged that the compounds of the invention will be useful in treating other conditions which result from disorders in proliferation or survival such as viral infections, and neurodegenerative diseases for example. PKB plays an important role in maintaining the survival of immune cells during an immune response and therefore PKB inhibitors could be particularly beneficial in immune disorders including autoimmune conditions.

Therefore, PKB inhibitors could be useful in the treatment of diseases in which there is a disorder of proliferation, apoptosis or differentiation.

PKB inhibitors may also be useful in diseases resulting from insulin resistance and insensitivity, and the disruption of glucose, energy and fat storage such as metabolic disease and obesity.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chrome myelogenous leukaemias, myelodysplastic syndrome, or promyelocytic leukaemia; thyroid follicular cancer; a tumour of mesenchymal origin, for example fibro sarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include breast cancer, ovarian cancer, colon cancer, prostate cancer, oesophageal cancer, squamous cancer and non-small cell lung carcinomas.

A further subset of cancers includes breast cancer, ovarian cancer, prostate cancer, endometrial cancer and glioma.

It is also possible that some protein kinase B inhibitors can be used in combination with other anticancer agents. For example, it may be beneficial to combine of an inhibitor that induces apoptosis with another agent which acts via a different mechanism to regulate cell growth thus treating two of the characteristic features of cancer development. Examples of such combinations are set out below.

Immune Disorders

Immune disorders for which PKA and PKB inhibitors may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses

PKB plays a role in apoptosis, proliferation, differentiation and therefore PKB inhibitors could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example osteoporosis and arthritis, aspirin-sensitive rhinosinusitis, cystic fibrosis, multiple sclerosis, kidney diseases.

Methods of Treatment

It is envisaged that the compounds of the formula (I) will useful in the prophylaxis or treatment of a range of disease states or conditions mediated by protein kinase A and/or protein kinase B. Examples of such disease states and conditions are set out above.

Compounds of the formula (I) are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile manner.

A typical daily dose of the compound can be in the range from 100 picograms to 100 milligrams per kilogram of body weight, typically 10 nanograms to 10 milligrams per kilogram of bodyweight, more typically 1 microgram to 10 milligrams although higher or lower doses may be administered where required. Ultimately, the quantity of compound administered will be commensurate with the nature of the disease or physiological condition being treated and will be at the discretion of the physician.

The compounds of the formula (I) can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Radiotherapy.

For the case of protein kinase A inhibitors or protein kinase B inhibitors combined with other therapies the two or more treatments may be given in individually varying dose schedules and via different routes.

Where the compound of the formula (I) is administered in combination therapy with one or more other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against protein kinase A and/or protein kinase B.

For example, a biological sample taken from a patient may be analysed to determine whether a condition or disease, such as cancer, that the patient is or may be suffering from is one which is characterised by a genetic abnormality or abnormal protein expression which leads to up-regulation of PKA and/ or PKB or to sensitisation of a pathway to normal PKA and/or PKB activity, or to upregulation of a signal transduction component upstream of PKA and/or PKB such as, in the case of PKB, P13K, GF receptor and PDK 1 & 2.

Alternatively, a biological sample taken from a patient may be analysed for loss of a negative regulator or suppressor of the PKB pathway such as PTEN. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of PKA and/or PKB. The term diagnosis includes screening. By marker we include genetic markers including, for example, the measurement of DNA composition to identify mutations of PKA and/or PKB. The term marker also includes markers which are characteristic of up regulation of PKA and/or PKB, including enzyme activity, enzyme levels, enzyme state (e.g. phosphorylated or not) and mRNA levels of the aforementioned proteins.

The above diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of an individual carrying a mutation in PKA and/or PKB or a rearrangement of TCL-1 or loss of PTEN expression may mean that the patient would be particularly suitable for treatment with a PKA and/or PKB inhibitor. Tumours may preferentially be screened for presence of a PKA and/or PKB variant prior to treatment. The screening process will typically involve direct sequencing, oligonucleotide micro array analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR.

Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of PKB, or detection of PKB variants could be applicable in the present case.

Therefore all of these techniques could also be used to identify tumours particularly suitable for treatment with PKA and/or PKB inhibitors.

For example, as stated above, PKB beta has been found to be upregulated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330). Therefore it is envisaged that PKB inhibitors, and in particular inhibitors of PKB beta, may be used to treat ovarian and pancreatic cancers.

PKB alpha is amplified in human gastric, prostate and breast cancer (Staal 1987, PNAS 84, 5034-5037; Sun et al 2001, Am. J. Pathol. 159, 431-437). Therefore it is envisaged that PKB inhibitors, and in particular inhibitors of PKB alpha, may be used to treat human gastric, prostate and breast cancer.

Increased PKB gamma activity has been observed in steroid independent breast and prostate cell lines (Nakatani et al 1999, J. Biol. Chem. 274, 21528-21532). Therefore it is envisaged that PKB inhibitors, and in particular inhibitors of PKB gamma, may be used to treat steroid independent breast and prostate cancers.

EXPERIMENTAL

The invention will now be illustrated, but not limited, by reference to the specific embodiments described in the following procedures and examples.

The starting materials for each of the procedures described below are commercially available unless otherwise specified.

In the examples, the compounds prepared were characterised by liquid chromatography, mass spectroscopy and $^1$H nuclear magnetic resonance spectroscopy using the systems and operating conditions set out below.

Proton magnetic resonance ($^1$H NMR) spectra were recorded on a Bruker AV400 instrument operating at 400.13 MHz, in Me-d$_3$-OD at 27 C, unless otherwise stated and are reported as follows: chemical shift δ/ppm (number of protons, multiplicity where s=singlet, d=doublet, t=triplet, q=quartet, m=multiplet, br=broad). The residual protic solvent MeOH ($δ_H$=3.31 ppm) was used as the internal reference.

For the mass spectra, where chlorine is present, the mass quoted for the compound is for $^{35}$Cl.

In each of the examples, where the compounds are isolated or formed as the free base, they can be converted into a salt form such as an acetic acid or hydrochloric acid salt. Conversely, where the compounds are isolated or formed as a salt, the salt can be converted into the corresponding free base by methods well known to the skilled person, and then optionally converted to another salt.

A number of liquid chromatography systems were used and these are described below.

Platform System
HPLC System: Waters 2795
Mass Spec Detector: Micromass Platform LC
PDA Detector: Waters 2996 PDA
Acidic Analytical Conditions 1:
Eluent A: H$_2$O (0.1% Formic Acid)
Eluent B: CH$_3$CN (0.1% Formic Acid)
Gradient: 5-95% eluent B over 3.5 minutes
Flow: 1.5 ml/min
Column: Phenomenex Synergi 4μ Max-RP 80A, 50×4.6 mm
Acidic Analytical Conditions 2:
Eluent A. H$_2$O (0.1% Formic Acid)
Eluent B: CH$_3$CN (0.1% Formic Acid)
Gradient: 5-95% eluent B over 3.5 minutes
Flow: 0.8 ml/min
Column: Phenomenex Synergi 4μ Max-RP 80A, 50×2.0 mm
Acidic Analytical Conditions 3:
Eluent A: H2O (0.1% Formic Acid)
Eluent B: CH$_3$CN (0.1% Formic Acid)
Gradient: 5-95% eluent B over 15 minutes
Flow: 0.4 ml/min
Column: Phenomenex Synergi 4μ Max-RP 80A, 50×2.0 mm
Basic Analytical Conditions 1:
Eluent A: H$_2$O (10 mM NH$_4$HCO$_3$ buffer adjusted to pH=9.5 with NH$_4$OH)
Eluent B: CH$_3$CN
Gradient: 05-95% eluent B over 3.5 minutes
Flow: 1.5 ml/min
Column: Waters XTerra MS C$_{18}$ 5 μm 4.6×50 mm
Basic Analytical Conditions 2:
Eluent A. H$_2$O (10 mM NH$_4$HCO$_3$ buffer adjusted to pH=9.5 with NH$_4$OH)
Eluent B: CH$_3$CN
Gradient: 05-95% eluent B over 3.5 minutes
Flow: 0.8 ml/min
Column: Thermo Hypersil-Keystone BetaBasic-18 5 μm, 50×2.1 mm
Basic Analytical Conditions 3:
Eluent A. H$_2$O (10 mM NH$_4$HCO$_3$ buffer adjusted to pH=9.5 with NH$_4$OH)
Eluent B: CH$_3$CN
Gradient: 05-95% eluent B over 3.5 minutes
Flow: 0.8 ml/min
Column: Phenomenex Luna C18(2) 5 μm, 50×2.0 mm
Basic Analytical Conditions 4:
Eluent A. H$_2$O (10 mM NH$_4$HCO$_3$ buffer adjusted to pH=9.2 with NH$_4$OH)
Eluent B: CH$_3$CN
Gradient: 05-95% eluent B over 15 minutes
Flow: 0.8 ml/min
Column: Phenomenex Luna C18(2) 5 μm, 150×2.0 mm
Polar Analytical Conditions:
Eluent A: H$_2$O (0.1% Formic Acid)
Eluent B: CH$_3$CN (0.1% Formic Acid)
Gradient: 00-50% eluent B over 3 minutes
Flow: 1.5 ml/min
Column: Phenomenex Synergi 4μ Hydro 80A, 50×4.6 mm
MS Conditions:
Capillary voltage: 3.5 kV or 3.6 kV
Cone voltage: 30 V
Source Temperature: 120° C.
Scan Range: 165-700 amu
Ionisation Mode: Electro Spray Negative, Positive or Positive & Negative
Fraction Lynx System
System: Waters FractionLynx (dual analytical/prep)
HPLC Pump: Waters 2525
Injector-Auto sampler: Waters 2767
Mass Spec Detector: Waters-Micromass ZQ
PDA Detector: Waters 2996 PDA
Acidic Analytical Conditions:
Eluent A: H$_2$O (0.1% Formic Acid)
Eluent B: CH$_3$CN (0.1% Formic Acid)
Gradient: 5-95% eluent B over 5 minutes
Flow: 2.0 ml/min
Column: Phenomenex Synergi 4μ Max-RP 80A, 50×4.6 mm
Polar Analytical Conditions:
Eluent A: H$_2$O (0.1% Formic Acid)
Eluent B: CH$_3$CN (0.1% Formic Acid)
Gradient: 00-50% eluent B over 5 minutes
Flow: 2.0 ml/min
Column: Phenomenex Synergi 4μ Max-RP 80A, 50×4.6 mm
MS Parameters for Acidic and Polar Analytical Conditions:
Capillary voltage: 3.5 kV
Cone voltage: 25 V
Source Temperature: 120° C.
Scan Range: 125-800 amu
Ionisation Mode: Electro Spray Positive or Electro Spray Positive & Negative
Chiral Analytical Conditions:
Eluent: MeOH+0.1% NH4/TFA
Flow: 1.2 ml/min
Total time: 16.00 min
Inj. Volume: 10 μL
Sample conc. 2 mg/ml
Column: Astec, Chirobiotic V; 250×4.6 mm
Mass spectrometer was taken off-line.
Agilent System
HPLC System. Agilent 1100 series
Mass Spec Detector: Agilent LC/MSD VL
Multi Wavelength Detector: Agilent1100 series MWD
Software: HP Chemstation
Chiral Analytical Conditions:
Eluent: MeOH+0.2% NH4/AcOH at room Temperature
Flow: 2.0 ml/min
Total time: 8.5 min
Inj. Volume: 20 uL
Sample Conc: 2 mg/ml
Column: Astec, Chirobiotic V; 250×4.6 mm Chiral Preparative Conditions 1:
Eluent: MeOH+0.1% NH4/TFA at room Temperature
Flow: 6.0 ml/min
Total time: 10 min
Inj. Volume: 100 uL
Sample Conc: 20 mg/ml
Column: Astec, Chirobiotic V; 250×10 mm
Chiral Preparative Conditions 2:
Eluent: MeOH+0.2% NH4/AcOH at room Temperature
Flow: 20.0 ml/min
Total time: 19 min
Inj. Volume: 950 uL
Sample Conc: 25 mg/ml
Column: Astec, Chirobiotic V2; 250×21.2 mm
MS Conditions (Just Analytical Method):
Capillary voltage: 3000 V
Fragmentor: 150
Gain: 1.00
Drying gas: 12.0 L/min
Drying gas T: 350° C.
Nebulizer pressure: 35 (psig)
Scan Range: 125-800 amu
Ionisation Mode Electro Spray Positive In the examples below, the following key is used to identify the LCMS conditions used:
PS-A Platform System—acidic analytical conditions 1
PS-A2 Platform System—acidic analytical conditions 2
PS-A3 Platform System—acidic analytical conditions 3
PS-B Platform System—basic analytical conditions 1
PS-B2 Platform System—basic analytical conditions 2
PS-B3 Platform System—basic analytical conditions 3
PS-B4 Platform System—basic analytical conditions 4
PS-P Platform System—polar analytical conditions
FL-A FractionLynx System—acidic analytical conditions
FL-P FractionLynx System—polar analytical conditions
FL-C FractionLynx System—chiral analytical conditions
AG-CA Agilent System—chiral analytical conditions
AG-CP1 Agilent System—chiral preparative conditions 1
AG-CP2 Agilent System—chiral preparative conditions 2

Example 1

2-Phenyl-2-[4-(1H-pyrazol-4-yl)-phenyl]-ethylamine

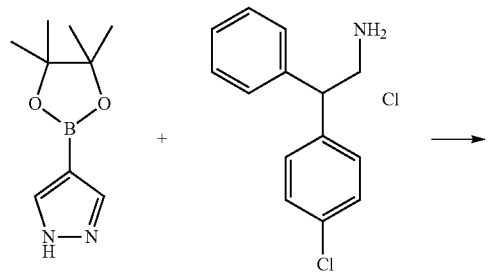

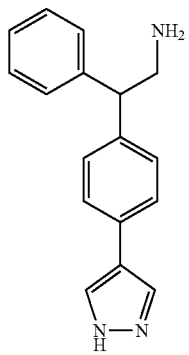

To a suspension of 2-(4-chlorophenyl)-2-phenylethylamine hydrochloride (134 mg, 0.5 mmol, 1.0 equiv.) (Array PPA-Q02-1) in toluene (0.8 ml) was added bis(tri-t-butylphosphine)palladium (0) (3 mg, 1 mol %) (Strem) and the mixture was purged with nitrogen. A suspension of 4-(4,4,5,5-tetramethyl-1,3,2-dioxaborolan-2-yl)-1H-pyrazole (107 mg, 0.55 mmol, 1:1 equiv.) (Aldrich 52, 505-7) in ethanol (0.8 ml) was added followed by potassium carbonate (415 mg, 3.0 mmol, 6 equiv.) in water (2.5 ml). The mixture was purged with nitrogen and sealed. The reaction mixture was heated in a CEM Explorer™ microwave to 135° C. for 15 minutes using 50 watts power. The solvents were removed and the residue was partitioned between ethyl acetate and 2N NaOH. The aqueous layer was extracted with ethyl acetate and the combined organic layers were washed with brine, dried (MgSO$_4$) and concentrated under reduced pressure. The crude reaction mixture was purified by column chromatography (SiO$_2$), eluting with a mixture of dichloromethane (90 ml):methanol (18 ml):acetic acid (3 ml):H$_2$O (2 ml) to afford the title compound 14 mg (9%); LCMS (PS-A) R$_t$ 1.79 min; m/z [M+H]$^+$ 264.

Example 2

3-Phenyl-2-[3-(1H-pyrazol-4-yl)-phenyl]-propionitrile 2A. 2-(3-Bromo-phenyl)-3-phenyl-propionitrile

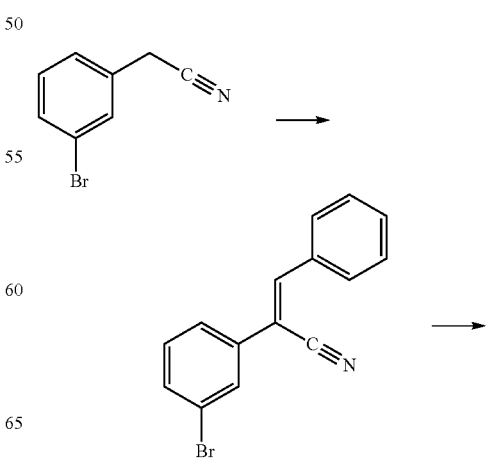

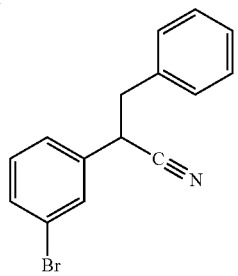

A solution of 40% KOH (2.83 g in 5.0 ml of H₂O) in ethanol (13 ml) was added to a solution of benzaldehyde (2.85 ml, 28.05 mmol) and 3-bromophenylacetonitrile (5 g, 25.50 mmol) in ethanol (9 ml). The reaction mixture was then stirred at room temperature for 2 hours and the precipitate was collected by suction filtration and washed with cold ethanol (6.68 g, 92%). The crude product (3.45 g, 12.14 mmol) was then dissolved methanol (35 ml) and heated to 65° C. Sodium borohydride (459 mg, 12.14 mmol) was added in portions and the reaction mixture was maintained at this temperature for a further 2 hours. Upon cooling, water (10 ml) was added and the solvent was removed under reduced pressure. The residue was partitioned between water (100 ml) and ethyl acetate (100 ml). The organic layer was separated, dried (MgSO₄), filtered and concentrated to afford the desired product (1.80 g, 52%), which was used without purification.

2B. 3-Phenyl-2-[3-(1H-pyrazol-4-yl)-phenyl]-propionitrile

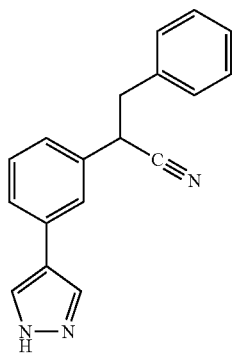 [SMILES: N#CC(Cc1ccccc1)c1cccc(-c2cn[nH]c2)c1]

2-(3-Bromo-phenyl)-3-phenyl-propionitrile was reacted with 4-(4,4,5,5-tetramethyl-1,3,2-dioxaborolan-2-yl)-1H-pyrazole following the procedure set out in Example 1 to give the title compound. (LC/MS: (PS-A) $R_t$ 2.98 $[M+H]^+$ 274).

Example 3

2-[4-(3,5-Dimethyl-1H-pyrazol-4-yl)-phenyl]-2-phenyl-ethylamine

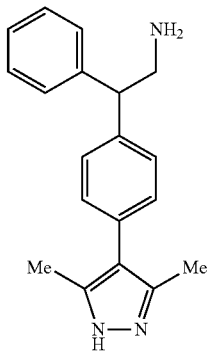 [SMILES: Cc1n[nH]c(C)c1-c1ccc(C(CN)c2ccccc2)cc1]

Following the procedure of Example 1 but using 3,5-dimethyl-4-(4,4,5,5-tetramethyl-[1,3,2]dioxaborolan-2-yl)-1H-pyrazole (Boron Molecular D03-BM152) instead of 4-(4,4,5,5-tetramethyl-1,3,2-dioxaborolan-2-yl)-1H-pyrazole gave the title compound. (LC/MS: (PS-A) $R_t$ 1.79 $[M+H]^+$ 292.

Example 4

2-(4-Chloro-phenyl)-2-[4-(1H-pyrazol-4-yl)-phenyl]-ethylamine

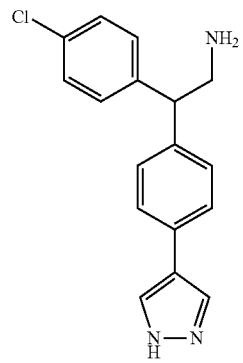 [SMILES: NCC(c1ccc(Cl)cc1)c1ccc(-c2cn[nH]c2)cc1]

Following the procedure of Example 1 but using 2,2-bis-(4-chloro-phenyl)-ethylamine in place of 2-(4-chlorophenyl)-2-phenylethylamine hydrochloride* gave the title compound. (LC/MS. (PS-A) $R_t$ 1.99 $[M+H]^+$ 298).

*This starting material can be made by the method described in *J. Amer. Chem. Soc.*, 1983, 105, 3183-3188.

Example 5

2-[3-(3,5-Dimethyl-1H-pyrazol-4-yl)-phenyl]-1-phenyl-ethylamine 5A. 2-(3-Bromo-phenyl)-1-phenyl-ethylamine

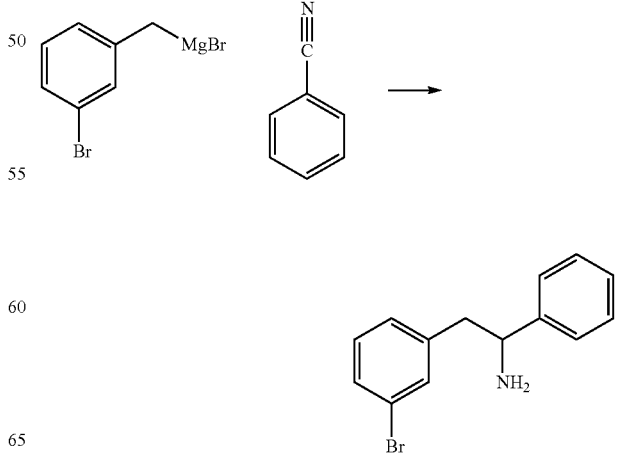

Benzonitrile (500 mg, 4.849 mmol) was added dropwise to a solution of 3-bromobenzylmagnesium bromide (0.275 M solution in diethyl ether, 21.1 ml, 5.818 mmol) under an atmosphere of nitrogen at room temperature. The reaction mixture was then heated to reflux for a period of 2 hours then allowed to cool. Lithium aluminium hydride (1.0 M in THF, 4.85 ml, 4.849 mmol) was then added cautiously and the reaction mixture was allowed to heat at reflux for a further 16 hours. Upon cooling, the reaction was quenched by cautious and dropwise addition of water (5 ml) and then partitioned between water (20 ml) and ethyl acetate (100 ml). The organic layer was separated, dried (MgSO$_4$), filtered and concentrated. Purification by ion exchange chromatography afforded the desired compound (420 mg, 31%).

5B. 2-[3-(3,5-Dimethyl-1H-pyrazol-4-yl)-phenyl]-1-phenyl-ethylamine

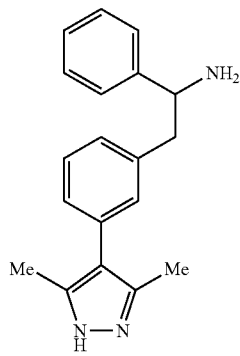 [SMILES: Cc1n[nH]c(C)c1-c1cccc(CC(N)c2ccccc2)c1]

The product of 5B was reacted with 3,5-dimethyl-4-(4,4,5,5-tetramethyl-[1,3,2]dioxaborolan-2-yl)-1H-pyrazole following the procedure set out in Example 1 to give the title compound. (LC/MS: (PS-B) R$_t$ 2.54 [M+H]$^+$ 292).

Example 6

3-Phenyl-2-[3-(1H-pyrazol-4-yl)-phenyl]-propylamine

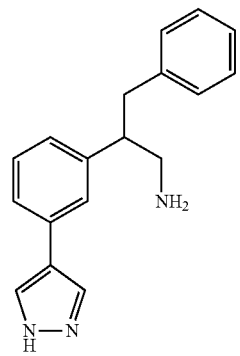 [SMILES: NCC(Cc1ccccc1)c1cccc(-c2cn[nH]c2)c1]

To a solution of the product of Example 2 (70 mg, 0.256 mmol, 1.0 equiv) in ethanol (25 ml) was added concentrated ammonia (0.5 ml) and Raney Nickel (approximately 0.5 ml of the water suspension) and the reaction mixture was subjected to a hydrogen atmosphere for 17 hours. The mixture was filtered through Celite® and the mother liquor was concentrated under reduced pressure to give the title compound which was purified by preparative liquid chromatography. (LC/MS: (PS-A) R$_t$ 1.89 [M+H]$^+$ 278.

Example 7

3-Phenyl-2-[4-(1H-pyrazol-4-yl)-phenyl]-propylamine 7A. 2-(4-Bromo-phenyl)-3-phenyl-propionitrile

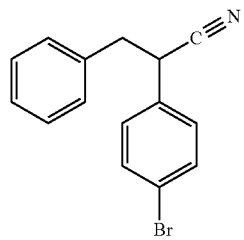 [SMILES: N#CC(Cc1ccccc1)c1ccc(Br)cc1]

Following the procedure described in Example 2A but substituting 4-bromophenylacetonitrile for 3-bromophenylacetonitrile gave the title compound was obtained which was used in the next step without further purification.

7B. 3-Phenyl-2-[4-(1H-pyrazol-4-yl)-phenyl]-propionitrile

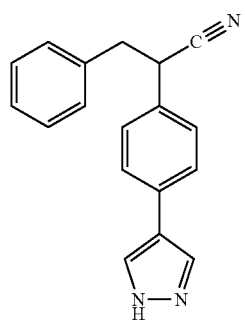 [SMILES: N#CC(Cc1ccccc1)c1ccc(-c2cn[nH]c2)cc1]

By following the procedure described in Example 1 but substituting 2-(4-Bromo-phenyl)-3-phenyl-propionitrile for 2-(4-chlorophenyl)-2-phenylethylamine, the title compound was obtained.

7C. 3-Phenyl-2-[4-(1H-pyrazol-4-yl)-phenyl]-propylamine

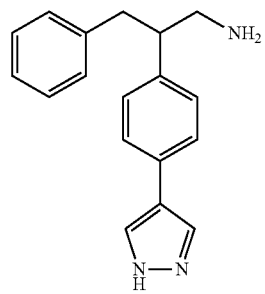 [SMILES: NCC(Cc1ccccc1)c1ccc(-c2cn[nH]c2)cc1]

The nitrile product of Example 7B was reduced using the conditions described in Example 6 to give the title compound. (LC/MS: (PS-B) R$_t$ 3.03 [M+H]$^+$ 278.

Example 8

{3-(4-Chloro-phenyl)-3-[4-(1H-pyrazol-4-yl)-phenyl]-propyl}-methyl-amine 8A. 3-(4-Bromo-phenyl)-2-cyano-acrylic acid ethyl ester (J. Med. Chem., 1983, 26, 935-947)

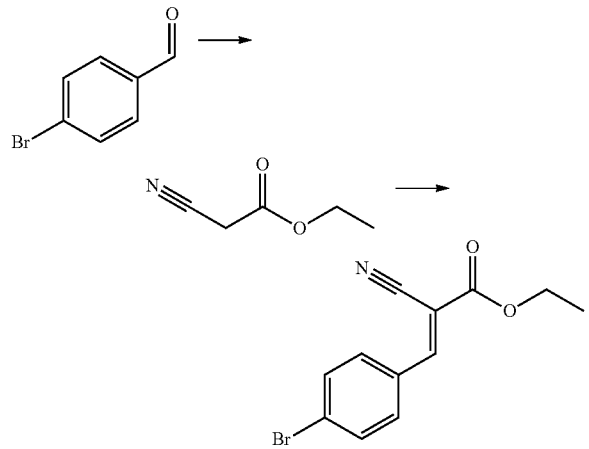

4-Bromobenzaldehyde (3 g, 16.21 mmol) and ethyl cyanoacetate (1.9 ml, 17.84 mmol) in toluene was added piperidine (27 μl) and the reaction mixture was refluxed for 1 hour with a Dean-Stark separator. The solvent was removed under reduced pressure, the residue triturated with warm ethyl acetate, filtered to yield the desired product as a yellow solid (4.03 g, 89% yield). LC/MS: (PS-A2) R$_t$ 3.44.

8B. 3-(4-Bromo-phenyl)-3-(4-chloro-phenyl)-2-cyano-propionic acid ethyl ester

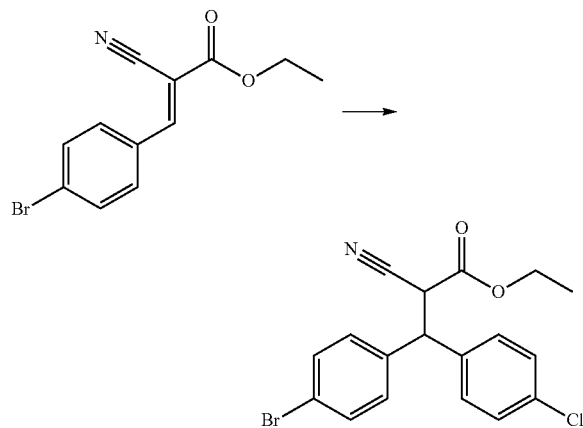

A solution of 3-(4-bromo-phenyl)-2-cyano-acrylic acid ethyl ester (1.5 g, 5.36 mmol) in dry toluene (12 ml) was added dropwise to 4-chlorophenylmagnesium bromide (0.5 M solution in tetrahydrofuran, 6.96 ml, 6.96 mmol) at 0° C. The reaction mixture was heated to 85° C. for 3 hours, poured onto ice, acidified with 1N HCl and extracted with ethyl acetate. The organic layer was separated, dried (MgSO$_4$), filtered and concentrated, the crude product was purified over flash silica chromatography eluting with petroleum ether to ethyl acetate/petroleum ether (5:95) to afford the desired product (1.91 g, 91% yield). LC/MS: (PS-A2) R$_t$ 3.78 [M+H]$^-$ 391.93.

8C. 3-(4-Bromo-phenyl)-3-(4-chloro-phenyl)-propionic acid

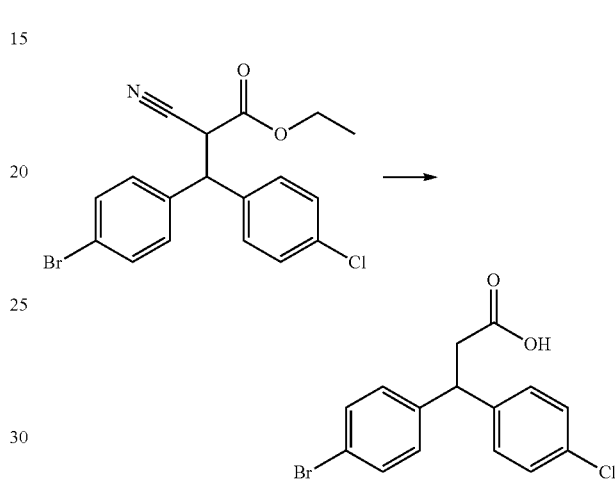

A mixture of 3-(4-bromo-phenyl)-3-(4-chloro-phenyl)-2-cyano-propionic acid ethyl ester (1.91, 4.87 mmol), acetic acid (10 ml), concentrated sulfuric acid (5 ml) and water (5 ml) were refluxed for 2 hours. Reaction mixture was poured into iced water and extracted with ethyl acetate. The organic layer was separated, dried (MgSO$_4$), filtered and concentrated, the crude product was purified over flash silica chromatography eluting with ethyl acetate/petroleum ether (1:1) to afford the desired product (0.82 g, 50% yield). LC/MS: (PS-A2) R$_t$ 3.39 [M+H]$^-$ 338.86.

8D. 3-(4-Bromo-phenyl)-3-(4-chloro-phenyl)-N-methyl-propionamide

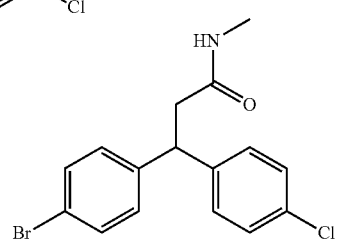

A mixture of 3-(4-bromo-phenyl)-3-(4-chloro-phenyl)-propionic acid (0.25 g, 0.74 mmol) and 1-hydroxybenatriazole (0.12 g, 0.88 mmol) in dichloromethane (3 ml) was stirred for 15 minutes before addition of methylamine (40% solution in water, 0.11 μl, 1.47 mmol) and 1-(3-dimethylaminopropyl)-ethylcarbodiimide hydrochloride (0.17 g, 0.88 mmol). The reaction mixture was stirred for 16 hours, solvent removed under reduced pressure and the residue partitioned between ethyl acetate and 1N HCl. The organic layer was separated, washed with saturated sodium hydrogen carbonate, brine, dried (MgSO$_4$), filtered and concentrated to yield the title compound which was used in the next step without further purification. LC/MS: (PS-A2) R$_t$ 3.20 [M+H]$^+$ 353.95.

8E. [3-(4-Bromo-phenyl)-3-(4-chloro-phenyl)-propyl]-methyl-amine

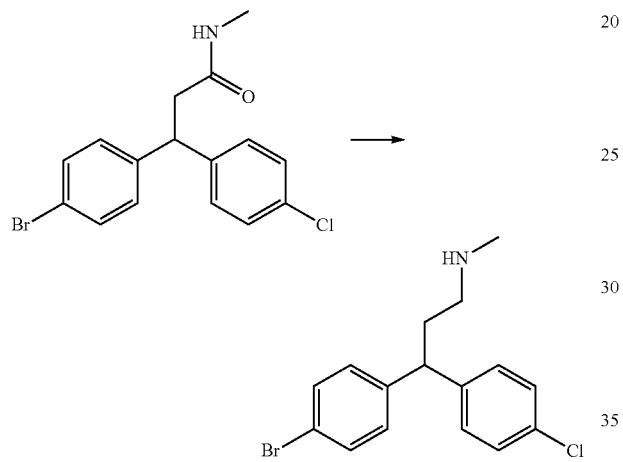

Under a nitrogen atmosphere, the crude 3-(4-bromo-phenyl)-3-(4-chloro-phenyl)-N-methyl-propionamide was cooled to 0° C., lithium aluminum hydride (0.075 g, 1.97 mmol) and diethyl ether (3 ml) were added. With cooling, aluminum chloride (0.23 g, 1.69 mmol) was dissolved in diethyl ether (2 ml) and added. The reaction mixture was stirred for 16 hours, quenched with addition of water, basified (2N NaOH) and extracted with ethyl acetate. The organic layer was separated, dried (MgSO$_4$), filtered and concentrated, the crude product was purified over Phenomenex_Strata_SCX column chromatography eluting with methanol followed by 2N ammonia in methanol to afford the desired product (0.254 g, 62% yield for steps 1D and 1E combined). LC/MS: (PS-B3) R$_t$ 3.20 [M+H]$^+$ 339.85.

8F. {3-(4-Chloro-phenyl)-3-[4-(1H-pyrazol-4-yl)-phenyl]-propyl}-methyl-amine

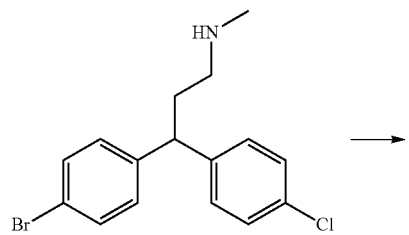

-continued

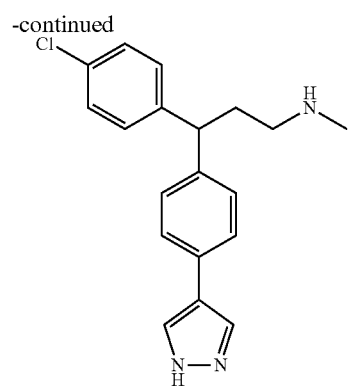

[3-(4-Bromo-phenyl)-3-(4-chloro-phenyl)-propyl]methyl-amine was reacted with 4-(4,4,5,5-tetramethyl-1,3,2-dioxaborolan-2-yl)-1H-pyrazole following the procedure set out in Example 1 to give the title compound. LC/MS: (PS-B3) R$_t$ 2.63 [M+H]$^+$ 326.00. $^1$H NMR (Me-d$_3$-OD) δ 2.37-2.47 (2H, m), 2.66 (3H, s), 2.91 (2H, t), 4.05 (1H, t), 7.25-7.34 (6H, m), 7.54 (2H, d), 7.92 (2H, s), 8.51 (1H, br s—due to formic acid).

Example 9

{3-(3,4-Difluoro-phenyl)-3-[4-(1H-pyrazol-4-yl)-phenyl]-propyl}-methyl-amine

9A. 3-(4-Bromo-phenyl)-3-(3,4-difluoro-phenyl)-N-methyl-propionamide

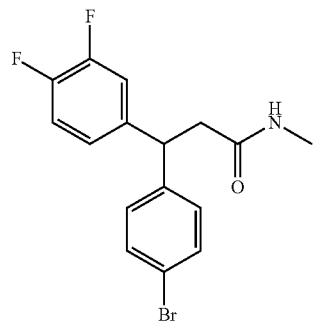 [SMILES: CNC(=O)CC(c1ccc(Br)cc1)c1ccc(F)c(F)c1]

By following the procedure described in Example 8A through to Example 8C but substituting 4-chlorophenylmagnesium bromide for 3,4-difluorophenylmagnesium bromide, the title compound was obtained. LC/MS: (PS-A2) R$_t$ 3.12 [M+H]$^+$ 355.84.

9B. 3-(3,4-Difluoro-phenyl)-N-methyl-3-[4-(1H-pyrazol-4-yl)-phenyl]-propionamide

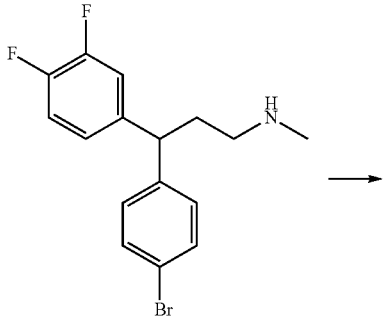

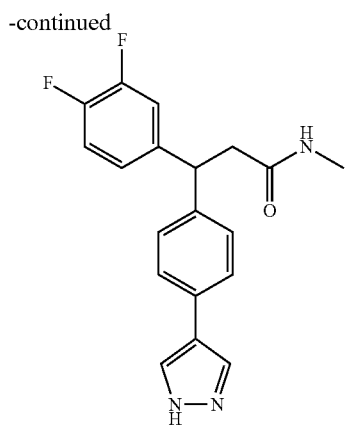

3-(4-Bromo-phenyl)-3-(3,4-difluoro-phenyl)-N-methyl-propionamide was reacted with 4-(4,4,5,5-tetramethyl-1,3,2-dioxaborolan-2-yl)-1H-pyrazole following the procedure set out in Example 1 to give the title compound. LC/MS: (PS-A2) R$_t$ 2.55 [M+H]$^+$ 341.93.

9C. {3-(3,4-Difluoro-phenyl)-3-[4-(1H-pyrazol-4-yl)-phenyl]-propyl}-methyl-amine

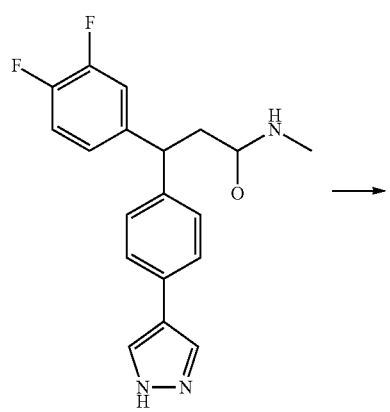

Lithium aluminium hydride was added to a suspension of 3-(3,4-Difluoro-phenyl)-N-methyl-3-[4-(1H-pyrazol-4-yl)-phenyl]-propionamide in diethyl ether, followed by a solution of aluminium chloride in diethyl ether at 0° C., under a nitrogen atmosphere. Toluene was added and the reaction mixture was heated at 70° C. for 18 hours. Upon cooling the reaction was quenched with addition of water, basified (2N NaOH) and extracted with ethyl acetate. The organic layer was separated, dried (MgSO$_4$), filtered and concentrated to afford the desired compound. LC/MS: (PS-A2) R$_t$ 2.15 [M+H]$^+$ 328.06. $^1$H NMR (Me-d$_3$-OD) δ 2.19-2.29 (2H, m), 2.35 (3H, s), 2.51 (2H, t), 4.00 (1H, t), 7.06-7.24 (3H, m), 7.27 (2H, d), 7.52 (2H, d), 7.92 (2H, s).

Example 10

{3-(3-Chloro-phenyl)-3-[4-(1H-pyrazol-4-yl)-phenyl]-propyl}-methyl-amine

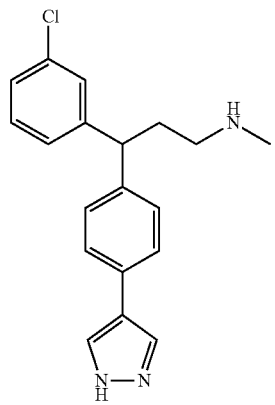 [SMILES: CNCCC(c1ccc(-c2cn[nH]c2)cc1)c1cccc(Cl)c1]

By following the procedure described in Example 8 but substituting 4-chlorophenylmagnesium bromide for 3-chlorophenylmagnesium bromide, the title compound was obtained. LC/MS: (PS-B3) R$_t$ 2.67 [M+H]$^+$ 326.00. $^1$H NMR (Me-d$_3$-OD) δ 2.43-2.50 (2H, m), 2.68 (3H, s), 2.94 (2H, m), 4.13 (1H, t), 7.24 (1H, m), 7.27-7.36 (3H, m), 7.41 (2H, d), 7.66 (2H, d), 8.50 (2H, s).

Example 11

3-(4-Chloro-phenyl)-3-[4-(1H-pyrazol-4-yl)-phenyl]-propionamide

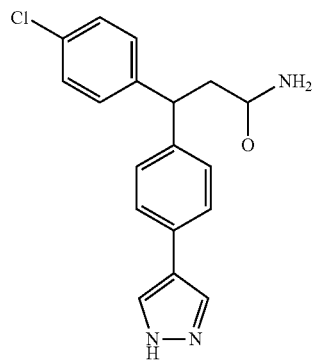 [SMILES: NC(O)CC(c1ccc(Cl)cc1)c1ccc(-c2cn[nH]c2)cc1]

By following the procedure described in Example 9A and 9B but substituting 3,4-difluorophenylmagnesium bromide for 4-chlorophenylmagnesium bromide, the title compound was obtained. LC/MS: (PS-A2) $R_t$ 2.54 [M+H]$^+$ 326. $^1$H NMR (Me-d$_3$-OD) δ 2.95 (2H, d), 4.53 (1H, t), 7.27 (6H, m), 7.50 (2H, d), 7.91 (2H, s).

Example 12

3-(4-Chloro-phenyl)-3-[4-(1H-pyrazol-4-yl)-phenyl]-propylamine

12A. 3-(4-Bromo-phenyl)-3-(4-chloro-phenyl)-propionamide

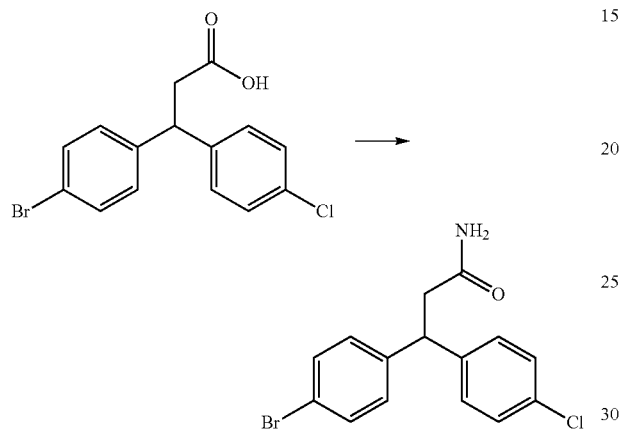

A solution of 3-(4-Bromo-phenyl)-3-(4-chloro-phenyl)-propionic acid* (0.25 g, 0.74 mmol) and 1,1'-carbonyldiimidazole (0.24 g, 1.47 mmol) in dichloromethane was stirred for 45 minutes before the addition of ammonia (2M solution in methanol, 3.68 ml, 7.36 mmol). The reaction mixture was stirred for 2 hours, solvent removed under reduced pressure and residue was purified over flash silica chromatography eluting with ethyl acetate/petroleum ether (1:4) to afford the title compound (0.091 g, 36% yield). LC/MS: (PS-A2)$R_t$ 3.08 [M+H]$^+$ 339.93.

*This starting material can be made by the method described in Example 8A through to 8C.

12B. 3-(4-Bromo-phenyl)-3-(4-chloro-phenyl)-propylamine

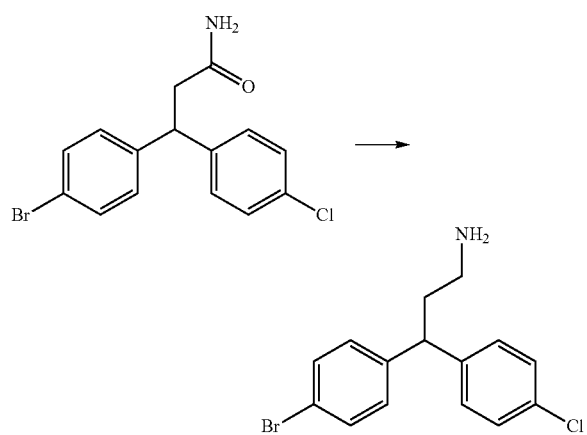

By following the procedure described in Example 8E but substituting 3-(4-Bromo-phenyl)-3-(4-chloro-phenyl)-propionamide for 3-(4-Bromo-phenyl)-3-(4-chloro-phenyl)-N-methyl-propionamide, the title compound was obtained. LC/MS: (PS-B2) $R_t$ 3.88 [M+H]$^+$ 359.87.

12C. 3-(4-Chloro-phenyl)-3-[4-(1H-pyrazol-4-yl)-phenyl]-propylamine

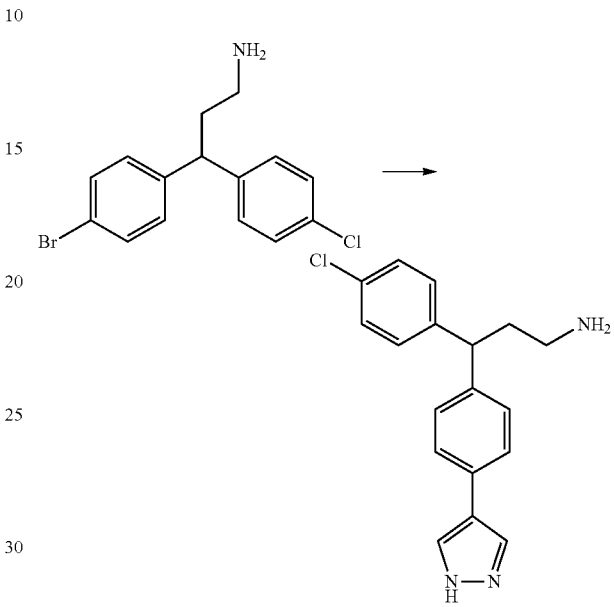

3-(4-Bromo-phenyl)-3-(4-chloro-phenyl)-propylamine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.54 [M+H]$^+$ 312.04. $^1$H NMR (Me-d$_3$-OD) δ 2.39 (2H, m), 2.84 (2H, t), 4.06 (1H, t), 7.27-7.33 (6H, m), 7.54 (2H, d), 7.91 (2H, s).

Example 13

3-(3,4-Dichloro-phenyl)-3-[4-(1H-pyrazol-4-yl)-phenyl]-propylamine

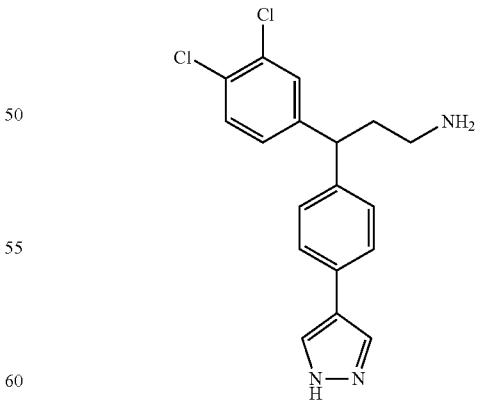

By following the procedure described in Example 12 but substituting 4-chlorophenylmagnesium bromide for 3,4-dichlorophenylmagnesium bromide, the title compound was obtained. LC/MS: (PS-A2) $R_t$ 2.17 [M+H]$^+$ 345.95. $^1$H NMR (Me-d$_3$-OD) δ 2.39 (2H, m), 2.84 (2H, t), 4.07 (1H, t), 7.24-7.31 (4H, m), 7.45-7.49 (2H, m), 7.56 (2H, d), 7.93 (2H, s).

Example 14

4-(4-Chloro-phenyl)-4-[4-(1H-pyrazol-4-yl)-phenyl]-piperidine

14A. 4-(4-Bromo-phenyl)-4-(4-chloro-phenyl)-piperidine

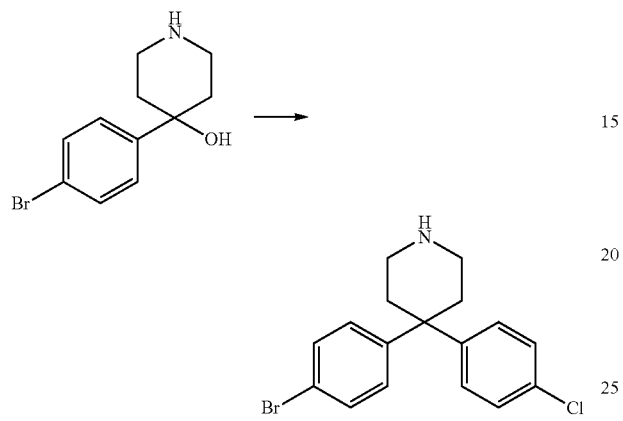

A suspension of 4-(4-Bromo-phenyl)-piperidin-4-ol (4.02 g, 15.7 mmol) in chlorobenzene (30 ml) was added dropwise to a suspension of aluminium chloride (7.32 g, 54.9 mmol) in chlorobenzene (10 ml) at 0° C. The reaction mixture was stirred at 0° C. for 2 hours, quenched by addition of ice then methyl t-butyl ether added. After stirring for 1 hour the precipitate was collected by filtration washed with water, methyl t-butyl ether and water to afford the title compound (5.59 g, 92% yield). LC/MS: (PS-B3) $R_t$ 3.57 [M+H]$^+$ 350, 352.

14B. 4-(4-Chloro-phenyl)-4-[4-(1H-pyrazol-4-yl)-phenyl]-piperidine

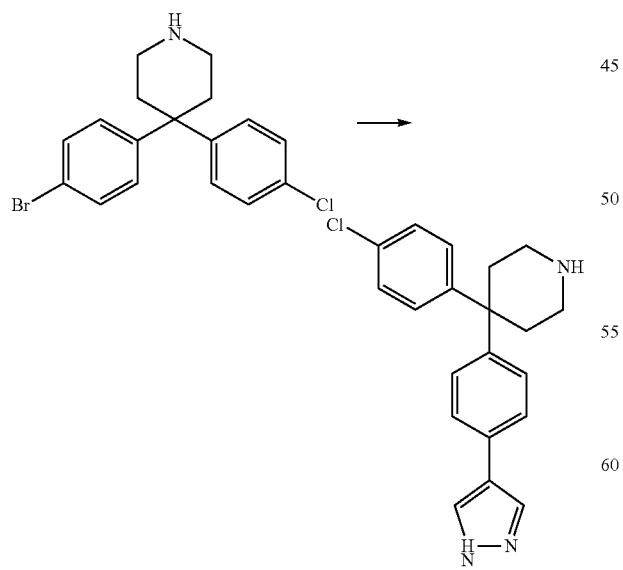

4-(4-Bromo-phenyl)-4-(4-chloro-phenyl)-piperidine was reacted with 4-(4,4,5,5-tetramethyl-1,3,2-dioxaborolan-2-yl)-1H-pyrazole following the procedure set out in Example 1 to give the title compound. LC/MS: (PS-A3) $R_t$ 7.22 [M+H]$^+$ 338.08 $^1$H NMR (Me-d$_3$-OD) δ 2.64-2.74 (4H, m), 3.22-3.25 (4H, m), 7.33-7.45 (6H, m), 7.65 (2H, d), 8.37 (2H, s).

Example 15

4-(4-Methoxy-phenyl)-4-[4-(1H-pyrazol-4-yl)-phenyl]-piperidine

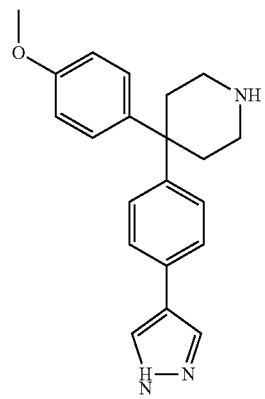 [SMILES: COc1ccc(C2(c3ccc(-c4cn[nH]c4)cc3)CCNCC2)cc1]

By following the procedure described in Example 14 but substituting chlorobenzene for anisole, the title compound was obtained. LC/MS: (PS-B3) $R_t$ 2.42 [M+H]$^+$ 334.00. $^1$H NMR (Me-d$_3$-OD) δ 2.69 (4H, m), 3.23 (4H, m), 3.76 (3H, s), 6.90 (2H, d), 7.28 (2H, d), 7.40 (2H, d), 7.65 (2H, d), 8.53 (2H, s).

Example 16

4-(4-Chloro-phenyl)-1-methyl-4-[4-(1H-pyrazol-4-yl)-phenyl]-piperidine

16A. 4-(4-Bromo-phenyl)-4-(4-chloro-phenyl)-piperidine-1-carboxylic acid ethyl ester

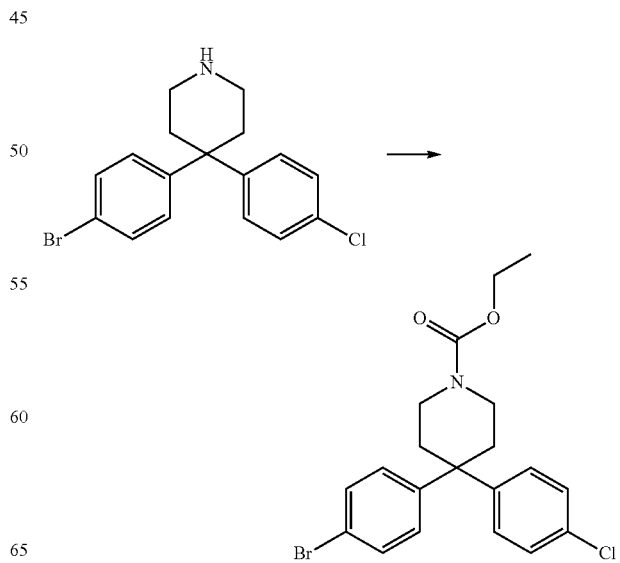

To a stirring suspension of 4-(4-Bromo-phenyl)-4-(4-chloro-phenyl)-piperidine* (0.28 g, 0.80 mmol) in dichloromethane (10 ml), were added triethylamine (0.45 ml, 3.2 mmol) and ethyl chloroformate (0.085 ml, 0.88 mmol). The reaction mixture was stirred for 3 hours, diluted with ethyl acetate and washed with 1N HCl, saturated sodium hydrogen carbonate and brine. The organic layer was separated, dried (MgSO$_4$), filtered and concentrated to afford the title compound (0.29 g, 94% yield). LCMS: (PS-A2), R$_t$ 4.02 [M+H]$^+$ 422, 424.

*This starting material can be made by the method described in Example 14A

16B. 4-(4-Bromo-phenyl)-4-(4-chloro-phenyl)-1-methyl-piperidine

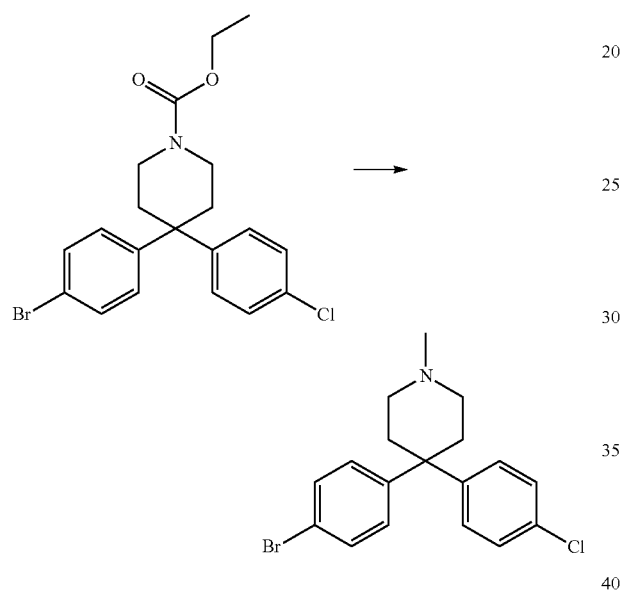

Under a nitrogen atmosphere 4-(4-Bromo-phenyl)-4-(4-chloro-phenyl)-piperidine-1-carboxylic acid ethyl ester (0.28 g, 0.66 mmol) and lithium aluminum hydride (0.051 g) were suspended in tetrahydrofuran (5 ml) and stirred for 2 hours. The reaction mixture was quenched with addition of water, solvent removed under reduced pressure, the residue was partitioned between ethyl acetate and 2N NaOH. The organic layer was washed with brine, dried (MgSO$_4$), filtered and concentrated to afford the desired product (0.241 g, 99% yield). LC/MS: (PS-B3) R$_t$ 3.78 [M+H]$^+$ 363.95, 365.73.

16C. 4-(4-Chloro-phenyl)-1-methyl-4-[4-(1H-pyrazol-4-yl)-phenyl]-piperidine

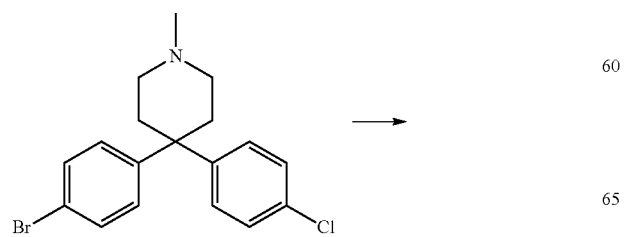

-continued

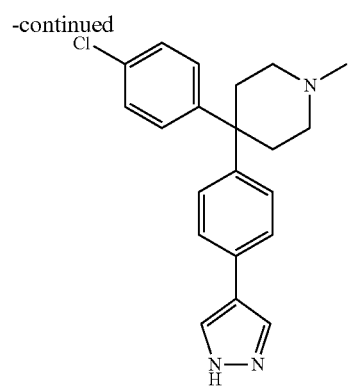

4-(4-Bromo-phenyl)-4-(4-chloro-phenyl)-1-methyl-piperidine was reacted with 4-(4,4,5,5-tetramethyl-1,3,2-dioxaborolan-2-yl)-1H-pyrazole following the procedure set out in Example 1 to give the title compound. LC/MS: (PS-B3) R$_t$ 2.90 [M+H]$^+$ 352. $^1$H NMR (Me-d$_3$-OD) δ 2.41-2.53 (2H, m), 2.82 (3H, d), 2.97-3.12 (4H, m), 3.56-3.59 (2H, m), 7.28 (2H, s), 7.34 (1H, m), 7.42 (1H, d), 7.49 (1H, d), 7.54 (1H, d), 7.61 (1H, d), 7.75 (1H, d), 8.52 (2H, d).

Example 17

4-Phenyl-4-[4-(1H-pyrazol-4-yl)-phenyl]-piperidine

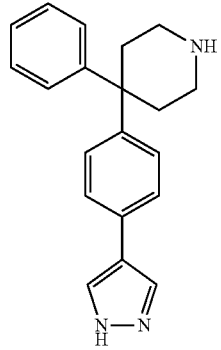 [SMILES: c1ccc(C2(c3ccc(-c4cn[nH]c4)cc3)CCNCC2)cc1]

By following the procedure described in Example 1 but substituting 2-(4-chlorophenyl)-2-phenylethylamine hydrochloride for 4-(4-Chloro-phenyl)-4-phenyl-piperidine, the title compound was obtained. LC/MS: (PS-A2) R$_t$ 1.88 [M+H]$^+$ 304. $^1$H NMR (Me-d$_3$-OD) δ 2.65-2.71 (4H, m), 3.21 (4H, t), 7.18-7.22 (1H, m), 7.32-7.38 (6H, m), 7.55 (2H, d), 7.93 (2H, s).

Example 18

4-[4-(3,5-Dimethyl-1H-pyrazol-4-yl)-phenyl]-4-phenyl-piperidine

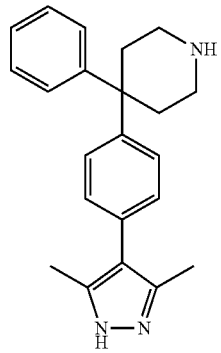 [SMILES: Cc1n[nH]c(C)c1-c1ccc(C2(c3ccccc3)CCNCC2)cc1]

By following the procedure described in Example 1 but substituting 2-(4-chlorophenyl)-2-phenylethylamine hydrochloride and 4-(4,4,5,5-tetramethyl-1,3,2-dioxaborolan-2-yl)-1H-pyrazole for 4-(4-chloro-phenyl)-4-phenyl-piperidine and 3,5-dimethyl-4-(4,4,5,5-tetramethyl-[1,3,2]dioxaborolan-2-yl)-1H-pyrazole, the title compound was obtained. LC/MS: (PS-A2) R$_t$ 2.95 [M+H]$^+$ 315. $^1$H NMR (Me-d$_3$-OD) δ 2.22 (6H, s), 2.66-2.76 (4H, m), 3.16-3.28 (4H, m), 7.19-7.44 (9H, m).

Example 19

Dimethyl-{3-[4-(1H-pyrazol-4-yl)-phenyl]-3-pyridin-2-yl-propyl}-amine

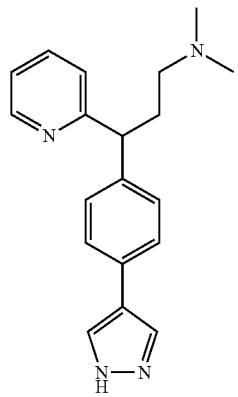 [SMILES: CN(C)CCC(c1ccc(-c2cn[nH]c2)cc1)c1ccccn1]

By following the procedure described in Example 1 but substituting 2-(4-chlorophenyl)-2-phenylethylamine hydrochloride for brompheniramine maleate, the title compound was obtained. LC/MS: (PS-B2) R$_t$ 2.29 [M+H]$^+$ 307. $^1$H NMR (Me-d$_3$-OD) δ 2.44-2.54 (1H, m), 2.59-2.70 (1H, m), 2.77 (6H, s), 2.93-3.01 (2H, m), 4.20 (1H, t), 7.25-7.28 (1H, m), 7.32-7.36 (3H, m), 7.54 (2H, d), 7.75 (1H, dt), 7.94 (2H, br s).

Example 20

{2-(4-Chloro-phenyl)-2-[4-(1H-pyrazol-4-yl)-phenyl]-ethyl}-dimethyl-amine 20A.
2,2-Bis-(4-chloro-phenyl)-N,N-dimethyl-acetamide

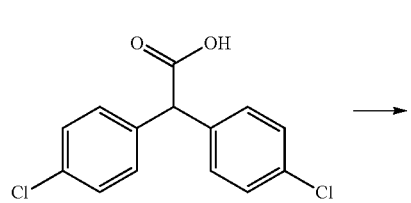

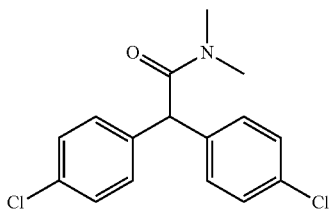

Bis-(4-chloro-phenyl)-acetic acid was reacted with dimethylamine following the procedure set out in Example 8D to give the title compound. LC/MS: (PS-A2) R$_t$ 3.40 [M+H]$^+$ 309.95.

20B.
[2,2-Bis-(4-chloro-phenyl)-ethyl]-dimethyl-amine

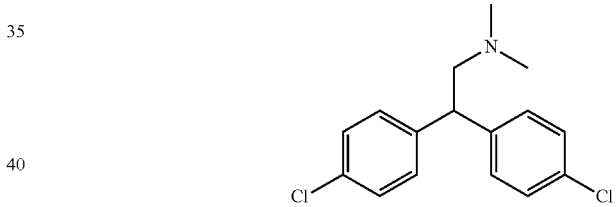

By following the procedure described in Example 8E but substituting 3-(4-Bromo-phenyl)-3-(4-chloro-phenyl)-N-methyl-propionamide for 2,2-Bis-(4-chloro-phenyl)-N,N-dimethyl-acetamide, the title compound was obtained. LC/MS: (PS-B2) R$_t$ 375 [M+H]$^+$ 295.99.

20C. {2-(4-Chloro-phenyl)-2-[4-(1H-pyrazol-4-yl)-phenyl]-ethyl}-dimethyl-amine

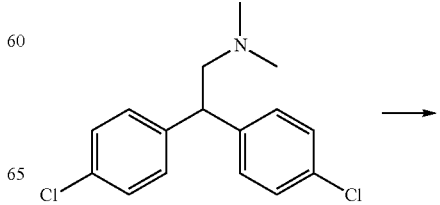

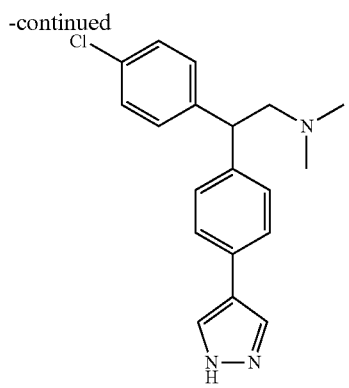

[2,2-Bis-(4-chloro-phenyl)-ethyl]-dimethyl-amine was reacted with 4-(4,4,5,5-tetramethyl-1,3,2-dioxaborolan-2-yl)-1H-pyrazole following the procedure set out in Example 1 to give the title compound. LC/MS: (PS-B2) $R_t$ 3.07 [M+H]$^+$ 325.99. $^1$H NMR (Me-d$_3$-OD) δ 2.5 (6H, s), 2.98 (2H, dd), 4.34 (1H, t), 7.31-7.36 (6H, m), 7.50 (2H, d), 7.92 (2H, s).

Example 21

{2-(4-Chloro-phenyl)-2-[4-(1H-pyrazol-4-yl)-phenyl]-ethyl}-methyl-amine

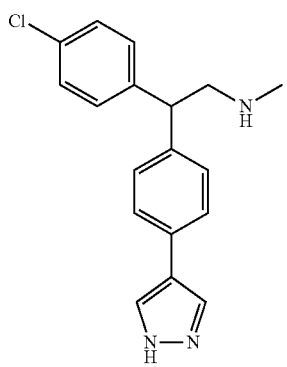 [SMILES: CNCC(c1ccc(Cl)cc1)c1ccc(-c2cn[nH]c2)cc1]

By following the procedure described in Example 20 but substituting dimethylamine for methylamine, the title compound was obtained. LC/MS: (PS-B2) $R_t$ 2.83 [M+H]$^+$ 312.07. $^1$H NMR (Me-d$_3$-OD) δ 2.42 (3H, s), 3.20-3.23 (2H, dd), 4.18 (1H, t), 7.27-7.33 (6H, m), 7.54 (2H, d), 7.92 (2H, br s).

Example 22

{2-(4-Chloro-phenyl)-2-[4-(1H-pyrazol-4-yl)-phenyl]-ethyl}-methyl-amine (R)

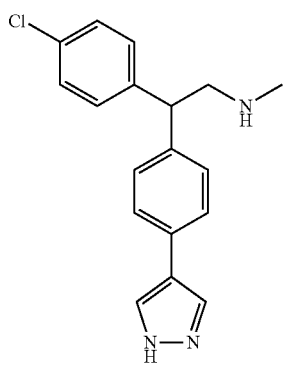 [SMILES: CNCC(c1ccc(Cl)cc1)c1ccc(-c2cn[nH]c2)cc1]

Prepared using the same procedure as Example 21 but enantiomers separated by chiral preparative HPLC using method AG-CP2. LCMS: (AG-CA) $R_t$ 5.58 min, 97.4% ee. $^1$H NMR (Me-d$_3$-OD) δ 2.75 (3H, s), 3.78 (2H, d), 4.43 (1H, t), 7.39 (4H, s), 7.44 (2H, d), 7.69 (2H, d), 8.43 (2H, s).

Example 23

{2-(4-Chloro-phenyl)-2-[4-(1H-pyrazol-4-yl)-phenyl]-ethyl}-methyl-amine (S)

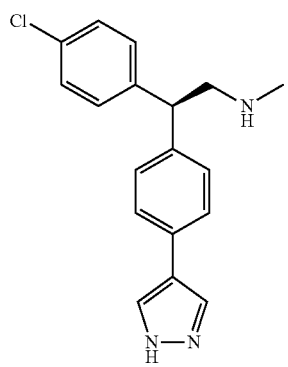 [SMILES: CNC[C@H](c1ccc(Cl)cc1)c1ccc(-c2cn[nH]c2)cc1]

Prepared using the same procedure as Example 21 but enantiomers separated by chiral preparative HPLC using method AG-CP2. LCMS: (AG-CA) $R_t$ 4.51 min, 98.0% ee. $^1$H NMR (Me-d$_3$-OD) δ 2.75 (3H, s), 3.79 (2H, d), 4.51 (1H, t), 7.37-7.43 (4H, m), 7.49 (2H, d), 7.73 (2H, d), 8.66 (2H, s).

Example 24

4-{2-(4-Chloro-phenyl)-2-[4-(1H-pyrazol-4-yl)-phenyl]-ethyl}-morpholine

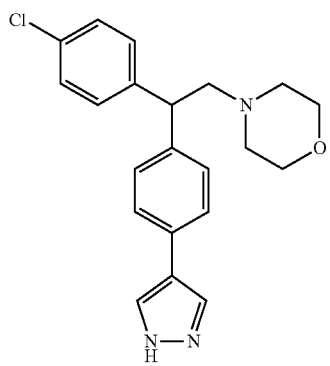 [SMILES: Clc1ccc(C(CN2CCOCC2)c2ccc(-c3cn[nH]c3)cc2)cc1]

By following the procedure described in Example 20 but substituting dimethylamine for morpholine, the title compound was obtained. LC/MS: (PS-B3) $R_t$ 3.07 [M+H]$^+$ 368.05. $^1$H NMR (Me-d$_3$-OD) δ 2.50 (4H, m), 2.97 (2H, m), 3.60 (4H, t), 4.26 (1H, t), 7.27 (6H, m), 7.49 (2H, d), 7.89 (2H, s).

Example 25

4-{4-[1-(4-Chloro-phenyl)-2-pyrrolidin-1-yl-ethyl]-phenyl}-1H-pyrazole

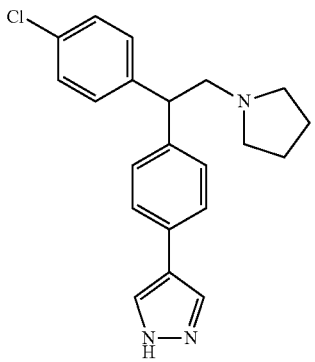 [SMILES: Clc1ccc(C(CN2CCCC2)c2ccc(-c3cn[nH]c3)cc2)cc1]

By following the procedure described in Example 20 but substituting dimethylamine for pyrrolidine, the title compound was obtained. LC/MS: (PS-A2) $R_t$ 2.06 [M+H]$^+$ 354.01. $^1$H NMR (Me-d$_3$-OD) δ 1.85 (4H, m), 2.87 (4H, m), 3.47 (2H, d), 4.31 (1H, t), 7.30-7.37 (6H, m), 7.54 (2H, d), 7.92 (2H, s).

Example 26

{2-(4-Chloro-phenyl)-2-[4-(1H-pyrazol-4-yl)-phenyl]-ethyl}-isopropyl-amine

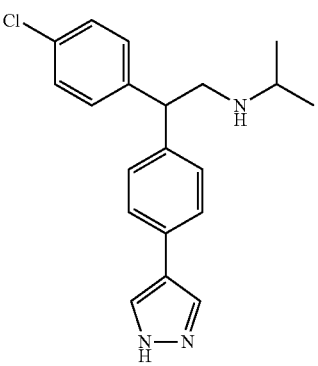 [SMILES: CC(C)NCC(c1ccc(Cl)cc1)c1ccc(-c2cn[nH]c2)cc1]

By following the procedure described in Example 20 but substituting dimethylamine for isopropylamine, the title compound was obtained. LC/MS: (PS A2) $R_t$ 2.10 [M+H]$^+$ 340. $^1$H NMR (Me-d$_3$-OD) δ 1.31 (6H, d), 3.38-3.45 (1H, m), 3.65-3.74 (2H, m), 4.39 (1H, br t), 7.37 (6H, m), 7.59 (2H, d), 7.94 (2H, s).

Example 27

Dimethyl-{2-phenyl-2-[4-(1H-pyrazol-4-yl)-phenyl] ethyl}-amine

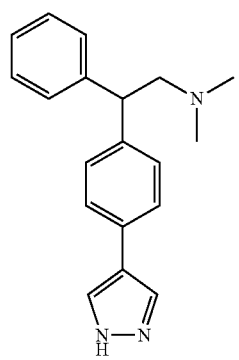 [SMILES: CN(C)CC(c1ccccc1)c1ccc(-c2cn[nH]c2)cc1]

By following the procedure described in Example 20, the title compound was obtained. LC/MS: (PS-B2) $R_t$ 2.82 [M+H]$^+$ 292.11 $^1$H NMR (Me-d$_3$-OD) δ 2.25 (6H, s), 2.95-3.04 (2H, m), 4.20 (1H, t), 7.16 (1H, t), 7.26-7.33 (6H, m), 7.49 (2H, d), 7.89 (2H, s).

Example 28

{2,2-Bis-[4-(1H-pyrazol-4-yl)-phenyl]-ethyl}-dimethyl-amine

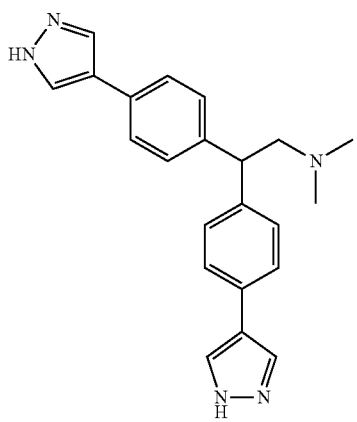 [SMILES: CN(C)CC(c1ccc(-c2cn[nH]c2)cc1)c1ccc(-c2cn[nH]c2)cc1]

By following the procedure described in Example 20, the title compound was obtained. LC/MS: (PS-B2) $R_t$ 2.45 [M+H]$^+$ 358.11. $^1$H NMR (Me-d$_3$-OD) δ 2.69 (6H, s), 3.59 (2H, d), 4.43 (1H, t), 7.39 (4H, d), 7.57 (4H, d), 7.93 (4H, s).

Example 29

{2,2-Bis-[4-(1H-pyrazol-4-yl)-phenyl]ethyl}-methyl-amine

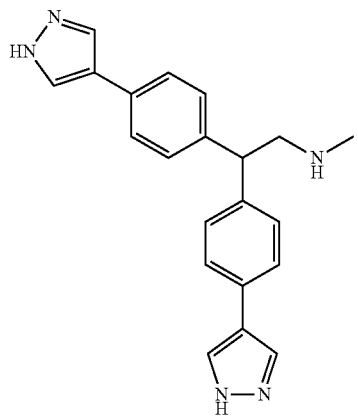 [SMILES: CNCC(c1ccc(-c2cn[nH]c2)cc1)c1ccc(-c2cn[nH]c2)cc1]

By following the procedure described in Example 21, the title compound was obtained. LC/MS: (PS-B2) $R_t$ 2.18 [M+H]$^+$ 344.11. $^1$H NMR (Me-d$_3$-OD) δ 2.65 (3H, s), 3.60 (2H, d), 4.34 (1H, t), 7.36 (4H, d), 7.59 (4H, d), 7.94 (4H, s).

Example 30

2-(4-Chloro-phenyl)-2-[4-(1H-pyrazol-4-yl)-phenyl]ethylamine (R)

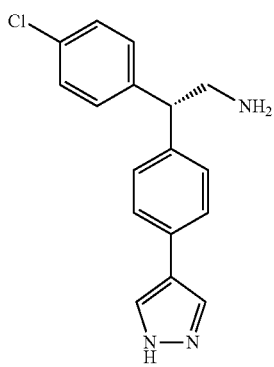 [SMILES: NC[C@@H](c1ccc(Cl)cc1)c1ccc(-c2cn[nH]c2)cc1]

Prepared using the same procedure as Example 4 but enantiomers separated by chiral preparative HPLC using method AG-CP1. LCMS: (FL-C)$R_t$ 10.97 min, 95.7% ee. $^1$H NMR (Me-d$_3$-OD) δ 3.65 (2H, m), 4.30 (1H, t), 7.35-7.40 (6H, m), 7.64 (2H, d), 8.16 (2H, s).

Example 31

2-(4-Chloro-phenyl)-2-[4-(1H-pyrazol-4-yl)-phenyl]-ethylamine (S)

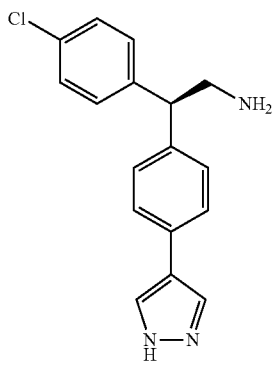 [SMILES: NC[C@H](c1ccc(Cl)cc1)c1ccc(-c2cn[nH]c2)cc1]

Prepared using the same procedure as Example 4 but enantiomers separated by chiral preparative HPLC using method AG-CP1. LCMS: (FL-C) $R_t$ 9.63 min, 100% ee. $^1$H NMR (Me-d$_3$-OD) δ 3.66 (2H, m), 4.30 (1H, t), 7.35-7.40 (6H, m), 7.64 (2H, d), 8.15 (2H, s).

Example 32

2-(4-Chloro-phenyl)-2-[4-(1H-pyrazol-4-yl)-phenyl]-acetamide

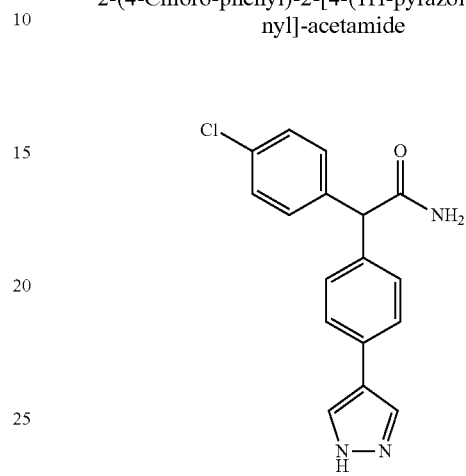

By following the procedure described in Example 12A followed by 12C but substituting 3-(4-Bromo-phenyl)-3-(4-chloro-phenyl)-propionic acid for Bis-(4-chloro-phenyl)-acetic acid, the title compound was obtained. LC/MS: (PS-A2) $R_t$ 2.53 [M+H]$^+$ 312. $^1$H NMR (Me-d$_3$-OD) δ 4.99 (1H, s), 7.30-7.33 (6H, m), 7.55 (2H, d), 7.86-8.02 (2H, br s).

Example 33

1-{2-(4-Chloro-phenyl)-2-[4-(1H-pyrazol-4-yl)-phenyl]-ethyl}-piperazine

37A. Bis-(4-chloro-phenyl)-acetaldehyde

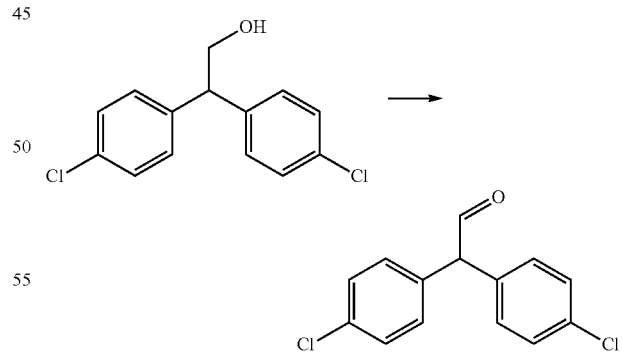

Dess-Martin periodinane (3.17 g, 7.49 mmol) was added to a solution of 2,2-Bis-(4-chloro-phenyl)-ethanol in dichloromethane (40 ml). The reaction mixture was stirred at room temperature for 17 hours under nitrogen, 2N NaOH added (15 ml) and the organic layer was separated, dried (MgSO4), filtered and concentrated to afford the title compounds which was used in the next step without further purification. LC/MS: (PS-B3) $R_t$ 3.62 [M+H]$^+$ 262.91.

33B. 4-[2,2-Bis-(4-chloro-phenyl)-ethyl]-piperazine-1-carboxylic acid tert-butyl ester

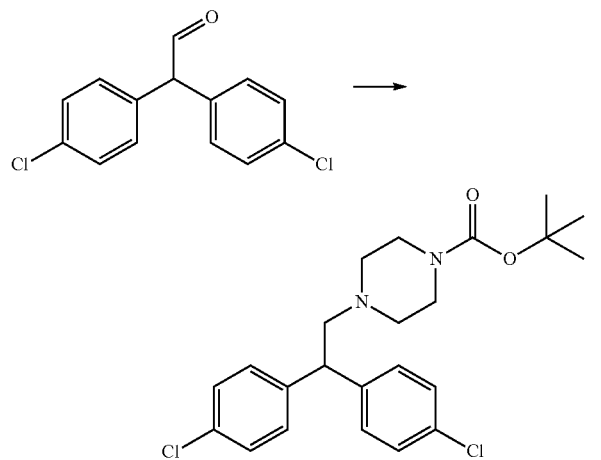

To a solution of bis-(4-chloro-phenyl)-acetaldehyde (3.74 mmol) in methanol under a nitrogen atmosphere, N—BOC-piperazine (1.05 g, 5.61 mmol) was added ???, the reaction mixture was stirred for 1 hour before addition of sodium cyanoborohydride (0.28 g, 4.49 mmol). The reaction mixture was stirred for 18 hours, water added (3 ml) and the solvent removed under reduced pressure. The residue was partitioned between dichloromethane and water, the organic layer was separated, dried (MgSO4), filtered and concentrated. Purified over flash silica chromatography eluting with ethyl acetate/petroleum ether (3:7) to yield the title compound (0.18 g, 11% yield for steps 30A and 30B combined). LC/MS: (PS-A2) $R_t$ 2.66 [M−BOC+H]$^+$ 335.02.

33C. 1-[2,2-Bis-(4-chloro-phenyl)-ethyl]-piperazine

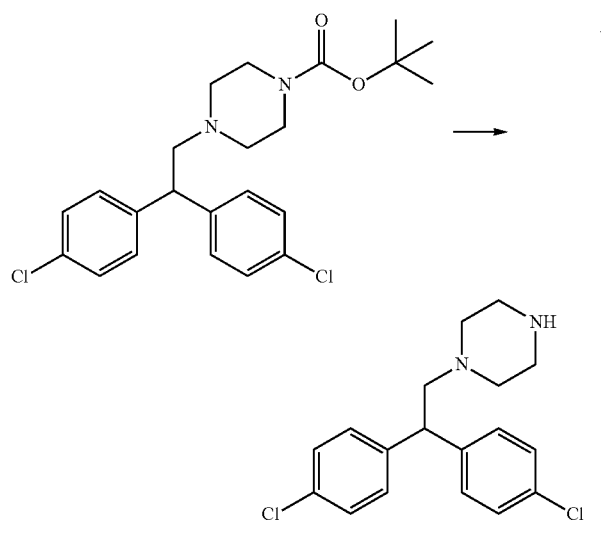

4-[2,2-Bis-(4-chloro-phenyl)-ethyl]-piperazine-1-carboxylic acid tert-butyl ester was treated with HCl in ethyl acetate (saturated, 5 ml) for 1 hour, solvent removed under reduced pressure to afford the title compound as the HCl salt

33D. 1-{2-(4-Chloro-phenyl)-2-[4-(1H-pyrazol-4-yl)-phenyl]-ethyl}-piperazine

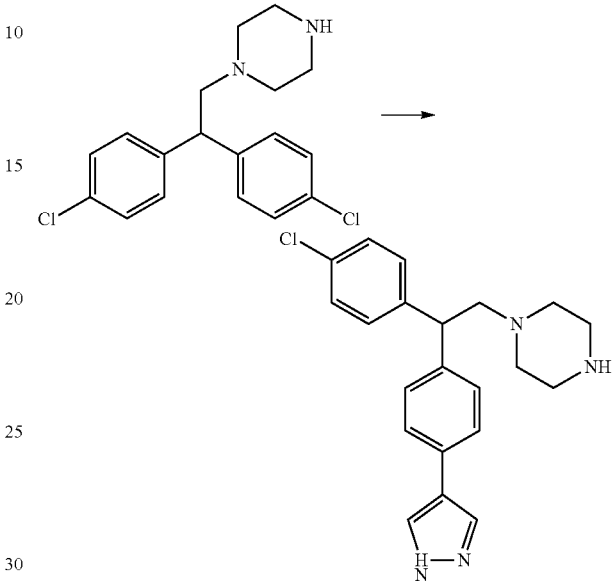

1-[2,2-Bis-(4-chloro-phenyl)-ethyl]-piperazine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.63 [M+H]$^+$ 326.00. $^1$H NMR (Me-d$_3$-OD) δ 3.55-3.68 (8H, m), 3.74 (1H, t), 4.10-4.17 (2H, m), 7.39 (2H, d), 7.48 (2H, d), 7.54 (2H, d), 7.70 (2H, d), 8.57 (2H, br s).

Example 34

1-{2-(4-Chloro-phenyl)-2-[4-(1H-pyrazol-4-yl)-phenyl]-ethyl}-piperidine

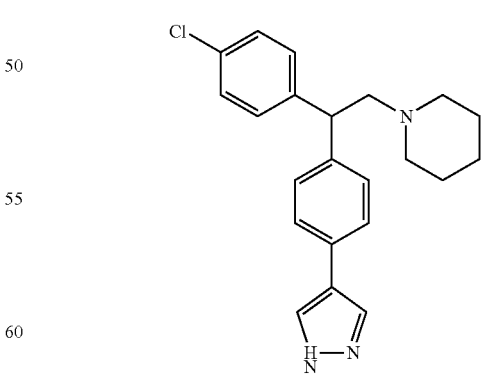

By following the procedure described in Example 33A, 33B and 33D but substituting piperidine for N—BOC-piperazine, the title compound was obtained. LC/MS: (PS-A2) $R_t$ 2.21 [M+H]$^+$ 366.09. $^1$H NMR (Me-d$_3$-OD) δ 1.44 (2H, m), 1.53 (4H, m), 2.39-2.57 (4H, m), 2.94-3.09 (2H, m), 4.26 (1H, t), 7.22-7.35 (6H, m), 7.50 (2H, d), 7.91 (2H, s).

Example 35

4-{4-[2-Azetidin-1-yl-1-(4-chloro-phenyl)-ethyl]-phenyl}-1H-pyrazole 35A. 2-(4-Chloro-phenyl)-2-[4-(1H-pyrazol-4-yl)-phenyl]-ethanol

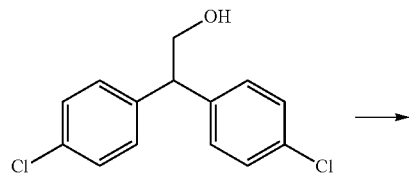

2,2-Bis-(4-chloro-phenyl)-ethanol was reacted with 4-(4,4,5,5-tetramethyl-1,3,2-dioxaborolan-2-yl)-1H-pyrazole following the procedure set out in Example 1 to give the title compound. LC/MS: (PS-A2) R$_t$ 2.72 [M+H]$^+$ 299.00.

35B. (4-Chloro-phenyl)-[4-(1H-pyrazol-4-yl)-phenyl]-acetaldehyde

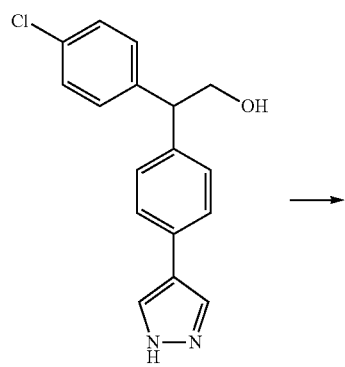

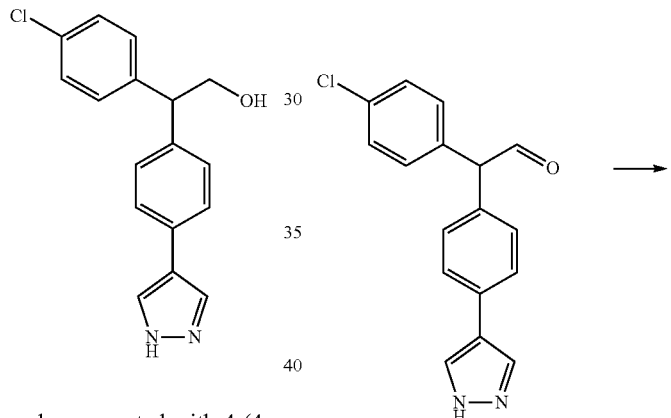

By following the procedure described in Example 33A but substituting 2,2-Bis-(4-chloro-phenyl)-ethanol for 2-(4-Chloro-phenyl)-2-[4-(1H-pyrazol-4-yl)-phenyl]-ethanol, the title compound was obtained. LC/MS. (PS-B3) R$_t$ 2.97 [M+H]$^-$ 294.98.

35C. 4-{4-[2-Azetidin-1-yl-1-(4-chloro-phenyl)-ethyl]-phenyl}-1H-pyrazole

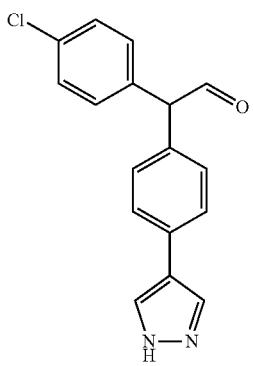

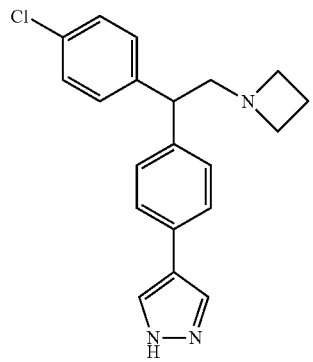

By following the procedure described in Example 33B but replacing bis-(4-chloro-phenyl)-acetaldehyde and N—BOC-piperazine with (4-Chloro-phenyl)-[4-(1H-pyrazol-4-yl)-phenyl]-acetaldehyde and azetidine, the title compound was obtained. LC/MS: (PS-B3) R$_t$ 2.99 [M+H]$^+$ 338.09. $^1$H NMR (Me-d$_3$-OD) δ 3.57-3.60 (1H, m), 3.63-3.70 (2H, m), 3.71-

3.77 (1H, m), 4.01 (2H, m), 4.14 (2H, m), 4.40 (1H, t), 7.40 (4H, br s), 7.49 (2H, d), 7.73 (2H, d), 8.69 (2H, br s).

Example 36

1-Phenyl-2-[4-(1H-pyrazol-4-yl)-phenyl]-ethylamine

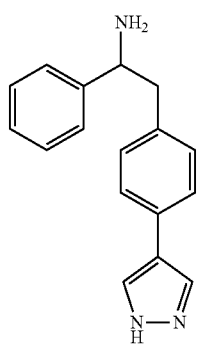 [SMILES: NC(Cc1ccc(-c2cn[nH]c2)cc1)c1ccccc1]

By following the procedure described in Example 5 but replacing 3-bromobenzylmagnesium bromide and 3,5-dimethyl-4-(4,4,5,5-tetramethyl-[1,3,2]dioxaborolan-2-yl)-1H-pyrazole with 4-bromobenzylmagnesium bromide and 4-(4,4,5,5-tetramethyl-1,3,2-dioxaborolan-2-yl)-1H-pyrazole, the title compound was obtained. LC/MS: (PS-B2) $R_t$ 2.44 [M+H]$^+$ 264.04. $^1$H NMR (Me-d$_3$-OD) δ 2.99 (2H, d), 4.13 (1H, t), 7.10 (2H, d), 7.20-7.38 (5H, m), 7.45 (2H, d), 7.91 (2H, s).

Example 37

[4-(5-Methyl-3-trifluoromethyl-1H-pyrazol-4-yl)-phenyl]-acetonitrile 37A. 4-Bromo-5-methyl-1-(tetrahydro-pyran-2-yl)-3-trifluoromethyl-1H-pyrazole

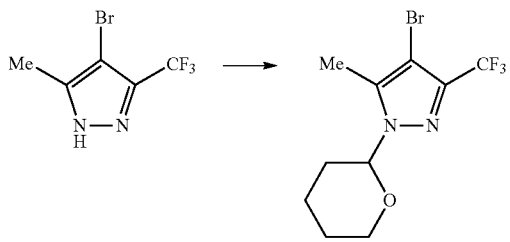 [SMILES: Cc1[nH]nc(C(F)(F)F)c1Br ; Cc1c(Br)c(C(F)(F)F)nn1C1CCCCO1]

To a solution of 4-bromo-5-methyl-3-trifluoromethyl-1H-pyrazole (1.4 g, 6.2 mmol, 1.0 equiv) in chloroform (31 ml) was added p-toluene sulphonic acid monohydrate (118 mg, 0.62 mmol, 0.1 equiv). The solution was cooled to 0° C. and 3,4-dihydro-2H-pyran (0.85 ml, 9.3 mmol, 1.5 equiv) was added drop-wise over 5 minutes. The mixture was allowed to warm to room temperature for 1 hour and the solvents were removed under reduced pressure. The crude mixture was purified by column chromatography (SiO$_2$), eluting with 0→25% EtOAc-petrol over a linear gradient to afford the title compound 1.4 g (59%), LCMS (PS-A) $R_t$ 3.72 mm [M+H]$^+$ 314.

37B. {4-[5-Methyl-1-(tetrahydro-pyran-2-yl)-3-trifluoromethyl-1H-pyrazol-4-yl]-phenyl}-acetonitrile

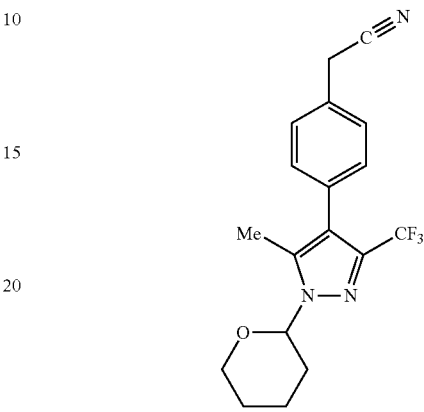

The product of Example 37A, 4-bromo-5-methyl-1-(tetrahydro-pyran-2-yl)-3-trifluoromethyl-1H-pyrazole, was reacted with 4-(cyanomethylphenyl)boronic acid (Combi-Blocks, San Diego, USA Cat. No. 2444-001) under the conditions described in Example 1, to give the title compound.

37C. [4-(5-Methyl-3-trifluoromethyl-1H-pyrazol-4-yl)-phenyl]-acetonitrile

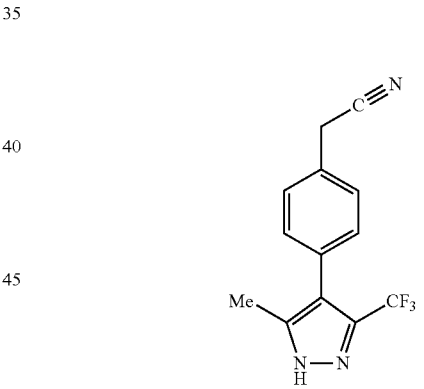

To {4-[5-Methyl-1-(tetrahydro-pyran-2-yl)-3-trifluoromethyl-1H-pyrazol-4-yl]-phenyl}-acetonitrile (Example 8B) (35 mg, 0.1 mmol, 1.0 equiv) in ethyl acetate (1 ml) was added HCl in ethyl acetate (1 ml) and the mixture was stirred for 1 hour.

The solvents were removed under reduced pressure and the title compound was purified by column chromatography (SiO$_2$) eluting with a linear gradient (0→30% ethyl acetate-petrol) 16 mg (60%); LCMS (PS-A) $R_t$ 2.85 min [M+H]$^+$ 266.

37D. Preparation of Compounds of the Formula (I) from [4-(5-Methyl-3-trifluoromethyl-1H-pyrazol-4-yl)-phenyl]-acetonitrile (i) The product of Example 37B can be reacted with benzaldehyde under the conditions described in Example 2 to give 2-[4-(5-methyl-1-(tetrahydro-pyran-2-yl)-3-trifluoromethyl-1H-pyrazol-4-yl)-phenyl]-3-phenyl-propionitrile which can be deprotected by removal of the 1-tetrahydropyranyl group under the conditions set out in Example 37C to give 2-[4-(5-methyl-3-trifluoromethyl-1H-pyrazol-4-yl)-phenyl]-3-phenyl-propionitrile.

2-[4-(5-Methyl-3-trifluoromethyl-1H-pyrazol-4-yl)-phenyl]-3-phenyl-propionitrile or its 1-tetrahydropyranyl derivative can be reduced according to the method of Example 6 (and thereafter where necessary deprotected according to the method of Example 41C) to give 2-[4-(5-methyl-3-trifluoromethyl-1H-pyrazol-4-yl)-phenyl]-3-phenyl-propylamine.

The product of Example 37B can also be reacted with benzyl magnesium bromide or phenyl magnesium bromide under the Grignard reaction conditions described in Example 5 to give (following deprotection by the method of Example 37C) 1-benzyl-2-[4-(5-methyl-3-trifluoromethyl-1H-pyrazol-4-yl)-phenyl]-ethylamine and 2-[4-(5-methyl-3-trifluoromethyl-1H-pyrazol-4-yl)-phenyl]-1-phenyl-ethylamine respectively.

Example 38

Construction of Pyrazole Ring System

38A. Synthesis of 4-(4-Bromo-phenyl)-3-methyl-1H-pyrazole

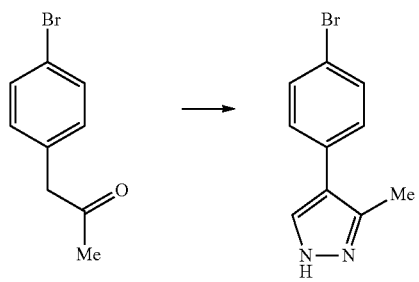 [SMILES: CC(=O)Cc1ccc(Br)cc1 ; Cc1n[nH]cc1-c1ccc(Br)cc1]

To 4-bromophenylacetone (5.0 g, 23.5 mmol, 1.0 equiv) (Acros Organics 34216) was added N,N-dimethylformamide dimethyl acetal (11.3 ml, 84.6 mmol, 3.6 equiv) and the mixture was heated to 90° C. for 6 hours. The solvents were removed and the resulting gum was dissolved in ethanol (235 ml) with additional heating. Hydrazine hydrate (1.37 ml, 28.2 mmol, 1.2 equiv) was added and the mixture was heated to reflux for 15 hours. The solvents were removed under reduced pressure and the solid was triturated with dichloromethane to afford the title compound, 2.24 g (40%); LCMS (PS-A) R$_t$ 2.87 min [M+H]$^+$ 238. Further material could be isolated from the mother liquor.

38B. Conversion of 4-(4-Bromo-phenyl)-3-methyl-1H-pyrazole to compounds of the Formula (I)

(i) 4-(4-Bromo-phenyl)-3-methyl-1H-pyrazole can be protected at the 1-position of the pyrazole ring by formation of the tetrahydropyranyl (THP) derivative by following the procedure set out in Example 38A. A Grignard reagent can then be prepared from the bromo-phenyl moiety by treating the protected derivative with magnesium in an ether solvent in standard fashion (see J. March, *Advanced Organic Chemistry*, 4$^{th}$ Edition, 1992, John Wiley, New York, pages 622-625). The Grignard reagent can be reacted with nitrostyrene (the nitrostyrene having been prepared by a standard method such as the method described in *Organic Syntheses*, Collective Volume 1, page 413) and the resulting nitroethyl compound reduced to give 2-{4-[3-methyl-1-(tetrahydro-pyran-2-yl)-1H-pyrazol-4-yl]-phenyl}-2-phenyl-ethylamine. Removal of the tetrahydropyranyl group using the method of Example 8C gives 2-{4-[3-methyl-1H-pyrazol-4-yl]-phenyl}-2-phenyl-ethylamine.

(ii) The bromo-compound of Example 38A can be converted into compounds of the formula (I) in which the group A contains a nitrogen atom which is attached to the group E. The introduction of a nitrogen containing entity can be accomplished by reaction of the compound of Example 38A with [3-(4-chloro-phenylamino)-propyl]-methyl-carbamic acid tert-butyl ester under palladium catalysed amination conditions of the type described in *Organic Letters*, 2002, vol. 4, No. 17, pp 2885-2888, followed by removal of the t-butyloxycarbonyl protecting group by standard methods.

Example 39

[3-(1H-Pyrazol-4-yl)-phenyl]-acetonitrile

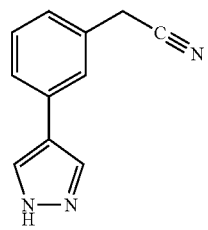 [SMILES: N#CCc1cccc(-c2cn[nH]c2)c1]

By following the procedure set out in Example 1 but using 3-bromophenyl-acetonitrile instead of 2-(4-chlorophenyl)-2-phenylethylamine, the title compound was obtained. LCMS (PS-A) 2.35 min [M+H]$^+$ 184.

3-(1H-Pyrazol-4-yl)-phenyl]-acetonitrile can be used as an intermediate in the preparation of compounds of the formula (I), for example by means of an aldehyde condensation reaction as described in Example 2 or a Grignard reaction as described in Example 5.

Example 40

2-(4-Chloro-phenyl)-N-methyl-2-[4-(1H-pyrazol-4-yl)-phenyl]-acetamide

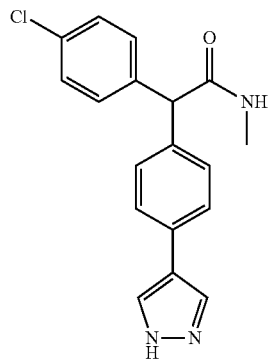 [SMILES: CNC(=O)C(c1ccc(Cl)cc1)c1ccc(-c2cn[nH]c2)cc1]

By following the procedure described in Example 12A followed by 12C but substituting 3-(4-Bromo-phenyl)-3-(4-chloro-phenyl)-propionic acid for Bis-(4-chloro-phenyl)-acetic acid and ammonia for methyl amine, the title compound was obtained. LC/MS: (PS-A2): R$_t$ 2.64 [M+H]$^+$ 326. $^1$H NMR (Me-d$_3$-OD) δ 2.79 (3H, s), 4.94, (1H, br s), 7.26-7.35 (6H, m), 7.55-7.57 (2H, m), 7.96 (2H, br s)

Example 41

N-Methyl-2,2-bis-[4-(1H-pyrazol-4-yl)-phenyl]-acetamide

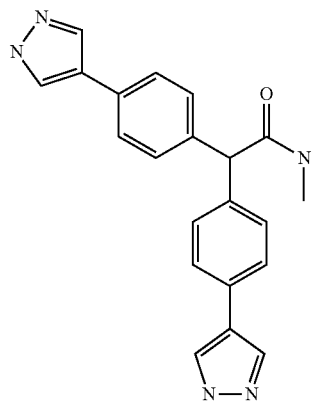 [SMILES: CNC(=O)C(c1ccc(-c2cn[nH]c2)cc1)c1ccc(-c2cn[nH]c2)cc1]

By following the procedure described in Example 40, the title compound was obtained. LC/MS: (PS-A2): R$_t$ 2.19 [M+H]$^+$ 358. $^1$H NMR (Me-d$_3$-OD) δ 2.80 (3H, s), 4.95, (1H, br s), 7.32 (4H, d), 7.56 (4H, d), 7.98 (4H, br s)

Example 42

{2-(4-Chloro-phenyl)-2-[4-(1H-pyrazol-4-yl)-phenyl]-ethyl}-methyl-amine

42A. 1-(4-Bromo-phenyl)-2-methylamino-ethanol

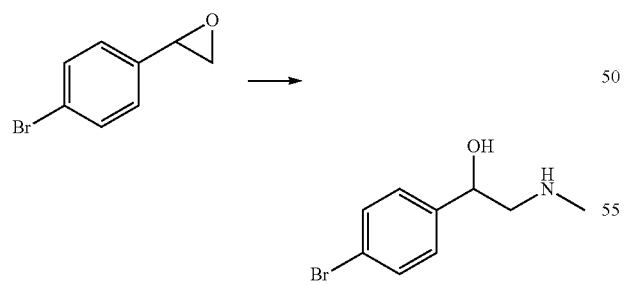

A solution of 2-(4-bromophenyl)-oxirane (0.5 g, 2.51 mmol) in methylamine (6.6 ml, 33% by volume in ethanol. 25.12 mmol) was stirred at room temperature under an atmosphere of nitrogen. After 18 hours the solvent was removed in vacuo and the residue was purified over flash silica eluting with dichloromethane:methanol:acetic acid:water (120:15:3:2) to afford the desired compound as the acetic acid salt. Further purification over a Phenomenex_Strata_SCX column eluting with methanol followed by 2N ammonia in methanol gave the desired product. LC/MS: (PS-B3) R$_t$ 2.52 [M+H]$^+$ 230.

42B. [2-(4-Bromo-phenyl)-2-(4-chloro-phenyl)-ethyl]-methyl-amine

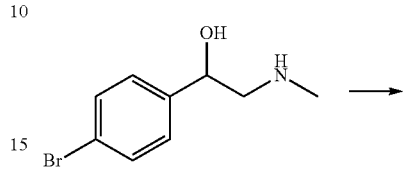

Aluminium chloride (278 mg, 2.087 mmol) was added portionwise to a stirred solution of 1-(4-Bromo-phenyl)-2-methylamino-ethanol (160 mg, 0.696 mmol) in chlorobenzene (3 ml) and the reaction mixture stirred at room temperature for 17 hours. Water (2 ml) was added dropwise and the reaction mixture was then partitioned between dichloromethane (100 ml) and saturated NaHCO$_3$ (30 ml). The organic layer was dried (MgSO$_4$), filtered and concentrated under reduced pressure. The crude product was then purified by Phenomenex_Strata_SCX column chromatography eluting with methanol followed by 2N ammonia in methanol to afford the desired product. LC/MS: (PS-B3) R$_t$ 3.58 [M+H]$^+$ 324.

42C. {2-(4-Chloro-phenyl)-2-[4-(1H-pyrazol-4-yl)-phenyl]-ethyl}-methyl-amine

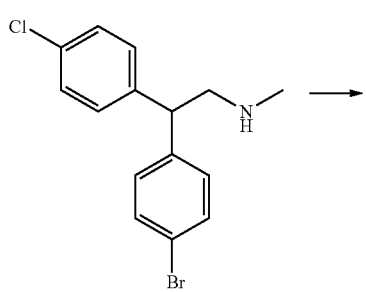

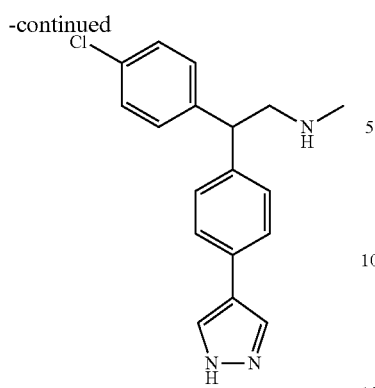

A solution of [2-(4-Bromo-phenyl)-2-(4-chloro-phenyl)-ethyl]-methyl-amine (6.1 g, 13.716 mmol), 4-(4,4,5,5-tetramethyl-1,3,2-dioxaborolan-2-yl)-1H-pyrazole (5.3 g, 27.431 mmol) and $K_3PO_4$ (10.19 g, 48.00 mmol) in ethanol (7.5 ml), methanol (11.5 ml), toluene (7.5 ml) and water (11.5 ml) was purged with nitrogen for 2 minutes. Bis(tri-t-butylphosphine)palladium (0) (175 mg, 2.5 mol %) was then added and the reaction mixture purged with nitrogen for a further 2 minutes. The mixture was then heated to 80° C., under nitrogen for a period of 17 hours. The solvents were removed and the residue was partitioned between ethyl acetate and 2N NaOH. The aqueous layer was extracted with ethyl acetate and the combined organic layers were washed with brine, dried ($MgSO_4$) and concentrated under reduced pressure. The crude reaction mixture was purified by column chromatography ($SiO_2$), eluting with dichloromethane:methanol:acetic acid:water (90:18:3:2) to afford the title compound (3.6 g); LCMS (PS-A2) $R_t$ 2.08 min [M+H]$^+$ 312.

Example 43

{2-(4-Chloro-phenyl)-2-[4-(1H-pyrazol-4-yl)-phenyl]-ethyl}-ethyl-amine

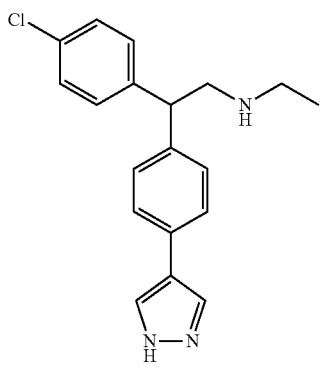

By following the procedures described in Examples 42A through to 42C but substituting methylamine for ethylamine, the title compound was obtained. LC/MS: (PS-A2) $R_t$ 2.11 [M+H]$^+$ 326. $^1$H NMR (Me-$d_3$-OD) δ 1.15 (3H, t), 2.83 (2H, q), 3.35-3.43 (2H, m), 4.25 (1H, t), 7.30-7.48 (6H, m), 7.57 (2H, d), 7.95 (2H, s).

Example 44

4-{4-[1-(4-Chloro-phenyl)-2-imidazol-1-yl-ethyl]-phenyl}-1H-pyrazole

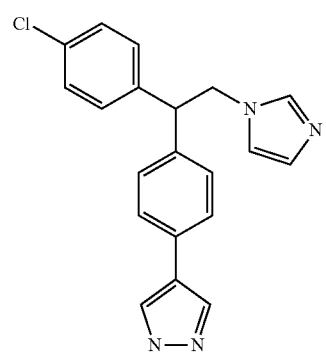 [SMILES: Clc1ccc(C(Cn2ccnc2)c2ccc(-c3cn[nH]c3)cc2)cc1]

By following the procedures described in Examples 42A through to 42C but substituting methylamine for imidazole, the title compound was obtained. LC/MS: (PS-B3) $R_t$ 2.73 [M+H]$^+$ 349. $^1$H NMR ($d_6$-DMSO) δ 4.60 (1H, t), 4.95 (2H, d), 7.32 (2H, d), 7.42 (4H, s), 7.53-7.60 (3H, m), 7.70 (1H, s), 8.05 (2H, s), 9.0 (1H, s).

Example 45

Methyl-{2-(4-phenoxy-phenyl)-2-[4-(1H-pyrazol-4-yl)-phenyl]-ethyl}-amine

45A. [2-(4-Bromo-phenyl)-2-(4-phenoxy-phenyl)-ethyl]-methyl-amine

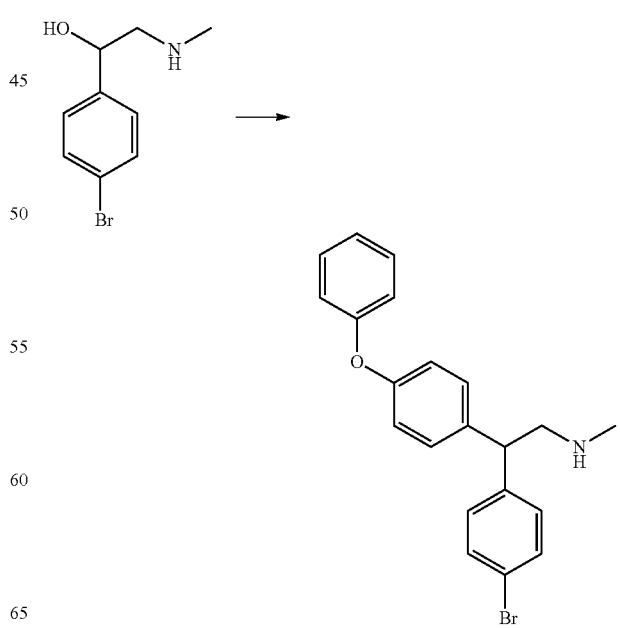

By following the procedure described in Example 42B but substituting chlorobenzene for diphenyl ether and employing nitrobenzene as solvent, the title compound was obtained. LC/MS: (PS-A2) $R_t$ 2.54 [M+H]$^+$ 382.

45B Methyl-{2-(4-phenoxy-phenyl)-2-[4-(1H-pyrazol-4-yl)-phenyl]-ethyl}-amine

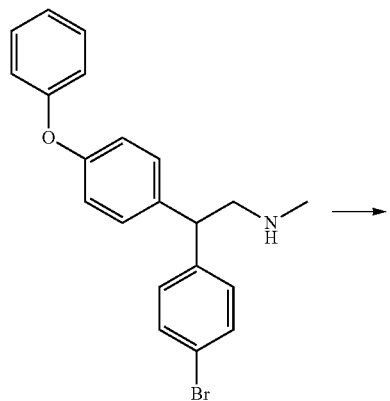

By following the procedure described in Example 42C but substituting [2-(4-Bromo-phenyl)-2-(4-chloro-phenyl)-ethyl]-methyl-amine for [2-(4-Bromo-phenyl)-2-(4-phenoxy-phenyl)-ethyl]-methyl-amine, the title compound was obtained. LC/MS: (PS-B3) $R_t$ 3.04 [M+H]$^+$ 370. $^1$H NMR (Me-d$_3$-OD) δ 2.75 (3H, s), 3.75 (2H, d), 4.38 (1H, t), 6.98 (4H, dd), 7.12 (1H, t), 7.33-7.40 (6H, m), 7.61 (2H, d), 7.95 (2H, s).

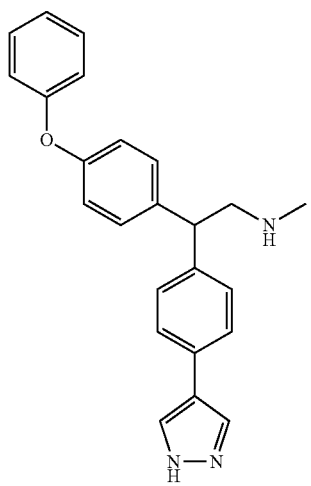

Example 46

{2-(4-Methoxy-phenyl)-2-[4-(1H-pyrazol-4-yl)-phenyl]-ethyl}-methyl-amine

46A. [2-(4-Bromo-phenyl)-2-(4-methoxy-phenyl)-ethyl]-methyl-amine

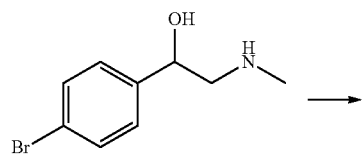

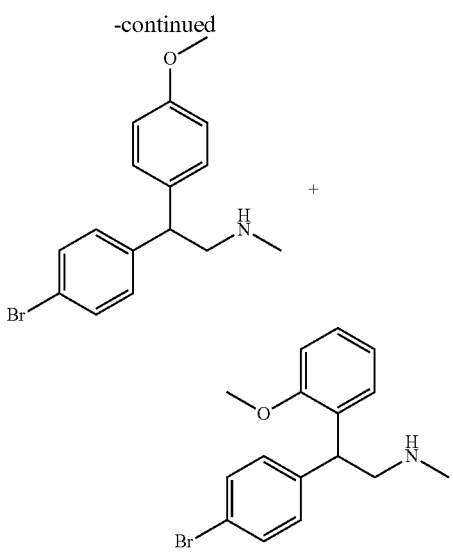

By following the procedure described in Example 42B but substituting chlorobenzene for anisole, the title compound was obtained as a mixture of regioisomers (ca 4:1) with the corresponding ortho-methoxy analogue. LC/MS: (PS-B3) $R_t$ 3.24 [M+H]$^+$ 320.

46B. [2-(4-Bromo-phenyl)-2-(4-methoxy-phenyl)-ethyl]-methyl-amine

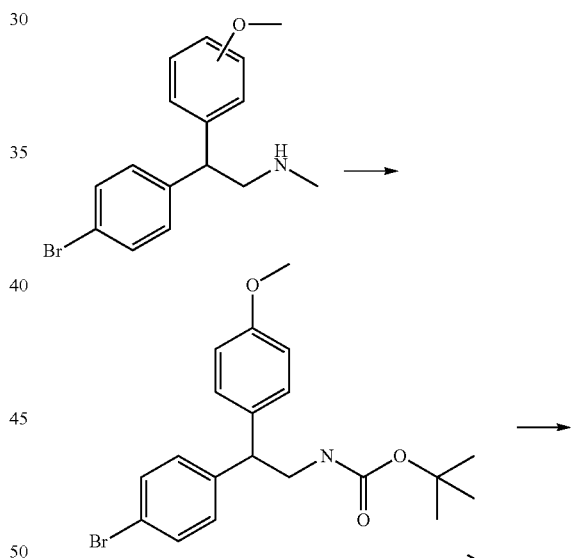

BOC$_2$O (941 mg, 4.309 mmol) was added to a solution of [2-(4-Bromo-phenyl)-2-(4-methoxy-phenyl)-ethyl]-methyl-amine (and its regioisomer) (1.38 g, 4.309 mmol) in dichloromethane (10 ml). After stirring at room temperature for 16 hours the solvent was removed under reduced pressure and the crude product was purified by flash chromatography eluting with ethyl acetate/petroleum ether (1:9) to yield the intermediate BOC protected compound as the desired single isomer (540 mg). The product was then stirred in a saturated solution of HCl in diethyl ether (30 ml) for 3 days. Removal of the solvent under reduced pressure afforded the title compound as the HCl salt. LC/MS: (PS-B3) $R_t$ 3.21 [M+H]$^+$ 320.

46C. {2-(4-Methoxy-phenyl)-2-[4-(1H-pyrazol-4-yl)-phenyl]-ethyl}-methyl-amine

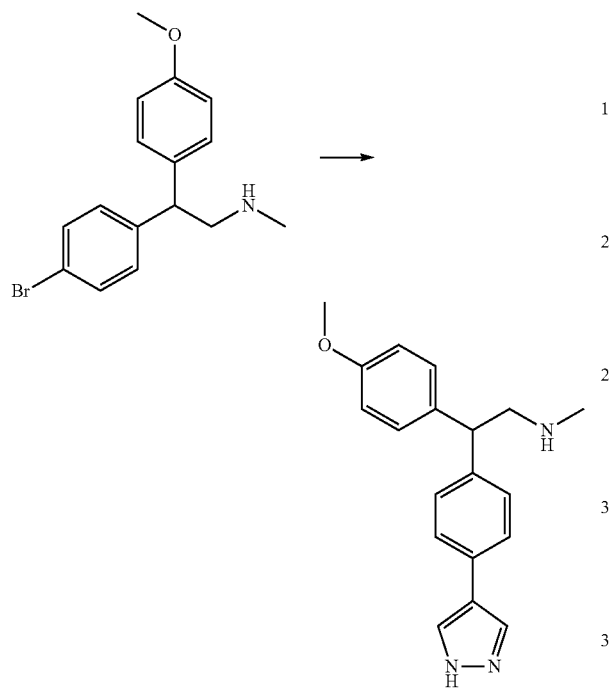

By following the procedure described in example 42C but substituting [2-(4-Bromo-phenyl)-2-(4-chloro-phenyl)-ethyl]-methyl-amine for [2-(4-Bromo-phenyl)-2-(4-methoxy-phenyl)-ethyl]-methyl-amine, the title compound was obtained. LC/MS: (PS-B3) $R_t$ 2.52 [M+H]$^+$ 308. $^1$H NMR (Me-d$_3$-OD) δ 2.75 (3H, s), 3.75 (2H, dd), 3.80 (3H, s), 4.38 (1H, t), 6.95 (2H, d), 7.32 (2H, d), 7.45 (2H, d), 7.70 (2H, d), 8.52 (2H, s).

Example 47

Methyl-{2-[4-(pyrazin-2-yloxy)-phenyl]-2-[4-(1H-pyrazol-4-yl)-phenyl]-ethyl}-amine

47A. 4-[1-(4-Bromo-phenyl)-2-methylamino-ethyl]-phenol

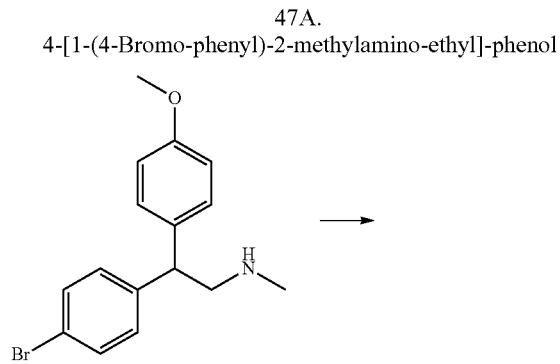

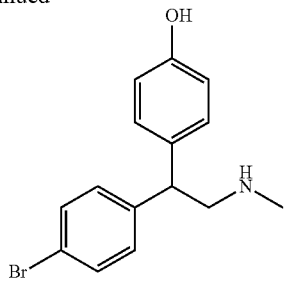

Boron tribromide (7.8 ml, 1.0M in dichloromethane) was added slowly to a solution of [2-(4-Bromo-phenyl)-2-(4-methoxy-phenyl)-ethyl]-methyl-amine (500 mg, 1.56 mmol) in dichloromethane (8 ml) at 0° C., under an atmosphere of nitrogen. The reaction mixture was allowed to warm to room temperature and then stirred for a further hour. The mixture was poured on to ice and then diluted with dichloromethane and saturated NaHCO$_3$ solution. The organic layer was dried (MgSO$_4$), filtered and concentrated to afford the desired product. LC/MS: (PS-B3) $R_t$ 2.76 [M+H]$^+$ 306.

47B. [2(4-Bromo-phenyl)-2(4-hydroxy-phenyl)-ethyl]-methyl-carbamic acid tert-butyl ester

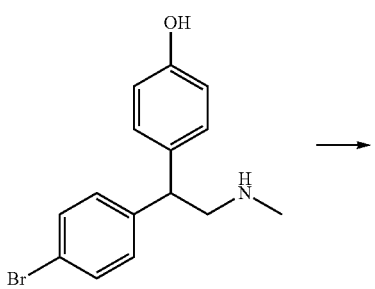

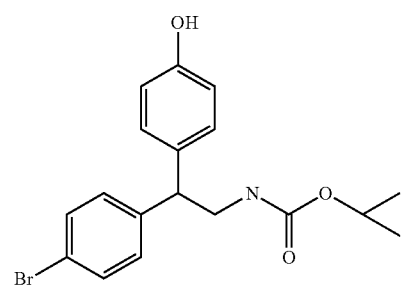

BOC$_2$O (269 mg, 1.23 mmol) was added to a solution of 4-[1-(4-Bromo-phenyl)-2-methylamino-ethyl]-phenol (360 mg, 1.18 mmol) in dichloromethane (20 ml). After stirring at room temperature for 16 hours the solvent was removed under reduced pressure and the crude product was purified by column chromatography (SiO$_2$), eluting with ethyl acetate/petroleum ether (1:4) to yield the title compound. LC/MS: (FL-A) R$_t$ 3.85 [M+H]$^+$ 406.

47C {2-(4-Bromo-phenyl)-2-[4-(pyrazin-2-yloxy)-phenyl]-ethyl}-methyl-amine

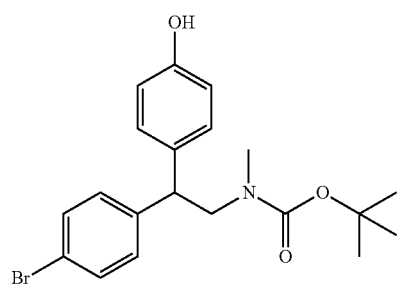

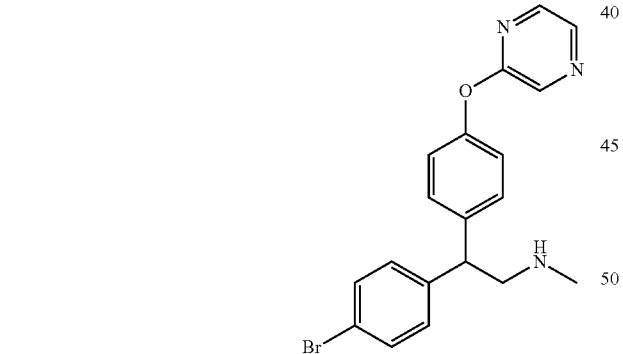

A solution of [2-(4-Bromo-phenyl)-2-(4-hydroxy-phenyl)-ethyl]-methyl-carbamic acid tert-butyl ester (125 mg, 0.31 mmol), 2-chloropyrazine (35.2 mg, 0.31 mmol) and K$_2$CO$_3$ (213 mg, 1.54 mmol) in dimethylformamide (8 ml) was heated to 100° C. for 17 hours. Upon cooling, the solvent was removed under reduced pressure and the residue was partitioned between ethyl acetate and saturated NaHCO$_3$ solution. The organic layer was dried (MgSO$_4$), filtered and concentrated. The crude product was then treated with saturated HCl in diethyl ether (15 ml) and stirred at room temperature for 72 hours. The solvent was then removed under reduced pressure and the crude product was purified by Phenomenex_Strata_SCX column chromatography eluting with methanol followed by 2N ammonia in methanol to afford the desired product (82 mg). LC/MS: (PS-B3) R$_t$ 3.17 [M+H]$^+$ 384.

47D Methyl-{2-[4-(pyrazin-2-yloxy)-phenyl]-2-[4-(1H-pyrazol-4-yl)-phenyl]-ethyl}-amine By following the procedure described in Example 42C, but substituting [2-(4-Bromo-phenyl)-2-(4-chloro-phenyl)-ethyl]-methyl-amine for {2-(4-Bromo-phenyl)-2-[4-(pyrazin-2-yloxy)-phenyl]-ethyl}-methyl-amine, the title compound was obtained. LC/MS: (PS-B3) R$_t$ 2.48 [M+H]$^+$ 372. $^1$H NMR (Me-d$_3$-OD) δ 2.80 (3H, s), 3.75-3.90 (2H, m), 4.50 (1H, t), 7.23 (2H, d), 7.50 (4H, t), 7.75 (2H, d), 8.12 (1H, d), 8.33 (1H, d), 8.42 (2H, s), 8.48 (1H, s).

Example 48

Methyl-{2-phenoxy-2-[4-(1H-pyrazol-4-yl)-phenyl]-ethyl}-amine

48A. [2-(4-Bromo-phenyl)-2-hydroxy-ethyl]-methyl-carbamic acid tert-butyl ester

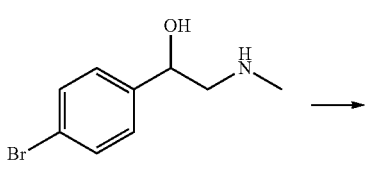

-continued

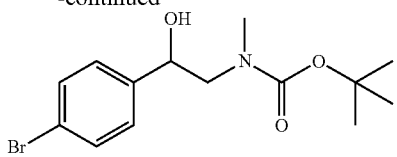

BOC₂O (1.90 g, 8.69 mmol) was added to a solution of 1-(4-Bromo-phenyl)-2-methylamino-ethanol (2.00 g, 8.69 mmol) in dichloromethane (20 ml). After stirring at room temperature for 16 hours the solvent was removed under reduced pressure and the crude product was purified by column chromatography (SiO₂), eluting with ethyl acetate/petroleum ether (1:4) to yield the desired product (2.1 g). LC/MS: (PS-B3) $R_t$ 3.16 [M+H]⁺ 330.

48B
[2-(4-Bromo-phenyl)-2-phenoxy-ethyl]-methyl-amine

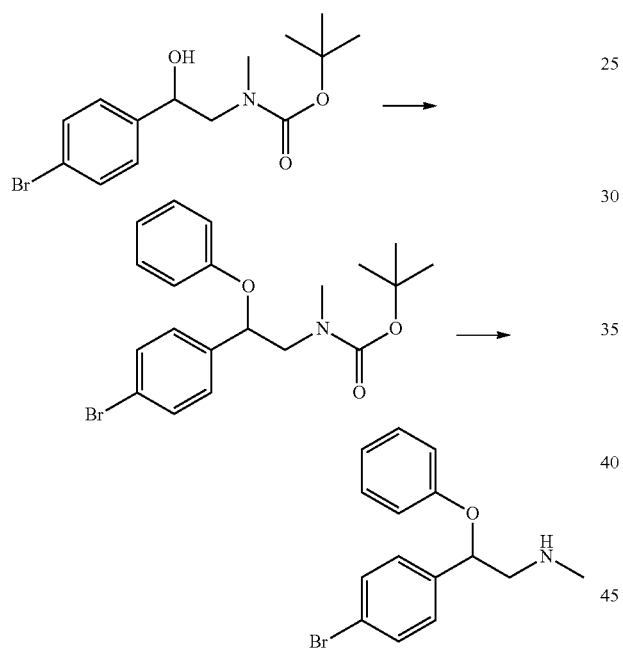

Diethyl azodicarboxylate (358 μl, 2.27 mmol) was added dropwise to a solution of [2-(4-Bromo-phenyl)-2-hydroxy-ethyl]-methyl-carbamic acid tert-butyl ester (500 mg, 1.5 μmol), triphenylphosphine (596 mg, 2.27 mmol) and phenol (285 mg, 3.03 mmol) in tetrahydrofuran (10 ml) and the reaction mixture stirred at room temperature, under an atmosphere of nitrogen, for 17 hours. The solvent was then removed under reduced pressure and the residue was partitioned between ethyl acetate and saturated NaHCO₃ solution. The organic layer was dried (MgSO₄), filtered and concentrated. The crude product was then purified by column chromatography (SiO₂), eluting with ethyl acetate/petroleum ether (1:9) to yield the intermediate BOC protected compound, which was then stirred in a saturated solution of HCl in diethyl ether (20 ml) for 24 hours. Removal of the solvent under reduced pressure afforded the title compound as the HCl salt. Further purification by Phenomenex_Strata_SCX column chromatography, eluting with methanol followed by 2N ammonia in methanol, afforded the desired product as the free base (94 mg). LC/MS: (PS-B3) $R_t$ 4.04 [M+H]⁺ 406.

48C Methyl-{2-phenoxy-2-[4-(1H-pyrazol-4-yl)-phenyl]-ethyl}-amine

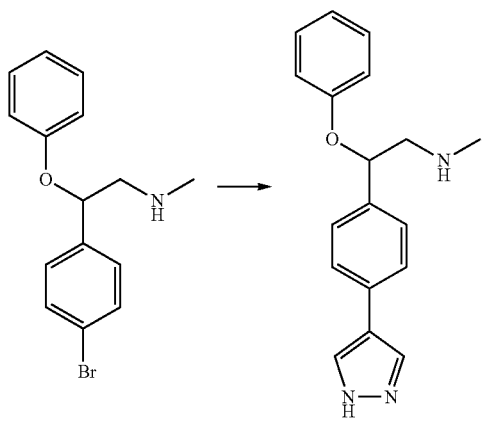 [SMILES: CNCC(Oc1ccccc1)c1ccc(Br)cc1 ; CNCC(Oc1ccccc1)c1ccc(-c2cn[nH]c2)cc1]

By following the procedure described in Example 42C, but substituting [2-(4-Bromo-phenyl)-2-(4-chloro-phenyl)-ethyl]-methyl-amine for [2-(4-Bromo-phenyl)-2-phenoxy-ethyl]-methyl-amine, the title compound was obtained. LC/MS: (PS-B3) $R_t$ 2.73 [M-PhO+H]⁺ 200. ¹H NMR (Me-d₃-OD) δ 2.50 (3H, s), 2.90 (1H, dd), 3.15 (1H, dd), 5.40 (1H, dd), 6.85 (1H, t), 6.90 (2H, d), 7.18 (2H, t), 7.40 (2H, d), 7.55 (2H, d), 7.93 (2H, s).

Example 49

2-{(4-Chloro-phenyl)-[4-(1H-pyrazol-4-yl)-phenyl]methoxy}-ethylamine 49A. (4-Bromo-phenyl)-(4-chloro-phenyl)-methanol

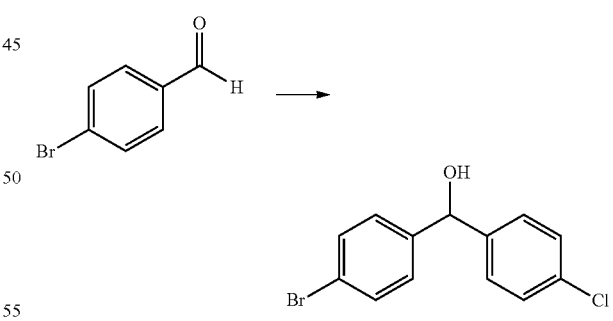

4-Chlorophenylmagnesium bromide (12.97 ml, 1M solution in diethyl ether) was added slowly to a solution of 4-bromobenzaldehyde (2.0 g, 10.81 mmol) in tetrahydrofuran (25 ml) at 0° C., under an atmosphere of nitrogen. The reaction mixture was allowed to warm to room temperature and was stirred for 17 hours. Water (3 ml) was then added and the solvent was removed under reduced pressure. The residue was then partitioned between ethyl acetate and 1N HCl solution. The organic layer was washed with brine, dried (MgSO₄), filtered and concentrated. The crude product was then purified by column chromatography (SiO₂), eluting with ethyl acetate/petroleum ether (1:9), to yield the title compound (2.30 g). LC/MS (PS-B3) $R_t$ 3.49 [M–H]$^+$ 297.

49B. 2-{2-[(4-Bromo-phenyl)-(4-chloro-phenyl)-methoxy]-ethyl}-isoindole-1,3-dione

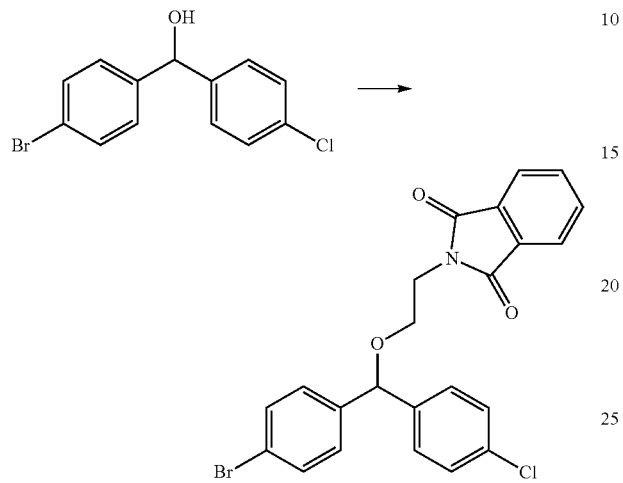

A mixture of (4-Bromo-phenyl)-(4-chloro-phenyl)-methanol (2.3 g, 7.73 mmol), N-(2-hydroxyethyl)phthalimide (1.4 g, 7.36 mmol) and para-toluenesulphonic acid monohydrate (560 mg, 2.94 mmol) in toluene (50 ml) was heated to reflux under Dean-Stark conditions for 17 hours. Upon cooling, the solvent was removed and the residue was partitioned between ethyl acetate and water. The organic layer was then dried (MgSO$_4$), filtered and concentrated. The crude product was purified by column chromatography (SiO$_2$), eluting with ethyl acetate/petroleum ether (1:4), to yield the title compound (1.95 g). LC/MS. (PS-B3) $R_t$ 4.07 no observable mass ion.

49C. N-(2-{(4-Chloro-phenyl)-[4-(1H-pyrazol-4-yl)-phenyl]-methoxy}-ethyl)-phthalamic acid

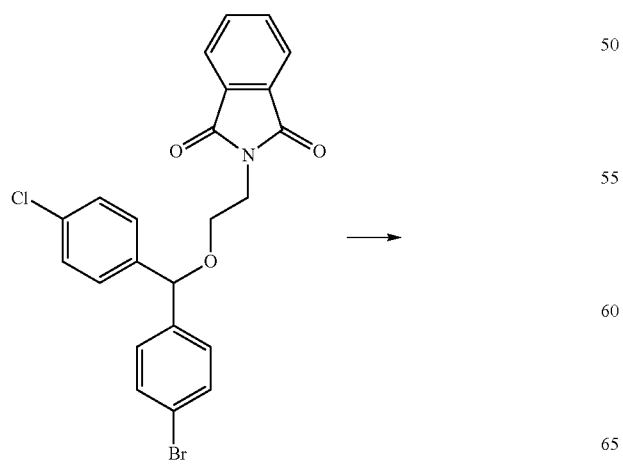

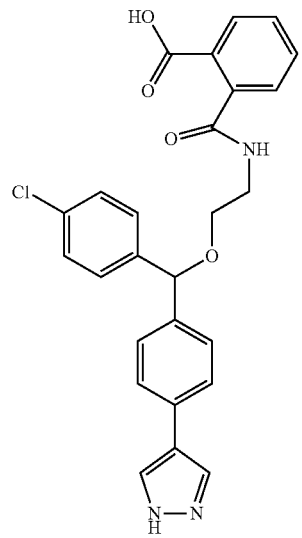

By following the procedure described in Example 42C, but substituting [2-(4-Bromo-phenyl)-2-(4-chloro-phenyl)-ethyl]-methyl-amine for 2-{2-[(4-Bromo-phenyl)-(4-chloro-phenyl)-methoxy]-ethyl}-isoindole-1,3-dione, the title compound was obtained. LC/MS: (FS-A) $R_t$ 2.85 [M–H]$^+$ 474.

49D. 2-{(4-Chloro-phenyl)-[4-(1H-pyrazol-4-yl)-phenyl]-methoxy}-ethylamine

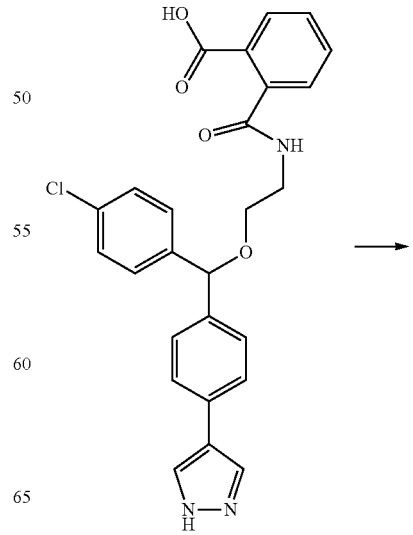

2.4-2.5 (2H, m), 2.88-2.97 (2H, m), 3.02 (2H, dd), 3.52-3.61 (2H, m), 4.02 (1H, t), 7.25 (4H, q), 7.32 (2H, d), 7.55 (2H, d), 8.41 (2H, s).

Example 51

4-{4-[3-Azetidin-1-yl-1-(4-chloro-phenyl)-propyl]-phenyl}-1H-pyrazole

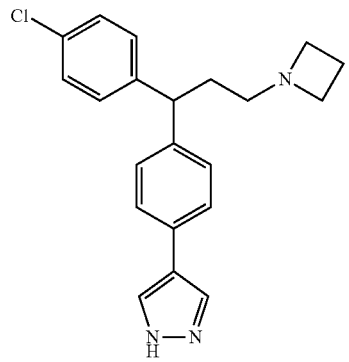 [SMILES: Clc1ccc(C(CCN2CCC2)c2ccc(-c3cn[nH]c3)cc2)cc1]

By following the procedure described in Example 8 but substituting methylamine for pyrrolidine, the title compound was obtained. LC/MS: (PS-A2) $R_t$ 2.18 [M+H]$^+$ 352. $^1$H NMR (Me-d$_3$-OD) δ 2.12-2.25 (2H, m), 3.00 (2H, t), 3.85-3.98 (5H, m), 4.05-4.17 (2H, m), 7.18 (2H, d), 7.19 (4H, s), 7.45 (2H, d), 7.83 (2H, s).

Example 52

Methyl-{3-naphthalen-2-yl-3-[4-(1H-pyrazol-4-yl)-phenyl]-propyl}-amine

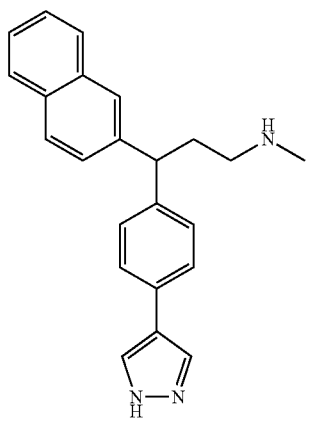 [SMILES: CNCCC(c1ccc(-c2cn[nH]c2)cc1)c1ccc2ccccc2c1]

By following the procedure described in Example 8 but substituting 4-chlorophenylmagnesium bromide for 2-naphthylmagnesium bromide, the title compound was obtained. LC/MS: (PS-A2) $R_t$ 2.26 [M+H]$^+$ 342. $^1$H NMR (Me-d$_3$-OD)

---

-continued

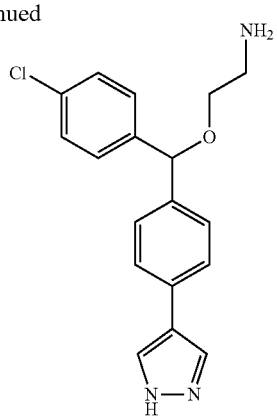

Hydrazine monohydrate (159 μl, 3.28 mmol) was added to a solution of N-(2-{(4-Chloro-phenyl)-[4-(1H-pyrazol-4-yl)-phenyl]-methoxy}-ethyl)-phthalamic acid (260 mg, 0.55 mmol) in methanol (6 ml) and the reaction mixture stirred at 80° C. for 16 hours. Upon cooling, the solvent was removed under reduced pressure and the crude product was purified by column chromatography (SiO$_2$), eluting with dichloromethane:methanol:acetic acid:water (90:18:3:2). Further purification by Phenomenex_Strata_SCX column chromatography, eluting with methanol followed by 2N ammonia in methanol, afforded the desired product as the free base (120 mg). LC/MS: (FL-A) $R_t$ 2.07 [M-NH$_2$CH$_2$CH$_2$O+H]$^+$ 267. $^1$H NMR (Me-d$_3$-OD) δ 2.85 (2H, t), 3.55 (2H, t), 5.45 (1H, s), 7.35-7.40 (6H, m), 7.58 (2H, d), 7.95 (2H, s).

Example 50

4-{4-[1-(4-Chloro-phenyl)-3-pyrrolidin-1-propyl]-phenyl}-1H-pyrazole

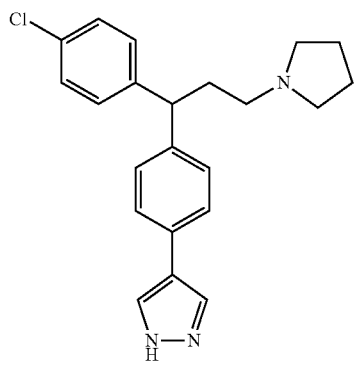

By following the procedure described in Example 8 but substituting methylamine for pyrrolidine, the title compound was obtained. LC/MS: (PS-A2) $R_t$ 2.25 [M+H]$^+$ 366. $^1$H NMR (Me-d$_3$-OD) δ 1.83-1.95 (2H, m), 1.95-2.09 (2H, m), δ 2.57-2.70 (2H, m), 2.70 (3H, s), 2.90-3.10 (2H, m), 4.32 (1H, t), 7.40-7.52 (5H, m), 7.70 (2H, m), 7.80-7.90 (4H, m), 8.70 (2H, s).

Example 53

Dimethyl-(4-{3-methylamino-1-[4-(1H-pyrazol-4-yl)-phenyl]-propyl}-phenyl)-amine

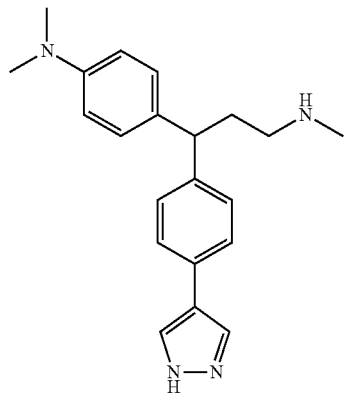

By following the procedure described in Example 8 but substituting 4-chlorophenylmagnesium bromide for 4-(N,N-dimethyl)anilinemagnesium bromide, the title compound was obtained. LC/MS: (PS-A2) $R_t$ 1.55 [M+H]$^+$ 335. $^1$H NMR (Me-d$_3$-OD) δ 2.46-2.60 (2H, m), 2.69 (3H, s), 2.95 (2H, t), 3.27 (6H, s), 4.25 (1H, t), 7.45 (2H, d), 7.60-7.72 (6H, m), 8.50 (2H, s).

Example 54

{3-(4-Fluoro-phenyl)-3-[4-(1H-pyrazol-4-yl)-phenyl]-propyl}-methyl-amine

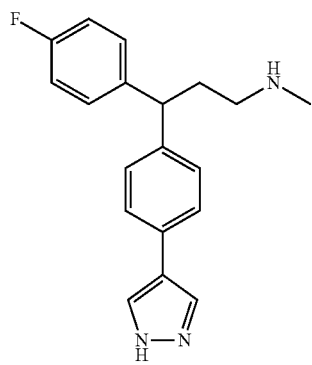 [SMILES: CNCCC(c1ccc(F)cc1)c1ccc(-c2cn[nH]c2)cc1]

By following the procedure described in Example 8 but substituting 4-chlorophenylmagnesium bromide for 4-fluorophenylmagnesium bromide, the title compound was obtained. LC/MS: (PS-A2) $R_t$ 2.05 [M+H]$^+$ 310. $^1$H NMR (Me-d$_3$-OD) δ 2.40-2.55 (2H, d), 2.70 (3H, s), 2.90-3.0 (2H, m), 4.12 (1H, t), 7.05 (2H, t), 7.32-7.40 (4H, m), 7.63 (21-1, d), 8.33 (2H, s).

Example 55

4-{4-[4-(4-Chloro-phenyl)-piperidin-4-yl]-phenyl}-1H-pyrazole-3-carbonitrile

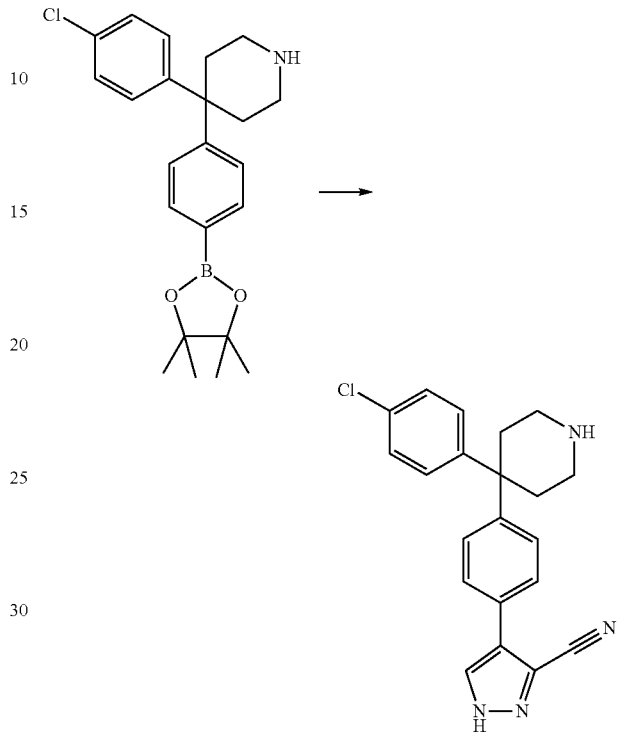

Following the procedure of Example 1 but using 4-(4-Chloro-phenyl)-4-[4-(4,4,5,5-tetramethyl-[1,3,2]dioxaborolan-2-yl)-phenyl]-piperidine instead of 4-(4,4,5,5-tetramethyl-1,3,2-dioxaborolan-2-yl)-1H-pyrazole and 4-bromo-1H-pyrazole-3-carbonitrile instead of 2-(4-chlorophenyl)-2-phenylethylamine hydrochloride gave the title compound. LC/MS: (PS-A2) $R_t$ 2.22 [M+H]$^+$ 363. $^1$H NMR (Me-d$_3$-OD) δ 2.52-2.70 (4H, m), 3.10-3.20 (4H, m), 7.25 (4H, s), 7.37 (2H, d), 7.58 (2H, d), 8.02 (1H, s).

Example 56

3-(4-Phenoxy-phenyl)-3-[4-(1H-pyrazol-4-yl)-phenyl]-propylamine

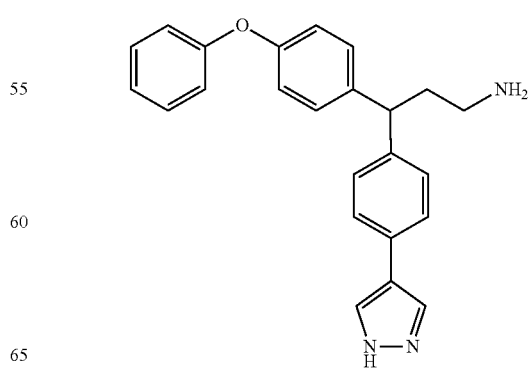

By following the procedure described in Example 8 but substituting 4-chlorophenylmagnesium bromide for 4-phenoxyphenylmagnesium bromide and methylamine for ammonia the title compound was obtained. LC/MS: (PS-A2) $R_t$ 2.28 [M+H]$^+$ 370.34. $^1$H NMR (Me-d$_3$-OD) δ 2.38-2.46 (2H, m), 2.85-2.92 (2H, t), 4.03-4.10 (1H, t), 6.94-7.0 (4H, d), 7.08-7.14 (1H, t), 7.30-7.39 (6H, m), 7.55-7.58 (2H, d), 7.90-7.97 (2H, br s), 8.54-8.60 (1H, br s).

Example 57

1-{(4-Chloro-phenyl)-[4-(1H-pyrazol-4-yl)-phenyl]-methyl}-piperazine

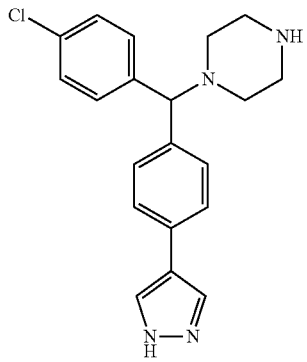 [SMILES: Clc1ccc(C(c2ccc(-c3cn[nH]c3)cc2)N2CCNCC2)cc1]

By following the procedure described in Example 1 but substituting 2-(4-chlorophenyl)-2-phenylethylamine hydrochloride for 1-(4,4'-dichloro-benzhydryl)-piperazine gave the title compound. LC/MS: (PS-B3) $R_t$ 2.82 [M−H]$^+$ 351.27. $^1$H NMR (Me-d$_3$-OD) δ 3.0-3.25 (4H, m), 3.45-3.65 (4H, m), 5.05-5.25 (1H, br s), 7.40-7.50 (2H, d), 7.65-7.83 (6H, m), 8.45 (2H, s).

Example 58

1-Methyl-4-{phenyl-[4-(1H-pyrazol-4-yl)-phenyl]-methyl}-[1,4]diazepane

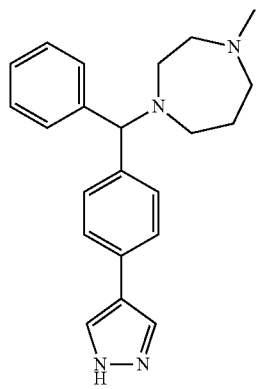 [SMILES: CN1CCCN(C(c2ccccc2)c2ccc(-c3cn[nH]c3)cc2)CC1]

By following the procedure described in Example 1 but substituting 2-(4-chlorophenyl)-2-phenylethylamine hydrochloride for 1-[p-chlorodiphenylmethyl]-4-methyl-1,4-diazacycloheptane dihydrochloride gave the title compound. LC/MS: (PS-B3) $R_t$ 2.85 [M+H]$^+$ 347.18. $^1$H NMR (Me-d$_3$-OD) δ 2.25-2.60 (2H, br m), 3.00 (3H, s), 3.40-4.18 (8H, br m), 5.78 (1H, s), 7.40-7.48 (1H, m), 7.49-7.55 (2H, t), 7.75-7.80 (2H, d), 7.82-7.98 (4H, m), 8.32 (2H, s).

Example 59

{3-(3-Chloro-phenoxy)-3-[4-(1H-pyrazol-4-yl)-phenyl]-propyl}-methyl-amine 59A. 1-(4-Bromo-phenyl)-3-chloro-propan-1-ol (J. Med. Chem, 2004, 47, 3924-3926)

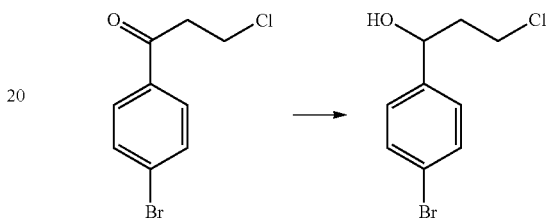

To a solution of 1-(4-Bromo-phenyl)-3-chloro-propan-1-one (1 g, 4.04 mmol) in tetrahydrofuran (9 ml) and water (0.58 ml) was added sodium borohydride (0.16 g, 4.28 mmol). The reaction mixture was stirred at room temperature for 2 hours, quenched with careful addition of water and extracted with ethyl acetate. The organic layers were separated, dried (MgSO$_4$), filtered and concentrated to afford the title compound, which was used in the next step without further purification. LC/MS: (PS-A2) $R_t$ 3.07 [M+H]$^+$ No Ionization.

59B. [3-(4-Bromo-phenyl)-3-(3-chloro-phenoxy)-propyl]chloride

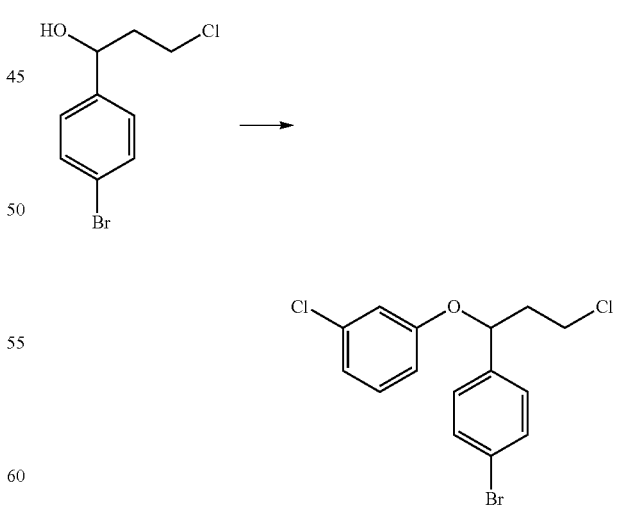

3-Chlorophenol was reacted with 1-(4-Bromo-phenyl)-3-chloro-propan-1-ol following the procedure set out in Example 48B to give the title compound, which was used in the next step without further purification.

59C. [3-(4-Bromo-phenyl)-3-(3-chloro-phenoxy)-propyl]methyl-amine

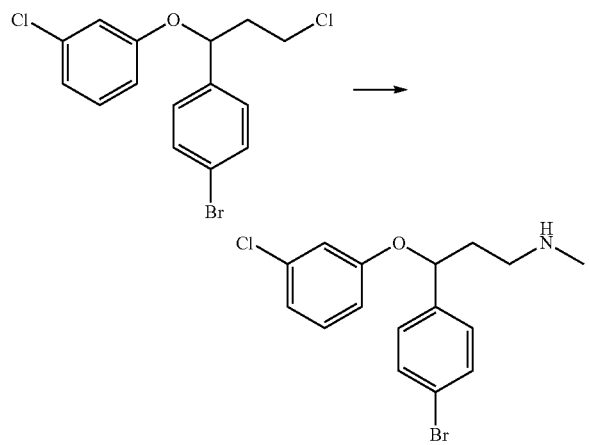

A solution of 3-(4-Bromo-phenyl)-3-(3-chloro-phenoxy)-propyl]-chloride in 33% methylamine in ethanol (4 ml) was heated in a CEM microwave at 100° C. for 30 minutes using 50 W power. Solvent was removed and the crude product was purified over Phenomenex_Strata_SCX ion exchange column eluting with methanol followed by 2N ammonia in methanol. The product was purified by column chromatography ($SiO_2$), eluting with dichloromethane to dichloromethane:methanol:acetic acid:water (90:18:3:2) using the SP4 biotage to afford the title compound. LC/MS: (PS-B3) $R_t$ 3.42 [M+H]$^+$ 356.19.

59D. {3-(3-Chloro-phenoxy)-3-[4-(1H-pyrazol-4-yl)-phenyl]-propyl}-methyl-amine

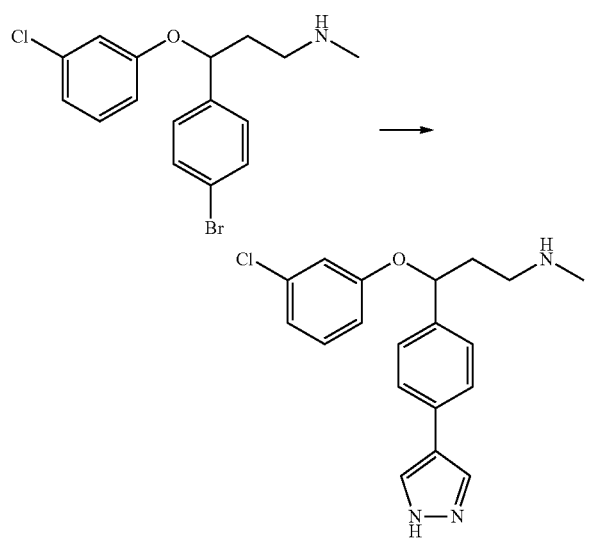

[3-(4-Bromo-phenyl)-3-(3-chloro-phenoxy)-propyl]-methyl-amine was reacted with 4-(4,4,5,5-tetramethyl-1,3,2-dioxaborolan-2-yl)-1H-pyrazole following the procedure set out in Example 1 to give the title compound. LC/MS: (PS-B3) $R_t$ 2.80 [M+H]$^+$ 342.26. $^1$H NMR (Me-$d_3$-OD) δ 2.19-2.30 (1H, m), 2.30-2.45 (1H, m), 2.72 (3H, s), 3.10-3.28 (2H, m), 5.40-5.47 (1H, m), 6.80-6.88 (1H, d), 6.88-6.94 (1H, d), 6.96 (1H, s), 7.15-7.20 (1H, t), 7.38-7.45 (2H, d), 7.57-7.65 (2H, d), 7.98 (2H, s).

Example 60

Methyl-{2-phenyl-2-[6-(1H-pyrazol-4-yl)-pyridin-3-yl]-ethyl}-amine 60A. 6-(3-Methyl-1-trityl-1H-pyrazol-4-yl)-nicotinonitrile

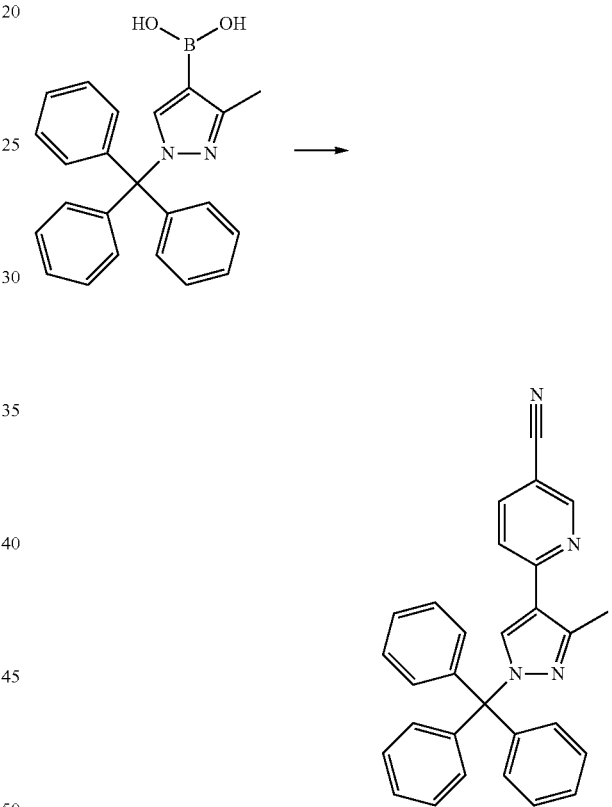

To a solution of 6-Chloro-nicotinonitrile (0.2 g, 1.49 mmol) and 3-methyl-1-trityl-1H-pyrazole-4-boronic acid* (0.5 g, 1.36 mmol) in ethylene glycol dimethyl ether (3 ml), was added sodium carbonate (0.36 g, 3.39 mmol) in water (1.5 ml). The reaction mixture was degassed with nitrogen before addition of tetrakis(triphenylphosphine)palladium (0) and then heated in a CEM microwave at 135° C. for 30 minutes (50 W power). Reaction partitioned between water and ethyl acetate, aqueous basified with 2N NaOH, organic extracts were combined, dried ($MgSO_4$) and solvent removed. Crude product suspended in small volume of methanol, white precipitate filtered to afford the title compound (0.32 g, 53% yield). LC/MS: (PS-A2) $R_t$ 4.52 [M+H]$^+$ 427.26.

*This starting material can be made by the method described in EP1382603A1

121
60B. (4-Chloro-phenyl)-[6-(3-methyl-1-trityl-1H-pyrazol-4-yl)-pyridin-3-yl]-methanone

122
60C. {2-(4-Chloro-phenyl)-2-[6-(3-methyl-1-trityl-1H-pyrazol-4-yl)-pyridin-3-yl]-vinyl}-methyl-(1-phenyl-ethyl)-amine

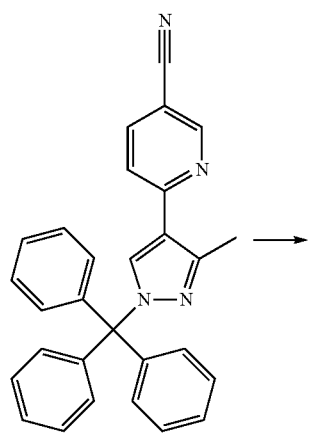

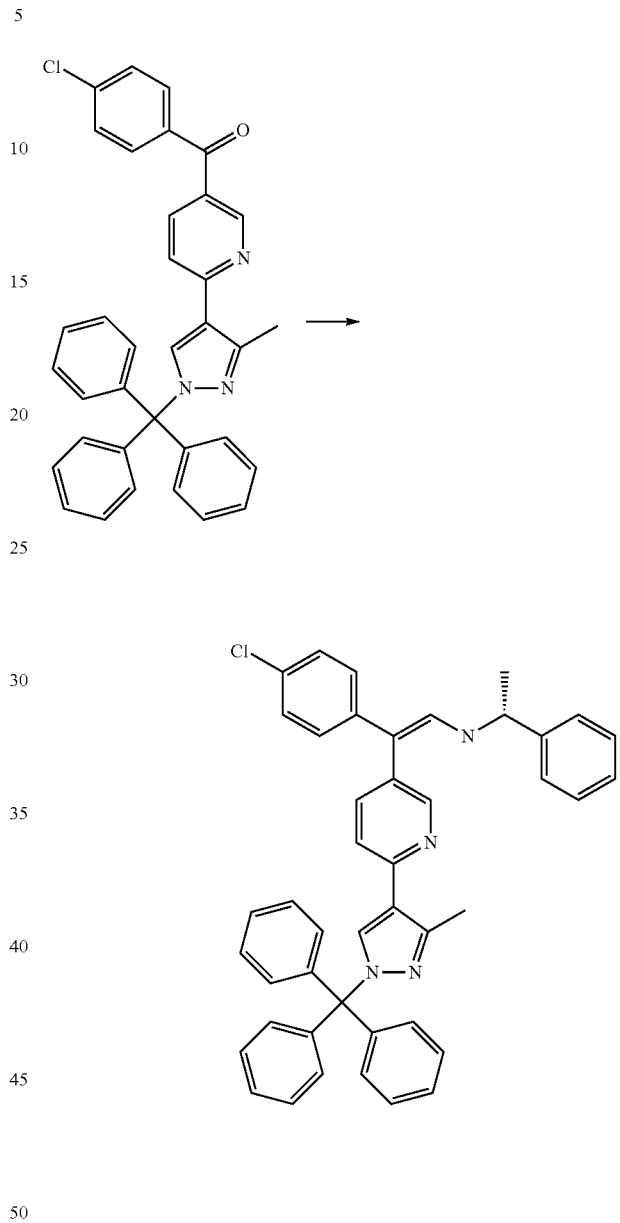

To a solution of 6-(3-Methyl-1-trityl-1H-pyrazol-4-yl)-nicotinonitrile (0.5 g, 1.17 mmol) in dry tetrahydrofuran (4 ml) was added 4-chlorobenzenemagnesium bromide (1.52 ml, 1.52 mmol, 1M in diethyl ether); the reaction mixture was stirred under nitrogen for 16 hours. The reaction was quenched to below pH 2 by the addition of 2N HCl and stirred for 1 hour. Then adjusted to pH 8 with saturated sodium bicarbonate and extracted with ethyl acetate. Organic extracts were combined, dried (MgSO$_4$), solvent removed and residue purified by column chromatography (SiO$_2$), eluting with petrol to ethyl acetate:petroleum ether (15:85) to yield the title compound (0.49 mg, 77% yield). LC/MS: (PS-A2) R$_t$ 4.45 [M+H]$^+$ 540.30, 542.28.

n-Butyllithium (0.47 ml, 0.76 mmol, 1.6M in Hexanes) was added dropwise to a solution of (R) (Diphenyl-phosphinoylmethyl)-methyl-(1-phenyl-ethyl)-amine* (0.18 g, 0.51 mmol) in dry tetrahydrofuran (9 ml) at −15° C. After 15 minutes a solution of (4-Chloro-phenyl)-[6-(3-methyl-1-trityl-1H-pyrazol-4-yl)-pyridin-3-yl]-methanone (0.14 g, 0.25 mmol) in tetrahydrofuran (0.9 ml) was added and the reaction mixture was stirred for a further 30 minutes at −15° C. before warming to room temperature over 1 hour. The reaction mixture was quenched with water, extracted with diethyl ether, organic extracts were combined, dried (MgSO$_4$) and concentrated to afford the title compound, which was used in the next step without further purification.

*This starting material can be made by the method described in Tetrahedron Asymmetry, 2003, 14, 1309-1316.

60D. Methyl-{2-phenyl-2-[6-(1H-pyrazol-4-yl)-pyridin-3-yl]-ethyl}-amine

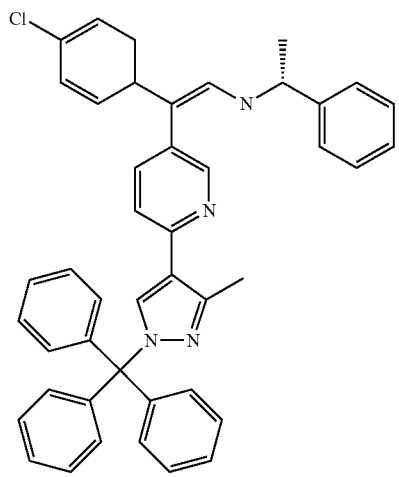

To a solution of {2-(4-Chloro-phenyl)-2-[6-(3-methyl-1-trityl-1H-pyrazol-4-yl)-pyridin-3-yl]-vinyl}-methyl-(1-phenyl-ethyl)-amine in ethanol was added palladium, 10 wt. % on activated carbon and the reaction mixture was subjected to a hydrogen atmosphere for 17 hours. The mixture was filtered through Celite®, the mother liquor was concentrated, the residue was purified by column chromatography (SiO$_2$), eluting with dichloromethane:methanol:acetic acid:water (240:20:3:2) to dichloromethane:methanol:acetic acid:water (90:18:3:2) to afford the title compound. LC/MS: (PS-A2) R$_t$ 1.59 [M+H]$^+$ 293.18. $^1$H NMR (Me-d$_3$-OD) δ 2.35 (3H, s), 2.40 (3H, s), 3.25 (2H, s), 4.15-4.20 (1H, t), 7.10-7.18 (1H, m), 7.25 (4H, m), 7.45 (1H, d), 7.67 (1H, dd), 7.80 (1H, s), 8.38 (1H, s).

Example 61

4-{4-[1-(4-Chloro-phenyl)-3-imidazol-1-yl-propyl]-phenyl}-1H-pyrazole

61A. 1-(4-Bromo-phenyl)-3-imidazol-1-yl-propan-1-ol

A solution of 1-(4-Bromo-phenyl)-3-chloro-propan-1-ol* (1.5 g, 6.01 mmol) and imidazole (1.23 g, 18.03 mmol) in dimethylformamide (18 ml) was heated at 100° C. for 18 hrs then partitioned between water and ethyl acetate. The organic extracts were combined, dried (MgSO$_4$), filtered, concentrated and purified by column chromatography (SiO$_2$), eluting with methanol:dichloromethane (2:98) to methanol:dichloromethane (6:94) to afford the title compound (0.75 g, 44% yield). LC/MS: (PS-B3) R$_t$ 2.48 [M+H]$^+$ 281.14, 283.11.

*This starting material can be made by the method described in Example 43A.

61B. 1-[3-(4-Bromo-phenyl)-3-(4-chloro-phenyl)-propyl]-1H-imidazole

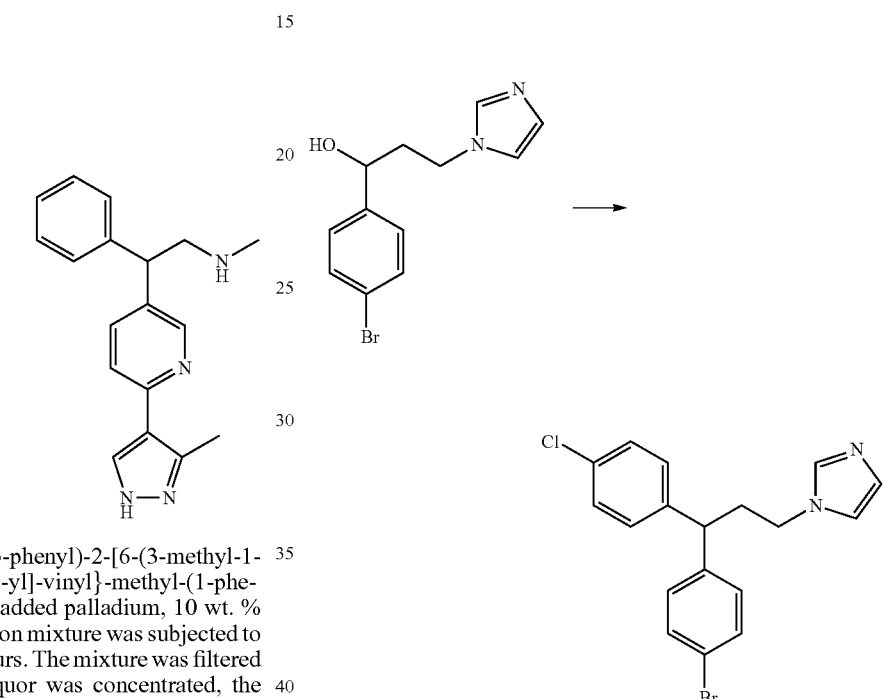

Chlorobenzene (5 ml) was reacted with 1-(4-Bromo-phenyl)-3-imidazol-1-yl-propan-1-ol (0.41 mg, 1.46 mmol) following the procedure set out in Example 42B to give the title compound (0.37 g, 67% yield). LC/MS: (PS-A2) R$_t$ 2.40 [M+H]$^+$ 375.16, 377.17.

61C. 4-{4-[1-(4-Chloro-phenyl)-3-imidazol-1-yl-propyl]-phenyl}-1H-pyrazole

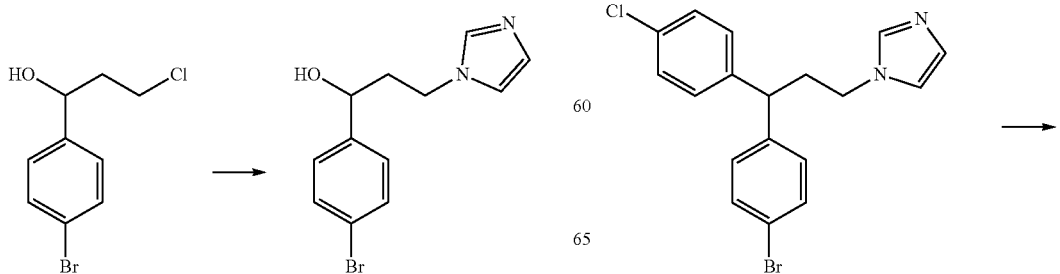

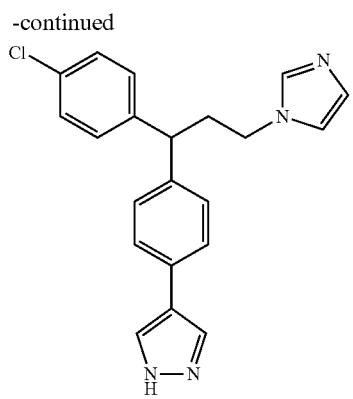

1-[3-(4-Bromo-phenyl)-3-(4-chloro-phenyl)-propyl]-1H-imidazole was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 2.21 [M+H]$^+$ 363.28. $^1$H NMR (Me-d$_3$-OD) δ 2.55-2.70 (2H, m), 3.85-3.95 (1H, m), 3.95-4.10 (2H, m), 7.05 (1H, s), 7.10-7.60 (9H, m), 7.65 (1H, s), 7.90-8.00 (2H, d).

Example 62

4-[4-(3-Imidazol-1-yl-1-phenoxy-propyl)-phenyl]-1H-pyrazole 62A. 1-[3-(4-Bromo-phenyl)-3-phenoxy-propyl]-1H-imidazole

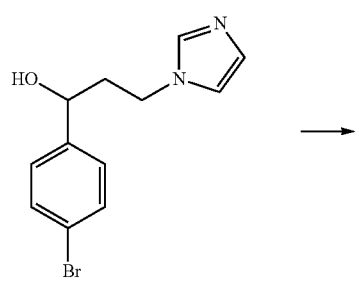

Phenol was reacted with 1-(4-Bromo-phenyl)-3-imidazol-1-yl-propan-1-ol* following the procedure set out in Example 48B to give the title compound. LC/MS: (PS-A2) $R_t$ 2.30 [M+H]$^+$ 357.26, 359.27.

*This starting material can be made by the method described in Example 47A.

62B. 4-[4-(3-Imidazol-1-yl-1-phenoxy-propyl)-phenyl]-1H-pyrazole

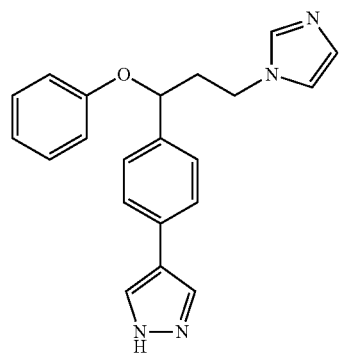

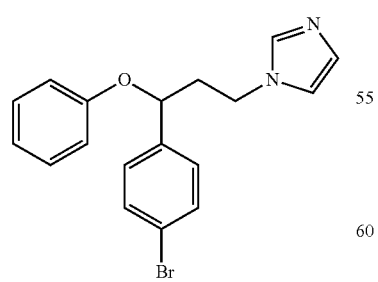

1-[3-(4-Bromo-phenyl)-3-phenoxy-propyl]-1H-imidazole was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 2.05 [M+H]$^+$ 345.30. $^1$H NMR (Me-d$_3$-OD) δ 2.30-2.55 (2H, m), 4.25-4.45 (2H, m), 5.10-5.15 (1H, m), 6.80-6.90 (3H, m), 7.10 (1H, s), 7.15-7.20 (2H, t), 7.25 (1H, s), 7.35-7.40 (2H, d), 7.55-7.60 (2H, d), 7.85 (1H, s), 7.95 (2H, s).

Example 63

4-{4-[4-(1H-Pyrazol-4-yl)-phenyl]-piperidin-4-yl}-phenol

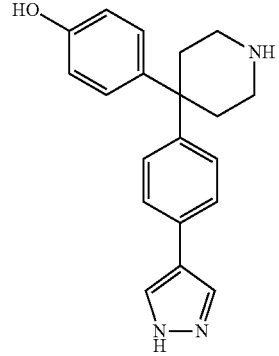 [SMILES: Oc1ccc(C2(c3ccc(-c4cn[nH]c4)cc3)CCNCC2)cc1]

By following the procedure described in Example 14 but substituting chlorobenzene for phenol using nitrobenzene as the solvent, the title compound was obtained. LC/MS: (PS- A3) $R_t$ 5.07 [M+H]$^+$ 320. $^1$H NMR (d$_6$-DMSO) δ 7.97 (2H, s), 7.49 (2H, d), 7.25 (2H, d), 7.10 (2H, d), 6.68 (2H, d), 2.840 (4H, bs), 2.376 (4H, bs).

Example 64

1-{(4-Chloro-phenyl)-[4-(1H-pyrazol-4-yl)-phenyl]-methyl}-piperazine

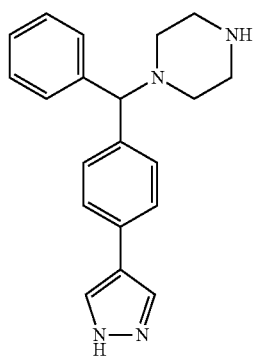 [SMILES: c1ccc(C(c2ccc(-c3cn[nH]c3)cc2)N2CCNCC2)cc1]

By following the procedure described in Example 57, the title compound was obtained. LCMS. (PS-A3) $R_t$ 6.38 [M+H]$^+$ 319. $^1$H NMR (Me-d$_3$-OD) δ 8.53 (2H, s), 7.90 (2H, d), 7.83 (2H, d), 7.71 (2H, d), 7.40-7.30 (3H, m), 5.70 (1H, s), 3.68 (4H, bs), 3.51-3.48 (4H, m).

Example 65

{2-(4-Fluoro-phenyl)-2-[4-(1H-pyrazol-4-yl)-phenyl]-ethyl}-methyl-amine

65A. [2-(4-Bromo-phenyl)-2-(4-fluoro-phenyl)-ethyl]-carbamic acid benzyl ester

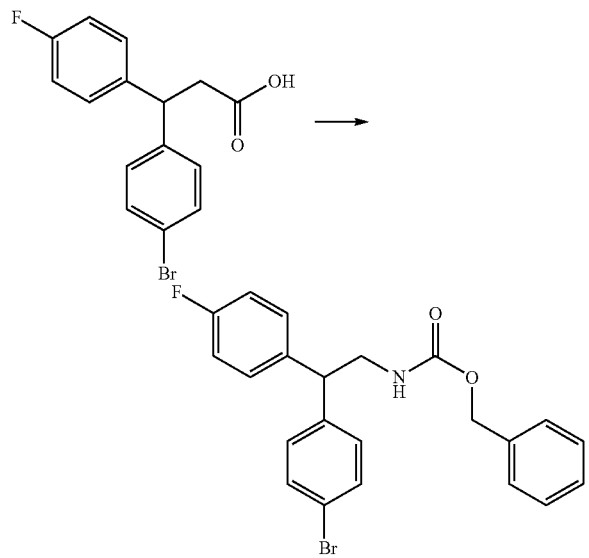

To a solution of 3-(4-fluorophenyl)-3-(4-bromophenyl) propionic acid* (1.0 g, 3.09 mmol) in acetone (4 ml) at 0° C. was sequentially added triethylamine (561 ul, 4.02 mmol) in acetone (1.6 ml) and ethyl chloroformate (443 ul, 4.64 mmol) in acetone (1.6 ml). The reaction was allowed to warm to room temperature, stirred for 30 minutes before cooling again to 0° C. and sodium azide (402 mg, 6.18 mmol) in water (1.6 ml) was added. The resultant brown solution was stirred for 45 minutes before addition of water (10 ml) and diethyl ether (10 ml). The aqueous layer was separated and extracted further with ethyl acetate (10 ml). The combined organic liquors were washed with saturated brine, dried (MgSO$_4$) and concentrating in vacuo. The residue was dissolved in anhydrous toluene (12 ml) before addition of benzyl alcohol (567 ul, 9.27 mmol) and heating to 80° C. for 40 minutes. The reaction was allowed to cool to room temperature before addition of ethyl acetate (50 ml) and saturated sodium bicarbonate (50 ml). The organic liquors were separated and washed with further bicarbonate solution (50 ml), hydrochloric acid (2N, 100 ml) and saturated brine (50 ml) before drying (MgSO$_4$) and concentrating in vacuo. The residue was purified by column chromatography (SiO$_2$), eluting with ethyl acetate/petrol (5:95) gradient to (15:85) to afford the title compound (594 mg, 45%). LC/MS: (PS-A2) $R_t$ 3.18 No Ionisation.

*This staffing material can be made by the method described in Example 8A to 8C, substituting 4-chlorophenylmagnesium bromide for 4-fluorophenylmagnesium bromide 65B. {2-(4-Fluoro-phenyl)-2-[4-(1H-pyrazol-4-yl)-phenyl]-ethyl}-carbamic acid benzyl ester

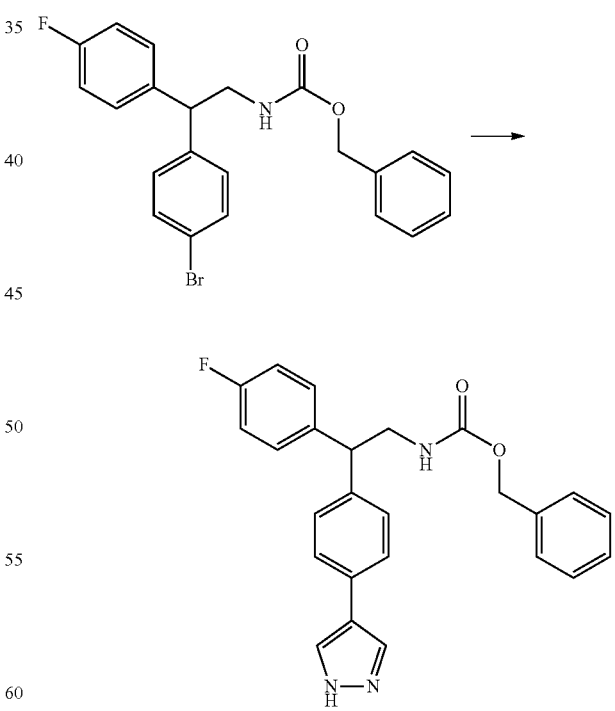

[2-(4-Bromo-phenyl)-2-(4-fluoro-phenyl)-ethyl]-carbamic acid benzyl ester was reacted with 4-(4,4,5,5-tetramethyl-1,3,2-dioxaborolan-2-yl)-1H-pyrazole following the procedure set out in Example 1 to give the title compound. LC/MS: (PS-A2) $R_t$ 3.20 [M+H]$^+$ 416.

65C. {2-(4-Fluoro-phenyl)-2-[4-(1H-pyrazol-4-yl)-phenyl]-ethyl}-methyl-amine

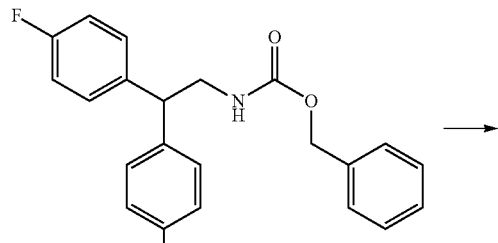

Lithium aluminium hydride (5.3 ml, 5.30 mmol, 1M in tetrahydrofuran) was slowly added to {2-(4-Fluoro-phenyl)-2-[4-(1H-pyrazol-4-yl)-phenyl]-ethyl}-carbamic acid benzyl ester (439 mg, 1.06 mmol) in tetrahydrofuran (5 ml) at 0° C. under nitrogen. The reaction mixture was allowed to warm to room temperature, stirred for 51 hours and quenched with water (5 ml), aqueous sodium hydroxide (2N, 5 ml) and ethyl acetate (10 ml). The aqueous layer was separated, extracted with ethyl acetate (2×20 ml). The combined organic liquors were washed with saturated aqueous brine then dried (MgSO$_4$) and concentrated in vacuo. The residue was purified by column chromatography (SiO$_2$), eluting with dichloromethane:methanol:acetic acid:water (120:15:3:2) gradient to (90:18:3:2) to afford the title compound, which was subsequently converted to the hydrochloride salt (100 mg, 32%). LC/MS: (PS-A2) R$_t$ 1.87 [M+H]$^+$ 296. $^1$H NMR (Me-d$_3$-OD) δ 8.20 (2H, s), 7.57 (2H, d), 7.34-7.29 (4H, m), 7.02 (2H, t), 4.32 (1H, t), 3.67 (2H, d), 2.65 (3H, s).

Example 66

{2-(3-Chloro-phenyl)-2-[4-(1H-pyrazol-4-yl)-phenyl]-ethyl}-methyl-amine

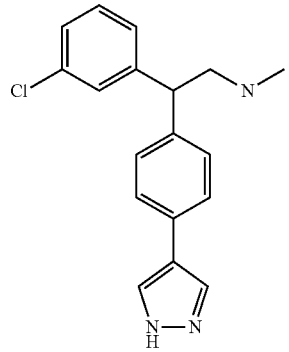 [SMILES: CNCC(c1ccc(-c2cn[nH]c2)cc1)c1cccc(Cl)c1]

By following the procedure described in Example 65 but substituting 4-fluorophenylmagnesium bromide for 3-chlorophenylmagnesium bromide the title compound was obtained. LC/MS: (PS-A3) R$_t$ 4.92 [M+H]$^+$ 312. $^1$H NMR (Me-d$_3$-OD) δ 8.50 (2H, s), 7.63 (2H, d), 7.39 (2H, d), 7.34 (1H, s), 7.30-7.20 (3H, m), 4.40 (1H, t), 3.70 (2H, d), 2.65 (3H, s).

Example 67

4-[4-(2-Methoxy-ethoxy)-phenyl]-4-[4-(1H-pyrazol-4-yl)-phenyl]-piperidine

67A. 4-(4-Bromo-phenyl)-4-(4-hydroxy-phenyl)-piperidine-1-carboxylic acid tert-butyl ester

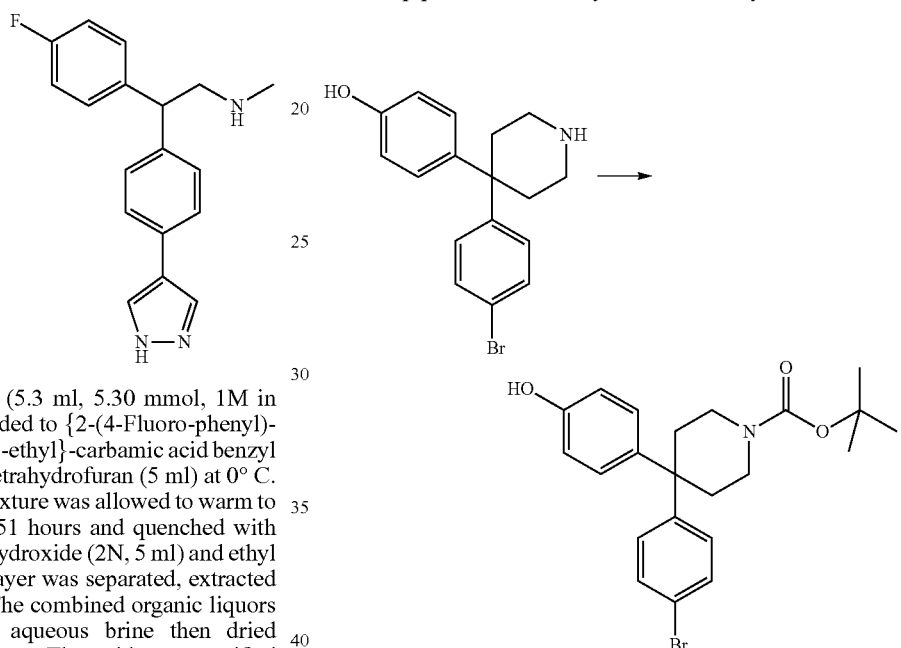

By following the procedure described in Example 47B but substituting 4-[1-(4-Bromo-phenyl)-2-methylamino-ethyl]-phenol for 4-[4-(4-Bromo-phenyl)-piperidin-4-yl]-phenol* the title compound was obtained. $^1$H NMR (d$_6$-DMSO) δ 7.45 (2H, d), 7.25 (2H, d), 7.11 (2H, d), 6.68 (2H, d), 3.35-3.18 (4H, m), 2.31-2.20 (4H, m), 1.38 (9H, s).

*This starting material can be made by the method described in Example 63

67B. 4-(4-Bromo-phenyl)-4-[4-(2-methoxy-ethoxy)-phenyl]-piperidine-1-carboxylic acid tert-butyl ester

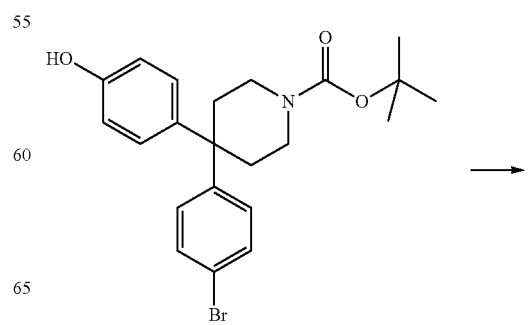

-continued

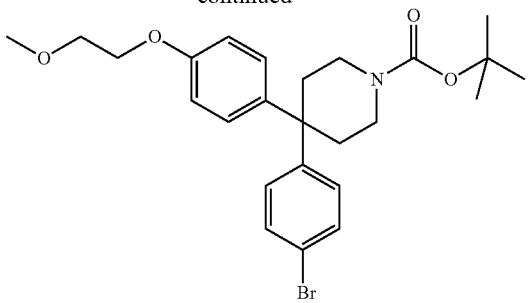

A solution of 4-(4-Bromo-phenyl)-4-(4-hydroxy-phenyl)-piperidine-1-carboxylic acid tert-butyl ester (100 mg, 0.23 mmol), 2-bromoethyl methylether (200 ul) and potassium carbonate (64 mg, 0.46 mmol) in dimethylformamide (2 ml) was heated in a CEM Explorer™ microwave to 50° C. for 30 minutes using 50 watts power. The reaction was poured into sodium hydroxide (2N, 4 ml), stirred for 5 minutes then extracted into ethyl acetate (2×30 ml). The combined organic liquors were dried (MgSO$_4$), concentrated and the residue was purified by column chromatography (SiO$_2$), eluting with ethyl acetate/petrol (25:75) gradient to (50:50) to afford the title compound (82 mg). LCMS: (PS-A2) R$_t$ 4.00 [M+H]$^+$ 490.

67C. 4-[4-(2-Methoxy-ethoxy)-phenyl]-4-[4-(1H-pyrazol-4-yl)-phenyl]-piperidine

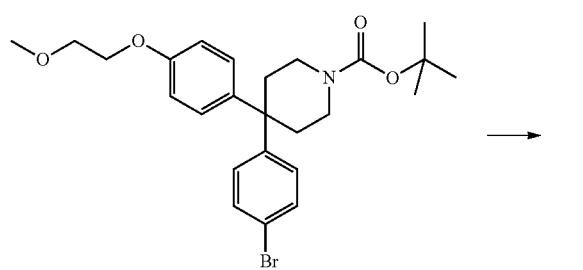

4-(4-Bromo-phenyl)-4-[4-(2-methoxy-ethoxy)-phenyl]-piperidine-1-carboxylic acid tert-butyl ester was reacted with 4-(4,4,5,5-tetramethyl-1,3,2-dioxaborolan-2-yl)1H-pyrazole following the procedure set out in Example 1, substituting tetrakis triphenylphosphine palladium (0) as catalyst, the title compound was obtained. LC/MS: (PS-A2) R$_t$ 3.27 [M+H]$^+$ 478.

67D. 4-[4-(2-Methoxy-ethoxy)-phenyl]-4-[4-(1H-pyrazol-4-yl)-phenyl]-piperidine

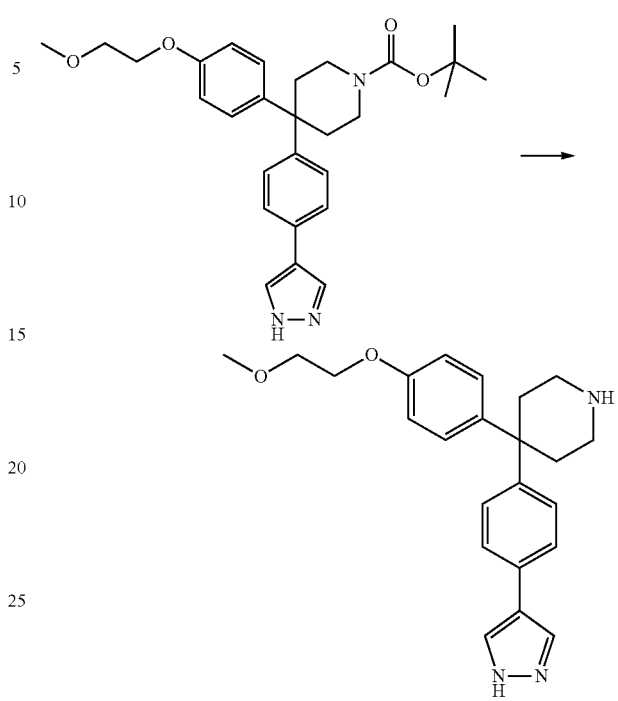

Trifluoroacetic acid (1 ml) was added to a solution of 4-[4-(2-Methoxy-ethoxy)-phenyl]-4-[4-(1H-pyrazol-4-yl)-phenyl]-piperidine (87 mg) in dichloromethane (1 ml). After 30 minutes at room temperature, the reaction was concentrated. The residue was dissolved methyl acetate then extracted into hydrochloric acid (2N, 2×20 ml). The combined aqueous fractions were washed with ethyl acetate then basified (2N NaOH) before back-extraction into ethyl acetate (2×20 ml). The combined organic liquors were washed with saturated brine solution then dried (MgSO$_4$) and concentrated to yield the title compound (66 mg). LCMS (PS-A3) R$_t$ 6.08 [M+H]$^+$ 378. $^1$H NMR (Me-d$_3$-OD) δ 7.92 (2H, s), 7.51 (2H, d), 7.31 (2H, d), 7.25 (2H, d). 6.89 (2H, d), 4.13 (2H, t), 3.73 (2H, t), 3.42 (3H, s). 2.94 (4H, bs), 2.44 (4H, bs).

Example 68

4-[4-(3-Methoxy-propoxy)-phenyl]-4-[4-(1H-pyrazol-4-yl)-phenyl]-piperidine

68A. 4-(4-Bromo-phenyl)-4-[4-(3-methoxy-propoxy)-phenyl]-piperidine-1-carboxylic acid tert-butyl ester

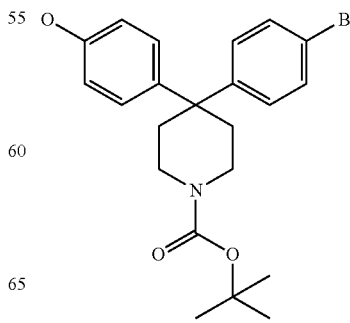

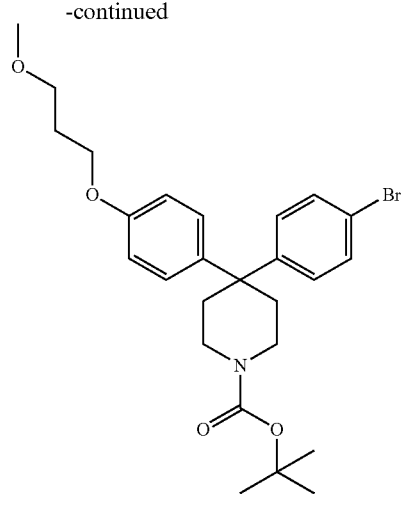

Tosyl chloride (572 mg, 3.0 mmol) was added to a solution of 3-methoxypropanol (191 ul, 2.0 mmol) in pyridine (1 ml). This was stirred at room temperature for 5.5 hours then diluted with ethyl acetate (20 ml) and washed with hydrochloric acid (2N, 3×10 ml) and saturated brine (10 ml). The liquors were dried (MgSO$_4$) and concentrated to furnish a colourless oil (600 mg). This oil was dissolved in dimethylformamide (2 ml) and to this solution was added potassium carbonate (64 mg, 0.46 mmol) and 4-(4-Bromo-phenyl)-4-(4-hydroxy-phenyl)-piperidine-1-carboxylic acid tert-butyl ester* (100 mg, 0.23 μmol). The resultant mixture was stirred at 100° C. for 4 hours. Once cooled, water (20 ml) was added and the mixture was extracted with ethyl acetate (3×10 ml). The combined organic liquors were washed with brine (10 ml) before drying (MgSO$_4$) and concentrating. The residue was purified by column chromatography (SiO$_2$), eluting with a gradient from 10-20% ethyl acetate/petrol to furnish the title compound as a colourless oil (131 mg). LCMS: R$_t$ 4.20 [M+H]$^+$ 504.
*This starting material can be made by the method described in Example 67A 68B. 4-[4-(3-Methoxy-propoxy)-phenyl]-4-[4-(1H-pyrazol-4-yl)-phenyl]-piperidine

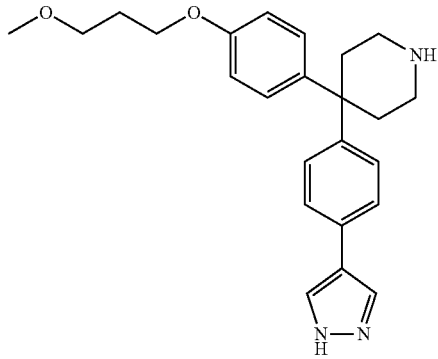 [SMILES: COCCCOc1ccc(C2(c3ccc(-c4cn[nH]c4)cc3)CCNCC2)cc1]

By following the procedure described in Example 67C and 67D but substituting 4-(4-Bromo-phenyl)-4-[4-(2-methoxy-ethoxy)-phenyl]-piperidine-1-carboxylic acid tert-butyl ester for 4-(4-Bromo-phenyl)-4-[4-(3-methoxy-propoxy)-phenyl]-piperidine-1-carboxylic acid tert-butyl ester the title compound was obtained. LCMS: R$_t$ 6.65 [M+H]$^+$ 392. $^1$H NMR (Me-d$_3$-OD) δ 7.94 (2H, s), 7.57 (2H, d), 7.34 (2H, d), 7.27 (2H, d), 6.91 (2H, d), 4.04 (2H, t), 3.56 (2H, t), 3.34-3.33 (5H, m), 3.24-3.22 (4H, m), 2.67-2.66 (4H, m)

Example 69

3-(3,4-Dichloro-phenyl)-3-[4-(1H-pyrazol-4-yl)-phenyl]-propionamide

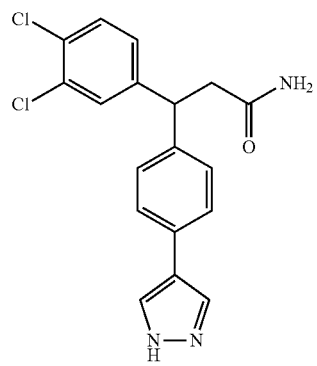 [SMILES: NC(=O)CC(c1ccc(-c2cn[nH]c2)cc1)c1ccc(Cl)c(Cl)c1]

By following the procedure described in Example 9A and 9B but substituting 3,4-difluorophenylmagnesium bromide for 3,4-dichlorophenylmagnesium bromide, the title compound was obtained. LC/MS: (PS-A3) R$_t$ 9.82 [M+H]$^+$ 360.14, 362.12. $^1$H NMR (Me-d$_3$-OD) δ 2.90-3.00 (2H, d), 4.50-4.60 (1H, t), 7.10-7.30 (3H, m), 7.40-7.45 (2H, d), 7.50-7.55 (2H, d), 7.85-8.05 (2H, br s).

Example 70

2-(4-{2-Methylamino-1-[4-(1H-pyrazol-4-yl)-phenyl]-ethyl}-phenoxy)-isonicotinamide

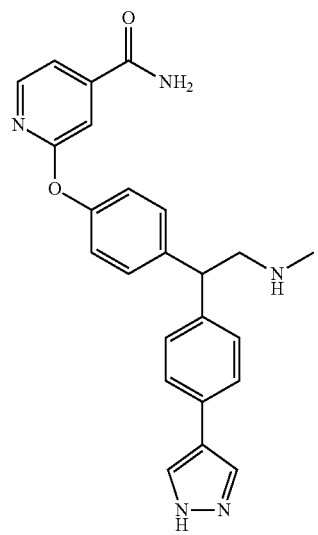 [SMILES: CNCC(c1ccc(Oc2cc(C(N)=O)ccn2)cc1)c1ccc(-c2cn[nH]c2)cc1]

By following the procedure described in Example 47, but substituting 2-chloropyrazine for 2-chloro-4-cyanopyridine, the title compound was obtained. LC/MS: (PS-B3) R$_t$ 2.27 [M+H]$^+$ 414. $^1$H NMR (Me-d$_3$-OD) δ 2.45 (3H, s), 3.55 (1H, dd), 3.65 (1H, dd), 4.25 (1H, t), 7.10 (2H, d), 7.30-7.38 (3H, m), 7.40 (2H, d), 7.48 (1H, d), 7.56 (2H, d), 7.95 (2H, s), 8.22 (1H, d).

Example 71

{2-(4-Chloro-phenoxy)-2-[4-(1H-pyrazol-4-yl)-phenyl]-ethyl}-methyl-amine

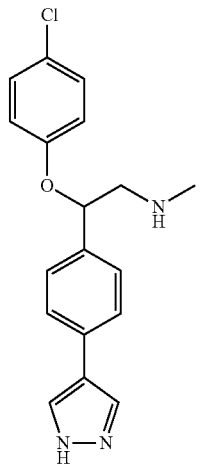 [SMILES: CNCC(Oc1ccc(Cl)cc1)c1ccc(-c2cn[nH]c2)cc1]

By following the procedure described in Example 48, but substituting phenol for 4-chlorophenol, the title compound was obtained. LC/MS: (PS-A3) $R_t$ 2.29 [M−ClPhO+H]⁺ 200. ¹H NMR (Me-$d_3$-OD) δ 2.50 (3H, s), 2.86 (1H, dd), 3.10 (1H, dd), 5.35 (1H, dd), 6.89 (2H, d), 7.17 (2H, d), 7.40 (2H, d), 7.57 (2H, d), 7.93 (2H, s).

Example 72

3-{2-(4-Chloro-phenyl)-2-[4-(1H-pyrazol-4-yl)-phenyl]-ethylamino}-propan-1-ol

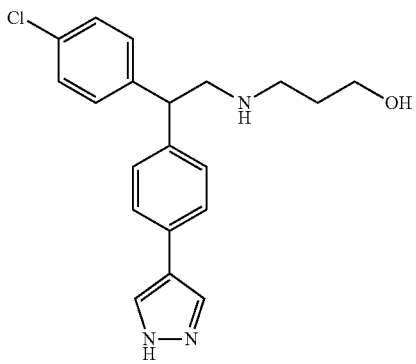 [SMILES: OCCCNCC(c1ccc(Cl)cc1)c1ccc(-c2cn[nH]c2)cc1]

By following the procedure described in Example 20 but substituting dimethylamine for 3-aminopropan-1-ol the title compound was obtained. LC/MS: (PS-A2) $R_t$ 2.05 [M+H]⁺ 356. ¹H NMR (Me-$d_3$-OD) δ 1.87 (2H, quintet), 1.98 (AcOH, s), 3.23 (2H, t), 3.68 (2H, t), 3.75 (2H, dd), 4.4 (1H, t), 7.36 (2H, d), 7.4 (4H, s), 7.62 (2H, d), 7.97 (2H, s).

Example 73

2-{2-(4-Chloro-phenyl)-2-[4-(1H-pyrazol-4-yl)-phenyl]-ethylamino}-ethanol

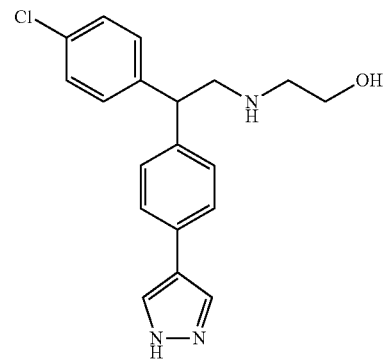 [SMILES: OCCNCC(c1ccc(Cl)cc1)c1ccc(-c2cn[nH]c2)cc1]

By following the procedure described in Example 20 but substituting dimethylamine for 2-aminoethan-1-ol the title compound was obtained. LC/MS: (PS-A2) $R_t$ 2.05 [M+H]⁺ 342. ¹H NMR (Me-$d_3$-OD) δ 1.98 (AcOH, s), 310 (2H, s), 3.69 (2H, dd), 378, (2H, t), 4.39 (1H, t), 7.36 (2H, d), 7.38 (4H, s), 7.61 (2H, d), 7.97 (2H, s).

Example 74

{2-(4-Chloro-phenyl)-2-[4-(1H-pyrazol-4-yl)-phenyl]-ethyl}-cyclopropylmethyl-amine

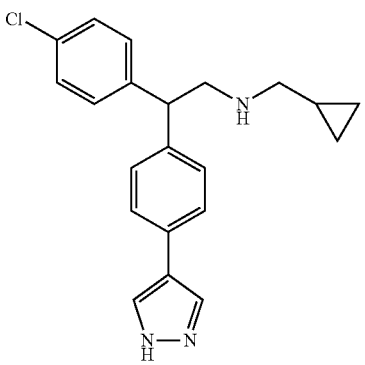 [SMILES: Clc1ccc(C(CNCC2CC2)c2ccc(-c3cn[nH]c3)cc2)cc1]

By following the procedure described in Example 20 but substituting dimethylamine for cyclopropylmethylamine the title compound was obtained. LC/MS: (PS-A2) $R_t$ 2.21 [M+H]⁺ 352. ¹H NMR (Me-$d_3$-OD) δ −0.4-0.3 (2H, m), 0.35-0.40 (2H, m), 0.78-0.87 (1H, m), 2.42 (2H, d), 3.15-3.25 (2H, m), 4.11 (1H, t), 7.16-7.27 (6H, m), 7.45 (2H, d), 7.82, (2H, s).

Example 75

Methyl-[2-[4-(1H-pyrazol-4-yl)-phenyl]-2-(4-pyridin-3-yl-phenyl)-ethyl]-amine

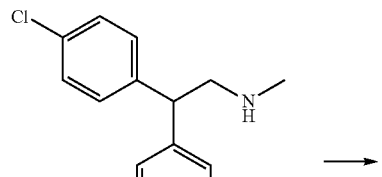
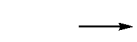

By following the procedure described in Example 1 but substituting 4-(4,4,5,5-tetramethyl-1,3,2-dioxaborolan-2-yl)-1H-pyrazole for 3-(4,4,5,5-Tetramethyl-[1,3,2]dioxaborolan-2-yl)-pyridine and coupling to {2-(4-Chloro-phenyl)-2-[4-(1H-pyrazol-4-yl)-phenyl]-ethyl}-methyl-amine*, the title compound was obtained. LC/MS: (PS-B3) $R_t$ 2.42 [M+H]$^+$ 355. $^1$H NMR (Me-d$_3$-OD) δ 1.94 (AcOH, s), 2.72 (3H, s), 3.73 (2H, d), 4.46 (1H, t), 7.41 (2H, d), 7.51-7.56 (3H, m), 7.63 (2H, d), 7.70 (2H, d), 7.96 (2H, s), 8.10 (1H, dt), 8.53 (1H, dd), 8.80 (1H, d).

*This starting material can be made by the method described in Example 21.

Example 76

4-{3-Methylamino-1-[4-(1H-pyrazol-4-yl)-phenyl]-propyl}-phenol

By following the procedure described in Example 8 but substituting 4-chlorophenylmagnesium bromide for 4-anisylmagnesium bromide, the title compound can be obtained LC/MS: (PS-A2) $R_t$ 1.82 [M+H]$^+$ 308. $^1$H NMR (Me-d$_3$-OD) δ 1.92 (AcOH, s), 2.34-2.43 (2H, m), 2.64 (3H, s), 2.86-2.92 (2H, m), 3.96 (1H, t), 6.75 (2H, d), 7.13 (2H, d), 7.29 (2H, d), 7.52 (2H, d), 7.93 (2H, d).

Example 77

3-(4-Methoxy-phenyl)-3-[4-(1H-pyrazol-4-yl)-phenyl]-propylamine

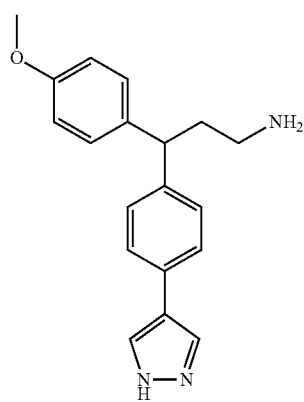 [SMILES: COc1ccc(C(CCN)c2ccc(-c3cn[nH]c3)cc2)cc1]

By following the procedure described in Example 8 but substituting 4-chlorophenylmagnesium bromide for 4-anisylmagnesium bromide and methylamine for ammonia (2M in methanol), the title compound was obtained. LC/MS: (PS-A2) $R_t$ 1.82 [M+H]$^+$ 308. $^1$H NMR (Me-d$_3$-OD) δ 2.23-2.32 (2H, m), 2.74 (2H, dd), 3.65 (3H, s), 3.89 (1H, t), 6.77 (2H, d), 7.11 (2H, s), 7.17 (2H, d), 7.41 (2H, d), 7.71 (2H, s), 8.41 (HCO$_2$H, br s).

Example 78

4-(4-Chloro-phenyl)-4-[4-(3-methyl-1H-pyrazol-4-yl)-phenyl]-piperidine 78A. 4-(4-Chloro-phenyl)-4-[4-(3-methyl-1-trityl-1H-pyrazol-4-yl)-phenyl]-piperidine

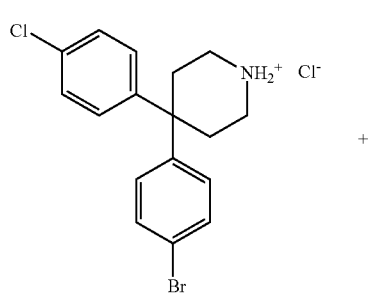

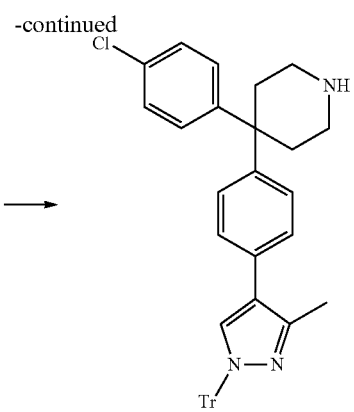

4-(4-bromo-phenyl)-4-(4-chloro-phenyl)-piperidine hydrochloride was reacted with 3-methyl-1-trityl-1H-pyrazole-4-boronic acid* following the procedure set out in Example 1, but using tetrakis(triphenylphosphine) palladium (0) as the catalyst to give the title compound. LC/MS: (PS-B3) $R_t$ 2.78 min [M+H]$^+$ 594.

*This starting material can be made by the method described in EP1382603

78B. 4-(4-Chloro-phenyl)-4-[4-(3-methyl-1H-pyrazol-4-yl)-phenyl]-piperidine

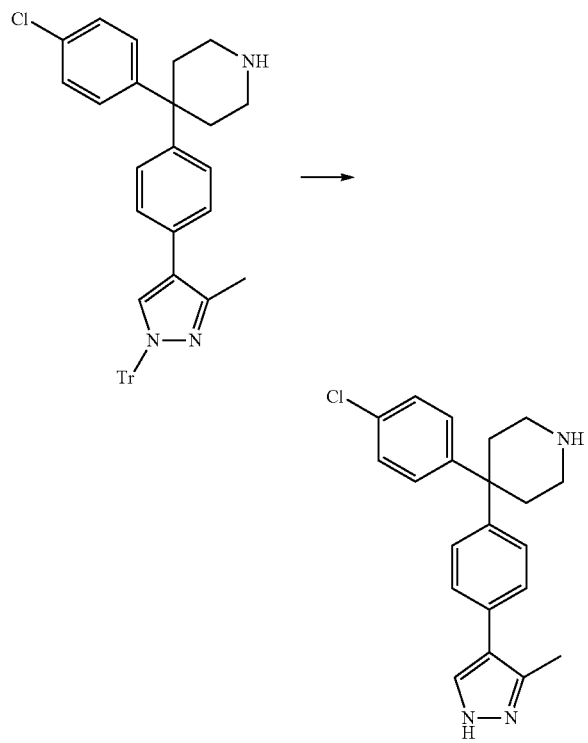

A suspension of 4-(4-chloro-phenyl)-4-[4-(3-methyl-1-trityl-1H-pyrazol-4-yl)-phenyl]-piperidine (178 mg, 0.30 mmol) in 5N hydrochloric acid (5 mL), THF (5 mL) and methanol (5 mL) was stirred for 140 minutes. The organic solvents were removed in vacuo then the resulting solution was diluted with 2N HCl and washed with ether. The aqueous phase was basified by addition of sodium hydroxide pellets then extracted with ethyl acetate. This organic extract was washed with brine, dried (MgSO$_4$), filtered and concentrated to give a residue which was purified by column chromatography (SiO$_2$), eluting with a gradient of 2M ammonia in methanol (5% to 7.5%) and dichloromethane. The product was further purified by preparative HPLC to give the title compound which was converted to its dihydrochloride salt (84 mg, 80%); LCMS (PS-A3) $R_t$ 6.86 min [M+H]$^+$ 352. $^1$H NMR (Me-d$_3$-OD) δ 2.55 (3H, s), 2.70-2.75 (4H, m), 3.22-3.27 (4H, m), 7.35-7.41 (4H, m), 7.47-7.54 (4H, m), 8.32 (2H, s).

Example 79

2-(4-Chloro-phenyl)-2-[4-(1H-pyrazol-4-yl)-phenyl]-morpholine

79A. 2-(4-Chloro-phenyl)-2-(4-iodo-phenyl)-oxirane

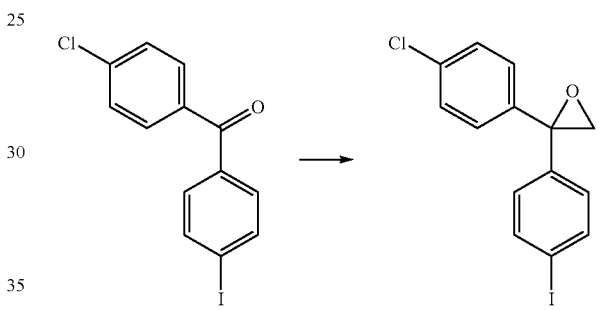

Sodium hydride (60% dispersion in oil, 128 mg, 3.2 mmol) was placed under N$_2$ then DMSO (5 mL) was added. Trimethylsulfonium iodide (0.66 g, 3.2 mmol) was added as a solid after 15 min, followed after a further 30 min by (4-chloro-phenyl)-(4-iodo-phenyl)-methanone. The mixture was stirred at room temperature for 24 hours then diluted with ethyl acetate and washed with 1:2 water/brine, water and brine (×2). The organic phase was dried (MgSO$_4$), filtered and concentrated to give the title compound (1.01 g, 97%), which was used without further purification. LCMS (PS-A2) $R_t$ 4.07 mm [M−H]$^-$ 355.

79B. 1-(4-Chloro-phenyl)-2-(2-hydroxy-ethylamino)-1-(4-iodo-phenyl)-ethanol

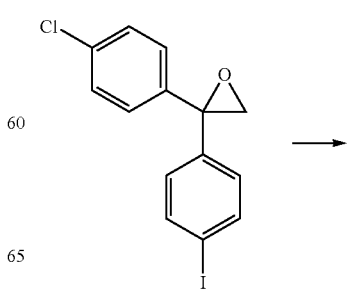

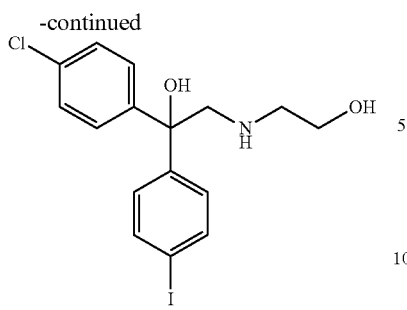

A solution of 2-(4-chloro-phenyl)-2-(4-iodo-phenyl)-oxime (0.60 g. 1.68 mmol), ethanolamine (0.5 mL, 8.3 mmol) and triethylamine (0.5 mL, 3.6 mmol) in iso-propanol (5 mL) was maintained at 50° C. for 72 hours then concentrated in vacuo. The residue was taken up in ethyl acetate and washed with saturated potassium carbonate solution/water (1:9). The aqueous phase was extracted a second time with ethyl acetate, then the combined extracts were washed with brine, dried (MgSO$_4$), filtered and concentrated to give the title compound (701 mg, quantitative); LCMS (PS-A2) R$_t$ 2.29 min [M+H]$^+$ 418, [M–H$_2$O+H]$^+$ 400.

79C. 2-(4-Chloro-phenyl)-2-(4-iodo-phenyl)-morpholine

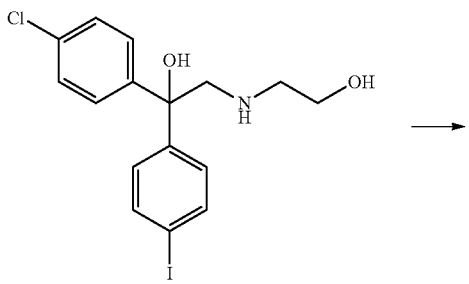

A solution of 1-(4-chloro-phenyl)-2-(2-hydroxy-ethylamino)-1-(4-iodo-phenyl)-ethanol (701 mg, 1.68 mmol) in DCM (10 mL) was treated with concentrated H$_2$SO$_4$ (0.1 mL, 1.9 mmol). After 20 hours, another portion of H$_2$SO$_4$ (1.0 mL, 19 mmol) was added and the mixture stirred for a further 2 hours. The mixture was diluted with ethyl acetate and washed with saturated potassium carbonate and brine then dried (MgSO$_4$), filtered and concentrated. The residue was purified by column chromatography (SiO$_2$), eluting with 0.5% tri- ethylamine in ethyl acetate to afford the title compound (290 mg, 43%); LCMS (PS-A2) R$_t$ 2.40 mm [M+H]$^+$ 400.

79D. 2-(4-Chloro-phenyl)-2-[4-(1H-pyrazol-4-yl)-phenyl]-morpholine

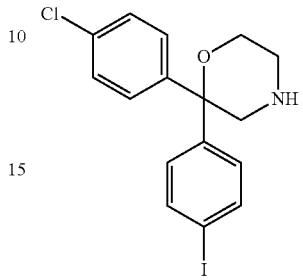

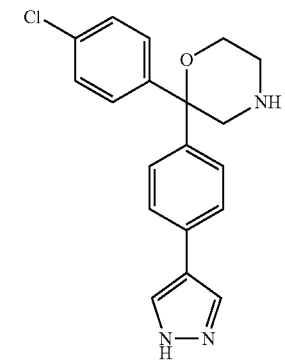

2-(4-chloro-phenyl)-2-(4-iodo-phenyl)-morpholine was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst to give the title compound. LCMS (PS-A3) R$_t$ 6.88 min [M+H]$^+$ 340. $^1$H NMR (Me-d$_3$-OD) δ 2.84-2.88 (2H, m), 3.32-3.36 (1H, m), 3.45-3.49 (1H, m), 3.69-3.72 (2H, m), 7.31 (2H, d), 7.40 (4H, apparent d), 7.56 (2H, d), 7.92 (2H, br.s).

Example 80

(4-{4-[4-(1H-Pyrazol-4-yl)-phenyl]-piperidin-4-yl}-phenoxy)-acetic acid and (4-{4-[4-(1H-Pyrazol-4-yl)-phenyl]-piperidin-4-yl}-phenoxy)-acetic acid, methyl ester 80A. {4-[4-(4-bromo-phenyl)-piperidin-4-yl]-phenoxy}-acetic acid ethyl ester

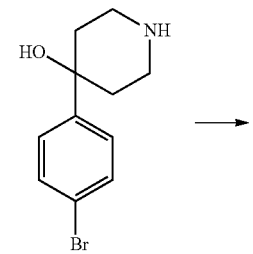

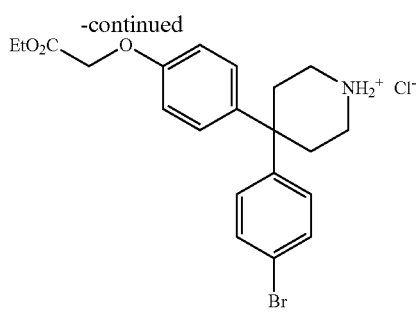

By following the procedure described in Example 42B but substituting chlorobenzene for ethyl phenoxyacetate and employing nitrobenzene as solvent, the title compound was obtained. LCMS (PS-A2) $R_t$ 2.37 min [M+H]$^+$ 418.

80B. (4-{4-[4-(1H-Pyrazol-4-yl)-phenyl]-piperidin-4-yl}-phenoxy)-acetic acid and (4-{4-[4-(1H-Pyrazol-4-yl)-phenyl]-piperidin-4-yl}-phenoxy)-acetic acid, methyl ester

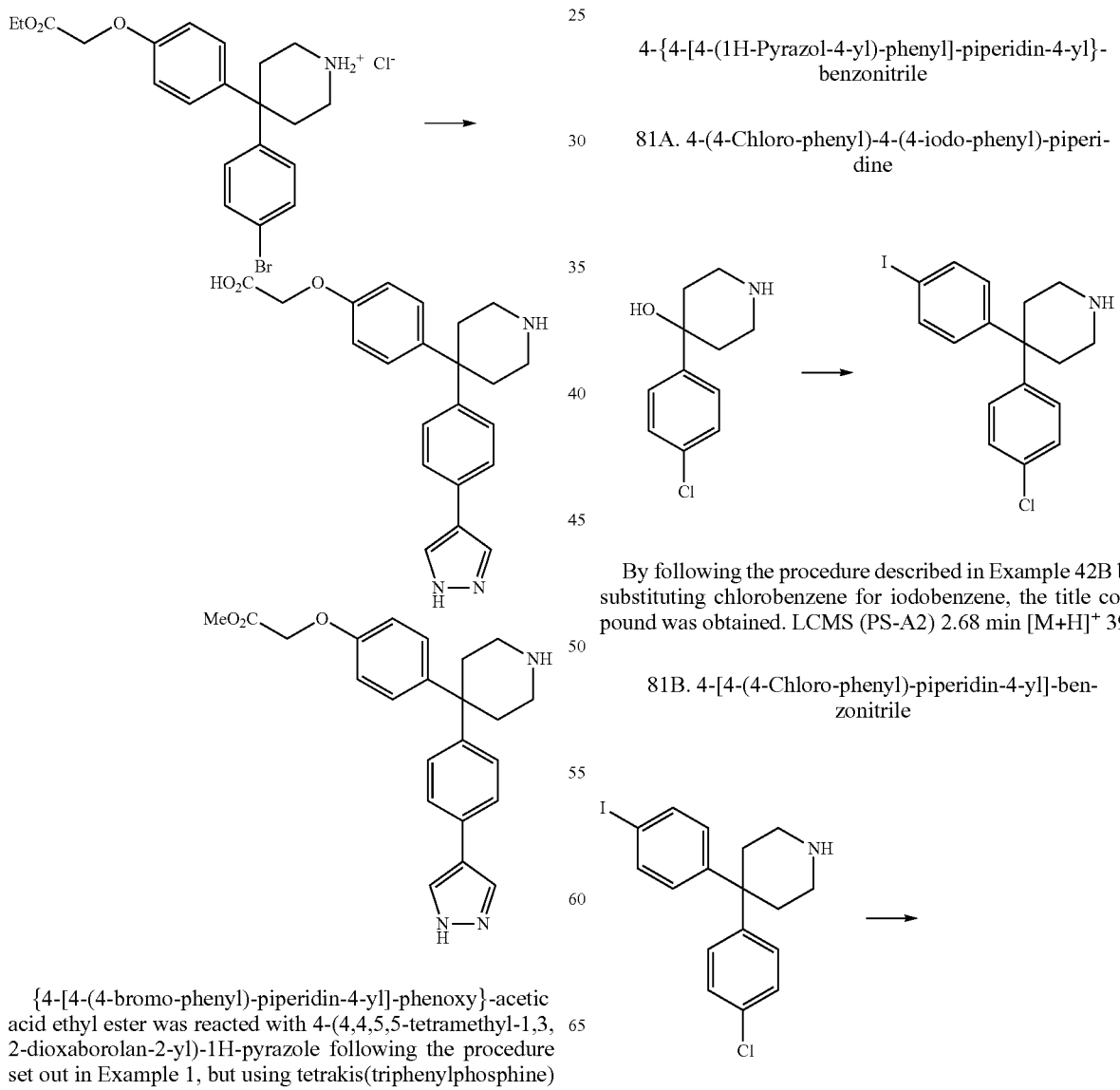

{4-[4-(4-bromo-phenyl)-piperidin-4-yl]-phenoxy}-acetic acid ethyl ester was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst and heating at 80° C. for 30 minutes, to yield a mixture of the title compounds. On work up the basic aqueous extract was neutralised with hydrochloric acid and extracted with ethyl acetate (×2), then these organic extracts were combined and washed with brine, dried (MgSO$_4$), filtered and concentrated to give a crude product that was recrystallised from water to afford (4-{4-[4-(1H-pyrazol-4-yl)-phenyl]-piperidin-4-yl}-phenoxy)-acetic acid (12 mg, 5%); LCMS (PS-A3) $R_t$ 5.33 min [M+H]$^+$ 378. $^1$H NMR (DMSO-d$_6$) δ 2.22-2.26 (4H, m), 2.67-2.71 (4H, m), 4.65 (2H, s) 6.67 (2H, d), 7.11 (2H, d), 7.24 (2H, d), 7.46 (2H, d), 7.96 (2H, br.s).

The material which was not extracted into base was converted on standing in methanol to a single compound, {4-[4-(1H-pyrazol-4-yl)-phenyl]-piperidin-4-yl}-phenoxy)-acetic acid, methyl ester. This was purified by preparative HPLC to afford the title compound (18 mg, 7%); LCMS (PS-A3) $R_t$ 6.13 min [M+H]$^+$ 392. $^1$H NMR (Me-d$_3$-OD) δ 2.34-2.45 (4H, m), 2.87 (4H, apparent t), 3.75 (3H, s), 6.83 (2H, d), 7.21 (2H, d), 7.26 (2H, d), 7.47 (2H, d), 7.89 (2H, s).

Example 81

4-{4-[4-(1H-Pyrazol-4-yl)-phenyl]-piperidin-4-yl}-benzonitrile 81A. 4-(4-Chloro-phenyl)-4-(4-iodo-phenyl)-piperidine By following the procedure described in Example 42B but substituting chlorobenzene for iodobenzene, the title compound was obtained. LCMS (PS-A2) 2.68 min [M+H]$^+$ 398.

81B. 4-[4-(4-Chloro-phenyl)-piperidin-4-yl]-benzonitrile

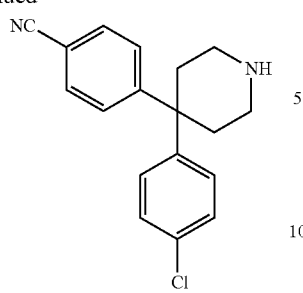

A mixture of 4-(4-chloro-phenyl)-4-(4-iodo-phenyl)-piperidine and copper (I) cyanide in DMF was heated at 140° C. under nitrogen for 6 hours then allowed to cool. The mixture was diluted with ethyl acetate, washed with a mixture of conc. ammonia and brine (×5), dried (MgSO₄), filtered and concentrated to give a residue which was partially purified by column chromatography (SiO₂), eluting with a gradient of 2M ammonia in methanol (5% to 10%) and dichloromethane to afford the title compound (46 mg, <16%). This was taken on to the next reaction without further purification. LCMS (PS-A2) $R_t$ 2.39 min [M+H]⁺ 297.

81C. 4-{4-[4-(1H-Pyrazol-4-yl)-phenyl]-piperidin-4-yl}-benzonitrile

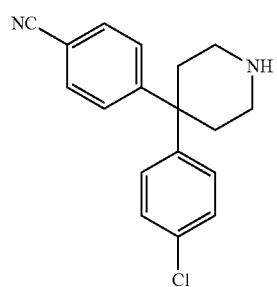
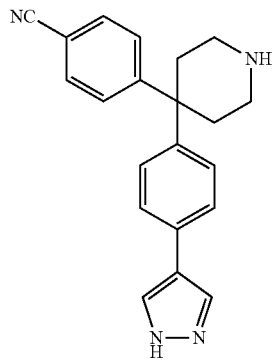

4-[4-(4-chloro-phenyl)-piperidin-4-yl]-benzonitrile was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst and heating at 100° C. for 15 minutes, to obtain the title compound. LCMS (PS-A3) $R_t$ 6.68 min [M+H]⁺ 329. ¹H NMR (Me-d₃-OD) δ 2.65-2.73 (4H, m), 2.77-2.85 (4H, m), 3.75 (3H, s), 7.46 (2H, d), 7.59 (2H, d), 7.68 (2H, d), 7.71 (2H, d), 8.42 (2H, br.s).

Example 82

{2-(4-Chloro-phenyl)-2-[4-(1H-pyrazol-4-yl)-phenyl]-propyl}-methyl-amine

82A. Bis-(4-chloro-phenyl)-acetic acid methyl ester

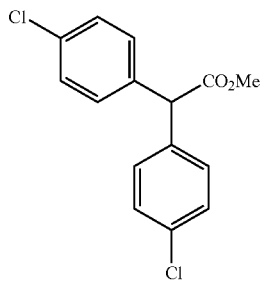

Bis-(4-chloro-phenyl)-acetic acid (4.33 g, 15.4 mmol) was suspended in anhydrous methanol (20 mL) and concentrated hydrochloric acid (5 drops) was added. After 1 day the reaction was quenched by the addition of saturated sodium bicarbonate solution, then the organic solvent was removed in vacuo. The residue was partitioned between ethyl acetate and 50% saturated potassium carbonate solution. The organic phase was washed with brine, dried (MgSO₄), filtered and concentrated to give a residue which was purified by column chromatography (SiO₂), eluting with 10% ethyl acetate/petrol, to afford the title compound as a colourless oil (3.57 g, 78%); LCMS (PS-B3) $R_t$ 3.79 min, No Ionisation. ¹H NMR (CDCl₃) δ 3.74 (3H, s), 4.96 (1H, s), 7.20-7.23 (4H, m), 7.28-7.32 (4H, m).

82B. 2,2-Bis-(4-chloro-phenyl)-propionic acid methyl ester

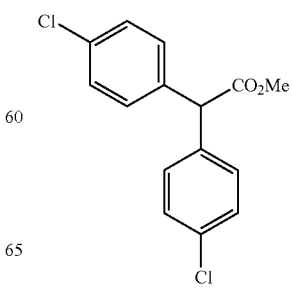

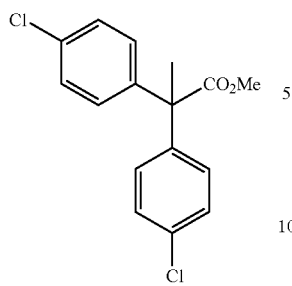

A solution of bis-(4-chloro-phenyl)-acetic acid methyl ester (1.19 g, 4.0 mmol) in THF (20 ml) was cooled to −78° C. under nitrogen. A solution of LDA (3.0 mL, 6.0 mmol, 2M in heptane/THF/ethylbenzene) was added over 5 minutes, then after a further 20 minutes, iodomethane (0.63 ml, 10.1 mmol) was added. After 4 hours the reaction was quenched by the addition of saturated ammonium chloride solution and allowed to warm to room temperature then concentrated in vacuo to remove organic solvents. The mixture was diluted with ethyl acetate/petrol 1:4 and washed with saturated ammonium chloride solution then brine, dried (MgSO$_4$), filtered and concentrated to give a residue which was purified by column chromatography (SiO$_2$), eluting with an ethyl acetate/petrol gradient (1% to 2%), to afford the title compound as a colourless oil (210 mg, 17%); LCMS (PS-B3) R$_t$ 4.01 min. No Ionisation. $^1$H NMR (CDCl$_3$) δ 1.88 (3H, s), 3.73 (3H, s), 7.11-7.14 (4H, m), 7.26-7.30 (4H, m).

82C. 2,2-Bis-(4-chloro-phenyl)-propionic acid

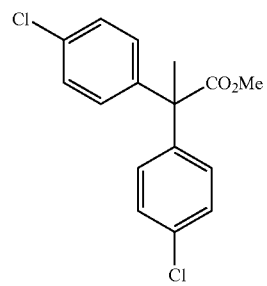

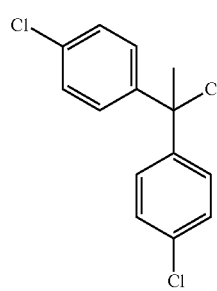

A solution of 2,2-bis-(4-chloro-phenyl)-propionic acid methyl ester (210 mg, 0.67 mmol) in THF/water/methanol (1:1:1, 18 mL) was stirred at room temperature for 5 days then concentrated in vacuo. The residue was partitioned between ethyl acetate and 2N hydrochloric acid, then the organic phase was washed with brine, dried (MgSO$_4$), filtered and concentrated to give the title compound (186 mg, 93%) as a yellow solid which was used without further purification. LCMS (PS-B3) R$_t$ 2.40 min [M−CO$_2$H]$^-$ 249.

82D. 2,2-Bis-(4-chloro-phenyl)-N-methyl-propionamide

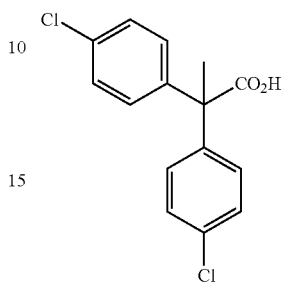

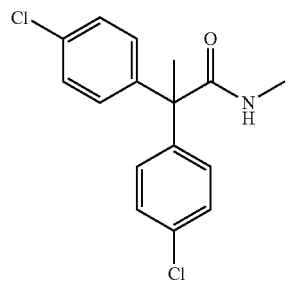

By following the procedure described in Example 8D but substituting 3-(4-bromo-phenyl)-3-(4-chloro-phenyl)-propionic acid for 2,2-bis-(4-chloro-phenyl)-propionic acid, the title compound was obtained. LCMS (PS-B3) R$_t$ 3.40 min [M+H]$^+$ 308.

82E. [2,2-Bis-(4-chloro-phenyl)-propyl]-methyl-amine

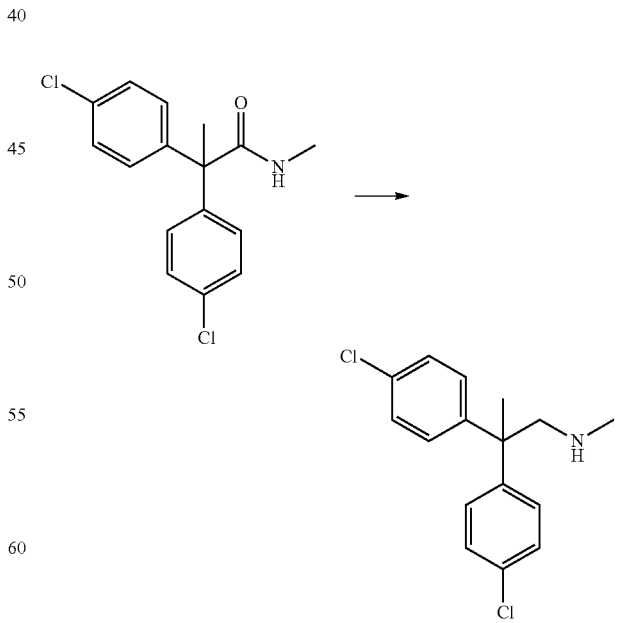

By following the procedure described in Example 8E but substituting 3-(4-Bromo-phenyl)-3-(4-chloro-phenyl)-N-methyl-propionamide for 2,2-Bis-(4-chloro-phenyl)-N-me-

82F. {2-(4-Chloro-phenyl)-2-[4-(1H-pyrazol-4-yl)-phenyl]-propyl}-methyl-amine

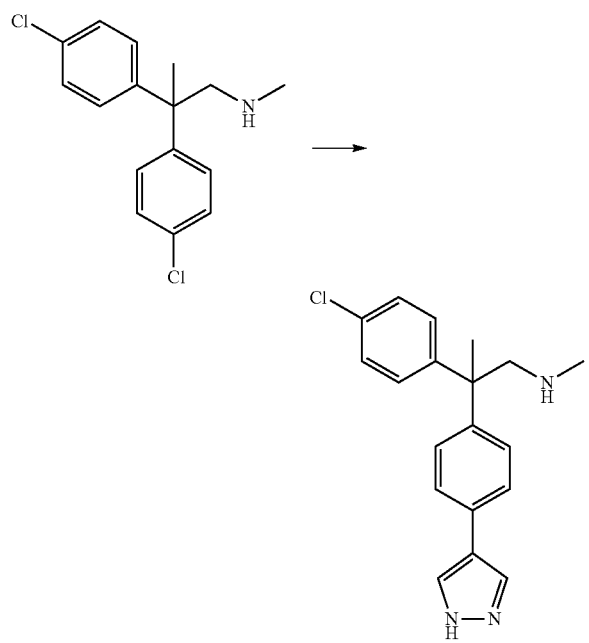

[2,2-Bis-(4-chloro-phenyl)-propyl]-methyl-amine was reacted with 4-(4,4,5,5-tetramethyl-1,3,2-dioxaborolan-2-yl)-1H-pyrazole following the procedure set out in Example 1 to give the title compound. LCMS (PS-A3) $R_t$ 6.94 min [M+H]$^+$ 326. $^1$H NMR (Me-d$_3$-OD) δ 1.86 (3H, s), 2.77 (3H, s), 3.89 (2H, s), 7.26-7.33 (4H, m), 737-7.40 (21-1, m), 7.68 (2H, d). 8.35 (2H, s).

Example 83

1-(4-Chloro-phenyl)-2-methylamino-1-[4-(1H-pyrazol-4-yl)-phenyl]-ethanol

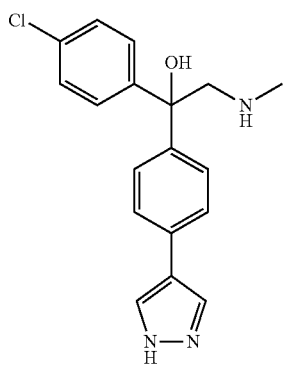 [SMILES: CNCC(O)(c1ccc(Cl)cc1)c1ccc(-c2cn[nH]c2)cc1]

By following the procedure described in Example 79A, 79B and 79D but substituting ethanolamine for methylamine, the title compound was obtained. LCMS (PS-A3) $R_t$ 5.28 min [M+H]$^+$ 328, [M−H$_2$O+H]$^+$ 310. $^1$H NMR (Me-d$_3$-OD) δ 2.38 (3H, s), 3.34 (2H, s), 7.28-7.31 (2H, m), 7.41-7.46 (4H, m), 7.51-7.54 (2H, m), 7.92 (2H, s).

Example 84

2-Amino-1-(4-chloro-phenyl)-1-[4-(1H-pyrazol-4-yl)-phenyl]-ethanol

84A. 2-[2-(4-Chloro-phenyl)-2-hydroxy-2-(4-iodo-phenyl)-ethyl]-1,3-dione

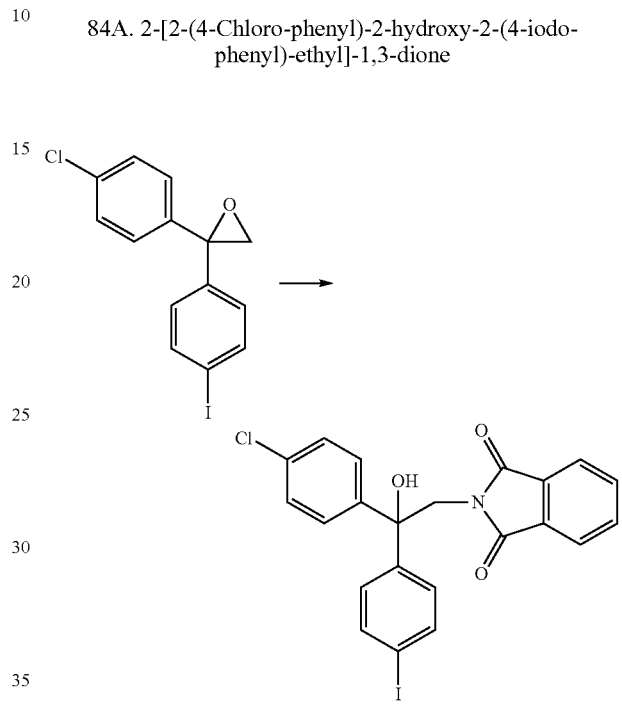

A mixture of 2-(4-chloro-phenyl)-2-(4-iodo-phenyl)-oxirane* (571 mg, 1.60 mmol) and potassium phthalimide (340 mg, 1.84 mmol) in THF (5 mL) and DMSO (2 mL) was heated at 100° C. for 20 hours. The mixture was concentrated in vacuo, diluted with ethyl acetate and washed with water and brine (×2), dried (MgSO$_4$), filtered and concentrated to give a crude product which was purified by column chromatography (SiO$_2$), eluting with a gradient of ethyl acetate/petrol (2.5% to 100%) then 10% methanol/dichloromethane to give the title compound (273 mg, 34%); LCMS (PS-A2) $R_t$ 3.22 min [M+H]$^+$ 504.

*This starting material can be made by the method described in Example 79A

84B. N-{2-(4-Chloro-phenyl)-2-hydroxy-2-[4-(1H-pyrazol-4-yl)-phenyl]-ethyl}-phthalamic acid

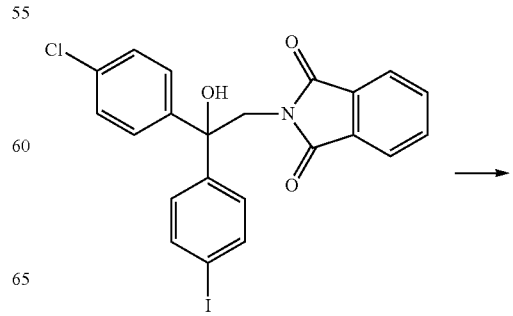

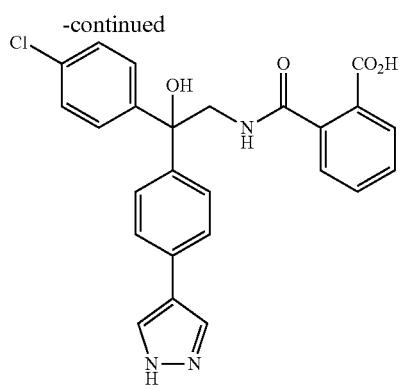

2-[2-(4-Chloro-phenyl)-2-hydroxy-2-(4-iodo-phenyl)-ethyl]-isoindole-1,3-dione was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst, to obtain the title compound. LCMS (PS-A2) $R_t$ 2.62 min [M−H]⁻ 460.

84C. 2-Amino-1-(4-chloro-phenyl)-1-[4-(1H-pyrazol-4-yl)-phenyl]-ethanol

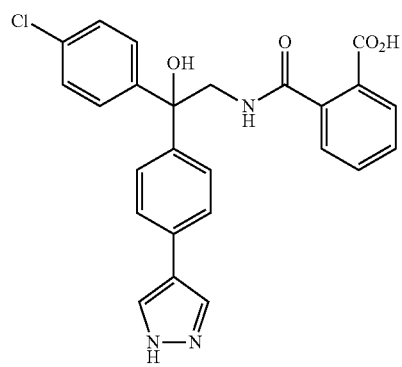

By following the procedure described in Example 49D but substituting N-(2-{(4-Chloro-phenyl)-[4-(1H-pyrazol-4-yl)-phenyl]-methoxy}-ethyl)-phthalamic acid for N-{2-(4-Chloro-phenyl)-2-hydroxy-2-[4-(1H-pyrazol-4-yl)-phenyl]-ethyl}-phthalamic acid, the title compound was obtained. LCMS (PS-A3) $R_t$ 6.29 min [M−H₂O+H]⁺ 296. ¹H NMR (Me-d₃-OD) δ 3.29-3.38 (2H, m), 7.32 (2H, d), 7.41-7.46 (4H, m). 7.55 (2H, d), 7.94 (2H, s).

Example 85

4-(3,4-Dichloro-phenyl)-4-[4-(1H-pyrazol-4-yl)-phenyl]-piperidine

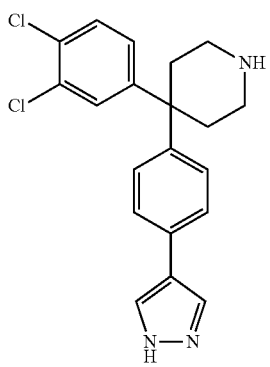 [SMILES: Clc1ccc(C2(c3ccc(-c4cn[nH]c4)cc3)CCNCC2)cc1Cl]

By following the procedure described in Example 14 but substituting chlorobenzene for 1,2-dichlorobenzene, the title compound was obtained. LCMS (PS-B4) $R_t$ 7.20 min [M+H]⁺ 372. ¹H NMR (Me-d₃-OD) δ 2.62-2.69 (2H, m), 2.73-2.81 (2H, m), 3.18-3.30 (4H, m), 7.34 (1H, dd), 7.46-7.52 (3H, m), 7.53 (1H, d), 7.72 (2H, d), 8.56 (2H, s).

Example 86

4-(3-Chloro-4-methoxy-phenyl)-4-[4-(1H-pyrazol-4-yl)-phenyl]-piperidine

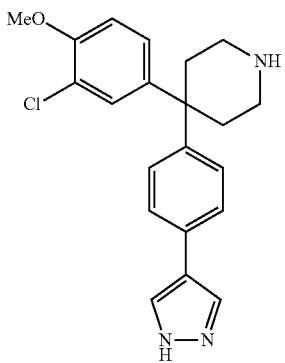

By following the procedure described in Example 14 but substituting chlorobenzene for 2-chloroanisole, the title compound was obtained. LCMS (PS-B4) $R_t$ 6.24 min [M+H]⁺ 368. ¹H NMR (Me-d₃-OD) δ 2.62-2.75 (4H, m), 3.23 (4H,

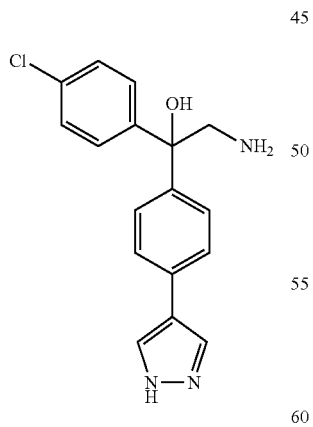

apparent t), 3.86 (3H, s), 7.06 (1H, d), 7.30 (1H, dd), 7.34 (1H, d), 7.45 (2H, d), 7.69 (2H, d), 8.57 (2H, s).

Example 87

4-(4-Chloro-3-fluoro-phenyl)-4-[4-(1H-pyrazol-4-yl)-phenyl]-piperidine 87A. 4-(4-Chloro-3-fluoro-phenyl)-4-hydroxy-piperidine-1-carboxylic acid tert-butyl ester

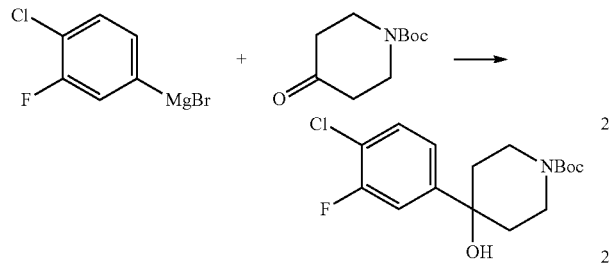

A solution of 4-chloro-3-fluorophenylmagnesium bromide (15 ml, 7.5 mmol, 0.5M in THF) was added, under nitrogen, to 4-oxo-piperidine-1-carboxylic acid tert-butyl ester (1.02 g, 5.1 mmol). After 24 hours, saturated ammonium chloride solution was added then the organic solvent was removed in vacuo. The mixture was extracted with ethyl acetate, then this extract was washed with brine, dried (MgSO$_4$), filtered and concentrated to afford a residue which was purified by column chromatography (SiO$_2$), eluting with gradient of ethyl acetate/petrol (0% to 20%) to afford the title compound (511 mg, 30%). $^1$H NMR (Me-d$_3$-OD) δ 1.48 (9H, s), 1.67 (2H, br.d), 1.92 (2H, td), 3.16-3.29 (2H, m), 3.99 (2H, br.d), 7.27 (1H, dd), 7.38 (1H, dd), 7.42 (1H, t).

87B. 4-(4-Bromo-phenyl)-4-(4-chloro-3-fluoro-phenyl)-piperidine

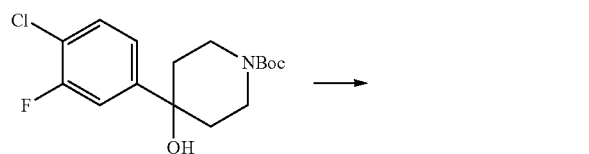

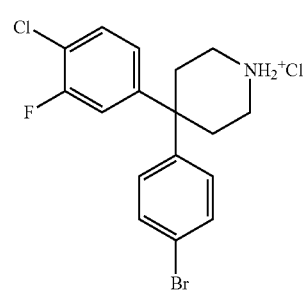

By following the procedure described in Example 42B but substituting chlorobenzene for bromobenzene, the title compound was obtained. LCMS (PS-A2) R$_t$ 2.43 min [M+H]$^+$ 368.

87C. 4-(4-Chloro-3-fluoro-phenyl)-4-[4-(1H-pyrazol-4-yl)-phenyl]-piperidine

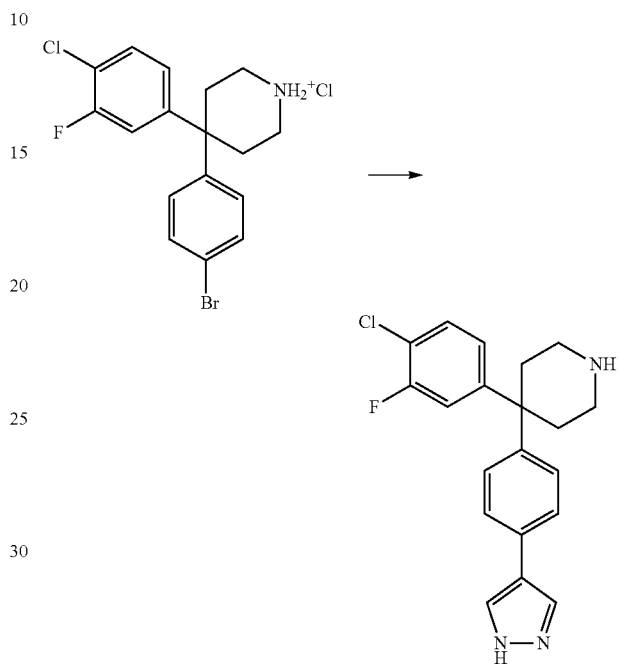

4-(4-Bromo-phenyl)-4-(4-chloro-3-fluoro-phenyl)-piperidine was reacted with 4-(4,4,5,5-tetramethyl-1,3,2-dioxaborolan-2-yl)-1H-pyrazole following the procedure set out in Example 1, but using tetrakis(triphenylphosphine) palladium (0) as the catalyst, to obtain the title compound. LCMS (PS-A3) R$_t$ 7.11 mm [M+H]$^+$ 356. $^1$H NMR (Me-d$_3$-OD) δ 2.62-2.80 (4H, m), 3.18-3.30 (partially overlaps with solvent, 4H, m), 7.23 (1H, t), 7.34-7.39 (1H, m), 7.22 (1H, dd), 7.30 (1H, dd), 7.43-7.49 (3H, m), 7.71 (2H, d), 8.55 (2H, s).

Example 88

4-{4-[4-(1H-Pyrazol-4-yl)-phenyl]-piperidin-4-yl}-benzoic acid 88A. 4-(4-carboxy-phenyl)-4-(4-chloro-phenyl)-piperidine-1-carboxylic acid tert-butyl ester

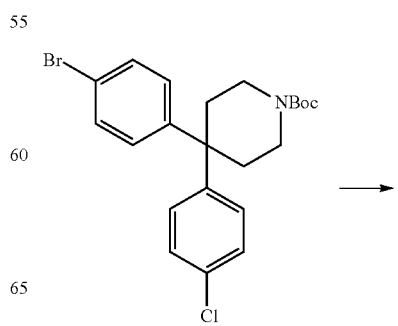

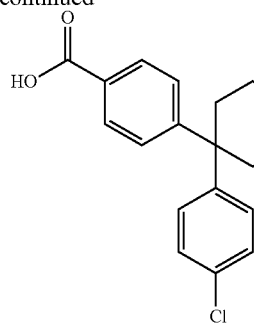

Under nitrogen, a solution of 4-(4-bromo-phenyl)-4-(4-chloro-phenyl)-piperidine-1-carboxylic acid tert-butyl ester* (888 mg, 1.97 mmol) in THF (5 mL) was cooled to –78° C. A solution of n-butyllithium (1.5 mL, 1.6M in hexanes) was added dropwise and the mixture maintained at this temperature for 25 minutes. Carbon dioxide gas (generated from dry ice and dried by passage through a column of calcium chloride pellets) was bubbled through the anion solution for 80 minutes then the mixture was allowed to warm to room temperature. The solvents were removed in vacuo then the residue was partitioned between 1N hydrochloric acid and diethyl ether. The organic phase was separated, dried (MgSO$_4$), filtered and concentrated. The combined aqueous phases were further extracted with ethyl acetate, this extract also being dried (MgSO$_4$), filtered, combined with the ethereal extract and concentrated to afford 4-(4-carboxy-phenyl)-4-(4-chloro-phenyl)-piperidine-1-carboxylic acid tert-butyl ester (889 mg); LCMS (PS-A2) R$_t$ 3.52 min [M–$^t$Bu+H]$^+$ 360.

*This starting material can be made by the method described in Example 14A followed by Example 48A

88B. 4-(4-Carboxy-phenyl)-4-[4-(1H-pyrazol-4-yl)-phenyl]-piperidine-1-carboxylic acid tert-butyl ester

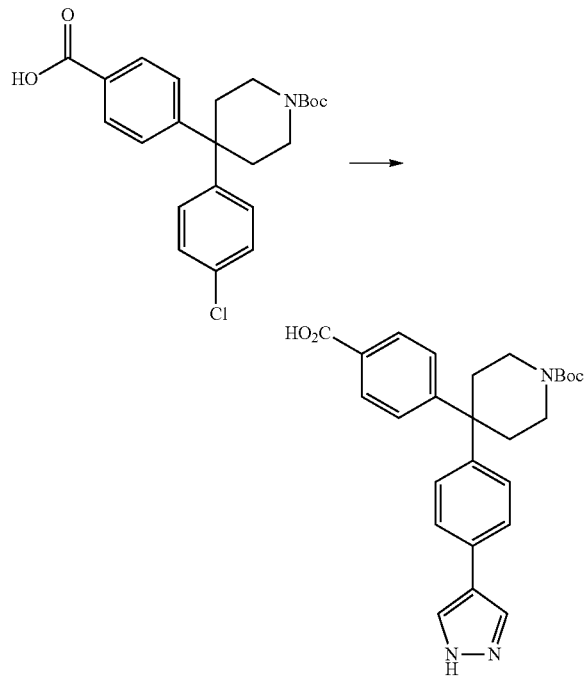

4-(4-Carboxy-phenyl)-4-(4-chloro-phenyl)-piperidine-1-carboxylic acid tert-butyl ester was reacted with 4-(4,4,5,5-tetramethyl-1,3,2-dioxaborolan-2-yl)-1H-pyrazole following the procedure set out in Example 1, to obtain the title compound. LCMS (PS-A2) R$_t$ 2.92 min [M+H]$^+$ 448.

88C. 4-{4-[4-(1H-Pyrazol-4-yl)-phenyl]-piperidin-4-yl}-benzoic acid

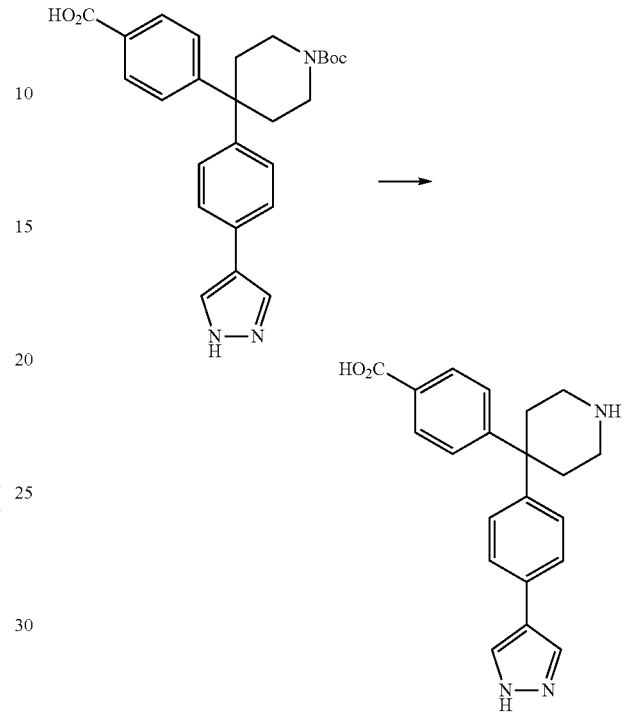

4-(4-Carboxy-phenyl)-4-[4-(1H-pyrazol-4-yl)-phenyl]-piperidine-1-carboxylic acid tert-butyl ester (26 mg, 0.06 mmol) was dissolved in dioxane (2 mL) and 1N hydrochloric acid (2 mL). After 24 hours the mixture was concentrated in vacuo and triturated with diethyl ether to afford the title compound as the dihydrochloride salt (22 mg, 90%); LCMS (PS-A3) R$_t$ 5.22 mm [M+H]$^+$ 348 $^1$H NMR (Me-d$_3$-OD) δ 2.70-2.82 (4H, m), 3.26 (4H, apparent t), 7.46 (2H, d), 7.51 (2H, m), 7.68 (2H, d), 8.00 (2H, d), 8.47 (2H, s).

Example 89

4-[4-(1H-Pyrazol-4-yl)-phenyl]-1,2,3,4,5,6-hexahydro-[4,4']bipyridinyl

89A. 4-(4-Chloro-phenyl)-3,4,5,6-tetrahydro-2H-[4,4']bipyridinyl carboxylic acid tert-butyl ester

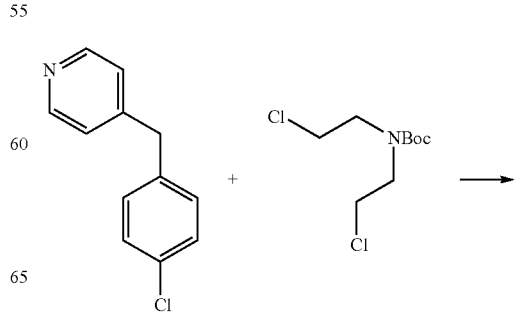

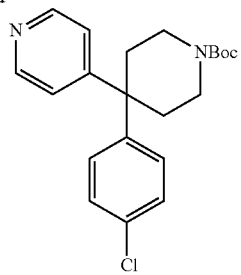

Under nitrogen, a solution of bis-(2-chloro-ethyl)-carbamic acid tert-butyl ester* (1.54 g, 6.36 mmol) in toluene (10 mL) was cooled in ice. 4-(4-Chloro-benzyl)-pyridine (1.30 g, 6.36 mmol) was added, followed over two minutes by sodium hexamethyldisilazide solution (10 mL, 20 mmol, 2M in THF). The mixture was stirred at 0° C. for 3.5 hours then allowed to warm to room temperature and stirred for a further 20 hours. Methanol was added then the mixture was concentrated in vacuo. The residue was taken up in ethyl acetate and washed with 1N hydrochloric acid (×3) and brine, dried (MgSO$_4$), filtered and concentrated to afford a residue which was purified by column chromatography (SiO$_2$), eluting with gradient of 2M methanolic ammonia in dichloromethane (1% to 5%). A second purification by column chromatography (SiO$_2$), eluting with 50% ethyl acetate/petrol gave the title compound (16 mg, 0.7%). LCMS (PS-A2) R$_t$ 2.65 min [M+H]$^+$ 373.

*This starting material can be made by the method described in J. Chem. Soc., Perkin Trans 1, 2000, p3444-3450

89B. 4-[4-(1H-Pyrazol-4-yl)-phenyl]-1,2,3,4,5,6-hexahydro-[4,4']bipyridinyl

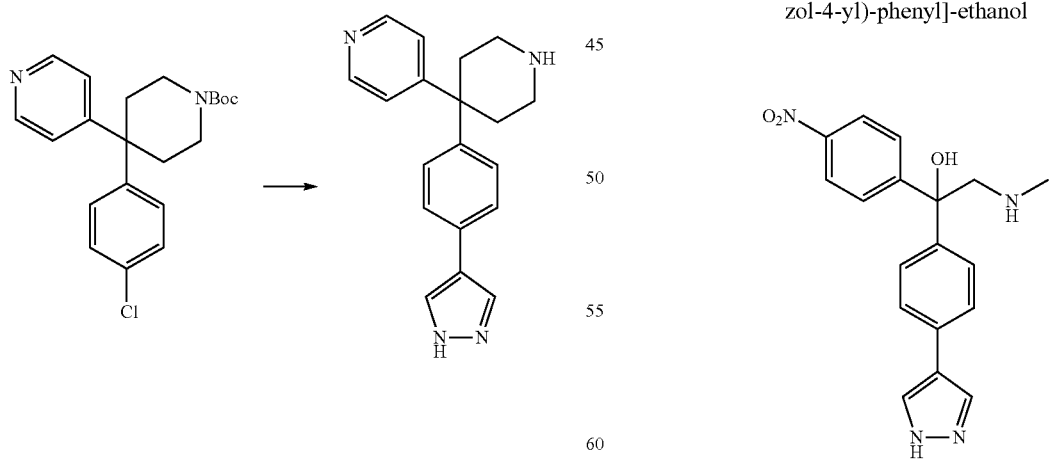

4-(4-Chloro-phenyl)-3,4,5,6-tetrahydro-2H-[4,4']bipyridinyl-1-carboxylic acid tert-butyl ester was reacted with 4-(4,4,5,5-tetramethyl-1,3,2-dioxaborolan-2-yl)-1H-pyrazole following the procedure set out in Example 1, followed by treatment with 4M HCl in dioxane, to obtain the title compound. LCMS (PS-B4) R$_t$ 4.28 min [M+H]$^+$ 305. $^1$H NMR (Me-d$_3$-OD) δ 2.76 (2H, br.t), 3.01 (2H, br.d), 3.24 (2H, br.t), 3.39 (2H, br.d), 7.58 (2H, d), 7.76 (2H, d), 8.17 (2H, d), 8.37 (2H, s), 8.82 (2H, d).

Example 90

3-(3-Chloro-phenyl)-3-[4-(1H-pyrazol-4-yl)-phenyl]-propylamine

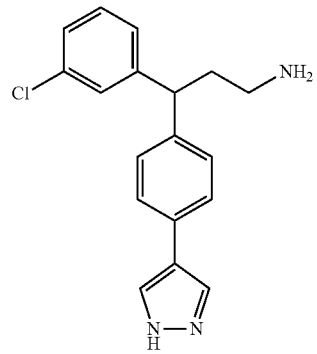 [SMILES: NCCC(c1ccc(-c2cn[nH]c2)cc1)c1cccc(Cl)c1]

By following the procedure described in Example 8 but substituting 4-chlorophenylmagnesium bromide for 3-chlorophenylmagnesium bromide and methylamine for ammonia the title compound was obtained. LCMS (PS-B3) R$_t$ 2.60 min [M+H]$^+$ 312. $^1$H NMR (Me-d$_3$-OD) δ 2.44 (2H, apparent qd), 2.87 (2H, dd), 4.14 (1H, t), 7.24 (1H, dt), 7.27-7.33 (2H, m), 7.34 (1H, t), 7.42 (2H, d), 7.68 (2H, d), 8.58 (2H, s).

Example 91

2-Methylamino-1-(4-nitro-phenyl)-1-[4-(1H-pyrazol-4-yl)-phenyl]-ethanol

By following the procedure described in Example 83 but substituting (4-chloro-phenyl)-(4-iodo-phenyl)-methanone for (4-Bromo-phenyl)-(4-nitro-phenyl)-methanone, the title compound was obtained. LCMS (PS-A) R$_t$ 1.79 [M+H]$^+$ 339. $^1$H NMR (Me-d$_3$-OD) δ 8.27 (2H, d), 7.98 (2H, s), 7.80 (2H, d), 7.65 (2H, d), 7.52 (2H, d), 4.00 (2H, dd), 2.73 (3H, s)—CH(OH) signal presumed to be under water peak.

Example 92

2-(3-Chloro-4-methoxy-phenyl)-2-[4-(1H-pyrazol-4-yl)-phenyl]-ethylamine

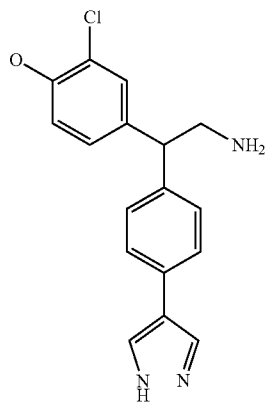 [SMILES: N=C/C(=C\N)c1ccc(C(CN)c2ccc(O)c(Cl)c2)cc1]

By following the procedure described in Example 87B and Example 42C but replacing 1-(4-bromo-phenyl)-2-methylamino-ethanol with 2-amino-1-(4-bromo-phenyl)-ethanol and chlorobenzene with 2-chloroanisole, the title compound was obtained. LCMS (PS-B3) $R_t$ 2.55 [M+H]$^+$ 328.20. $^1$H NMR (Me-d$_3$-OD) δ 3.65-3.70 (2H, d), 3.90 (3H, s), 4.30-4.35 (1H, t), 7.05-7.10 (1H, d), 7.30-7.35 (1H, d), 7.40 (1H, s), 7.45-7.50 (2H, d), 7.70-7.75 (2H, d), 8.60 (2H, s).

Example 93

2-(4-Chloro-phenyl)-2-fluoro-2-[4-(1H-pyrazol-4-yl)-phenyl]-ethylamine 93A. 2,2-Bis-(4-chloro-phenyl)-2-fluoro-ethylamine

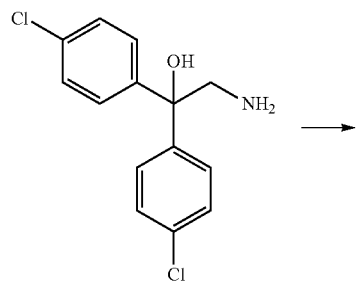

2-Amino-1,1-bis-(4-chloro-phenyl)-ethanol (293 mg, 1.04 mmol) was dissolved in pyridine-HF (2 ml) with cooling. After 24 hours the mixture was diluted into 1N sodium hydroxide solution and extracted with DCM (×3). Each extract was dried (MgSO$_4$) and filtered before being combined and concentrated to give a residue which was purified by column chromatography (SiO$_2$), eluting with 0.5% triethylamine in ethyl acetate to afford the title compound (192 mg, 65%; LCMS (PS-B3) $R_t$ 3.34 min [M−F$^-$]$^+$ 266. $^1$H NMR (DMSO-d$_6$) δ 3.41 (2H, d), 7.39-7.46 (8H, m).

93B. 2-(4-Chloro-phenyl)-2-fluoro-2-[4-(1H-pyrazol-4-yl)-phenyl]-ethylamine

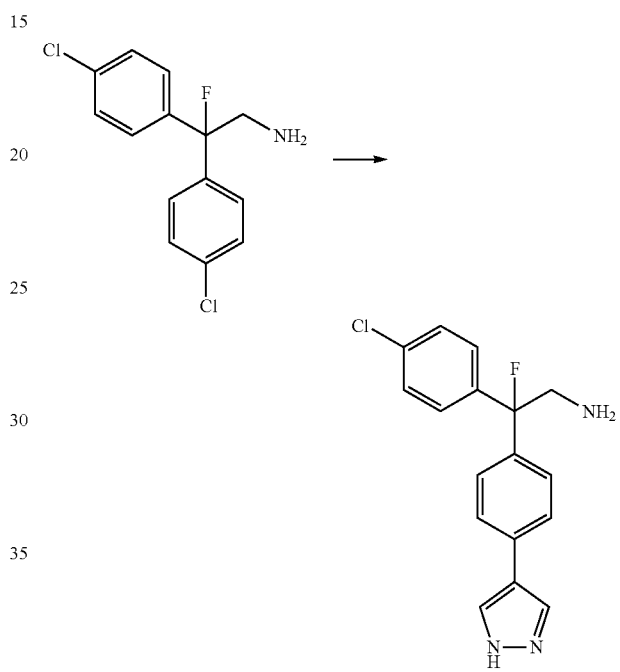

2,2-Bis-(4-chloro-phenyl)-2-fluoro-ethylamine was reacted with 4-(4,4,5,5-tetramethyl-1,3,2-dioxaborolan-2-yl)-1H-pyrazole following the procedure set out in Example 1 except that heating was carried out at 100° C. for 5 minutes using 300 W power in a CEM microwave, to obtain the title compound. LCMS (PS-B4) $R_t$ 6.69 min [M−F$^-$]$^+$ 296. $^1$H NMR (Me-d$_3$-OD) δ 4.04 (2H, d), 7.47-7.55 (6H, m), 7.77 (2H, d), 8.41 (2H, d).

Example 94

3-(3,4-Dichloro-phenyl)-3-[6-(1H-pyrazol-4-yl)-pyridin-3-yl]-propylamine

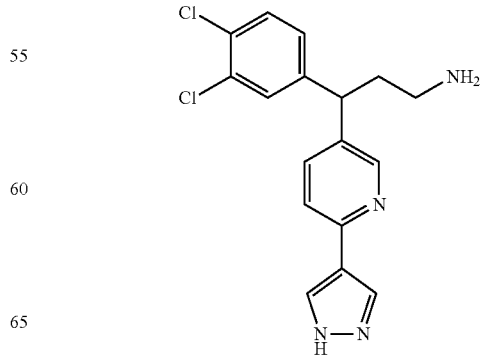

By following the procedure described in Example 60 but replacing 6-chloro-nicotinonitrile with 6-chloro-pyridine-3-carbaldehyde and replacing 3-methyl-1-trityl-1H-pyrazole-4-boronic acid with 1-trityl-1H-pyrazole-4-boronic acid, and then following the procedure described in Example 8, the title compound could be obtained.

Example 95

2-(4-Chloro-3-fluoro-phenyl)-2-[4-(1H-pyrazol-4-yl)-phenyl]-ethylamine

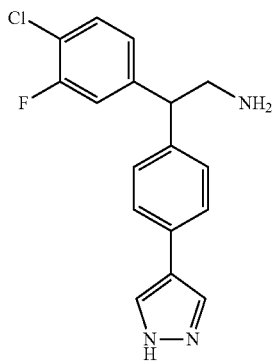 [SMILES: NCC(c1ccc(-c2cn[nH]c2)cc1)c1ccc(Cl)c(F)c1]

By following the procedure described in Example 87, but replacing 4-oxo-piperidine-1-carboxylic acid tert-butyl ester with (2-oxo-ethyl)-carbamic acid tert-butyl ester, the title compound could be obtained.

Example 96

4-(2-Chloro-3-fluoro-phenyl)-4-[4-(1H-pyrazol-4-yl)-phenyl]-piperidine

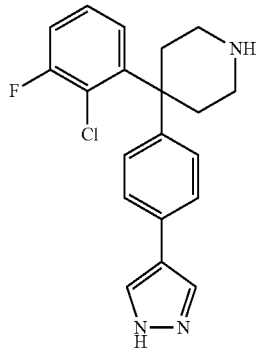 [SMILES: Fc1cccc(C2(c3ccc(-c4cn[nH]c4)cc3)CCNCC2)c1Cl]

By following the procedure described in Example 14, but replacing chlorobenzene with 1-chloro-2-fluorobenzene, the title compound can be obtained.

Example 97

1-{(3,4-Dichloro-phenyl)-[4-(1H-pyrazol-4-yl)-phenyl]-methyl}-piperazine 97A. (4-Chloro-phenyl)-(3,4-dichloro-phenyl)-methanol

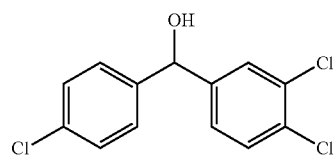 [SMILES: OC(c1ccc(Cl)cc1)c1ccc(Cl)c(Cl)c1]

Commercially available chlorophenyl magnesium bromide and 3,4-dichlorobenzaldehyde can be reacted together according to the method described in *J. Medicinal Chem.*, (2000), 43(21), 3878-3894 to give the title compound.

97B. 1,2-Dichloro-4-[chloro-(4-chloro-phenyl)-methyl]-benzene

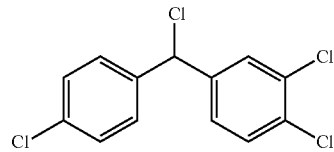 [SMILES: Clc1ccc(C(Cl)c2ccc(Cl)c(Cl)c2)cc1]

The product of Example 97A can be reacted with $SO_2Cl_2$ according to the method described in *Organic Letters*, (2003), 5(8), 1167-1169 to give the title compound.

97C. 1-{(3,4-Dichloro-phenyl)-[4-(1H-pyrazol-4-yl)-phenyl]-methyl}-piperazine

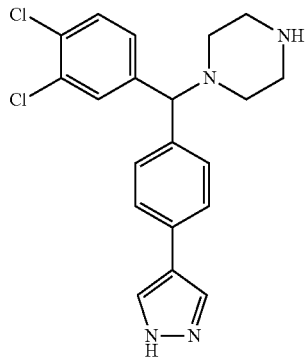

The title compound may be prepared from the compound of Example 97C by using the method and conditions described in *Zhongguo Yaowu Huaxue Zazhi* (2002), 12(3), 125-129.

Example 98

2-(3,4-Dichloro-phenyl)-2-[4-(1H-pyrazol-4-yl)-phenyl]-ethylamine

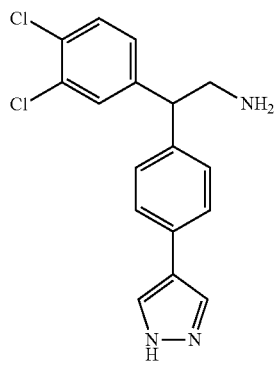 [SMILES: NCC(c1ccc(-c2cn[nH]c2)cc1)c1ccc(Cl)c(Cl)c1]

By following the procedure described in Example 42 but, in Example 42B, replacing chlorobenzene with 1,2-dichlorobenzene, the title compound can be obtained

Example 99

{2-(3-Chloro-4-methoxy-phenyl)-2-[4-(1H-pyrazol-4-yl)-phenyl]-ethyl}-methyl-amine

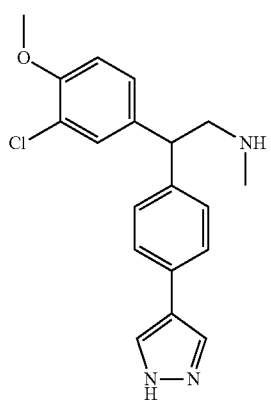 [SMILES: CNCC(c1ccc(-c2cn[nH]c2)cc1)c1ccc(OC)c(Cl)c1]

By following the procedure described in Example 42 but, in step 42B, substituting 2-chloroanisole for chlorobenzene, the title compound was obtained. LC/MS: (PS-A2) $R_t$ 2.03 [M+H]$^+$ 342. $^1$H NMR (Me-d$_3$-OD) δ 2.45 (3H, s), 3.22 (2H, d), 3.85 (3H, s), 4.15 (1H, t), 7.04 (1H, d), 7.33 (1H, d), 7.27-7.34 (3H, m), 7.55 (2H, d), 7.92 (2H, s).

Example 100

4-{4-[2-Azetidin-1-yl-1-(4-chloro-phenoxy)-ethyl]-phenyl}-1H-pyrazole

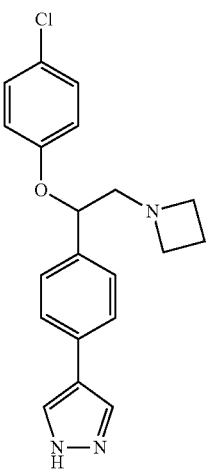 [SMILES: Clc1ccc(OC(CN2CCC2)c2ccc(-c3cn[nH]c3)cc2)cc1]

By following the procedure described in Example 42A, but replacing methylamine with azetidine and following the procedure in Example 45, the title compound could be obtained

Example 101

3-(3-Chloro-4-methoxy-phenyl)-3-[4-(1H-pyrazol-4-yl)-phenyl]-propylamine

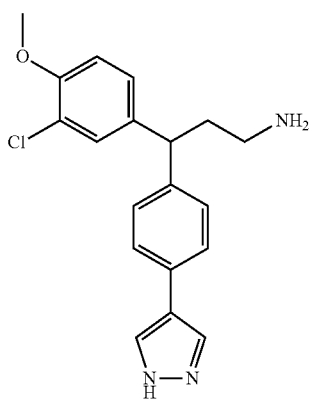 [SMILES: COc1ccc(C(CCN)c2ccc(-c3cn[nH]c3)cc2)cc1Cl]

By following the procedure described in Example 61, but replacing imidazole with potassium phthalimide in step 61A and replacing chlorobenzene with 1-chloro-2-methoxy-benzene in 61B, and then removing the phthaloyl protecting group under the conditions set out in Examples 84B and 84C, the title compound may be prepared.

Example 102

{3-(3-Chloro-4-methoxy-phenyl)-3-[4-(1H-pyrazol-4-yl)-phenyl]-propyl}-methyl-amine

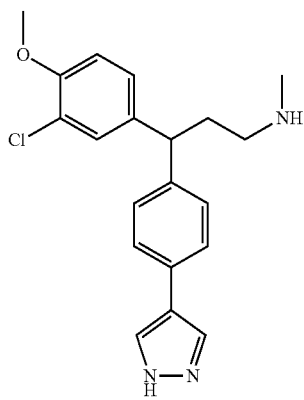 [SMILES: CNCCC(c1ccc(-c2cn[nH]c2)cc1)c1ccc(OC)c(Cl)c1]

By following the procedure described in Example 61, but substituting imidazole with methylamine in Example 61A and substituting chlorobenzene with 1-chloro-2-methoxy-benzene in Example 61B, the title compound may be obtained.

Example 103

1-[(3-Chloro-4-methoxy-phenyl)-(4-chloro-phenyl)-methyl]-piperazine 103A. (3-Chloro-4-methoxy-phenyl)-(4-chloro-phenyl)-methanol

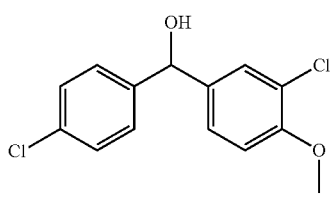 [SMILES: COc1ccc(C(O)c2ccc(Cl)cc2)cc1Cl]

The title compound can be prepared using the method of Example 97A but replacing 3,4-dichlorobenzaldehyde with 3-chloro-4-methoxybenzaldehyde.

103B. 2-Chloro-4-[chloro-(4-chloro-phenyl)-methyl]-1-methoxy-benzene

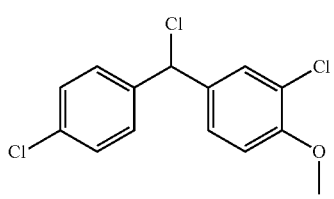 [SMILES: COc1ccc(C(Cl)c2ccc(Cl)cc2)cc1Cl]

The hydroxy compound of Example 103A can be converted into the title chloro compound by following the method of Example 97B.

103C. 1-[(3-Chloro-4-methoxy-phenyl)-(4-chloro-phenyl)-methyl]-piperazine

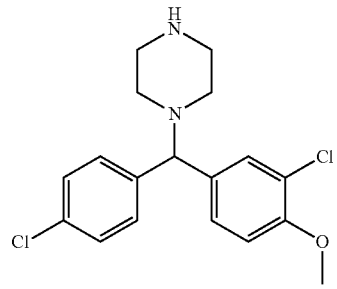 [SMILES: COc1ccc(C(c2ccc(Cl)cc2)N2CCNCC2)cc1Cl]

The title compound can be prepared from the product of Example 103B by following the method of Example 97C.

Example 104

C-(4-Chloro-phenyl)-C-[4-(1H-pyrazol-4-yl)-phenyl]-methylamine

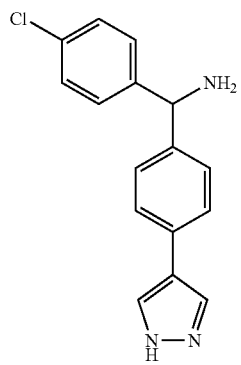 [SMILES: NC(c1ccc(Cl)cc1)c1ccc(-c2cn[nH]c2)cc1]

By following the procedure described in Example 1 but substituting 2-(4-chlorophenyl)-2-phenylethylamine hydrochloride with C,C-bis-(4-chloro-phenyl)-methylamine, the title compound could be obtained.

Example 105

{2-(4-Chloro-phenyl)-2-[4-(3-methyl-1H-pyrazol-4-yl)-phenyl]-ethyl}-methyl amine 105A. 2-(4-Chloro-phenyl)-N-methyl-2-[4-(3-methyl-1-trityl-1H-pyrazol-4-yl)-phenyl]-acetamide

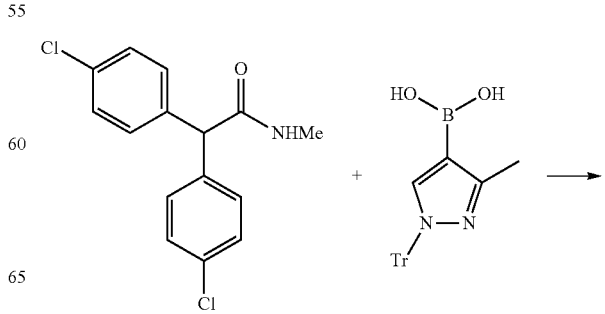

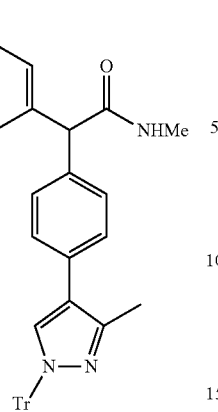

2,2-Bis-(4-chloro-phenyl)-N-methyl-acetamide was prepared by the reaction of the commercially available corresponding carboxylic acid with methylamine using the method of Example 21a. The N-methyl-acetamide compound was then converted to the title compound by the method described in Example 1.

LCMS (PS-B3) $R_t$ 4.21 min; m/z [M+H]$^+$ 582.

105B. 2-(4-Chloro-phenyl)-N-methyl-2-[4-(3-methyl-1H-pyrazol-4-yl)-phenyl]-acetamide

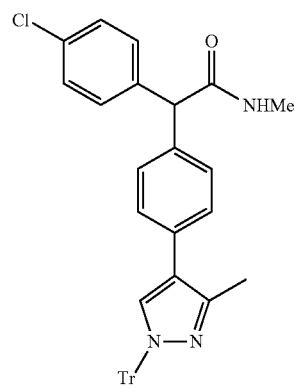 

The trityl-protected compound of example 104A was deprotected by the method described in example 60D to give the title compound.

LCMS (PS-B3) $R_t$ 2.41 min; m/z [M+H]$^+$ 340. $^1$H NMR (methanol-d$_4$) δ 2.40 (3H, s), 2.78 (3H, s), 4.95 (1H, s), 7.29-7.34 (6H, m), 7.41 (2H, d), 7.69 (1H, s).

105C. {2-(4-Chloro-phenyl)-2-[4-(3-methyl-1H-pyrazol-4-yl)-phenyl]-ethyl}-methyl-amine

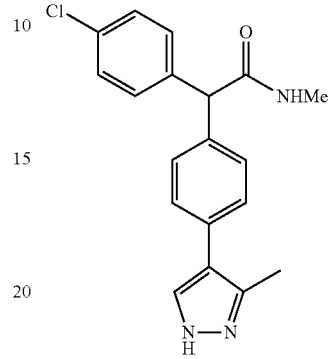 

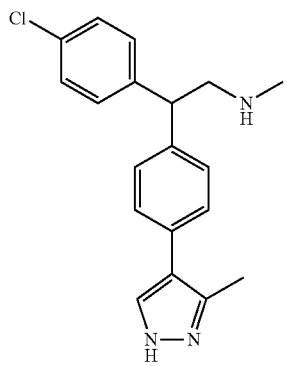

Following the procedure described in example 20B gave the title compound. LCMS (PS-B3) $R_t$ 2.80 min; m/z [M+H]$^+$ 326. $^1$H NMR (methanol-d$_4$) δ 2.52 (3H, s), 2.75 (3H, s), 3.80 (2H, d), 4.46 (1H, t), 7.41 (4H, s), 7.49 (2H, d), 7.54 (2H, d), 8.24 (1H, s).

Biological Activity

Example 106

Measurement of PKA Kinase Inhibitory Activity (IC$_{50}$)

Compounds of the invention can be tested for PK inhibitory activity using the PKA catalytic domain from Upstate Biotechnology (#14-440) and the 9 residue PKA specific peptide (GRTGRRNSI), also from Upstate Biotechnology (#12-257), as the substrate. A final concentration of 1 nM enzyme is used in a buffer that includes 20 mM MOPS pH 7.2, 40 μM ATP/γ$^{33}$P-ATP and 5 μM substrate. Compounds are added in dimethylsulphoxide (DMSO) solution to a final DMSO concentration of 2.5%. The reaction is allowed to proceed for 20 minutes before addition of excess orthophosphoric acid to quench activity. Unincorporated γ$^{33}$P-ATP is then separated from phosphorylated proteins on a Millipore MAPH filter plate. The plates are washed, scintillant is added and the plates are then subjected to counting on a Packard Topcount.

The % inhibition of the PKA activity is calculated and plotted in order to determine the concentration of test compound required to inhibit 50% of the PKB activity (IC$_{50}$).

The compounds of Examples 1, 4, 43, 44, 45, 46, 47, 48, 49, 52, 54, 59, 63, 66, 67, 73, 78, 79, 81, 82, 83, 84, 85, 86 and 90 have $IC_{50}$ values of less than 1 μM whereas the compounds of Examples 5, 7 and 80 have $IC_{50}$ values of less than 15 μM.

Example 107

Measurement of PKB Kinase Inhibitory Activity ($IC_{50}$)

The inhibition of protein kinase B (PKB) activity by compounds can be determined determined essentially as described by Andjelkovic et al. (Mol. Cell. Biol. 19, 5061-5072 (1999)) but using a fusion protein described as PKB-PIF and described in full by Yang et al (Nature Structural Biology 9, 940-944 (2002)). The protein is purified and activated with PDK1 as described by Yang et al. The peptide AKTide-2T (H-A-R-K-R-E-R-T-Y-S-F-G-H-H-A-OH) obtained from Calbiochem (#123900) is used as a substrate. A final concentration of 0.6 nM enzyme is used in a buffer that includes 20 mM MOPS pH 7.2, 30 μM ATP/$γ^{33}$P-ATP and 25 μM substrate. Compounds are added in DMSO solution to a final DMSO concentration of 2.5%. The reaction is allowed to proceed for 20 minutes before addition of excess orthophosphoric acid to quench activity. The reaction mixture is transferred to a phosphocellulose filter plate where the peptide binds and the unused ATP is washed away. After washing, scintillant is added and the incorporated activity measured by scintillation counting.

The % inhibition of the PKB activity is calculated and plotted in order to determine the concentration of test compound required to inhibit 50% of the PKB activity ($IC_{50}$).

Following the protocol described above, the $IC_{50}$ values of the compounds of Examples 1, 4, 8-10, 12-17, 20-23, 25-31, 33-35, 43, 44, 46, 47, 49-52, 54, 56, 57, 59, 61, 63, 65, 66, 69, 71-73, 76-79, 81-87, 90, 91, 94 and 104 have been found to be less than 1 μM whilst the compounds of Examples 2, 3, 5, 6, 7, 11, 18, 19, 24, 32, 36, 45, 48, 53, 55, 58, 60, 64, 67, 68, 75, 80 and 89 each have $IC_{50}$ values of less than 5 μM, and the compounds of Examples 40, 41, 62 and 70 each have $IC_{50}$ values of less than 50 μM.

Pharmaceutical Formulations

Example 108

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(iv) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A pharmaceutical composition comprising a pharmaceutically acceptable carrier and a compound having the formula (IV):

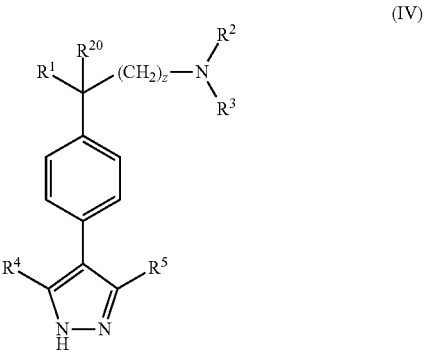

(IV)

or a salt or tautomer thereof,
wherein z is 0, 1 or 2;
$R^1$ is unsubstituted phenyl or phenyl substituted with 1, 2, 3 or 4 substituents independently selected from hydroxy, $C_{1-4}$ acyloxy, fluorine, chlorine, bromine, trifluoromethyl, cyano, $C_{1-4}$ hydrocarbyloxy and $C_{1-4}$ hydrocarbyl optionally substituted by $C_{1-2}$ alkoxy or hydroxy;
$R^2$ and $R^3$ are independently selected from hydrogen and methyl;
$R^4$ is selected from hydrogen and methyl;
$R^5$ is selected from hydrogen and methyl; and
$R^{20}$ is selected from hydrogen, methyl, hydroxy and fluorine, provided that when z is 0, $R^{20}$ is other than hydroxy.

2. A pharmaceutical composition according to claim 1 wherein the group $R^1$ has one or two substituents selected from fluorine, chlorine, trifluoromethyl, methyl and methoxy.

3. A pharmaceutical composition according to claim 2 wherein $R^1$ is a mono-chlorophenyl or dichlorophenyl group.

4. A pharmaceutical composition according to claim 1, wherein $R^2$ and $R^3$ are both hydrogen.

5. A pharmaceutical composition according to claim 1 wherein the compound of formula (IV) or the salt or tautomer thereof has a molecular weight less than 525.

6. A pharmaceutical composition according to claim 1 comprising a compound which is:

2-phenyl-2-[4-(1H-pyrazol-4-yl)-phenyl]-ethylamine;
2-[4-(3,5-dimethyl-1H-pyrazol-4-yl)-phenyl]-2-phenyl-ethylamine;
2-(4-chloro-phenyl)-2-[4-(1H-pyrazol-4-yl)-phenyl]-ethylamine;
{3-(4-chloro-phenyl)-3-[4-(1H-pyrazol-4-yl)-phenyl]-propyl}-methyl-amine;
{3-(3,4-difluoro-phenyl)-3-[4-(1H-pyrazol-4-yl)-phenyl]-propyl}-methyl-amine;
{3-(3-chloro-phenyl)-3-[4-(1H-pyrazol-4-yl)-phenyl]-propyl}-methyl-amine;
3-(4-chloro-phenyl)-3-[4-(1H-pyrazol-4-yl)-phenyl]-propylamine;
3-(3,4-dichloro-phenyl)-3-[4-(1H-pyrazol-4-yl)-phenyl]-propylamine;
{2-(4-chloro-phenyl)-2-[4-(1H-pyrazol-4-yl)-phenyl]-ethyl}-dimethyl-amine;
{2-(4-chloro-phenyl)-2-[4-(1H-pyrazol-4-yl)-phenyl]-ethyl}-methyl-amine;
{2-(4-chloro-phenyl)-2-[4-(1H-pyrazol-4-yl)-phenyl]-ethyl}-methyl-amine (R);
{2-(4-chloro-phenyl)-2-[4-(1H-pyrazol-4-yl)-phenyl]-ethyl}-methyl-amine (S);
dimethyl-{2-phenyl-2-[4-(1H-pyrazol-4-yl)-phenyl]-ethyl}-amine;
2-(4-chloro-phenyl)-2-[4-(1H-pyrazol-4-yl)-phenyl]-ethylamine (R);
2-(4-chloro-phenyl)-2-[4-(1H-pyrazol-4-yl)-phenyl]-ethylamine (S);
{2-(4-chloro-phenyl)-2-[4-(1H-pyrazol-4-yl)-phenyl]-ethyl}-methyl-amine;
{2-(4-methoxy-phenyl)-2-[4-(1-pyrazol-4-yl)-phenyl]-ethyl}-methyl-amine;
{3-(4-fluoro-phenyl)-3-[4-(1H-pyrazol-4-yl)-phenyl]-propyl}-methyl-amine;
{2-(4-fluoro-phenyl)-2-[4-(1H-pyrazol-4-yl)-phenyl]-ethyl}-methyl-amine;
{2-(3-chloro-phenyl)-2-[4-(1H-pyrazol-4-yl)-phenyl]-ethyl}-methyl-amine;
4-{3-methylamino-1-[4-(1H-pyrazol-4-yl)-phenyl]-propyl}-phenol;
3-(4-methoxy-phenyl)-3-[4-(1H-pyrazol-4-yl)-phenyl]-propylamine;
{2-(4-chloro-phenyl)-2-[4-(1H-pyrazol-4-yl)-phenyl]-propyl}-methyl-amine;
1-(4-chloro-phenyl)-2-methylamino-1-[4-(1H-pyrazol-4-yl)-phenyl]-ethanol;
2-amino-1-(4-chloro-phenyl)-1-[4-(1H-pyrazol-4-yl)-phenyl]-ethanol;
3-(3-chloro-phenyl)-3-[4-(1H-pyrazol-4-yl)-phenyl]-propylamine;
2-(3-chloro-4-methoxy-phenyl)-2-[4-(1H-pyrazol-4-yl)-phenyl]-ethylamine;
2-(4-chloro-phenyl)-2-fluoro-2-[4-(1H-pyrazol-4-yl)-phenyl]-ethylamine;
2-(4-chloro-3-fluoro-phenyl)-2-[4-(1H-pyrazol-4-yl)-phenyl]-ethylamine;
2-(3,4-dichloro-phenyl)-2-[4-(1H-pyrazol-4-yl)-phenyl]-ethylamine;
{2-(3-chloro-4-methoxy-phenyl)-2-[4-(1H-pyrazol-4-yl)-phenyl]-ethyl}-methyl-amine;
3-(3-chloro-4-methoxy-phenyl)-3-[4-(1H-pyrazol-4-yl)-phenyl]-propylamine; or
C-(4-chloro-phenyl)-C-[4-(1H-pyrazol-4-yl)-phenyl]-methylamine;
and salts and tautomers thereof.

7. A pharmaceutical composition according to claim 1 wherein the compound is in the form of a salt.

8. A pharmaceutical composition according to claim 1 wherein the compound is 2-amino-1-(4-chloro-phenyl)-1-[4-(1H-pyrazol-4-yl)-phenyl]-ethanol or a tautomer thereof.

9. A pharmaceutical composition according to claim 1 wherein the compound is a salt of 2-amino-1-(4-chloro-phenyl)-1-[4-(1H-pyrazol-4-yl)-phenyl]-ethanol or a tautomer thereof.

10. A pharmaceutical composition according to claim 1 wherein said composition is in a form suitable for oral administration.

11. A pharmaceutical composition according to claim 10 wherein the compound is 2-amino-1-(4-chloro-phenyl)-1-[4-(1H-pyrazol-4-yl)-phenyl]-ethanol or a salt or tautomer thereof.

12. A pharmaceutical composition according to claim 1 wherein said composition is in a form suitable for parenteral administration.

13. A pharmaceutical composition according to claim 12 wherein the compound is 2-amino-1-(4-chloro-phenyl)-1-[4-(1H-pyrazol-4-yl)-phenyl]-ethanol or a salt or tautomer thereof.

14. A pharmaceutical composition according to claim 1 wherein said composition is in a form suitable for intravenous administration.

15. A pharmaceutical composition according to claim 14 wherein the compound is 2-amino-1-(4-chloro-phenyl)-1-[4-(1H-pyrazol-4-yl)-phenyl]-ethanol or a salt or tautomer thereof.

16. A pharmaceutical composition according to claim 9 wherein the compound is a salt of 2-amino-1-(4-chloro-phenyl)-1-[4-(1H-pyrazol-4-yl)-phenyl]-ethanol.

17. A pharmaceutical composition according to claim 1 wherein the compound of formula (IV) is in the form of a hydrochloride salt.

18. A pharmaceutical composition according to claim 1 wherein the compound of formula (IV) is in the form of a dihydrochloride salt.

19. A pharmaceutical composition according to claim 9 wherein the compound is in the form of a hydrochloride salt.

20. A pharmaceutical composition according to claim 9 wherein the compound is in the form of a dihydrochloride salt.

* * * * *

UNITED STATES PATENT AND TRADEMARK OFFICE
CERTIFICATE OF CORRECTION

| | | |
|---|---|---|
| PATENT NO. | : 8,691,806 B2 | Page 1 of 1 |
| APPLICATION NO. | : 13/536174 | |
| DATED | : April 8, 2014 | |
| INVENTOR(S) | : Berdini et al. | |

It is certified that error appears in the above-identified patent and that said Letters Patent is hereby corrected as shown below:

In the Claims:

Column 171, Line 41: Claim 6, Delete "[4-(1-pyrazol-4-yl)-phenyl]" and insert -- [4-(1H-pyrazol-4-yl)-phenyl] --

Signed and Sealed this
Eighth Day of July, 2014

Michelle K. Lee
*Deputy Director of the United States Patent and Trademark Office*